United States Patent
Fujimori et al.

(10) Patent No.: US 9,546,181 B2
(45) Date of Patent: Jan. 17, 2017

(54) COMPOUND HAVING PERFLUOROALKYL TERMINAL GROUP AND CF$_2$O BONDING GROUP, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Sayaka Fujimori, Ichihara (JP); Hiroyuki Tanaka, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/951,104

(22) Filed: Nov. 24, 2015

(65) Prior Publication Data
US 2016/0152636 A1 Jun. 2, 2016

(30) Foreign Application Priority Data

Nov. 27, 2014 (JP) .................. 2014-239784

(51) Int. Cl.
| | | |
|---|---|---|
| C07D 309/06 | (2006.01) |
| C07D 319/06 | (2006.01) |
| C07D 237/06 | (2006.01) |
| C07D 213/30 | (2006.01) |
| C09K 19/20 | (2006.01) |
| C09K 19/30 | (2006.01) |
| C09K 19/34 | (2006.01) |
| C09K 19/54 | (2006.01) |
| C07D 497/08 | (2006.01) |
| C07D 239/26 | (2006.01) |
| C09K 19/32 | (2006.01) |
| C09K 19/04 | (2006.01) |
| C09K 19/12 | (2006.01) |

(52) U.S. Cl.
CPC ........... *C07D 497/08* (2013.01); *C07D 213/30* (2013.01); *C07D 239/26* (2013.01); *C07D 309/06* (2013.01); *C07D 319/06* (2013.01); *C09K 19/20* (2013.01); *C09K 19/3059* (2013.01); *C09K 19/3066* (2013.01); *C09K 19/3068* (2013.01); *C09K 19/32* (2013.01); *C09K 19/322* (2013.01); *C09K 19/3402* (2013.01); *C09K 19/3458* (2013.01); *C09K 2019/044* (2013.01); *C09K 2019/0466* (2013.01); *C09K 2019/122* (2013.01); *C09K 2019/123* (2013.01); *C09K 2019/301* (2013.01); *C09K 2019/3004* (2013.01); *C09K 2019/308* (2013.01); *C09K 2019/3009* (2013.01); *C09K 2019/3071* (2013.01); *C09K 2019/3077* (2013.01); *C09K 2019/3078* (2013.01); *C09K 2019/3083* (2013.01); *C09K 2019/3422* (2013.01); *C09K 2019/3425* (2013.01)

(58) Field of Classification Search
None
See application file for complete search history.

(56) References Cited

U.S. PATENT DOCUMENTS

| | | |
|---|---|---|
| 5,728,319 A | 3/1998 | Matsui et al. |
| 2009/0302273 A1 | 12/2009 | Tanaka |
| 2010/0127211 A1 | 5/2010 | Tanaka |
| 2011/0193022 A1 | 8/2011 | Tanaka et al. |

FOREIGN PATENT DOCUMENTS

| | | |
|---|---|---|
| WO | 96-11897 A1 | 4/1996 |
| WO | 2008-105286 A1 | 9/2008 |
| WO | 2009-150963 A1 | 12/2009 |
| WO | 2010-047260 A1 | 4/2010 |

*Primary Examiner* — Shean C Wu
(74) *Attorney, Agent, or Firm* — Hogan Lovells US LLP

(57) ABSTRACT

The subject is to provide a liquid crystal compound satisfying at least one of physical properties such as a high stability to heat or light, a high clearing point (or a high maximum temperature), a low minimum temperature of a liquid crystal phase, a small viscosity, a suitable optical anisotropy, a large dielectric anisotropy, a suitable elastic constant and an excellent compatibility with any other liquid crystal compound, a liquid crystal composition including this compound and a liquid crystal display device including this composition. The compound is represented by the following formula (1a):

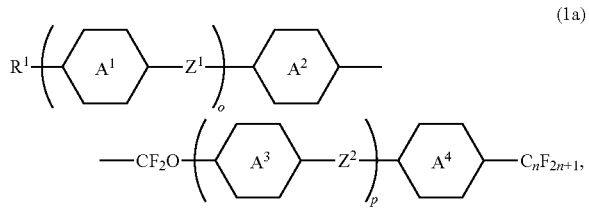

wherein $R^1$ is alkyl having 1 to 15 carbons or the like; ring $A^1$, ring $A^2$, ring $A^3$ and ring $A^4$ are independently 1,4-phenylene, naphthalene-2,6-diyl or the like; $Z^1$ and $Z^2$ are independently a single bond or the like; o and p are independently 0, 1 or 2; and n is an integer from 2 to 10.

16 Claims, No Drawings

COMPOUND HAVING PERFLUOROALKYL TERMINAL GROUP AND CF₂O BONDING GROUP, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. It relates especially to a liquid crystal compound having a perfluoroalkyl terminal group and a $CF_2O$ bonding group, a liquid crystal composition including this compound and having a nematic phase, and a liquid crystal display device including this composition.

A liquid crystal display device has been widely used as display for a personal computer, a television set and so forth. The device utilizes physical properties such as the optical anisotropy and the dielectric anisotropy of a liquid crystal compound. Operating modes for the liquid crystal display device includes modes such as PC (phase change), TN (twisted nematic), STN (super twisted nematic), BTN (bi-stable twisted nematic), ECB (electrically controlled birefringence), OCB (optically compensated bend), IPS (in-plane switching), VA (vertical alignment), FFS (Fringe Field Switching) and PSA (polymer sustained alignment).

A liquid crystal composition having suitable physical properties is used for such a liquid crystal display device. It is desirable that a liquid crystal compound included in the composition should have physical properties shown in the following items (1) to (8) in order to further improve the characteristics of the device: (1) a high stability to heat, light and so forth, (2) a high clearing point, (3) a low minimum temperature of a liquid crystal phase, (4) a small viscosity ($\eta$), (5) a suitable optical anisotropy ($\Delta n$), (6) a large dielectric anisotropy ($\Delta \in$), (7) a suitable elastic constant (K), and (8) an excellent compatibility with any other liquid crystal compound.

The effects of physical properties of a liquid crystal compound on the characteristics of a device are as follows. A compound having a high stability to heat, light and so forth described in item (1) increases the voltage holding ratio of a device. As a result, the service life of the device is increased. A compound having a high clearing point described in item (2) increases the temperature range in which the device can be used. A compound having a low minimum temperature of a liquid crystal phase such as a nematic phase or a smectic phase, especially having a low minimum temperature of a nematic phase, described in item (3) also increases the temperature range in which the device can be used. A compound having a small viscosity described in item (4) decreases the response time of the device.

A compound having a suitable optical anisotropy, namely a large optical anisotropy or a small optical anisotropy, is required depending on the design of the device. A compound having a large optical anisotropy is suitable when the response time is decreased by decreasing the cell gap of the device. A compound having a large dielectric anisotropy described in item (6) decreases the threshold voltage of the device. As a result, the electric power consumption of the device is decreased. In contrast, a compound having a small dielectric anisotropy decreases the response time of the device by decreasing the viscosity of the composition. This compound increases the temperature range in which the device can be used, by increasing the maximum temperature of a nematic phase.

With regard to item (7), a compound having a large elastic constant decreases the response time of the device. A compound having a small elastic constant decreases the threshold voltage of the device. Thus, a suitable elastic constant is required depending on the characteristics that should be improved. A compound having an excellent compatibility with any other liquid crystal compound described in item (8) is desirable. This is because the physical properties of the composition are adjusted by mixing liquid crystal compounds having different physical properties.

A variety of liquid crystal compounds having a large dielectric anisotropy have been prepared until now. A variety of liquid crystal compounds having a large optical anisotropy have been prepared until now. This is because excellent physical properties which are not possessed by conventional compounds can be expected from new compounds. This is because a suitable balance between at least two physical properties of a liquid crystal composition is expected by the addition of a new compound to the composition. In view of these situations, a compound having excellent physical properties and a suitable balance with regard to physical properties (1) to (8) described above has been expected.

PRIOR ART

Patent Document

Patent document No. 1: WO 1996/011897 A.
Patent document No. 2: WO 2009/150963 A.
Patent document No. 3: WO 2010/047260 A.
Patent document No. 4: WO 2008/105286 A.

SUMMARY OF THE INVENTION

Subject to be Solved by the Invention

The first subject is to provide a liquid crystal compound satisfying at least one of physical properties such as a high stability to heat or light, a high clearing point (or a high maximum temperature of a nematic phase), a low minimum temperature of a liquid crystal phase, a small viscosity, a suitable optical anisotropy, a large dielectric anisotropy, a suitable elastic constant and an excellent compatibility with any other liquid crystal compound. The subject is to provide a compound having an especially high maximum temperature. The second subject is to provide a liquid crystal composition including this compound and satisfying at least one of physical properties such as a high stability to heat or light, a high maximum temperature of a nematic phase, a low minimum temperature of a nematic phase, a small viscosity, a suitable optical anisotropy, a large dielectric anisotropy, a large specific resistance and a suitable elastic constant. The subject is to provide a liquid crystal composition having a suitable balance regarding at least two of the physical properties. The third subject is to provide a liquid crystal display device including this composition and having a wide temperature range in which the device can be used, a short response time, a large voltage holding ratio, a low threshold voltage, a large contrast ratio and a long service life.

Means for Solving the Subject

The invention concerns a compound represented by formula (1a), a liquid crystal composition including this compound, and a liquid crystal display device including this composition.

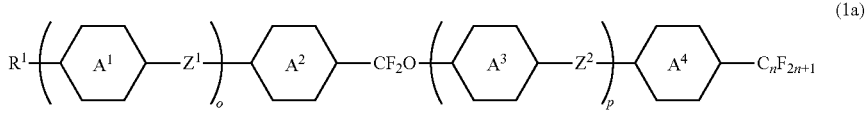

(1a)

In formula (1a),

R$^1$ is alkyl having 1 to 15 carbons, and in the alkyl at least one —CH$_2$— may be replaced by —O— or —S— and at least one —CH$_2$CH$_2$— may be replaced by —CH=CH—;

ring A$^1$, ring A$^2$ and ring A$^3$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl or 1,2,3,4-tetrahydronaphthalene-2,6-diyl, and in these rings at least one hydrogen may be replaced by fluorine or chlorine;

ring A$^4$ is 1,4-phenylene or naphthalene-2,6-diyl, and in these rings at least one hydrogen may be replaced by fluorine or chlorine;

Z$^1$ and Z$^2$ are independently a single bond, —CH$_2$CH$_2$—, —CH=CH—, —C≡C—, —COO—, —OCO—, —CH$_2$O—, —OCH$_2$—, —CF$_2$O—, —OCF$_2$— or —CF=CF—;

o and p are independently 0, 1 or 2, and the sum of o and p is 0, 1 or 2; and n is an integer from 2 to 10.

Effect of the Invention

The first advantage is to provide a liquid crystal compound satisfying at least one of physical properties such as a high stability to heat or light, a high clearing point (or a high maximum temperature of a nematic phase), a low minimum temperature of a liquid crystal phase, a small viscosity, a suitable optical anisotropy, a large dielectric anisotropy, a suitable elastic constant and an excellent compatibility with any other liquid crystal compound. The advantage is to provide a compound having an especially high maximum temperature (See Comparative Example 1). The second advantage is to provide a liquid crystal composition including this compound and satisfying at least one of physical properties such as a high stability to heat or light, a high maximum temperature of a nematic phase, a low minimum temperature of a nematic phase, a small viscosity, a suitable optical anisotropy, a large dielectric anisotropy, a large specific resistance and a suitable elastic constant. The advantage is to provide a liquid crystal composition having a suitable balance regarding at least two of the physical properties. The third advantage is to provide a liquid crystal display device including this composition and having a wide temperature range in which the device can be used, a short response time, a large voltage holding ratio, a low threshold voltage, a large contrast ratio and a long service life.

Embodiment to Carry Out the Invention

Usage of the terms in this specification is as follows. The terms, "liquid crystal compound", "liquid crystal composition" and "a liquid crystal display device" may be abbreviated to "compound", "composition" and "device", respectively. "Liquid crystal compound" is a generic term for a compound having a liquid crystal phase such as a nematic phase or a smectic phase, and for a compound having no liquid crystal phases but being mixed to a composition for the purpose of adjusting the physical properties of a composition, such as the maximum temperature, the minimum temperature, the viscosity and the dielectric anisotropy. This compound has a six-membered ring such as 1,4-cyclohexylene or 1,4-phenylene, and its molecular structure is rod-like. "Liquid crystal display device" is a generic term for a liquid crystal display panel and a liquid crystal display module. "Polymerizable compound" is a compound that is added to a composition in order to form a polymer in it.

A liquid crystal composition is prepared by mixing a plurality of liquid crystal compounds. The ratio of a liquid crystal compound (content) is expressed as a percentage by weight (% by weight) based on the weight of this liquid crystal composition. An additive such as a polymerizable compound, a polymerization initiator, a polymerization inhibitor, an optically active compound, an antioxidant, an ultraviolet light absorber, a light stabilizer, a thermal stabilizer, a coloring matter and an antifoaming agent is added to this composition as required. The ratio of the additive (added amount) is expressed as a percentage by weight (% by weight) based on the weight of the liquid crystal composition in the same manner as with the liquid crystal compound. Weight parts per million (ppm) is sometimes used. The ratio of the polymerization initiator or the polymerization inhibitor is exceptionally expressed on the basis of the weight of the polymerizable compound.

"Clearing point" is the transition temperature between a liquid crystal phase and an isotropic phase in a liquid crystal compound. "Minimum temperature of a liquid crystal phase" is the transition temperature between solids and a liquid crystal phase (a smectic phase, a nematic phase or the like) in a liquid crystal compound. "Maximum temperature of a nematic phase" is the transition temperature between a nematic phase and an isotropic phase in a mixture of a liquid crystal compound and mother liquid crystals or in a liquid crystal composition, and may be abbreviated to "maximum temperature". "Minimum temperature of a nematic phase" may be abbreviated to "minimum temperature". The expression "increase the dielectric anisotropy" means that its value increases positively when the composition has positive dielectric anisotropy, and that its value increases negatively when the composition has negative dielectric anisotropy.

A compound represented by formula (1a) is sometimes abbreviated to compound (1a). A compound selected from the group of compounds represented by formula sub formula (1a) is sometimes abbreviated to compound (1a). "Compound (1a)" means one compound, a mixture of two compounds or a mixture of three or more compounds, represented by formula (1a). These rules apply to a compound represented by another formula. In formula (1a), formula (1b) and formulas (2) to (15), the symbol such as A$^1$, B$^1$ or C$^1$ surrounded by a hexagon corresponds to a six-membered ring such as ring A$^1$, ring B$^1$ and ring C$^1$, respectively. The hexagon may represent a condensed ring such as naphthalene or a bridged ring such as adamantane.

The symbol for the terminal group, R$^1$, is used for a plurality of compounds in the chemical formulas of component compounds. In these compounds, two groups represented by two arbitrary R$^1$ may be the same or different. In one case, for example, R$^1$ of compound (1-1) is ethyl and R$^1$ of compound (1-2) is ethyl. In another case, R$^1$ of compound (1-1) is ethyl and R$^1$ of compound (1-2) is propyl. The same rule applies to symbols such as R$^{11}$ and Z$^{11}$. In compound (8), two of ring D$^1$ are present when i is 2. In this compound, two groups represented by two of ring D$^1$ may be the same or different. The same rule applies to arbitrary two of ring D$^1$, when i is greater than 2. The same rule also applies to other symbols.

The expression "at least one 'A'" means that the number of 'A' is arbitrary. The expression "at least one 'A' may be replaced by 'B'" means that the position of 'A' is arbitrary when the number of 'A' is one, and the positions can also be selected without restriction when the number of 'A' is two or more. This rule also applies to the expression "at least one 'A' has been replaced by 'B'." The expression "at least one 'A' may be replaced by 'B', 'C' or 'D'" includes cases where arbitrary 'A' has been replaced by 'B', and arbitrary 'A' has been replaced by 'C', and arbitrary 'A' has been replaced by 'D', and also cases where a plurality of 'A' has been replaced by at least two of 'B', 'C' and/or 'D'. For example, "alkyl in which at least one —CH$_2$— may be replaced by —O— or —CH=CH—" includes alkyl, alkoxy, alkoxyalkyl, alkenyl, alkoxyalkenyl and alkenyloxyalkyl. Incidentally, it is undesirable that two successive —CH$_2$— should be replaced by —O— to give —O—O—. It is also undesirable that —CH$_2$— of a methyl moiety (—CH$_2$—H) in alkyl and so forth should be replaced by —O— to give —O—H.

Halogen means fluorine, chlorine, bromine and iodine. Desirable halogen is fluorine and chorine. More desirable halogen is fluorine. The alkyl of a liquid crystal compound is straight-chain or branched-chain, and does not include cycloalkyl. Straight-chain alkyl is generally preferable to branched-chain alkyl. These apply to a terminal group such as alkoxy and alkenyl. With regard to the configuration of 1,4-cyclohexylene, trans is preferable to cis for increasing the maximum temperature. 2-Fluoro-1,4-phenylene means the two divalent groups described below. Fluorine may be facing left (L) or facing right (R) in a chemical formula. The same rule also applies to an asymmetric divalent group formed from a ring by removing two hydrogens, such as tetrahydropyran-2,5-diyl.

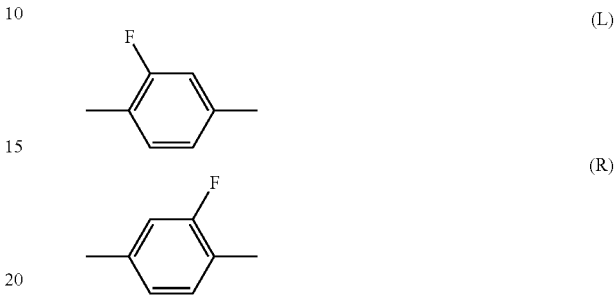

The invention includes the following items.

Item 1. A compound represented by formula (1a):

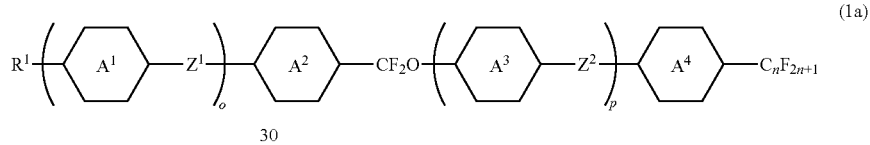

in formula (1a), $R^1$ is alkyl having 1 to 15 carbons, and in the alkyl at least one —CH$_2$— may be replaced by —O— or —S— and at least one —CH$_2$CH$_2$— may be replaced by —CH=CH—;

ring $A^1$, ring $A^2$ and ring $A^3$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl or 1,2,3,4-tetrahydronaphthalene-2,6-diyl, and in these rings at least one hydrogen may be replaced by fluorine or chlorine;

ring $A^4$ is 1,4-phenylene or naphthalene-2,6-diyl, and in these rings at least one hydrogen may be replaced by fluorine or chlorine;

$Z^1$ and $Z^2$ are independently a single bond, —CH$_2$CH$_2$—, —CH=CH—, —C≡C—, —COO—, —OCO—, —CH$_2$O—, —OCH$_2$—, —CF$_2$O—, —OCF$_2$— or —CF=CF—;

o and p are independently 0, 1 or 2, and the sum of o and p is 0, 1 or 2; and n is an integer from 2 to 10.

Item 2. The compound according to item 1, wherein in formula (1a) according to item 1, ring $A^3$ is 1,4-phenylene, 1,4-phenylene in which at least one hydrogen has been replaced by fluorine or chlorine, naphthalene-2,6-diyl or naphthalene-2,6-diyl in which at least one hydrogen has been replaced by fluorine or chlorine.

Item 3. The compound according to item 1 or 2, wherein the compound is represented by formula (1b):

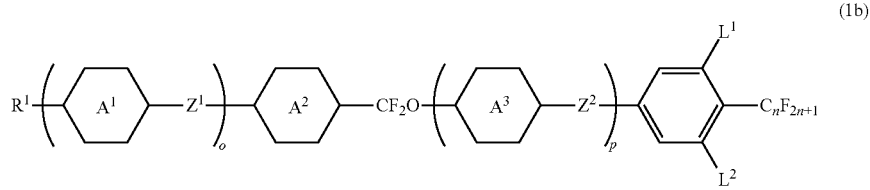

in formula (1b),

R¹ is alkyl having 1 to 15 carbons, and in the alkyl at least one —CH$_2$— may be replaced by —O— and at least one —CH$_2$CH$_2$— may be replaced by —CH=CH—;

ring A¹ is 1,4-cyclohexylene, 1,4-phenylene, 1,4-phenylene in which at least one hydrogen has been replaced by fluorine or chlorine, naphthalene-2,6-diyl, naphthalene-2,6-diyl in which at least one hydrogen has been replaced by fluorine or chlorine, 1,3-dioxane-2,5-diyl, tetrahydropyran-2,5-diyl or 2,6,7-trioxabicyclo[2.2.2]octane-1,4-diyl;

ring A² is 1,4-cyclohexylene, 1,4-phenylene, 1,4-phenylene in which at least one hydrogen has been replaced by fluorine or chlorine, naphthalene-2,6-diyl or naphthalene-2,6-diyl in which at least one hydrogen has been replaced by fluorine or chlorine;

ring A³ is 1,4-phenylene, 1,4-phenylene in which at least one hydrogen has been replaced by fluorine or chlorine, naphthalene-2,6-diyl or naphthalene-2,6-diyl in which at least one hydrogen has been replaced by fluorine or chlorine;

Z¹ and Z² are independently a single bond, —CH$_2$CH$_2$—, —CH=CH—, —C≡C—, —COO—, —OCO—, —CH$_2$O—, —OCH$_2$—, —CF$_2$O—, —OCF$_2$— or —CF=CF—;

L¹ and L² are independently hydrogen, fluorine or chlorine;

o and p are independently 0, 1 or 2, and the sum of o and p is 0, 1 or 2; and n is an integer from 2 to 10.

Item 4. The compound according to item 3, wherein in formula (1b) according to item 3, R¹ is alkyl having 1 to 15 carbons, alkoxy having 1 to 14 carbons, alkenyl having 2 to 15 carbons or alkenyloxy having 2 to 14 carbons; and Z¹ and Z² are independently a single bond, —CH$_2$CH$_2$—, —CH=CH—, —CF$_2$O— or —COO—.

Item 5. The compound according to any one of items 1 to 4, wherein the compound is represented by any one of formulas (1-1) to (1-4):

in formulas (1-1) to (1-4),

R¹ is alkyl having 1 to 15 carbons, alkoxy having 1 to 14 carbons, alkenyl having 2 to 15 carbons or alkenyloxy having 2 to 14 carbons;

ring A¹ is 1,4-cyclohexylene, 1,4-phenylene, 1,4-phenylene in which at least one hydrogen has been replaced by fluorine or chlorine, naphthalene-2,6-diyl, naphthalene-2,6-diyl in which at least one hydrogen has been replaced by fluorine or chlorine, 1,3-dioxane-2,5-diyl or tetrahydropyran-2,5-diyl;

ring A² is 1,4-cyclohexylene, 1,4-phenylene or 1,4-phenylene in which at least one hydrogen has been replaced by fluorine or chlorine, naphthalene-2,6-diyl or naphthalene-2,6-diyl in which at least one hydrogen has been replaced by fluorine or chlorine;

ring A³ is 1,4-phenylene or 1,4-phenylene in which at least one hydrogen has been replaced by fluorine or chlorine, naphthalene-2,6-diyl or naphthalene-2,6-diyl in which at least one hydrogen has been replaced by fluorine or chlorine;

Z¹ and Z² are independently a single bond, —CH$_2$CH$_2$— or —CH=CH—;

L¹ and L² are independently hydrogen or fluorine; and n is an integer from 2 to 10.

Item 6. The compound according to item 5, wherein in formulas (1-1) to (1-4) according to item 5, R¹ is alkyl having 1 to 15 carbons or alkenyl having 2 to 15 carbons.

Item 7. The compound according to any one of items 1 to 6, wherein the compound is represented by any one of formulas (1-5) to (1-37):

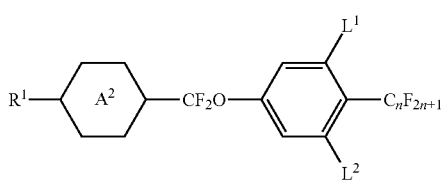

(1-1)

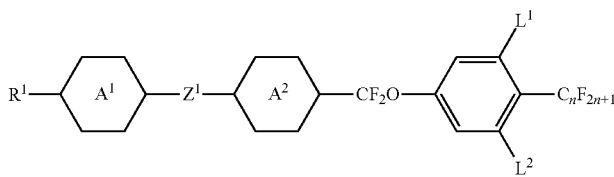

(1-2)

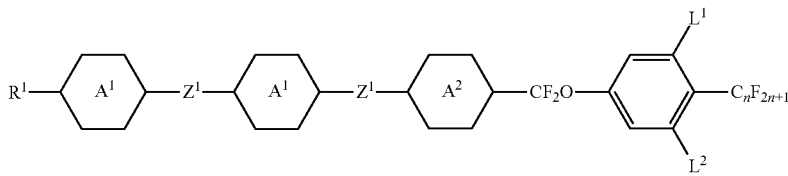

(1-3)

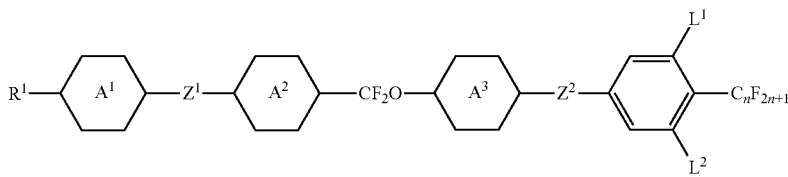

(1-4)

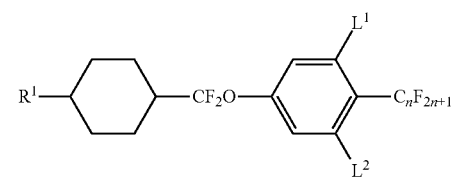 (1-5)
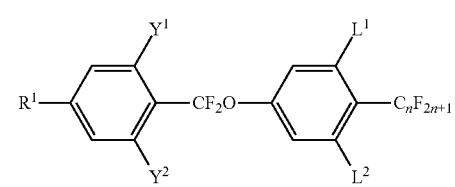 (1-6)
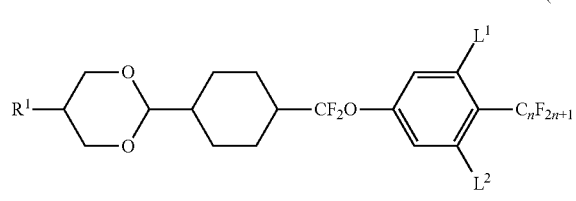 (1-7)
(1-8)
(1-9)
(1-10)
(1-11)
(10-12)
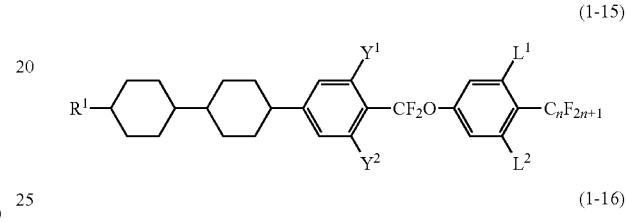 (1-13)
(1-14)
(1-15)
(1-16)
(1-17)
(1-18)
(1-19)
(1-20)
(1-21)

in formulas (1-5) to (1-37), $R^1$ is alkyl having 1 to 10 carbons or alkenyl having 2 to 10 carbons; $L^1$ and $L^2$ are independently hydrogen or fluorine; $Y^1$, $Y^2$, $Y^3$, $Y^4$, $Y^5$ and $Y^6$ are independently hydrogen or fluorine; $Z^1$ is a single bond, —$CH_2CH_2$— or —$CH$=$CH$—; and n is an integer from 2 to 10.

Item 8. The compound according to any one of items 1 to 7, wherein the compound is represented by any one of formulas (1-38) to (1-45):

-continued (1-39)
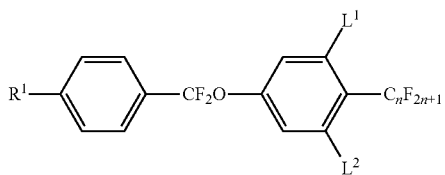

(1-40)
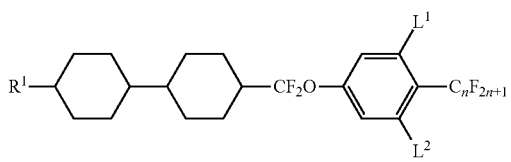

(1-41)
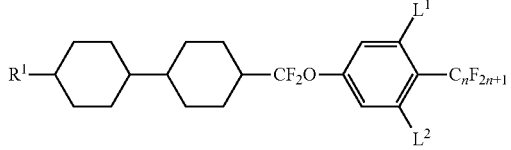

(1-42)
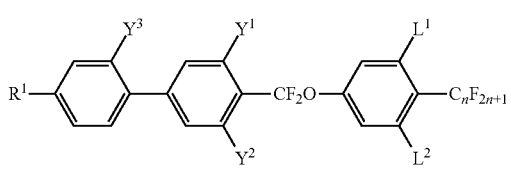

(1-43)
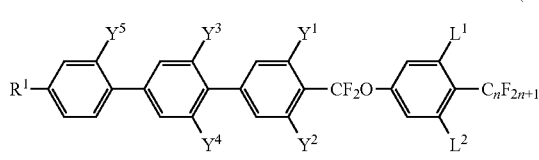

(1-44)
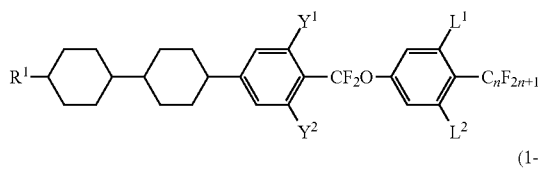

(1-45)
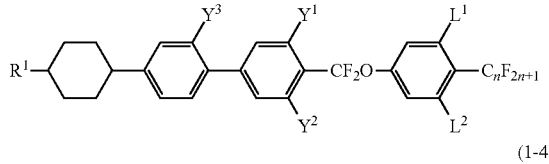

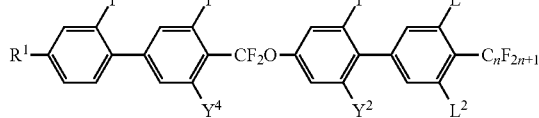

in formulas (1-38) to (1-45), $R^1$ is alkyl having 1 to 10 carbons or alkenyl having 2 to 10 carbons; $L^1$ and $L^2$ are independently hydrogen or fluorine; $Y^1$, $Y^2$, $Y^3$, $Y^4$ and $Y^5$ are independently hydrogen or fluorine; and n is an integer from 2 to 10.

Item 9. The compound according to item 8, wherein in formulas (1-38) to (1-45) according to item 8, $R^1$ is alkyl having 1 to 10 carbons; $L^1$ and $L^2$ are fluorine; and $Y^1$, $Y^2$, $Y^3$, $Y^4$, $Y^5$ and $Y^6$ are independently hydrogen or fluorine.

Item 10. A liquid crystal composition including at least one of compounds according to any one of items 1 to 9.

Item 11. The liquid crystal composition according to item 10, further including at least one compound selected from the group of compounds represented by formulas (2) to (4):

(2)
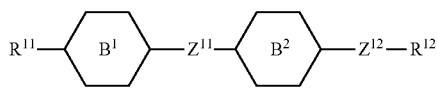

(3)
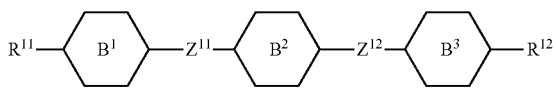

(4)
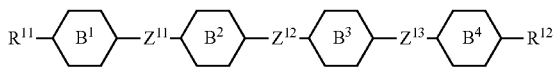

in formulas (2) to (4), $R^{11}$ and $R^{12}$ are independently alkyl having 1 to 10 carbons or alkenyl having 2 to 10 carbons, and in the alkyl and alkenyl at least one —$CH_2$— may be replaced by —O— and at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

Item 12. The liquid crystal composition according to item 10 or 11, further including at least one compound selected from the group of compounds represented by formulas (5) to (7):

(5)
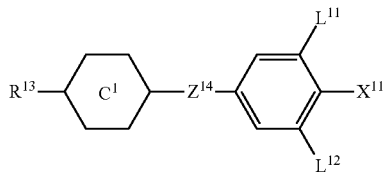

(6)
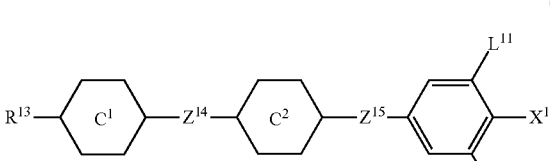

(7)
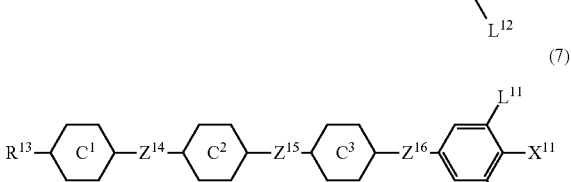

in formula (5) to (7), $R^{13}$ is alkyl having 1 to 10 carbons or alkenyl having 2 to 10 carbons, and in the alkyl and alkenyl at least one —$CH_2$— may be replaced by —O— and at least one hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and $L^{11}$ and $L^{12}$ are independently hydrogen or fluorine.

Item 13. The liquid crystal composition according to any one of items 10 to 12, further including at least one compound selected from the group of compounds represented by formula (8):

$Z^{17}$ is a single bond, —CH$_2$CH$_2$—, —C≡C—, —COO—, —CF$_2$O—, —OCF$_2$— or —CH$_2$O—;

$L^{13}$ and $L^{14}$ are independently hydrogen or fluorine; and i is 1, 2, 3 or 4.

Item 14. The liquid crystal composition according to any one of items 10 to 13, further including at least one compound selected from the group of compounds represented by formulas (9) to (15):

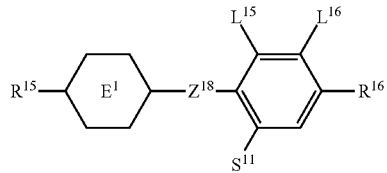
(9)

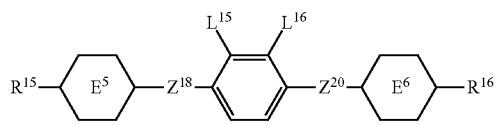
(10)

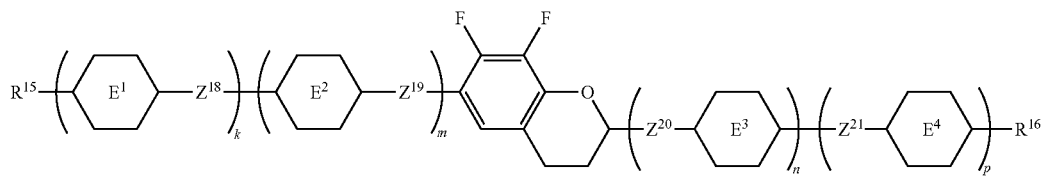
(11)

(12)

(13)

(14)

(15)

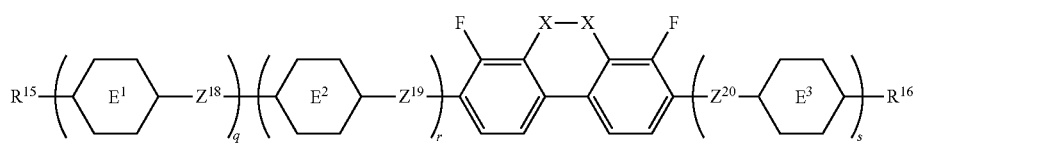
(8)

in formula (8), $R^{14}$ is alkyl having 1 to 10 carbons or alkenyl having 2 to 10 carbons, and in the alkyl and alkenyl at least one —CH$_2$— may be replaced by —O— and at least one hydrogen may be replaced by fluorine;

$X^{12}$ is —C≡N or —C≡C—C≡N;

ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

in formulas (9) to (15), $R^{15}$ and $R^{16}$ are independently alkyl having 1 to 10 carbons or alkenyl having 2 to 10 carbons, and in the alkyl and alkenyl at least one —CH$_2$— may be replaced by —O— and at least one hydrogen may be replaced by fluorine;

$R^{17}$ is hydrogen, fluorine, alkyl having 1 to 10 carbons or alkenyl having 2 to 10 carbons, and in the alkyl and alkenyl at least one —CH$_2$— may be replaced by —O— and at least one hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —CH$_2$CH$_2$—, —COO—, —CH$_2$O—, —OCF$_2$— or —OCF$_2$CH$_2$CH$_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, the sum of k, m, n and p is 1 or 2, and the sum of q, r and s is 0, 1, 2 or 3, and t is 1, 2 or 3.

Item 15. The liquid crystal composition according to any one of items 10 to 14, further including at least one additive selected from the group of a polymerizable compound, a polymerization initiator, a polymerization inhibitor, an optically active compound, an antioxidant, an ultraviolet light absorber, a light stabilizer, a thermal stabilizer, a coloring matter and an antifoaming agent.

Item 16. A liquid crystal display device including the liquid crystal composition according to any one of items 10 to 15.

The invention further includes the following items. (a) The liquid crystal composition described above, further including one, two or at least three additive selected from the group of a polymerizable compound, a polymerization initiator, a polymerization inhibitor, an optically active compound, an antioxidant, an ultraviolet light absorber, a light stabilizer, a thermal stabilizer, a coloring matter and an antifoaming agent. (b) The liquid crystal composition described above, wherein the maximum temperature of a nematic phase is 70° C. or higher, and the optical anisotropy (measured at 25° C.) at a wavelength of 589 nanometers is 0.07 or more, and the dielectric anisotropy (measured at 25° C.) at a frequency of 1 kHz is 2 or more. (c) The liquid crystal display device described above, wherein the operating mode of the liquid crystal display device is a TN mode, an ECB mode, an OCB mode, an IPS mode or a FPA mode, and the driving mode of the liquid crystal display device is an active matrix mode.

The aspects of compound (1a), the method for synthesizing compound (1a), the liquid crystal composition and the liquid crystal display device are explained in this order.

1. Aspects of Compound (1a)

Compound (1a) of the invention is characterized by an especially high maximum temperature, since it has a perfluoroalkyl terminal group and a $CF_2O$ bonding group (See Comparative Example 1). Desirable examples of compound (1a) will be explained. Desirable examples of a terminal group, a ring, a bonding group and a substituent in compound (1a) apply to the sub-formula of compound (1a). In compound (1a), the physical properties can be arbitrarily adjusted by a suitable combination of these groups. Compound (1a) may also contain isotopes such as $^2H$ (deuterium) and $^{13}C$ in a larger amount than the amount of the natural abundance, since there are no major differences in physical properties of the compound. Incidentally, the definition of compound (1a) is the same as that described in item 1.

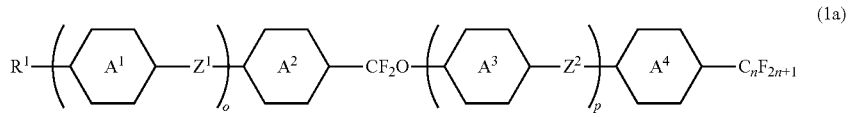
(1a)

An example of desirable compound (1a) is a compound where ring $A^3$ is 1,4-phenylene in which at least one hydrogen may be replaced by fluorine or chlorine, or is naphthalene-2,6-diyl in which at least one hydrogen may be replaced by fluorine or chlorine. A more desirable example is a compound where ring $A^4$ is 1,4-phenylene or 1,4-phenylene in which one or two hydrogens has been replaced by fluorine or chlorine. An especially desirable example is compound (1b) according to item 3.

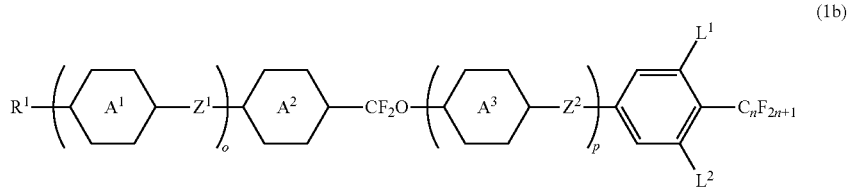
(1b)

In formula (1b), $R^1$ is alkyl having 1 to 15 carbons, and in the alkyl at least one —$CH_2$— may be replaced by —O— and at least one —$CH_2CH_2$— may be replaced by —CH=CH—.

An example of $R^1$ is alkyl, alkoxy, alkoxyalkyl, alkoxyalkoxy, alkenyl, alkenyloxy, alkenyloxyalkyl or alkoxyalkenyl. Desirable $R^1$ is alkyl, alkoxy, alkoxyalkyl, alkenyl or alkenyloxy. More desirable $R^1$ is alkyl, alkoxy, alkenyl or alkenyloxy. Especially desirable is alkyl or alkenyl. The most desirable $R^1$ is alkyl.

An example of alkyl is —$CH_3$, —$C_2H_5$, —$C_3H_7$, —$C_4H_9$, —$C_5H_{11}$, —$C_6H_{13}$ or —$C_7H_{15}$.

An example of alkoxy is —$OCH_3$, —$OC_2H_5$, —$OC_3H_7$, —$OC_4H_9$, —$OC_5H_{11}$, —$OC_6H_{13}$ or —$OC_7H_{15}$.

An example of alkoxyalkyl is —$CH_2OCH$, —$CH_2OC_2H_5$, —$CH_2OC_3H_7$, —$(CH_2)_2$—$OCH_3$, —$(CH_2)_2$—$OC_2H_5$, —$(CH_2)_2$—OCH, —$(CH_2)_3$—$OCH_3$, —$(CH_2)_4$—$OCH_3$ or —$(CH_2)_5$—$OCH_3$.

An example of alkenyl is —CH=$CH_2$, —CH=CH=$CH_3$, —$CH_2$CH=$CH_2$, —CH=CH$C_2H_5$, —$CH_2$CH=CH$CH_3$, —$(CH_2)_2$—CH=$CH_2$, —CH=CH$C_3H_7$, —$CH_2$CH=CH$C_2H_5$, —$(CH_2)_2$—C=CH=CH or —$(CH_2)_3$—CH=$CH_2$.

An example of alkenyloxy is —$OCH_2$CH=$CH_2$, —$OCH_2$CH=CH$CH_2$ or —$OCH_2$CH=CH$C_2H_5$.

Desirable $R^1$ is alkyl having 1 to 15 carbons, alkoxy having 1 to 14 carbons, alkenyl having 2 to 15 carbons or alkenyloxy having 2 to 14 carbons. More desirable $R^1$ is alkyl having 1 to 7 carbons, alkoxy having 1 to 7 carbons, alkenyl having 2 to 8 carbons or alkenyloxy having 2 to 8 carbons. Especially desirable $R^1$ is —$CH_3$, —$C_2H_5$, —$C_3H_7$, —$C_4H_9$, —$C_5H_{11}$, —$C_6H_{13}$, —$OCH_3$, —$OC_2H_5$, —OC$_3$H$_7$, —OC$_4$H$_9$, —OC$_5$H$_{11}$, —CH=CH$_2$, —CH=CHCH$_3$, —(CH$_2$)$_2$—CH=CH$_2$, —CH$_2$CH=CHC$_2$H$_5$, —(CH$_2$)$_2$—CH=CHCH$_3$, —OCH$_2$CH=CH$_2$, —OCH$_2$CH=CHCH$_3$ or —OCH$_2$CH=CHC$_2$H$_5$ The most desirable R$^1$ is —C$_3$H$_7$, —C$_4$H$_9$, —C$_5$H$_{11}$, —C$_6$H$_{13}$, —(CH$_2$)$_2$—CH=CH$_2$, —(CH$_2$)$_2$—CH=CHCH$_3$.

When R$^1$ is straight-chain, the temperature range of a liquid crystal phase is wide and the viscosity is small. When R$^1$ is branched-chain, the compatibility with any other liquid crystal compound is excellent. A compound where R$^1$ is optically active is useful as a chiral dopant. A reverse twisted domain which will occur in a liquid crystal display device can be prevented by the addition of this compound to a composition. A compound where R$^1$ is not optically active is useful as a component of a composition. A desirable configuration depends on the position of the double bond when R$^1$ is alkenyl. An alkenyl compound having a desirable configuration has a small viscosity, a high maximum temperature or a wide temperature range of a liquid crystal phase.

A desirable configuration of —CH=CH— in the alkenyl depends on the position of the double bond. The trans-configuration is preferable in the alkenyl having the double bond in the odd position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. The cis-configuration is preferable in the alkenyl having the double bond in the even position, such as —CH$_2$CH=CHCH$_3$, —CH$_2$CH=CHC$_2$H$_5$ and —CH$_2$CH=CHC$_3$H$_7$. An alkenyl compound having a desirable configuration has a high clearing point or a wide temperature range of a liquid crystal phase. For detailed explanation, see Mol. Cryst. Liq. Cryst., 1985, 131, 109 and Mol. Cryst. Liq. Cryst., 1985, 131, 327.

In formula (1b), ring A$^1$ is 1,4-cyclohexylene, 1,4-phenylene, 1,4-phenylene in which at least one hydrogen has been replaced by fluorine or chlorine, naphthalene-2,6-diyl, naphthalene-2,6-diyl in which at least one hydrogen has been replaced by fluorine or chlorine, 1,3-dioxane-2,5-diyl, tetrahydropyran-2,5-diyl or 2,6,7-trioxabicyclo[2.2.2]octane-1,4-diyl; ring A$^2$ is 1,4-cyclohexylene, 1,4-phenylene, 1,4-phenylene in which at least one hydrogen has been replaced by fluorine or chlorine, naphthalene-2,6-diyl or naphthalene-2,6-diyl in which at least one hydrogen has been replaced by fluorine or chlorine; ring A$^3$ is 1,4-phenylene, 1,4-phenylene in which at least one hydrogen has been replaced by fluorine or chlorine, naphthalene-2,6-diyl or naphthalene-2,6-diyl in which at least one hydrogen has been replaced by fluorine or chlorine.

A desirable example of 1,4-phenylene in which at least one hydrogen has been replaced by fluorine or chlorine is 2-fluoro-1,4-phenylene, 2-chloro-1,4-phenylene, 2,6-difluoro-1,4-phenylene, 2-chloro-6-fluoro-1,4-phenylene, 2,6-dichloro-1,4-phenylene or 2,3,5-trifluoro-1,4-phenylene. These groups mean two types of divalent groups in a chemical formula, since they are asymmetric. In these groups, fluorine (or chlorine) may be facing left or facing right. Desirable 2-fluoro-1,4-phenylene is facing left for increasing the dielectric anisotropy. This applies to any other divalent group. A more desirable example of 1,4-phenylene in which at least one hydrogen has been replaced by fluorine or chlorine is 2-fluoro-1,4-phenylene, 2-chloro-1,4-phenylene, 2,6-difluoro-1,4-phenylene or 2-chloro-6-fluoro-1,4-phenylene. A more desirable example is 2-fluoro-1,4-phenylene or 2,6-difluoro-1,4-phenylene.

Desirable ring A$^1$ is 1,4-cyclohexylene, 1,4-phenylene, 2-fluoro-1,4-phenylene, 2,6-difluoro-1,4-phenylene, 1,3-dioxane-2,5-diyl or tetrahydropyran-2,5-diyl. More desirable ring A$^1$ is 1,4-cyclohexylene, 1,4-phenylene, 2-fluoro-1,4-phenylene or 2,6-difluoro-1,4-phenylene. Especially desirable ring A$^1$ is 1,4-cyclohexylene, 1,4-phenylene or 2-fluoro-1,4-phenylene.

Desirable ring A$^2$ is 1,4-cyclohexylene, 1,4-phenylene, 2-fluoro-1,4-phenylene, 2-chloro-1,4-phenylene, 2,6-difluoro-1,4-phenylene or 2-chloro-6-fluoro-1,4-phenylene. More desirable ring A$^2$ is 1,4-cyclohexylene, 1,4-phenylene, 2-fluoro-1,4-phenylene, 2-chloro-1,4-phenylene or 2,6-difluoro-1,4-phenylene. Especially desirable ring A$^2$ is 1,4-cyclohexylene, 1,4-phenylene, 2-fluoro-1,4-phenylene or 2,6-difluoro-1,4-phenylene.

Desirable ring A$^3$ is 1,4-phenylene, 2-fluoro-1,4-phenylene, 2-chloro-1,4-phenylene, 2,6-difluoro-1,4-phenylene or 2-chloro-6-fluoro-1,4-phenylene. More desirable ring A$^3$ is 1,4-phenylene, 2-fluoro-1,4-phenylene, 2-chloro-1,4-phenylene or 2,6-difluoro-1,4-phenylene. Especially desirable ring A$^3$ is 1,4-phenylene, 2-fluoro-1,4-phenylene or 2,6-difluoro-1,4-phenylene.

When all of ring A$^1$, ring A$^2$ and ring A$^3$ are 1,4-cyclohexylene, the clearing point is high, and the viscosity is small. When at least one of ring A$^1$, ring A$^2$ and ring A$^3$ is 1,4-phenylene or is 1,4-phenylene in which at least one hydrogen has been replaced by fluorine or chlorine, the optical anisotropy is relatively large, and the orientational order parameter is relatively large. When ring A$^1$, ring A$^2$ and ring A$^3$ are 1,4-phenylene, 1,4-phenylene in which at least one hydrogen has been replaced by fluorine or chlorine, or any combination of these, the optical anisotropy is especially large. When at least one of ring A$^1$, ring A$^2$ and ring A$^3$ is 1,4-phenylene in which at least one hydrogen has been replaced by fluorine or chlorine, the dielectric anisotropy is large.

In formula (1b), Z$^1$ and Z$^2$ are independently a single bond, —CH$_2$CH$_2$—, —CH=CH—, —C≡C—, —COO—, —OCO—, —CH$_2$O—, —OCH$_2$—, —CF$_2$O—, —OCF$_2$— or —CF=CF—. Desirable Z$^1$ or Z$^2$ is a single bond, —CH$_2$CH$_2$—, —CH=CH—, —CF$_2$O— or —COO—. More desirable Z$^1$ or Z$^2$ is a single bond, —CH$_2$CH$_2$— or —CH=CH—. Especially desirable Z$^1$ or Z$^2$ is a single bond.

When Z$^1$ or Z$^2$ is a single bond, the chemical stability is high and the viscosity is small. When Z$^1$ or Z$^2$ is —C≡C—, the optical anisotropy and the dielectric anisotropy are large, and the maximum temperature is high.

In formula (1b), L$^1$ and L$^2$ are independently hydrogen, fluorine or chlorine. Desirable L$^1$ or L$^2$ is hydrogen or fluorine. A desirable combination of L$^1$ and L$^2$ is hydrogen and hydrogen, hydrogen and fluorine, or fluorine and fluorine. A more desirable combination is hydrogen and hydrogen in view of the ease of synthesis. A more desirable combination is hydrogen and fluorine or fluorine and fluorine in view of a large dielectric anisotropy. An especially large combination is fluorine and fluorine.

In formula (1b), o and p are independently 0, 1 or 2, and the sum of o and p is 0, 1 or 2. Desirable o is 1 or 2. More desirable o is 1. Desirable p is 0 or 1. Desirable p is 0. The sum of o and p is preferably 0 or 1 in view of a low minimum temperature or a small viscosity. The sum of o and p is preferably 1 or 2 in view of a high maximum temperature or a large dielectric anisotropy. The sum of o and p is preferably 1 in view of a balance between a low minimum temperature and a large compatibility.

In formula (1b), n is an integer from 2 to 10. n means the carbon number of perfluoroalkyl. Desirable n is 2 to 8, and more desirable n is 2 to 5.

2. Preparation of Compound (1a)

The method for synthesizing compound (1a) will be explained. Compound (1a) can be prepared by a suitable combination of methods in synthetic organic chemistry. Methods of introducing objective terminal groups, rings and bonding groups into starting materials are described in books such as "Organic Syntheses" (John Wiley & Sons, Inc.), "Organic Reactions" (John Wiley & Sons, Inc.), "Comprehensive Organic Synthesis" (Pergamon Press) and "Shin Jikken Kagaku Kouza" (New Experimental Chemistry Course, in English; Maruzen Co., Ltd., Japan).

2-1. Formation of Bonding Group $Z^1$ or $Z^2$

In compound (1a), the method for forming the bonding group is described in the schemes described below. In the schemes, $MSG^1$ (or $MSG^2$) is a monovalent organic group having at least one ring. Monovalent organic groups represented by a plurality of $MSG^1$ (or $MSG^2$) may be the same or different. Compounds (1A) to (1H) correspond to compound (1a).

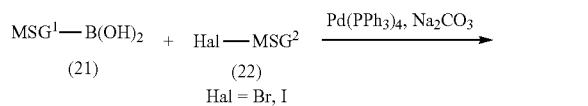

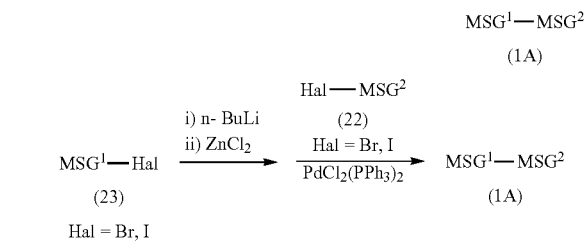

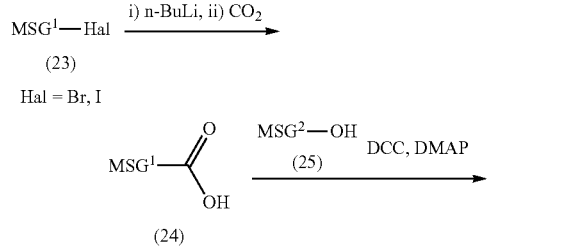

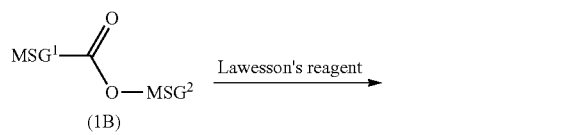

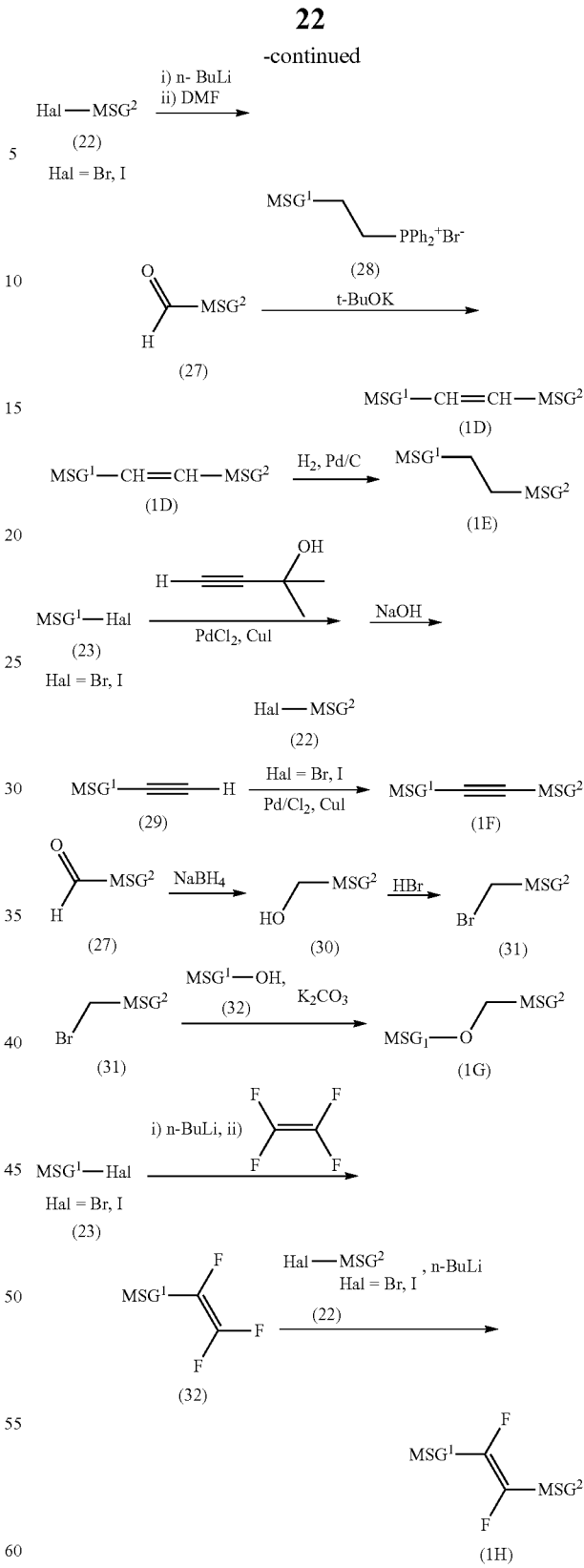

(I) Formation of a Single Bond

Compound (1A) is prepared by the reaction of arylboronic acid (21) with compound (22) in the presence of a carbonate and a tetrakis(triphenylphosphine)palladium catalyst. Compound (1A) is also be prepared by the reaction of compound

(23) with n-butyllithium, and then with zinc chloride, and by the reaction with compound (22) in the presence of a dichlorobis(triphenylphosphine)palladium catalyst.

(II) Formation of —COO— and —OCO—

Carboxylic acid (24) is prepared by the reaction of compound (23) with n-butyllithium and then with carbon dioxide. Dehydration of compound (24) and phenol (25) prepared by known methods from compound (21), in the presence of DCC (1,3-dicyclohexylcarbodiimide) and DMAP (4-dimethylaminopyridine) gives compound (1B).

(III) Formation of —CF$_2$O— and —OCF$_2$—

Sulfurization of compound (1B) with Lawesson's reagent gives compound (26). Fluorination of compound (26) with a HF-pyridine complex and NBS (N-bromosuccinimide) gives compound (1C). See M. Kuroboshi et al., Chem. Lett., 1992, 827. Compound (1C) is also prepared by fluorination of compound (26) with DAST [(diethylamino)sulfur trifluoride]. See W. H. Bunnelle et al., J. Org. Chem. 1990, 55, 768.

(32). Compound (22) is treated with n-Butyllithium, and reacted with compound (32) to give compound (1H).

2-2. Ring A$^1$ to Ring A$^4$

Starting materials are commercially available or methods are well known for the preparation of rings, such as 1,4-cyclohexylene, 1,4-phenylene, 2-fluoro-1,4-phenylene, 2,6-difluoro-1,4-phenylene, 1,3-dioxane-2,5-diyl, tetrahydropyran-2,5-diyl or 2,6,7-trioxabicyclo[2.2.2]octane-1,4-diyl.

2-3. Synthetic Examples

Examples of methods for synthesizing compound (1a) are as follows. Compound (51) can be prepared according to the synthetic method described in WO 96/011897 A. This compound is treated with butyllithum and iodine to give compound (52). Compound (52) is derivatized to compound (1a) by the reaction with 2,2'-bipyridine, copper powder and perfluoroalkyl iodide (53). In these compounds, the definition of symbols such as R$^1$ and ring A$^1$ is the same as that described in item 1 above.

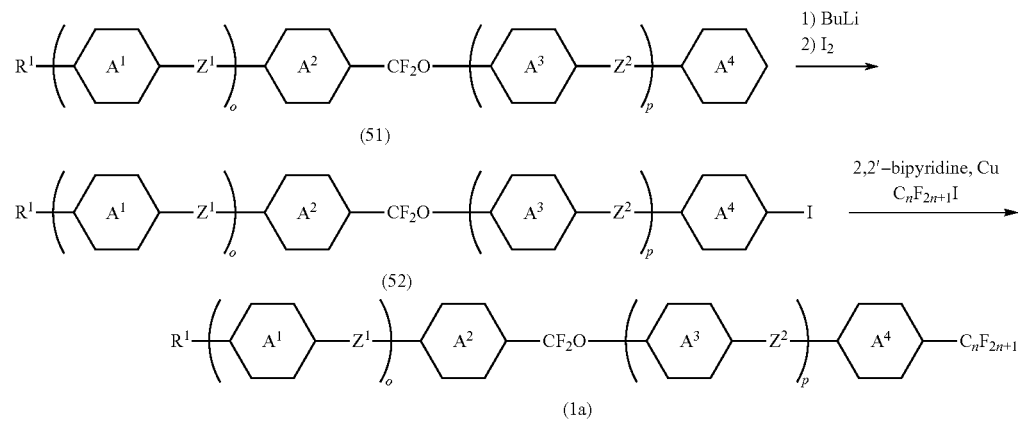

(IV) Formation of —CH═CH—

Compound (22) is treated with n-butyllithium, and then reacted with DMF (N,N-dimethylformamide) to give aldehyde (27). Aldehyde (27) is reacted with phosphorus ylide generated from the reaction of phosphonium salt (28) with potassium t-butoxide to give compound (1D). Since the cis-isomer is formed depending on the reaction conditions, the cis-isomer is isomerized to the trans-isomer by known methods as requested.

(V) Formation of —CH$_2$CH$_2$—

Compound (1E) is prepared by hydrogenation of compound (1D) in the presence of a palladium-carbon catalyst.

(VI) Formation of —C≡C—

The reaction of compound (23) with 2-methyl-3-butyn-2-ol in the presence of a catalyst of dichloropalladium and copper iodide, followed by the deprotection of the product under basic conditions gives compound (29). Compound (29) is reacted with compound (22) in the presence of a catalyst of dichlorobistriphenylphosphinepalladium and a copper halide to give compound (1F).

(VII) Formation of —CH$_2$O— and —OCH$_2$—

Compound (27) is reduced with sodium borohydride to give compound (30). Compound (30) is brominated with hydrobromic acid, giving compound (31). Compound (31) is allowed to react with compound (32) to give compound (1G).

(VIII) Formation of —CF═CF—

Compound (23) is treated with n-Butyllithium, which is allowed to react with tetrafluoroethylene to give compound 3. Liquid Crystal Compositions 3-1. Component Compounds The liquid crystal composition of the invention will be explained. The composition includes at least one of compound (1a) as component A. Compound (1a) is useful for increasing the maximum temperature of the composition. The composition may include two or more of compound (1a). The component of the composition may be compound (1a) alone. It is desirable that the composition should include at least one of compound (1a) in the range of 1% to 99% by weight in order to exhibit excellent physical properties. In a composition having positive dielectric anisotropy, a desirable content of compound (1a) is in the range of 5% by weight to 60% by weight. In a composition having negative dielectric anisotropy, a desirable content of compound (1a) is 30% by weight or less. The composition may include compound (1a) and a liquid crystal compound that is not described in this specification.

The composition includes compound (1a) as component A. It is desirable that the composition should further include a liquid crystal compound selected from components B, C, D and E described below. Component B is compounds (2) to (4). Component C is compounds (5) to (7). Component D is compound (8). Component E is compounds (9) to (15). This composition may include any other liquid crystal compound that is different from compounds (2) to (15). It is desirable that components B, C, D and E should be selected in consideration of the sign and magnitude of the dielectric anisotropy, when the composition is prepared. The composition in which the component is suitably selected has a high stability to heat or light, a high maximum temperature, a low minimum temperature, a small viscosity, a suitable optical anisotropy (that is to say, a large optical anisotropy or a small optical anisotropy), a large dielectric anisotropy, a large specific resistance, and a suitable elastic constant (that is to say, a large elastic constant or a small elastic constant).

Component B is a compound where two terminal groups are alkyl or the like. Desirable examples of component B include compounds (2-1) to (2-11), compounds (3-1) to (3-19) and compounds (4-1) to (4-7). In these compounds, $R^{11}$ and $R^{12}$ are independently alkyl having 1 to 10 carbons or alkenyl having 2 to 10 carbons, and in the alkyl and alkenyl at least one —$CH_2$— may be replaced by —O— and at least one hydrogen may be replaced by fluorine.

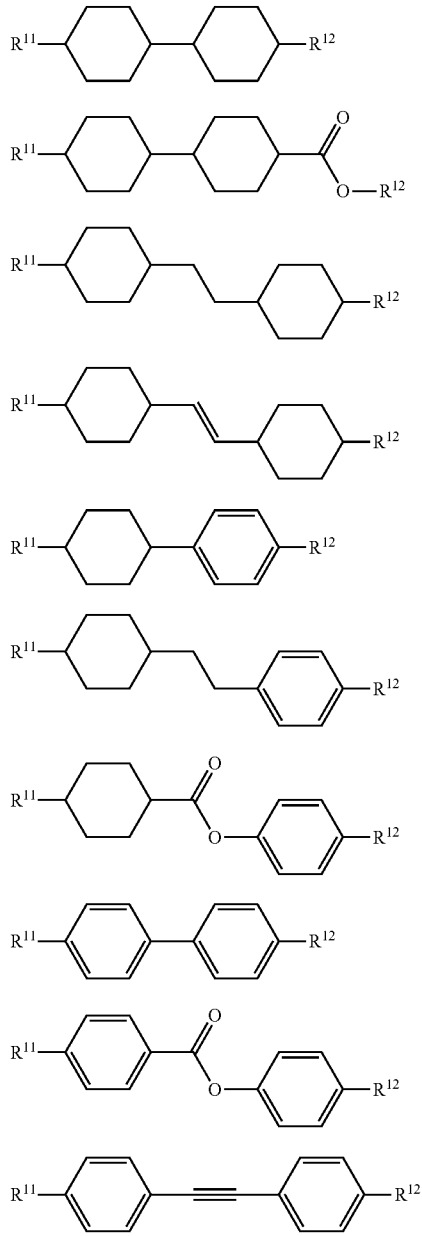

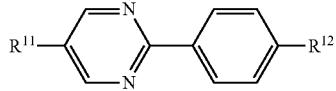
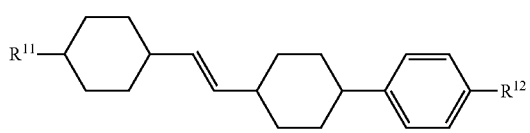
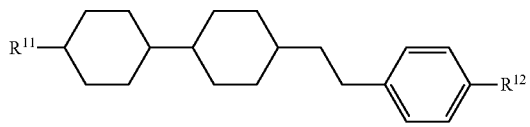
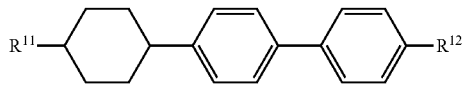
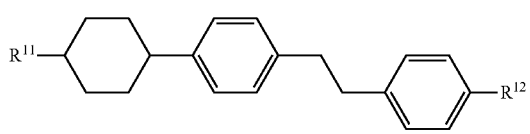
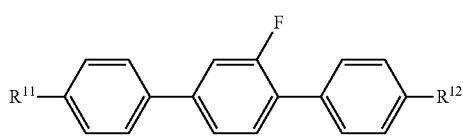
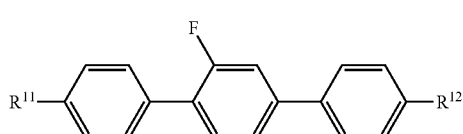
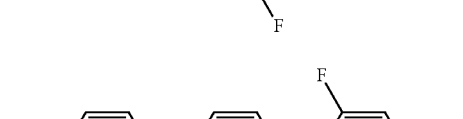
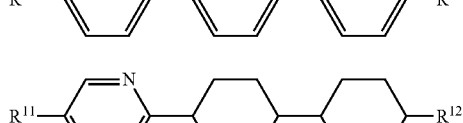
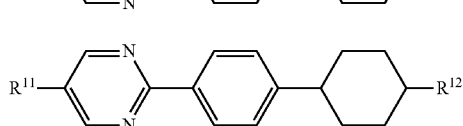
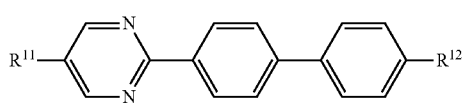

(3-12)
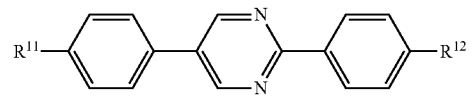

(3-13)

(3-14)
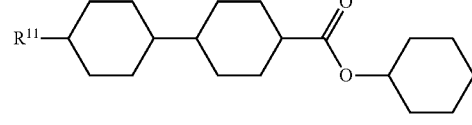

(3-15)
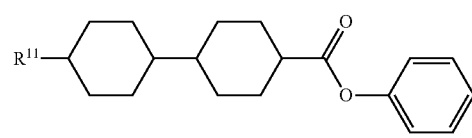

(3-16)
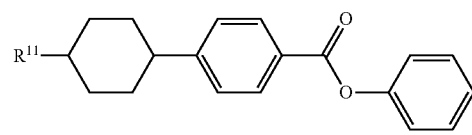

(3-17)
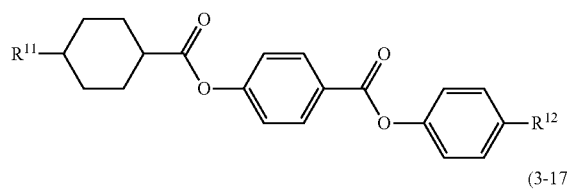

(3-18)
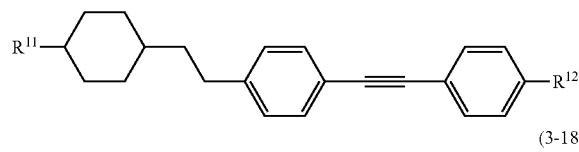

(3-19)
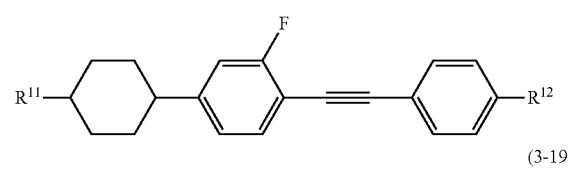

(4-1)
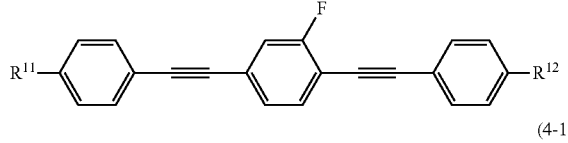

(4-2)
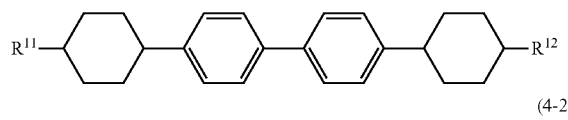

(4-3)
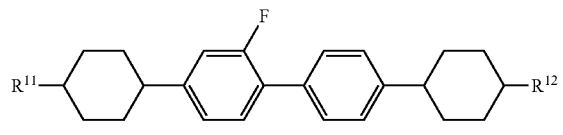

(4-4)
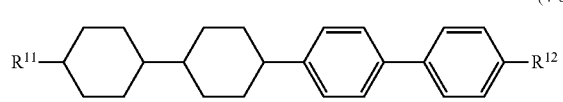

(4-5)
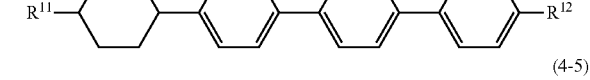

(4-6)
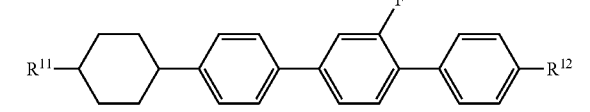

(4-7)
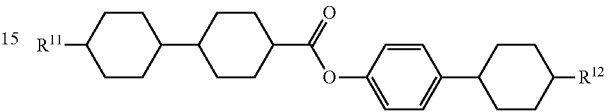

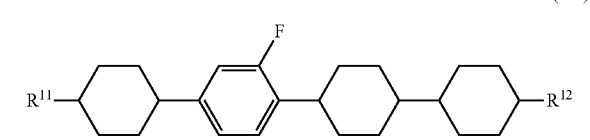

Component B has a small dielectric anisotropy. Component B is close to neutral. Compound (2) is effective in decreasing the viscosity or adjusting the optical anisotropy. Compounds (3) and (4) are effective in increasing the temperature range of a nematic phase that is caused by an increase in the maximum temperature, or adjusting the optical anisotropy.

As the content of component B is increased, the viscosity of the composition decreases. However, the dielectric anisotropy is decreased. Thus, it is desirable that the content should be increased as long as the required value of the threshold voltage is satisfied.

The content of component B is preferably 30% by weight or more, more preferably 40% by weight or more based on the weight of the composition, in the preparation of a composition for use in modes such as IPS and VA.

Component C is a compound having halogen or a fluorine-containing group at the far right. Desirable examples of component C include compounds (5-1) to (5-16), compounds (6-1) to (6-113) and compounds (7-1) to (7-57). In these compounds, $R^{13}$ is alkyl having 1 to 10 carbons or alkenyl having 2 to 10 carbons, and in the alkyl and alkenyl at least one —$CH_2$— may be replaced by —O— and at least one hydrogen may be replaced by fluorine; and $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

(5-1)

(5-2)
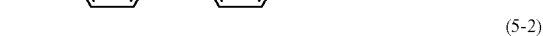

(5-3)
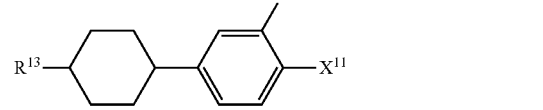

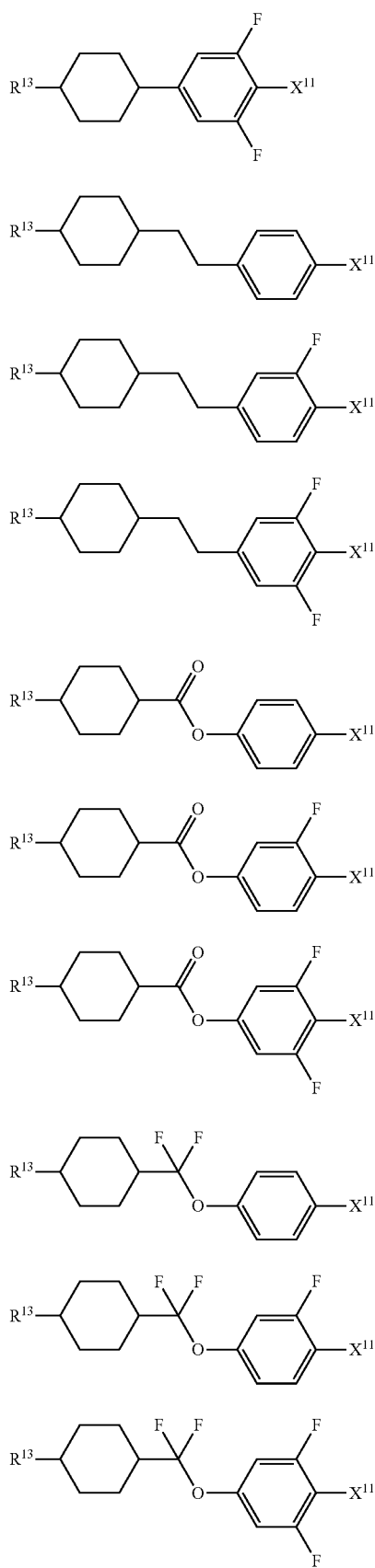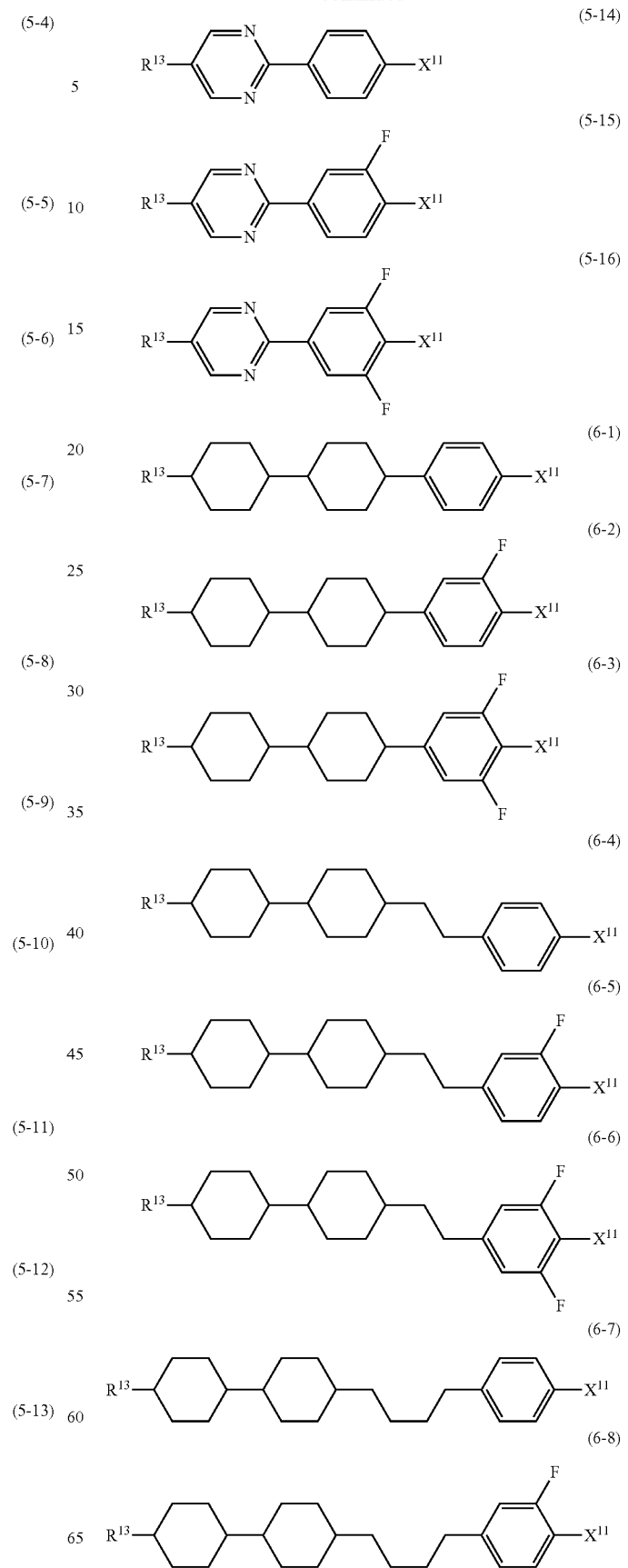

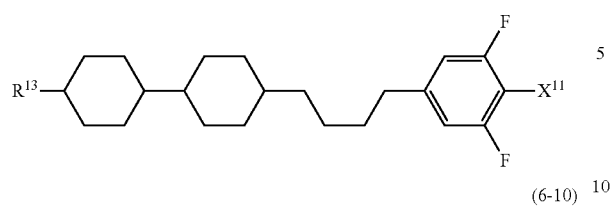
(6-9)
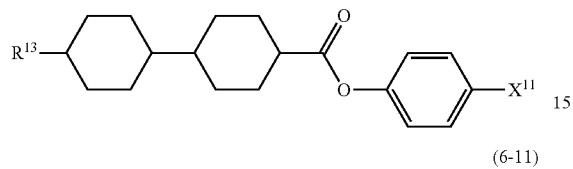
(6-10)
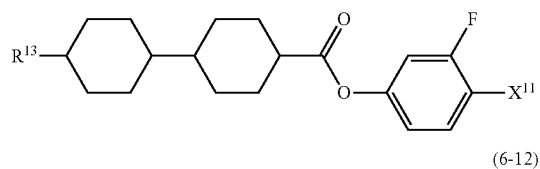
(6-11)
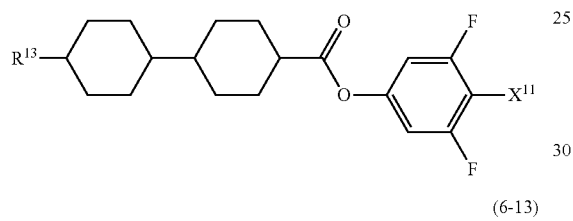
(6-12)
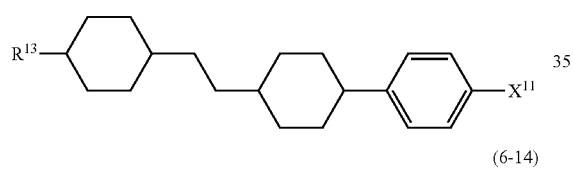
(6-13)
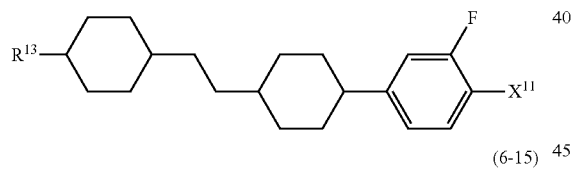
(6-14)
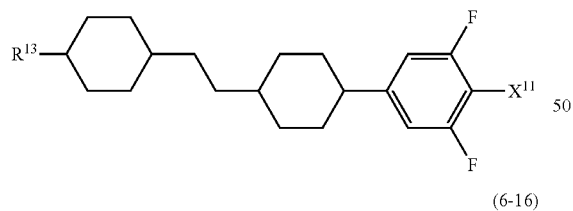
(6-15)
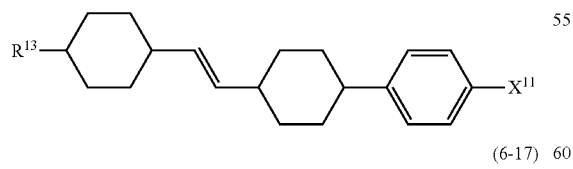
(6-16)
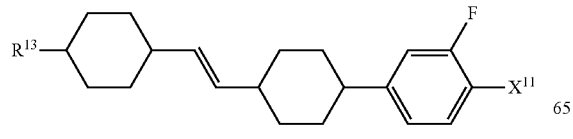
(6-17)
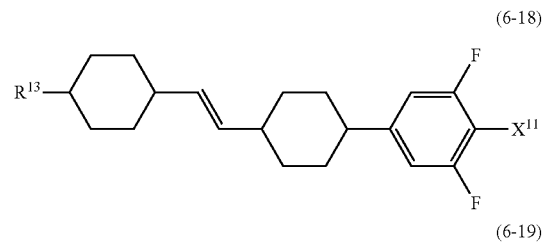
(6-18)
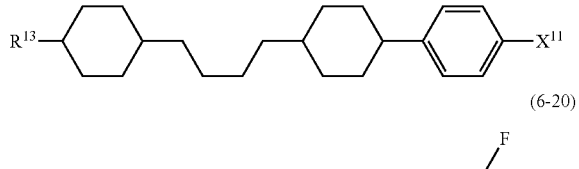
(6-19)
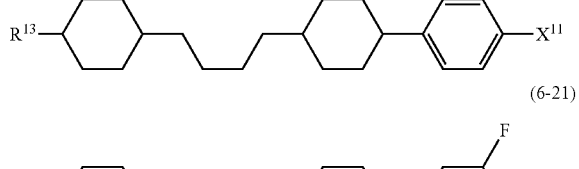
(6-20)
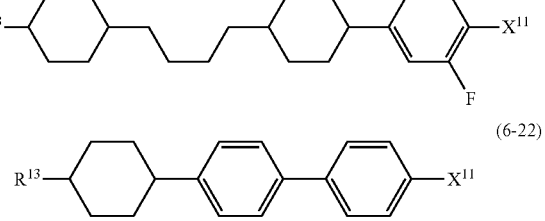
(6-21)
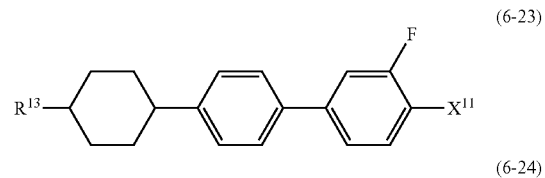
(6-22)
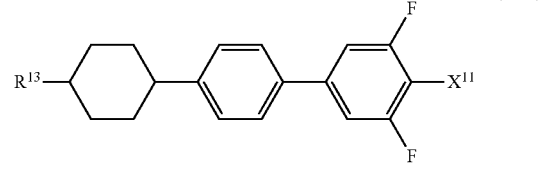
(6-23)
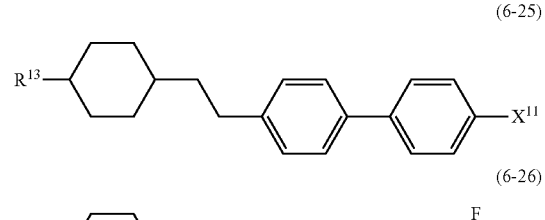
(6-24)
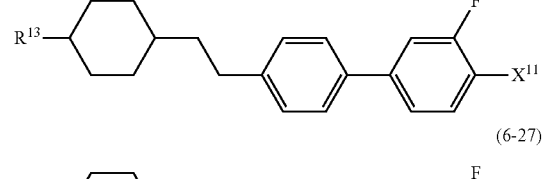
(6-25)
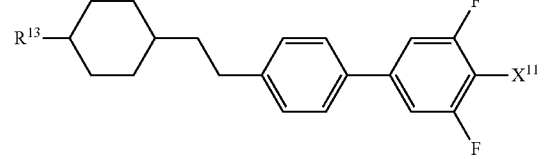
(6-26)
(6-27)

(6-28) 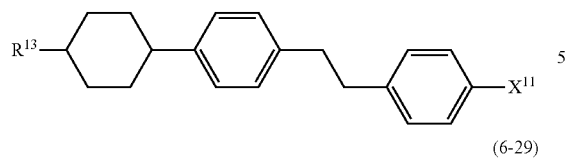
(6-29) 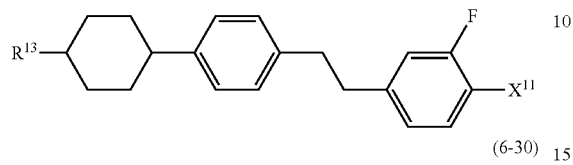
(6-30) 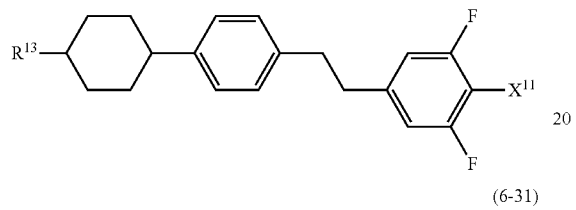
(6-31) 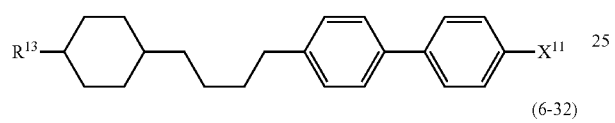
(6-32) 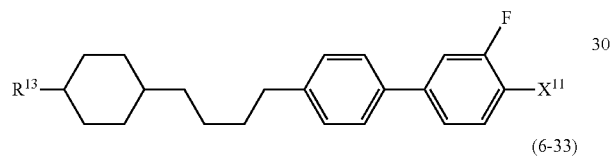
(6-33) 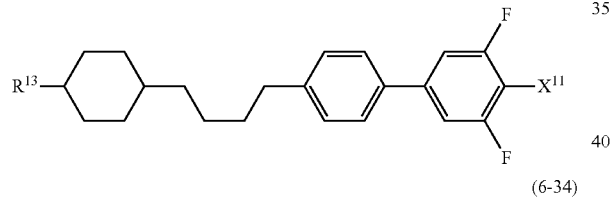
(6-34) 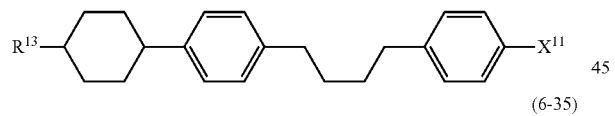
(6-35) 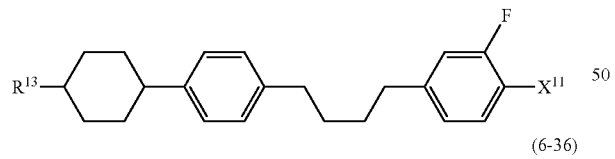
(6-36) 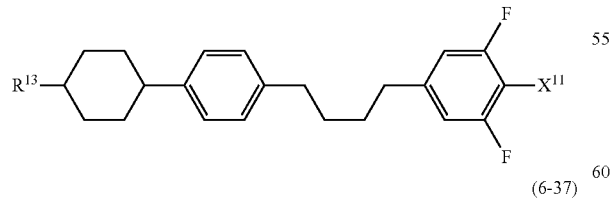
(6-37) 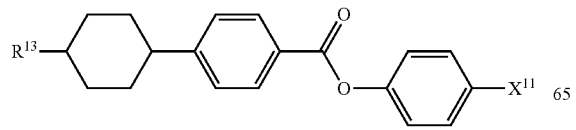
(6-38) 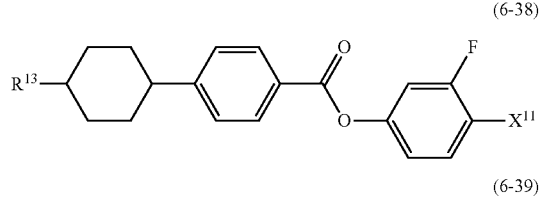
(6-39) 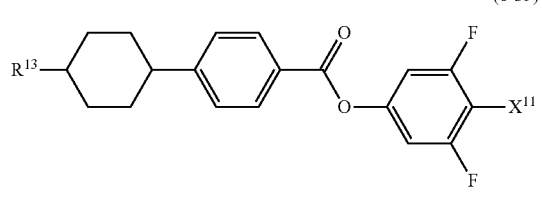
(6-40) 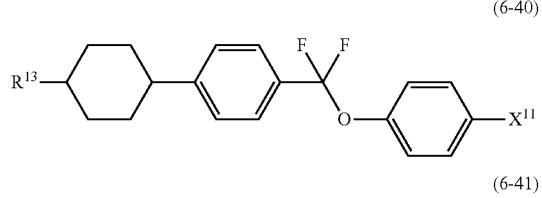
(6-41) 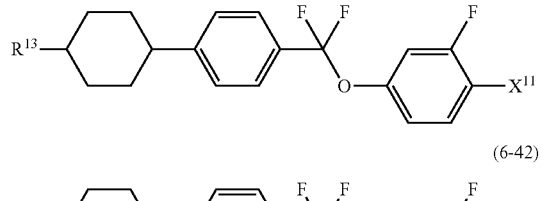
(6-42) 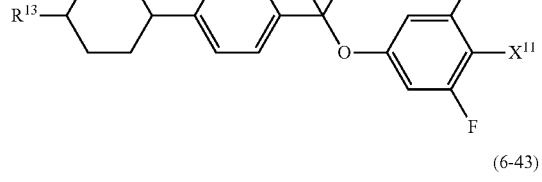
(6-43) 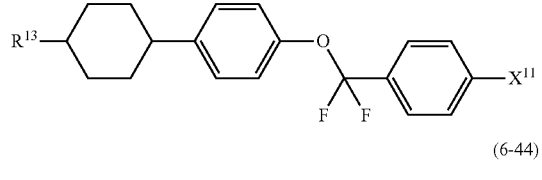
(6-44) 
(6-45) 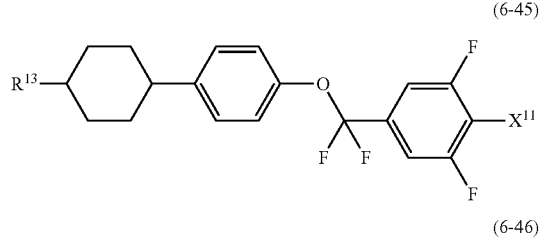
(6-46) 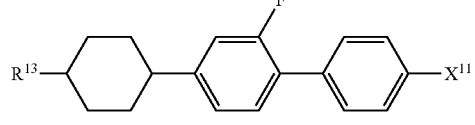

(6-47) 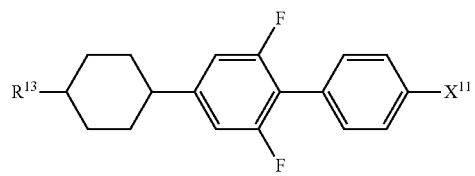
(6-48) 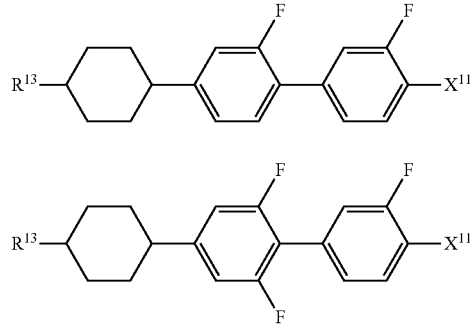
(6-49)
(6-50) 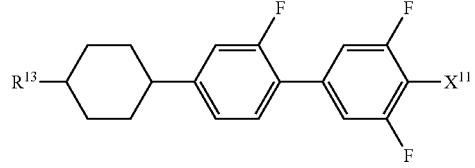
(6-51) 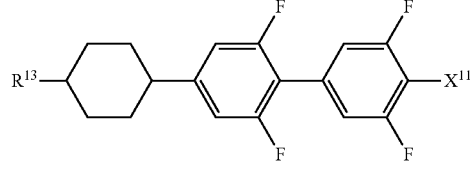
(6-52) 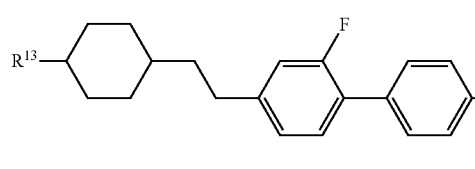
(6-53) 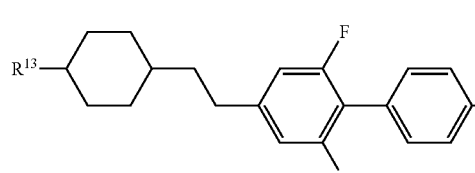
(6-54) 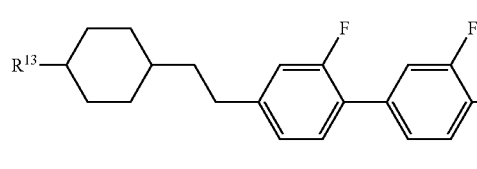
(6-55) 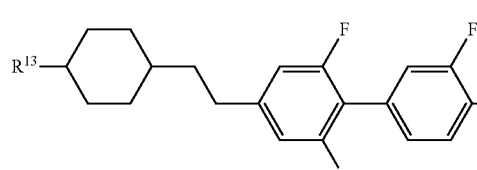
(6-56) 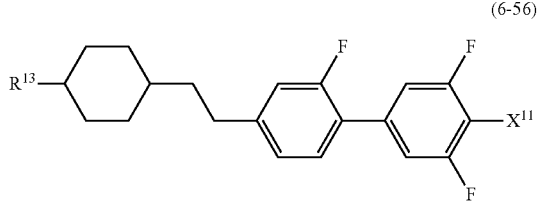
(6-57) 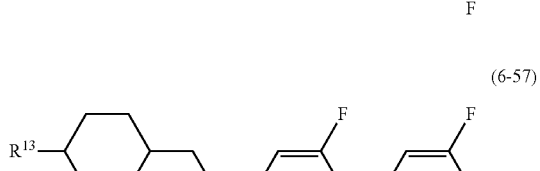
(6-58) 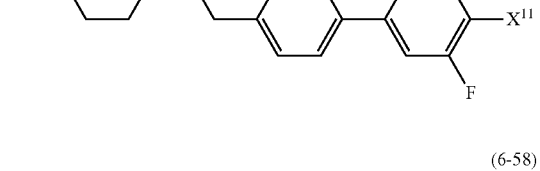
(6-59) 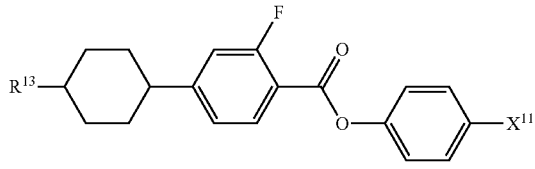
(6-60) 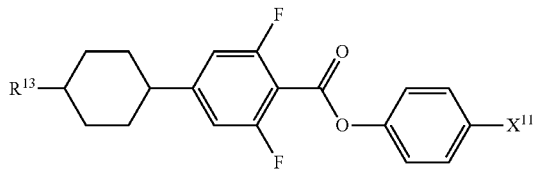
(6-61) 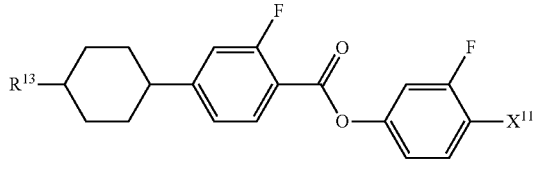
(6-62) 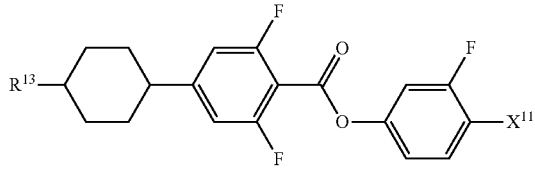

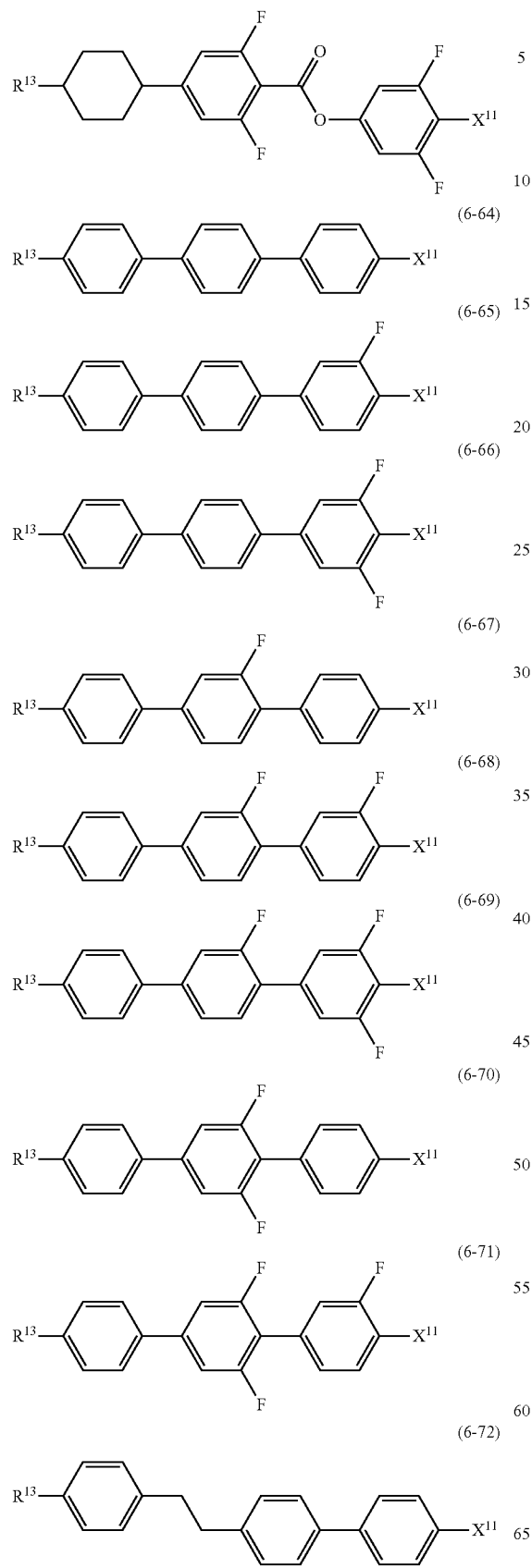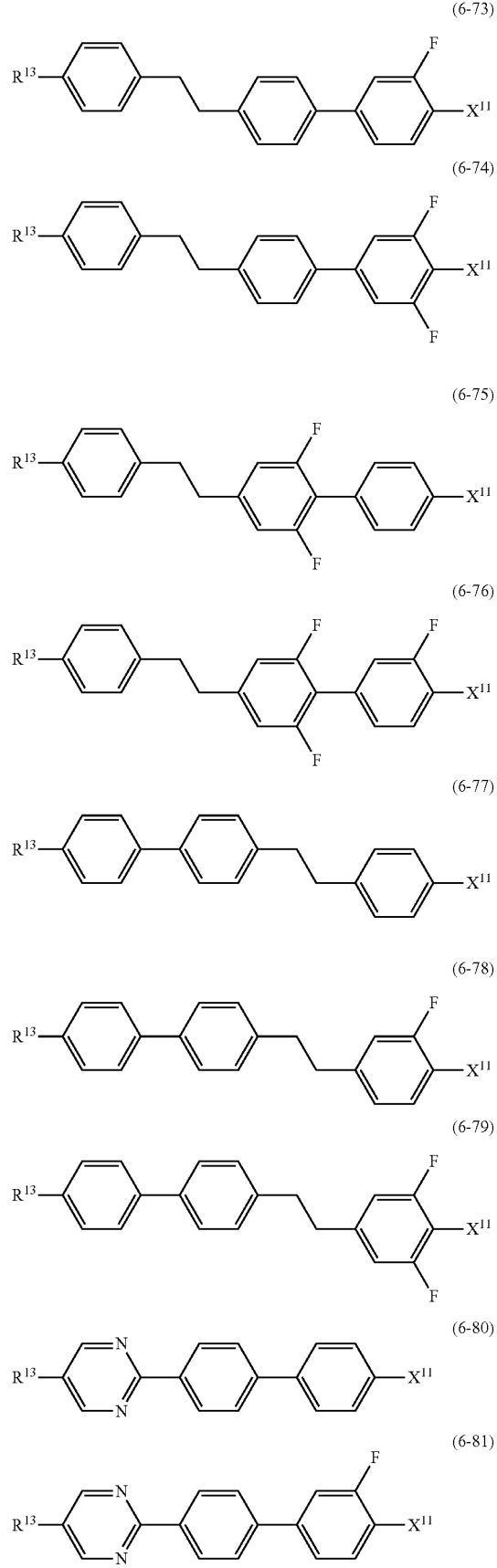

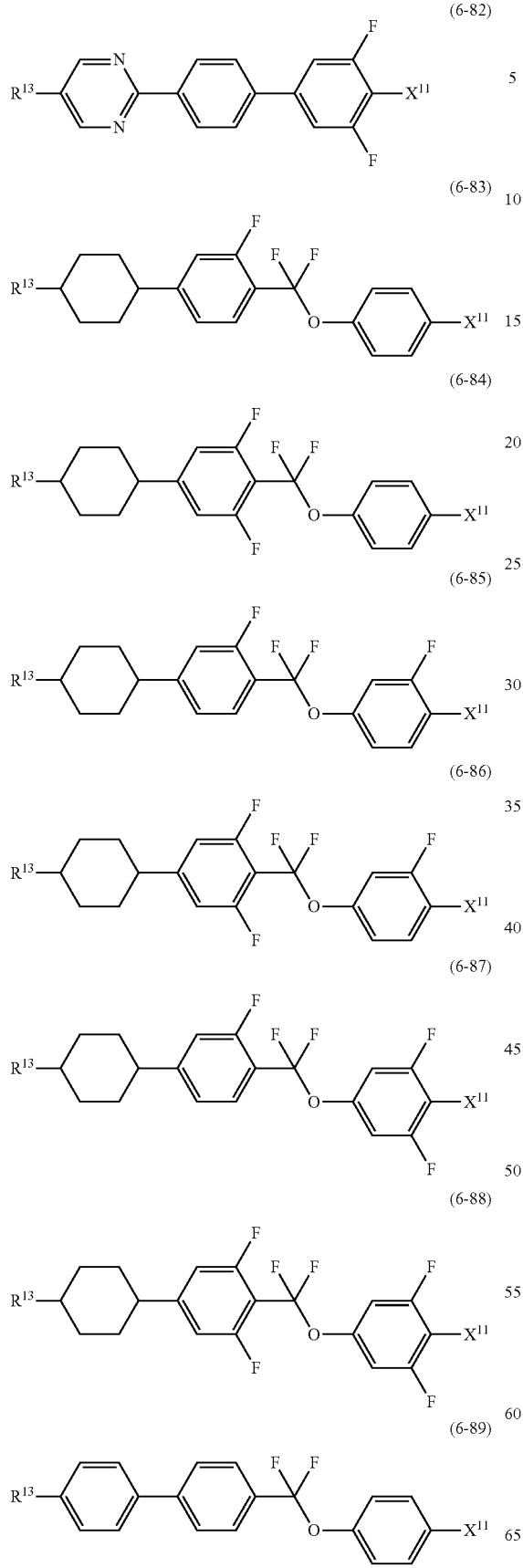
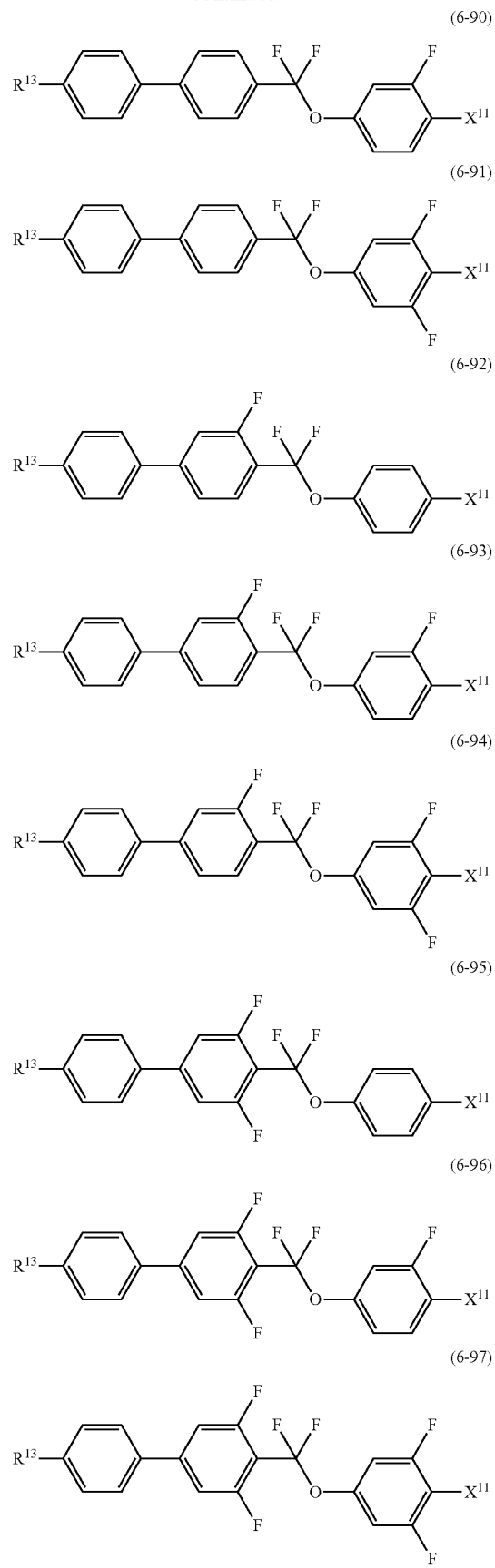

-continued
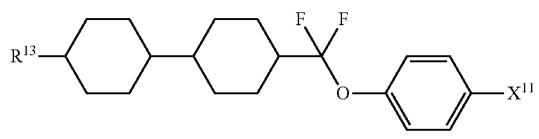
(6-98)
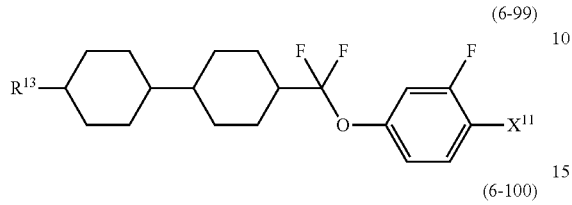
(6-99)
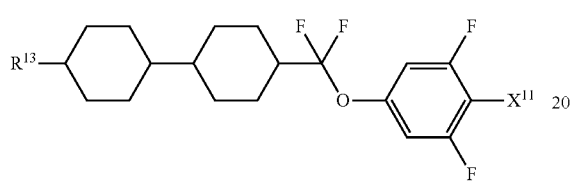
(6-100)
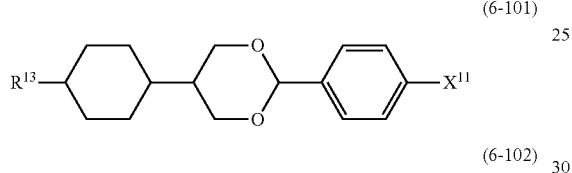
(6-101)
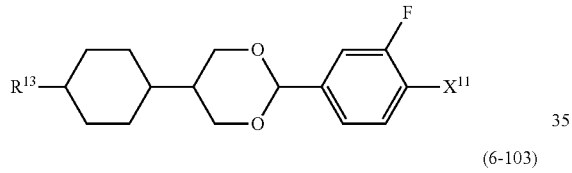
(6-102)
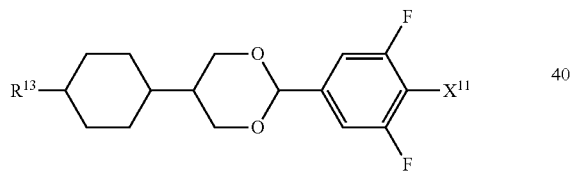
(6-103)
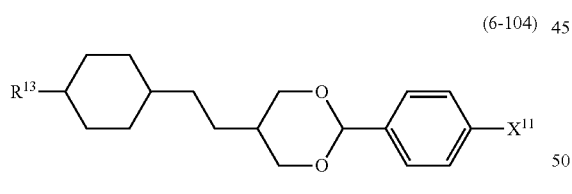
(6-104)
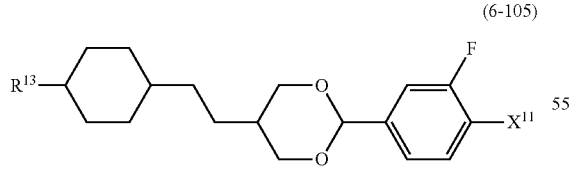
(6-105)
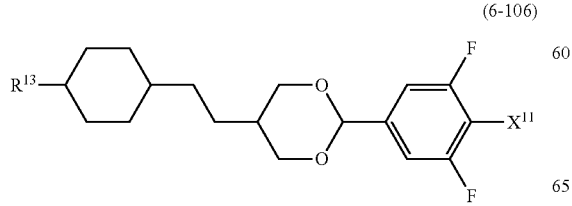
(6-106)
-continued
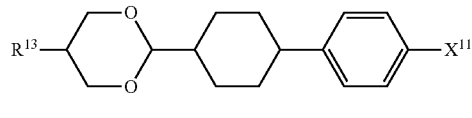
(6-107)
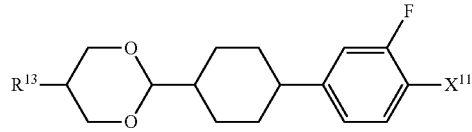
(6-108)
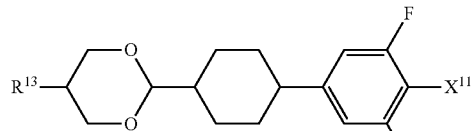
(6-109)
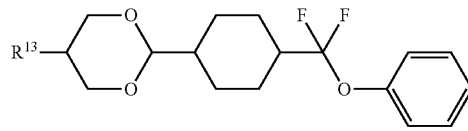
(6-110)
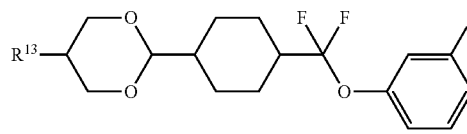
(6-111)
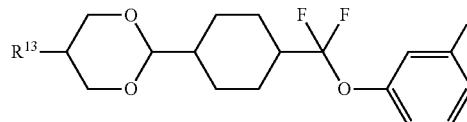
(6-112)
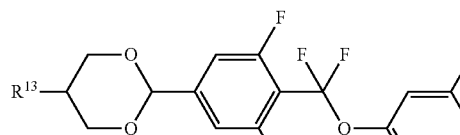
(6-113)
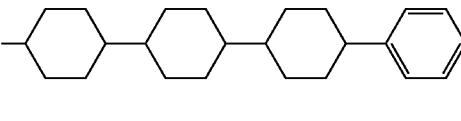
(7-1)
(7-2)

(7-3) 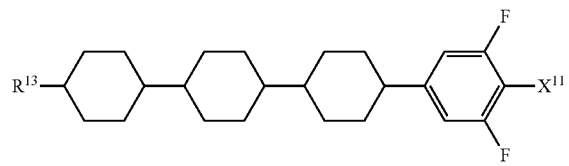
(7-4) 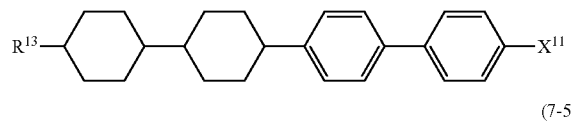
(7-5) 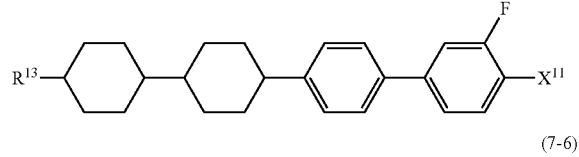
(7-6) 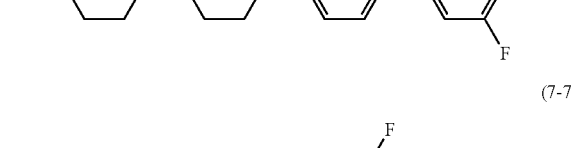
(7-7) 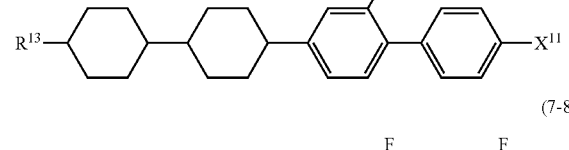
(7-8) 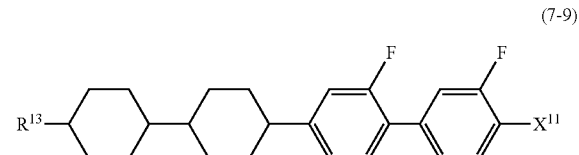
(7-9) 
(7-10) 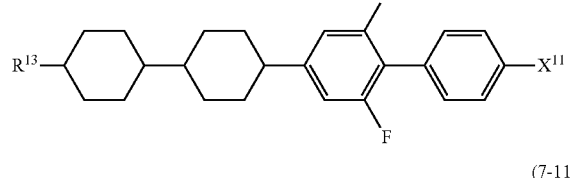
(7-11) 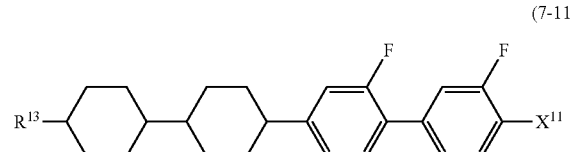
(7-12) 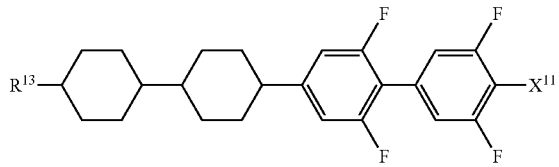
(7-13) 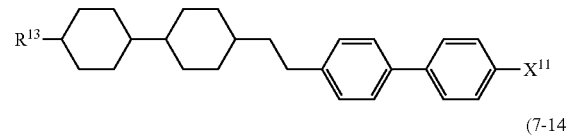
(7-14) 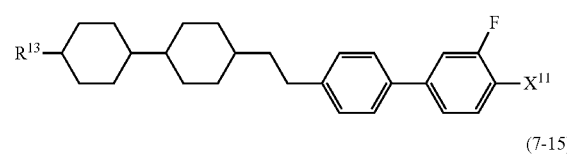
(7-15) 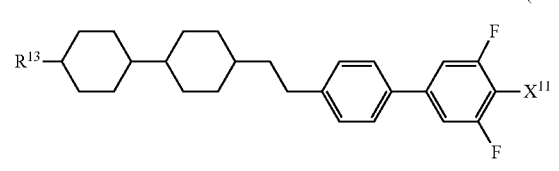
(7-16) 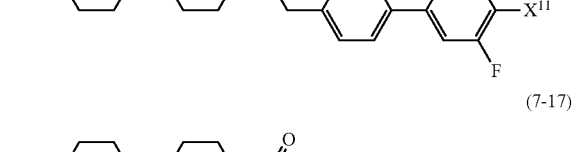
(7-17) 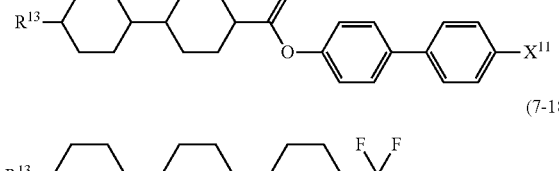
(7-18) 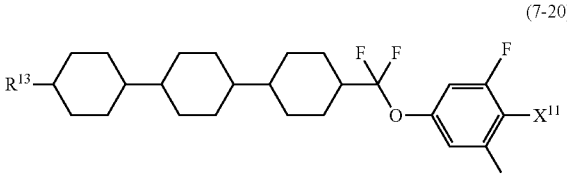
(7-19) 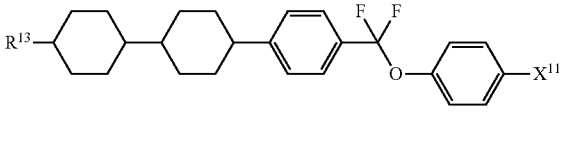
(7-20) 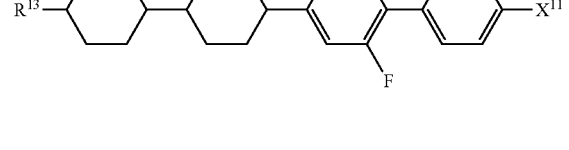
(7-21)

(7-22) 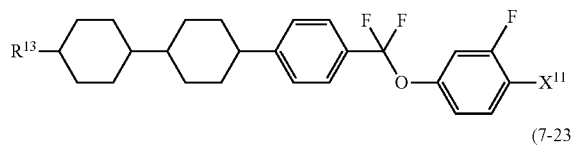
(7-23) 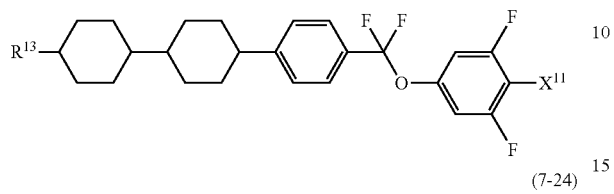
(7-24) 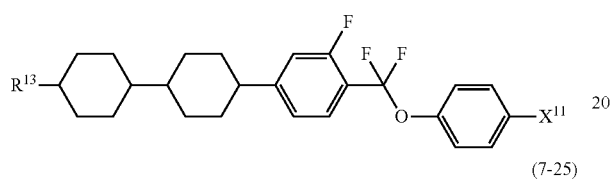
(7-25) 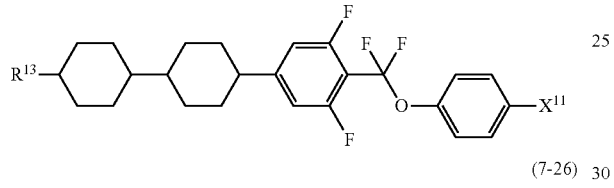
(7-26) 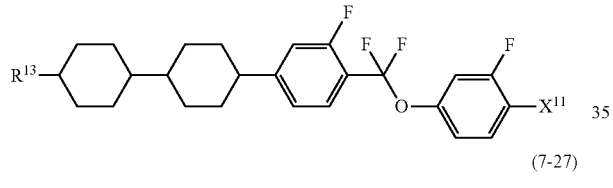
(7-27) 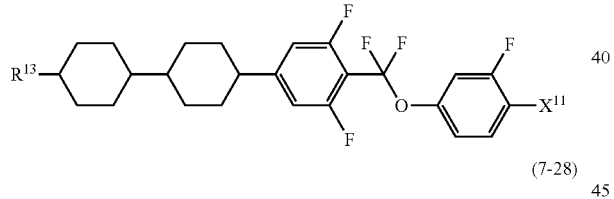
(7-28) 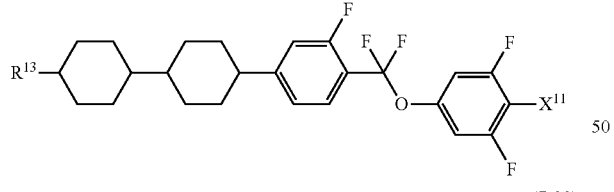
(7-29) 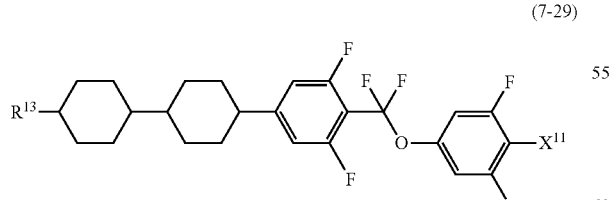
(7-30) 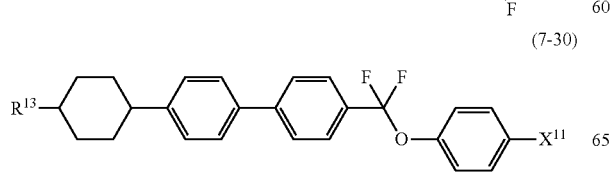
(7-31) 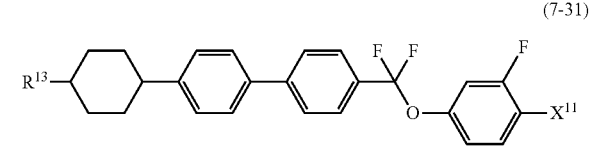
(7-32) 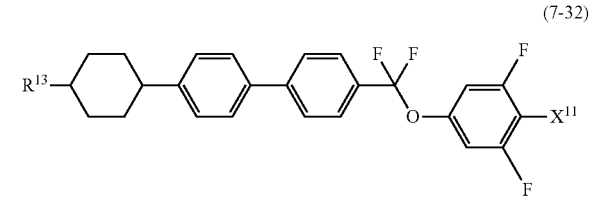
(7-33) 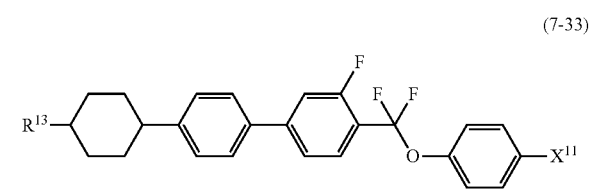
(7-34) 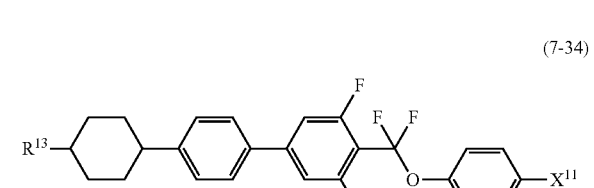
(7-35) 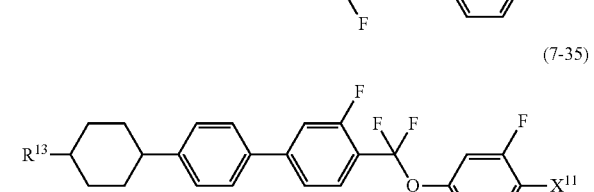
(7-36) 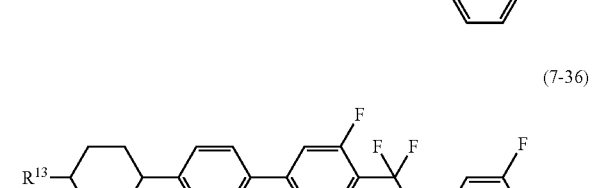
(7-37) 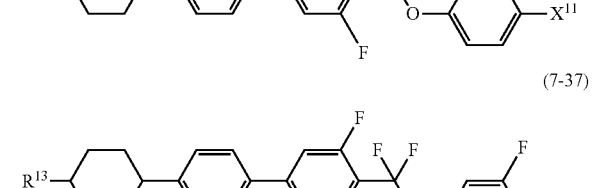
(7-38) 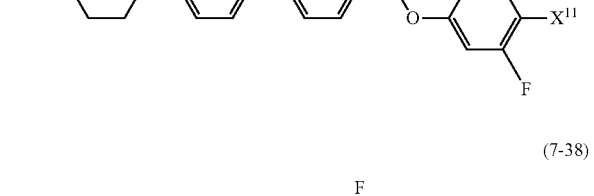
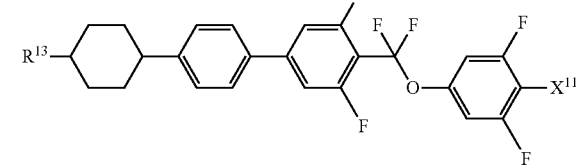

(7-39) 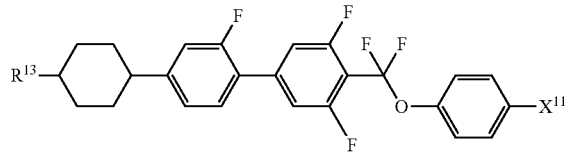
(7-40) 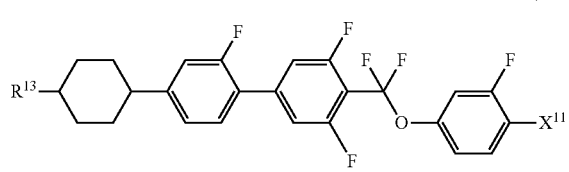
(7-41) 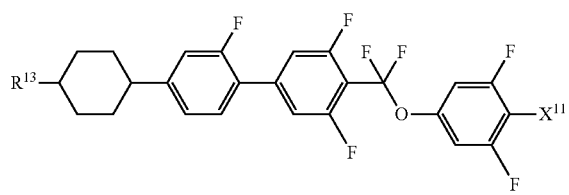
(7-42) 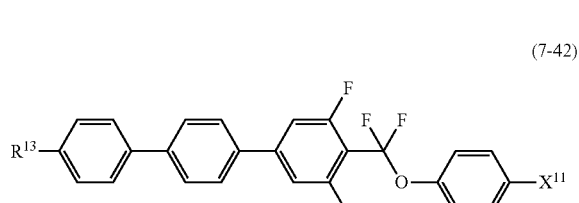
(7-43) 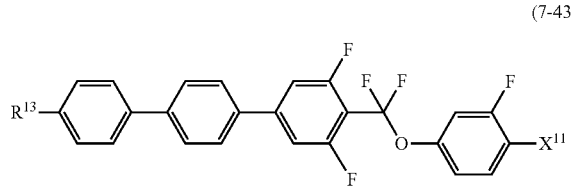
(7-44) 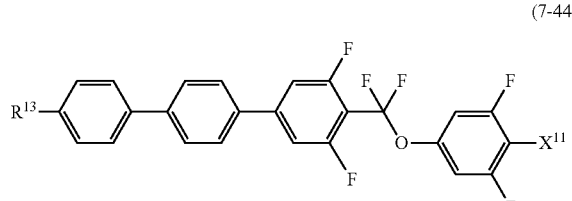
(7-45) 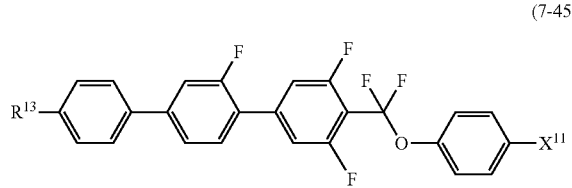
(7-46) 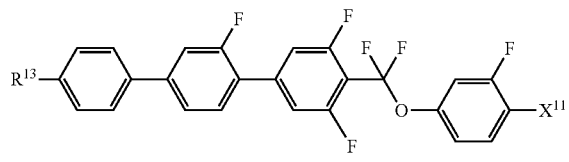
(7-47) 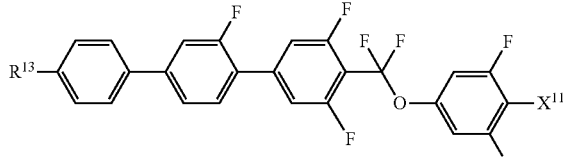
(7-48) 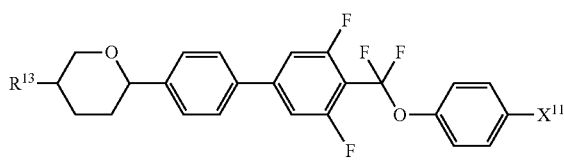
(7-49) 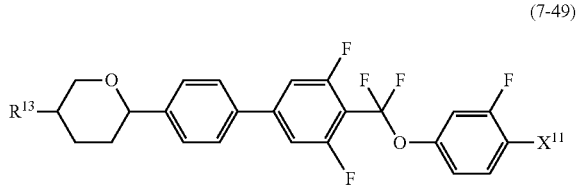
(7-50) 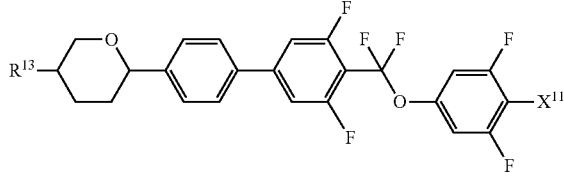
(7-51) 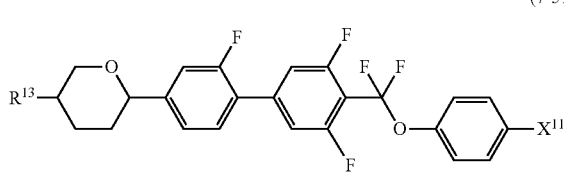
(7-52) 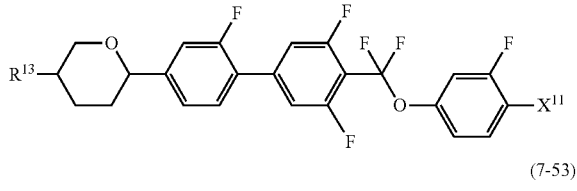
(7-53) 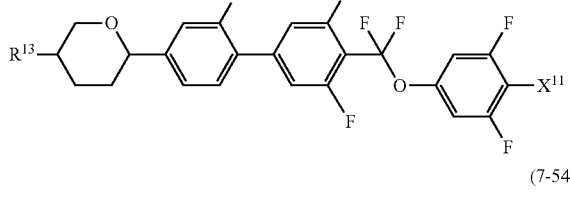
(7-54) 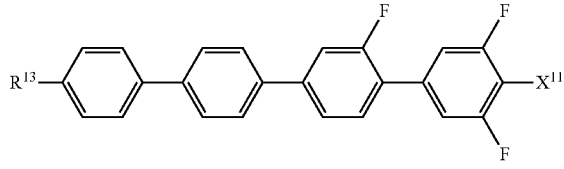

-continued (7-55)
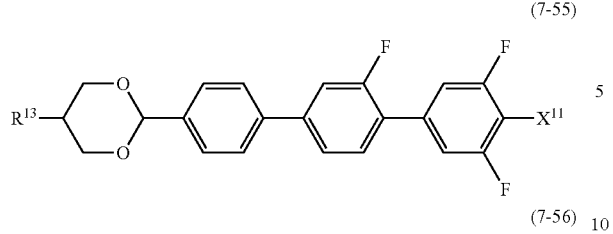

(7-56)
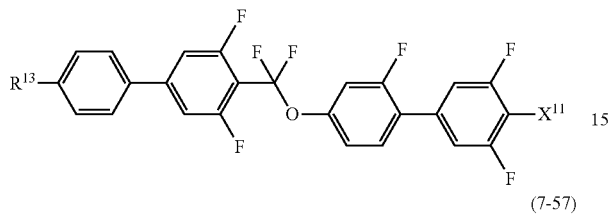

(7-57)
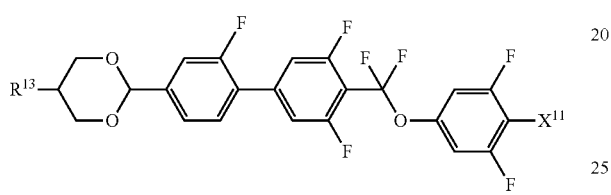

Component C is used for the preparation of a composition for use in modes such as IPS, FFS and OCB, since the dielectric anisotropy is positive and the stability to heat, light or the like is quite excellent. The content of component C is suitably in the range of 1% by weight to 99% by weight, preferably in the range of 10% by weight to 97% by weight, more preferably in the range of 40% by weight to 95% by weight, based on the weight of the liquid crystal composition. It is desirable that the content of component C should be 30% by weight or less when component C is added to a composition having negative dielectric anisotropy. The elastic constant of the composition can be adjusted and the voltage-transmission curve of the device can be adjusted, by the addition of component C.

Component D is compound (8) where the right-terminal group is —C≡N or —C≡C—C≡N. Desirable examples of component D include compounds (8-1) to (8-64). In these compounds, $R^{14}$ is alkyl having 1 to 10 carbons or alkenyl having 2 to 10 carbons, and in the alkyl and alkenyl at least one —CH$_2$— may be replaced by —O— and at least one hydrogen may be replaced by fluorine; and $X^{12}$ is —C≡N or —C≡C—C≡N.

(8-1)
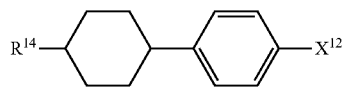

(8-2)
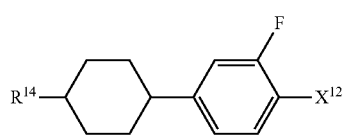

(8-3)
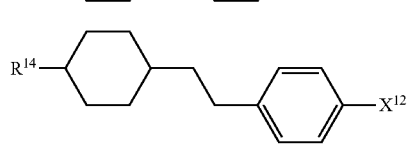

-continued (8-4)
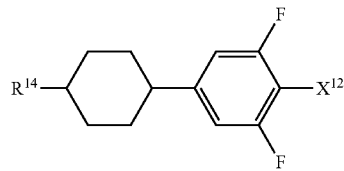

(8-5)
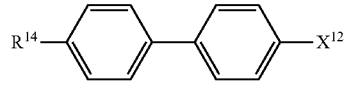

(8-6)
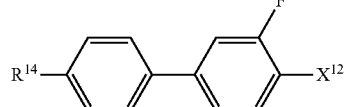

(8-7)
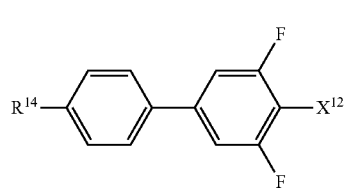

(8-8)
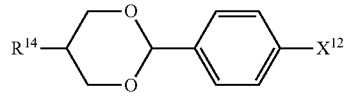

(8-9)
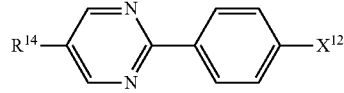

(8-10)
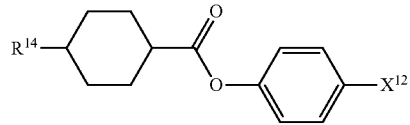

(8-11)
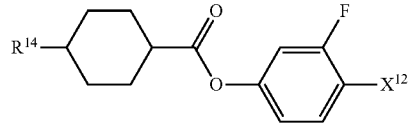

(8-12)
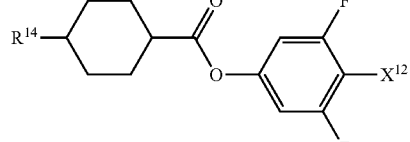

(8-13)
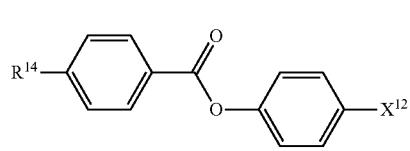

(8-14)
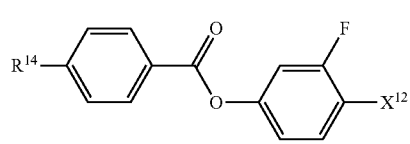

-continued
(8-15) 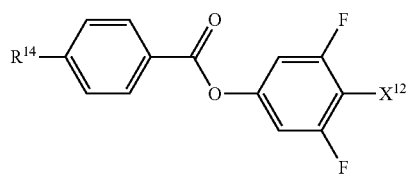
(8-16) 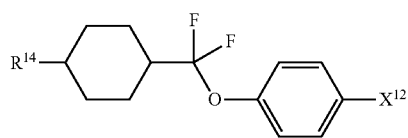
(8-17) 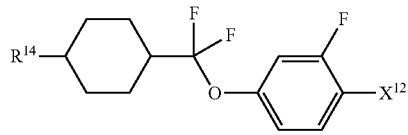
(8-18) 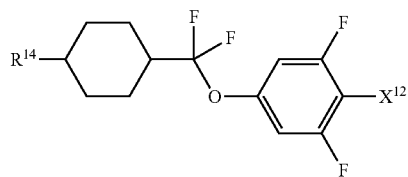
(8-19) 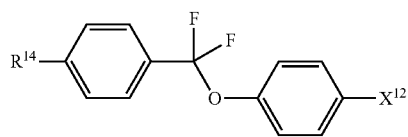
(8-20) 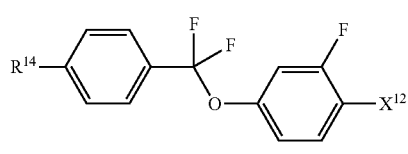
(8-21) 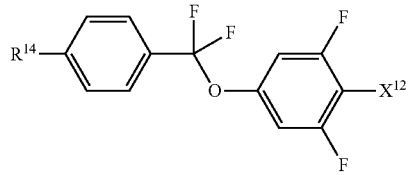
(8-22) 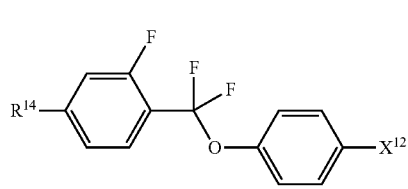
(8-23) 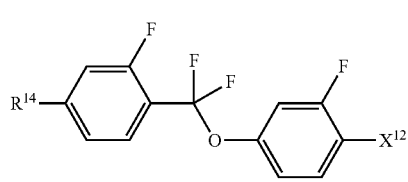
-continued
(8-24) 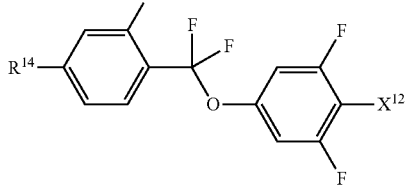
(8-25) 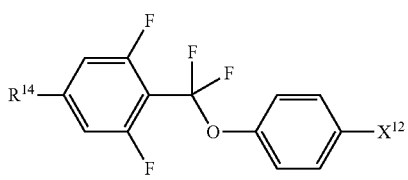
(8-26) 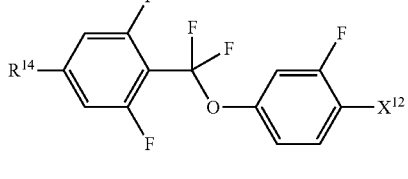
(8-27) 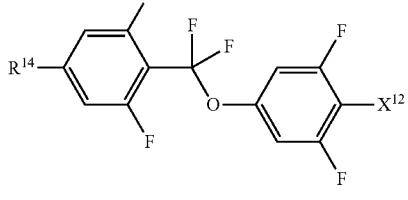
(8-28) 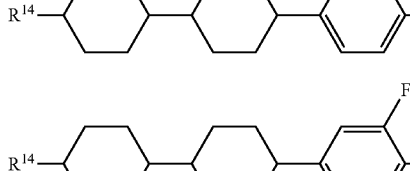
(8-29) 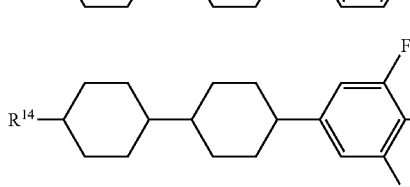
(8-30) 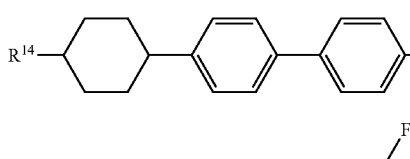
(8-31) 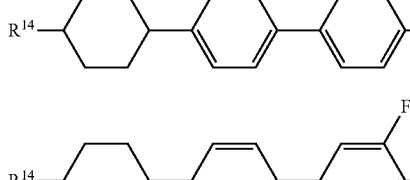
(8-32) 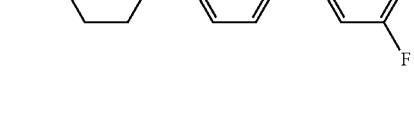
(8-33)

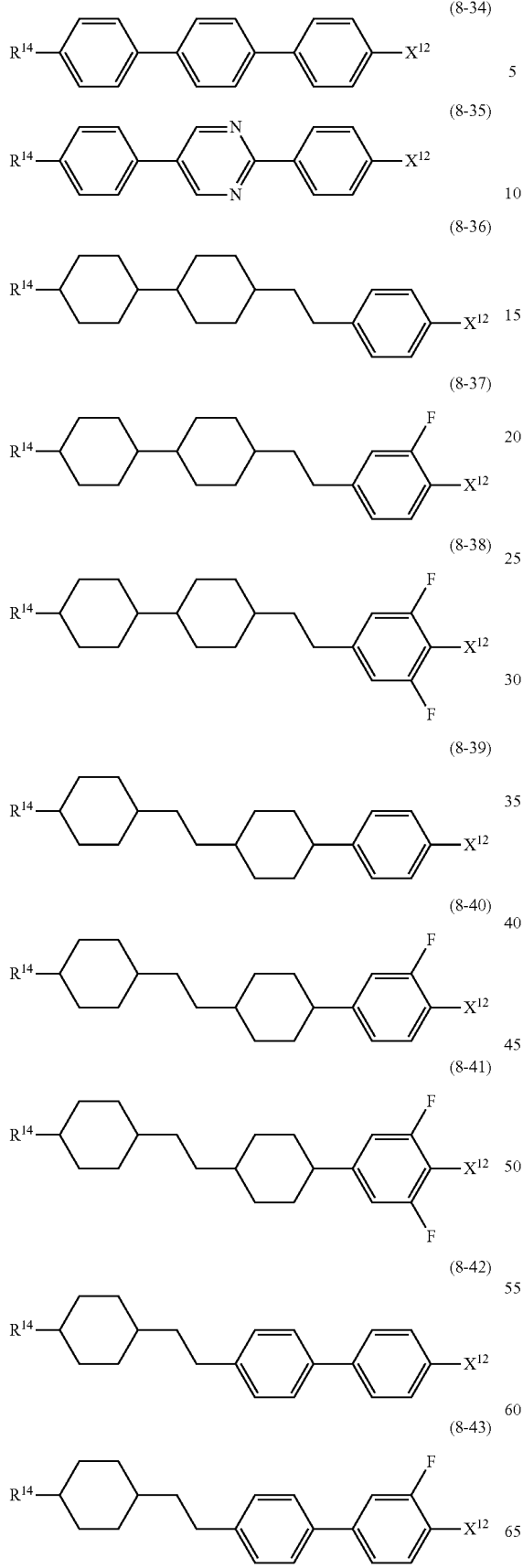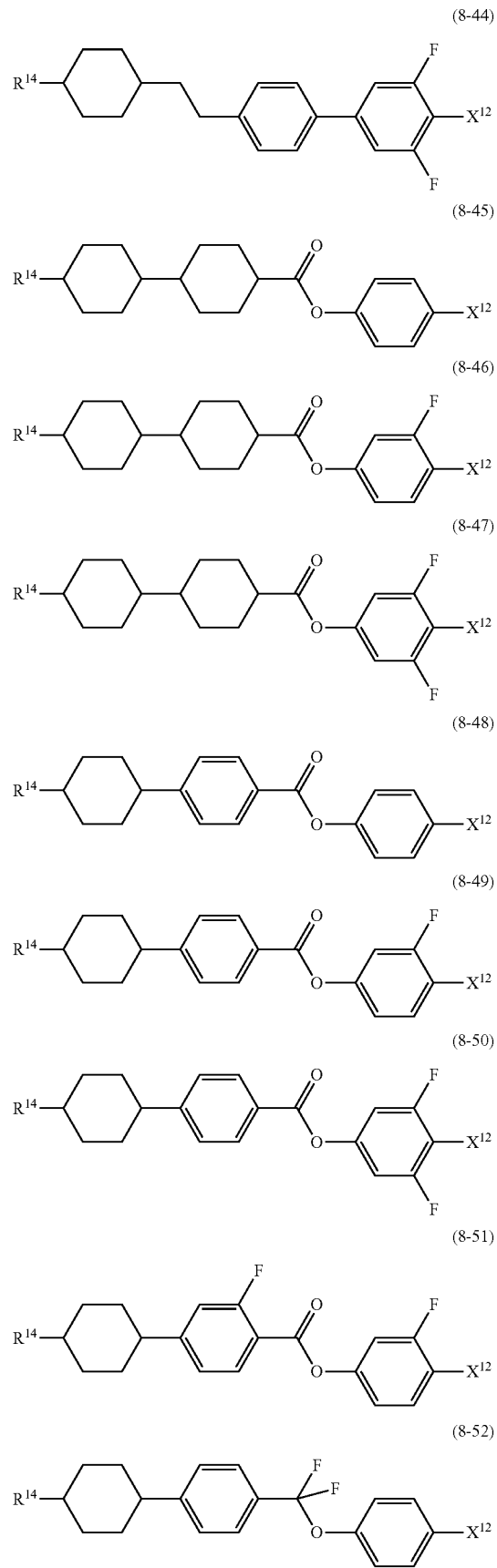

-continued

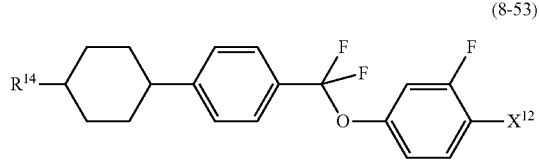
(8-53)

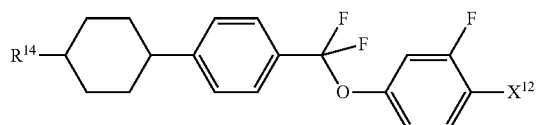
(8-54)

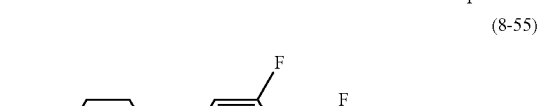
(8-55)

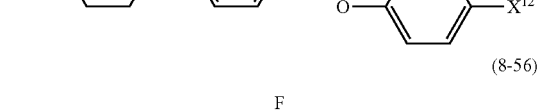
(8-56)

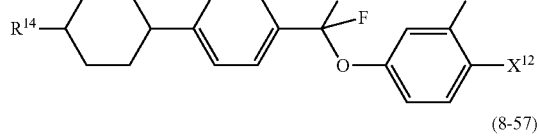
(8-57)

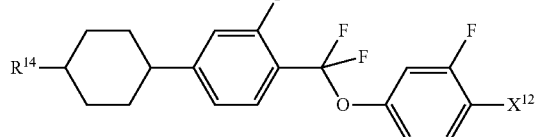
(8-58)

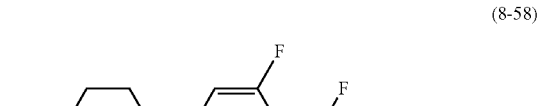
(8-59)

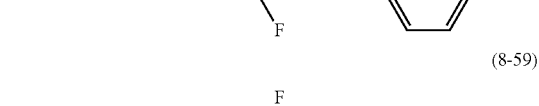
(8-60)

-continued

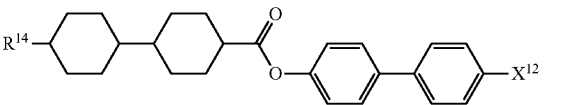
(8-61)

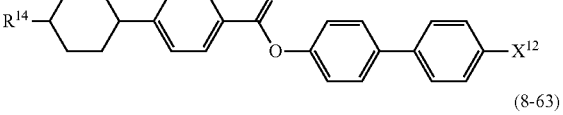
(8-62)

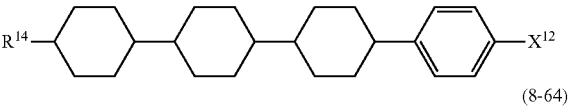
(8-63)

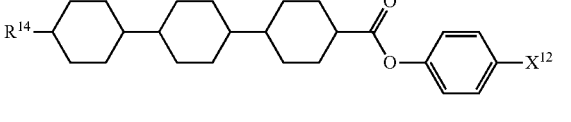
(8-64)

Component D is used for the preparation of a composition for use in modes such as TN, since the dielectric anisotropy is positive and its value is large. The dielectric anisotropy of the composition can be increased by the addition of component D. Component D has the effect of increasing the temperature range of a liquid crystal phase, adjusting the viscosity and adjusting the optical anisotropy. Component D is useful for adjusting the voltage-transmission curve of the device.

The content of component D is suitably in the range of 1% by weight to 99% by weight, preferably in the range of 10% by weight to 97% by weight, more preferably 40% by weight to 95% by weight based on the weight of the liquid crystal composition, in the preparation of a composition for use in modes such as TN. The content of component D is preferably 30% by weight or less when component D is added to a composition having negative dielectric anisotropy. The elastic constant of the composition can be adjusted and the voltage-transmission curve of the device can be adjusted by the addition of component D.

Component E is compounds (9) to (15). These compounds have phenylene substituted by two halogens in the lateral positions, such as 2,3-difluoro-1,4-phenylene. Desirable examples of component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In these compounds, $R^{15}$ and $R^{16}$ are independently alkyl having 1 to 10 carbons or alkenyl having 2 to 10 carbons, and in the alkyl and alkenyl at least one —$CH_2$— may be replaced by —O— and at least one hydrogen may be replaced by fluorine; and $R^{17}$ is hydrogen, fluorine, alkyl having 1 to 10 carbons or alkenyl having 2 to 10 carbons, and in the alkyl and alkenyl at least one —$CH_2$— may be replaced by —O— and at least one hydrogen may be replaced by fluorine.

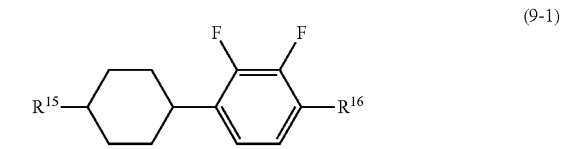
(9-1)

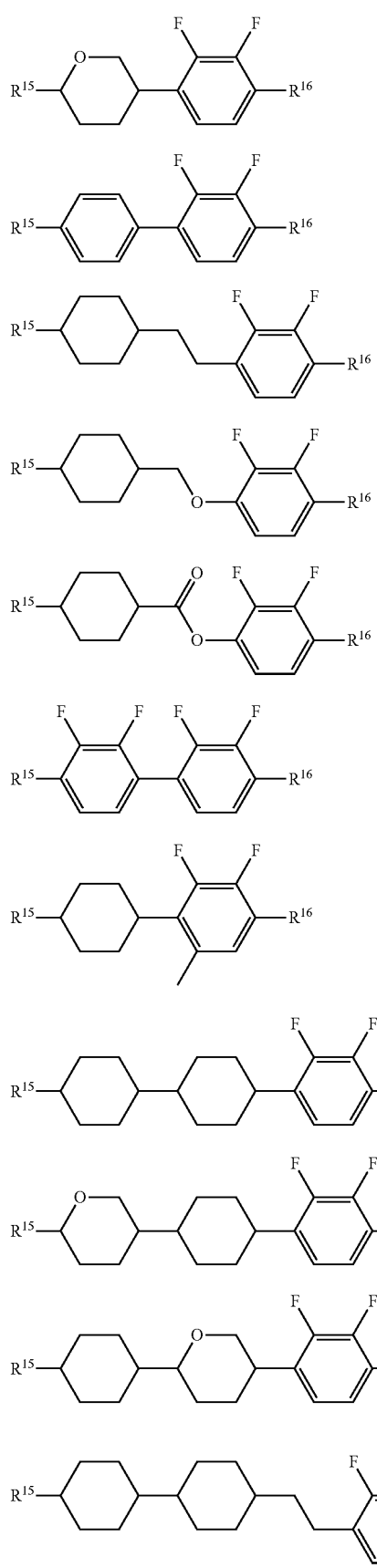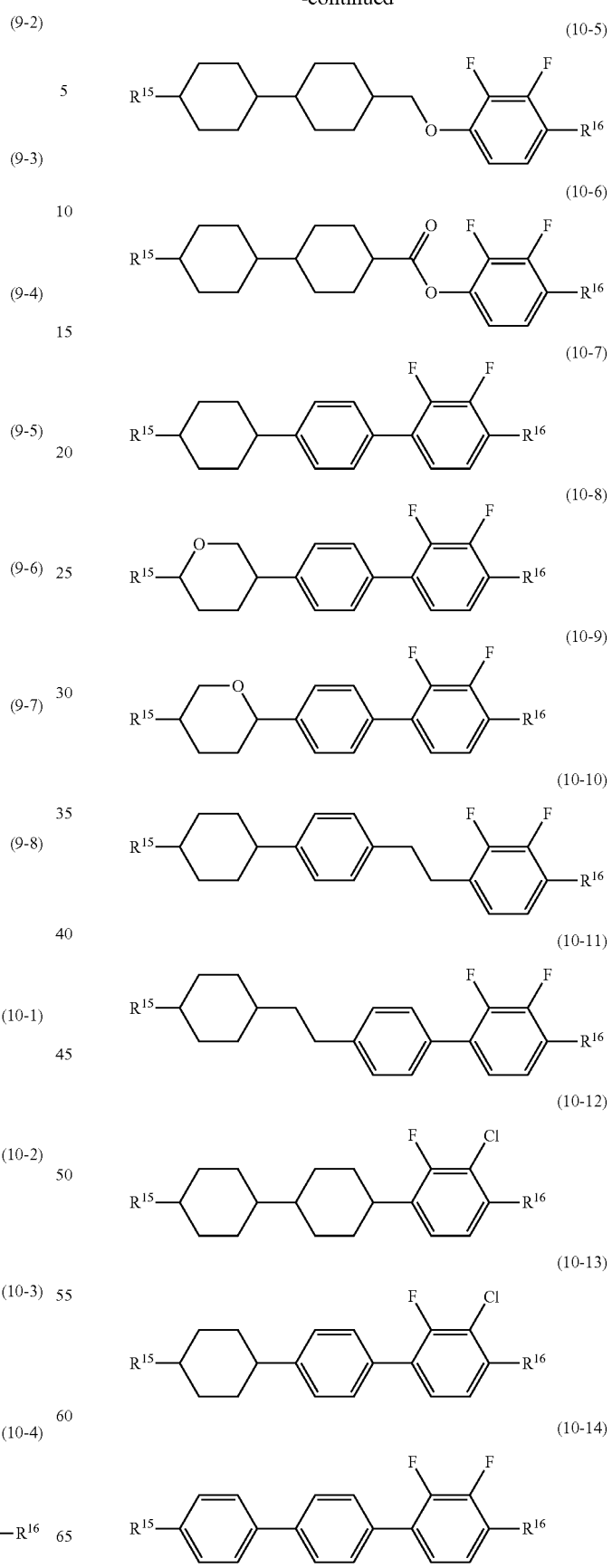

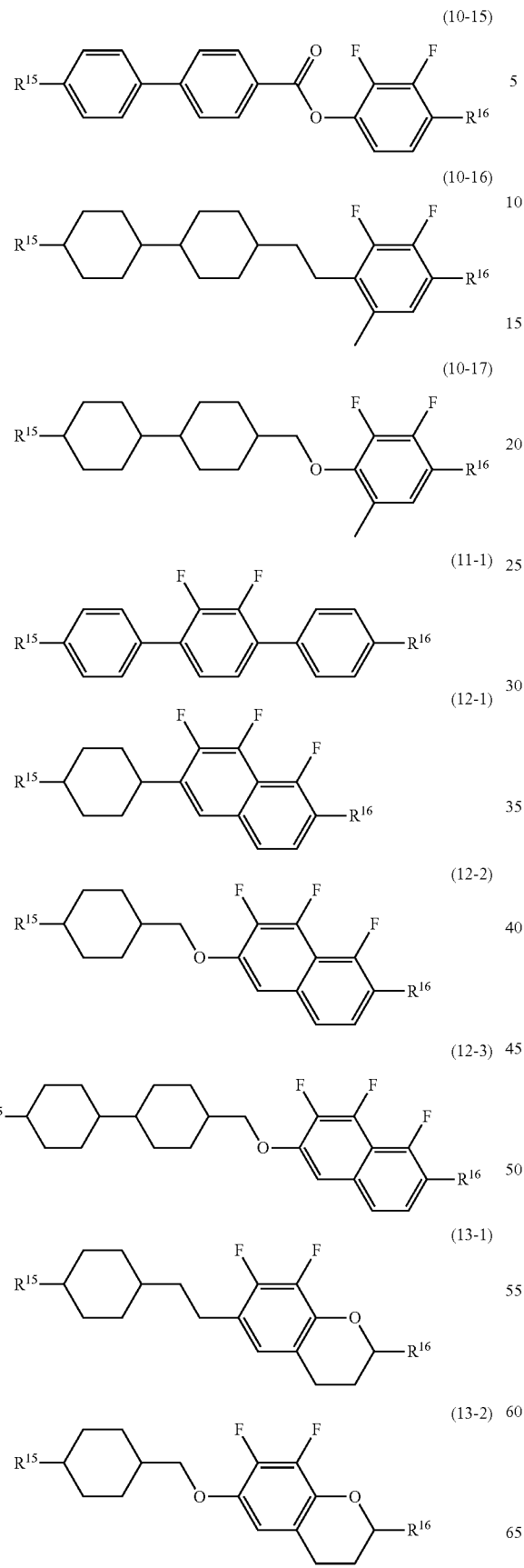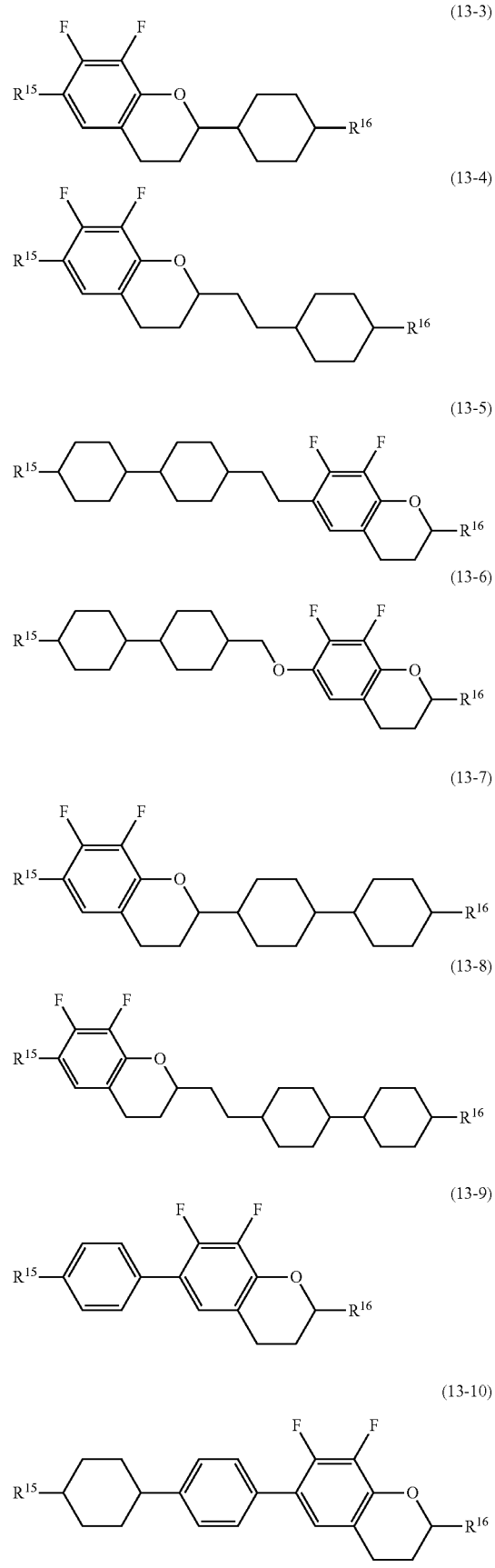

-continued (13-11)
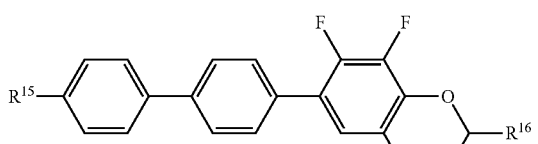

(14-1)
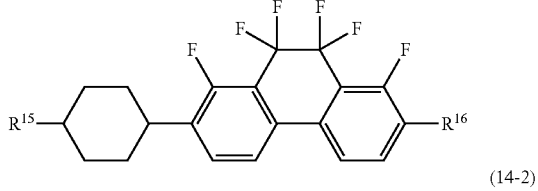

(14-2)
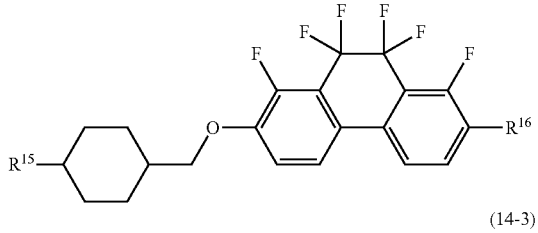

(14-3)
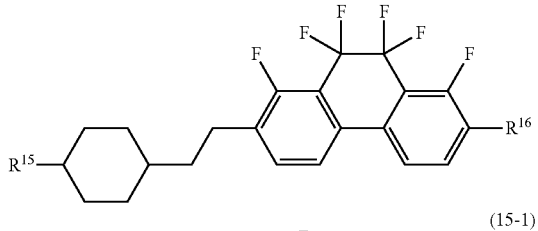

(15-1)
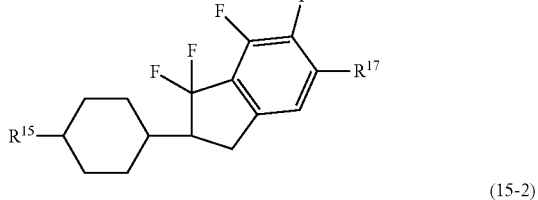

(15-2)
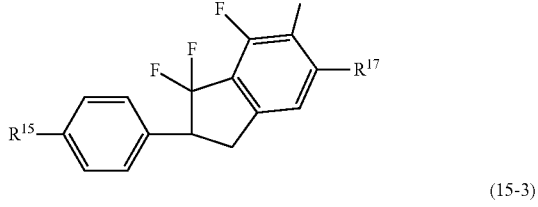

(15-3)
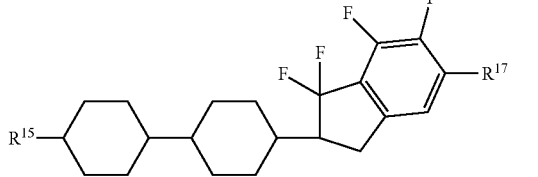

Component E has a large negative dielectric anisotropy. Component E is used for the preparation of a composition for use in modes such as IPS, VA and PSA. As the content of component E is increased, the dielectric anisotropy of the composition increases negatively. However, the viscosity increases. Thus, it is desirable that the content should be decreased as long as the required value of the threshold voltage of the device is satisfied. Accordingly, the content is preferably 40% by weight or more in order to ensure adequate voltage drive, in consideration that the value of the dielectric anisotropy is about −5.

In component E, compound (9) is effective in decreasing the viscosity, adjusting the optical anisotropy or increasing the dielectric anisotropy, since it is a two-ring compound. Compounds (10) and (11) are effective in increasing the maximum temperature, increasing the optical anisotropy or increasing the dielectric anisotropy, since it is a three-ring compound. Compounds (12) to (15) are effective in increasing the dielectric anisotropy.

The content of component E is preferably 40% by weight or more, more preferably in the range of 50% by weight to 95% by weight based on the weight of the liquid crystal composition, in the preparation of a composition for use in modes such as IPS, VA and PSA. It is desirable that the content of component E should be 30% by weight or less when component E is added to a composition having positive dielectric anisotropy. The elastic constant of the composition can be adjusted and the voltage-transmission curve of the device can be adjusted by the addition of component E.

A liquid crystal composition that satisfies at least one of physical properties such as a high stability to heat or light, a high maximum temperature, a low minimum temperature, a small viscosity, a suitable optical anisotropy, a large dielectric anisotropy, a large specific resistance, a suitable elastic constant can be prepared by suitably combining components B, C, D and E described above. A liquid crystal compound that is different from components B, C, D and E may be added as requested.

3-2. Additives

The liquid crystal composition is prepared according to known methods. For example, the component compounds are mixed and dissolved in each other by heating. An additive may be added to the composition depending on its intended use. Examples of the additive include a polymerizable compound, a polymerization initiator, a polymerization inhibitor, an optically active compound, an antioxidant, an ultraviolet light absorber, a light stabilizer, a thermal stabilizer, a coloring matter and an antifoaming agent. Such an additive is well-known to a person skilled in the art, and is described in the literature.

In a liquid crystal display device having PSA (polymer sustained alignment) mode, the composition includes a polymer. A polymerizable compound is added to the composition in order to form a polymer in it. A polymer is formed in the composition by the irradiation with ultraviolet light and by the polymerization of the polymerizable compound under conditions where a voltage is applied between the electrodes. A device is produced in which the response time is decreased and the image burn-in is improved, since a suitable pretilt is achieved by this method.

Desirable examples of the polymerizable compound include acrylates, methacrylates, vinyl compounds, vinyloxy compounds, propenyl ethers, epoxy compounds (oxiranes, oxetanes) and vinyl ketones. More desirable examples are a compound having at least one acryloyloxy and a compound having at least one metacryloyloxy. More desirable examples also include a compound having both acryloyloxy and metacryloyloxy.

More desirable examples are compounds (M-1) to (M-17). In these compounds, $R^{25}$ to $R^{31}$ are independently hydrogen or methyl; s, v and x are independently 0 or 1; t and u are independently an integer from 1 to 10. $L^{21}$ to $L^{26}$ are independently hydrogen or fluorine; and $L^{27}$ and $L^{28}$ are independently hydrogen, fluorine or methyl.

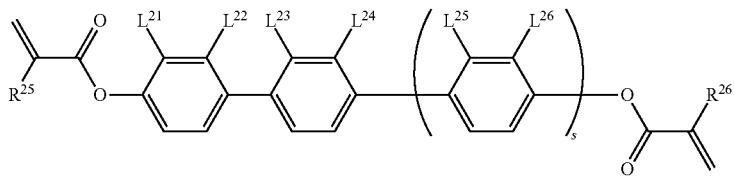
(M-1)
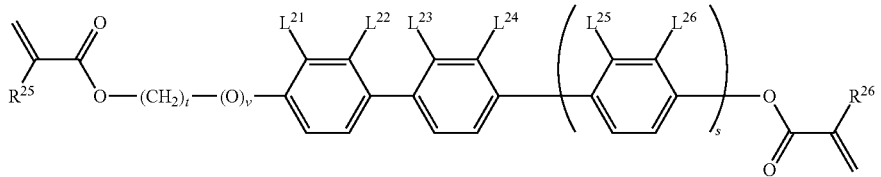
(M-2)
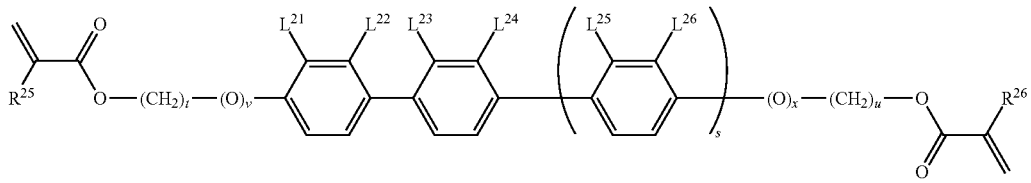
(M-3)
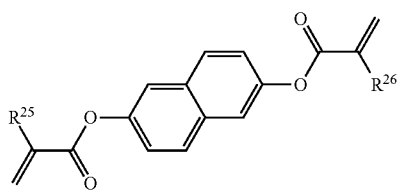
(M-4)
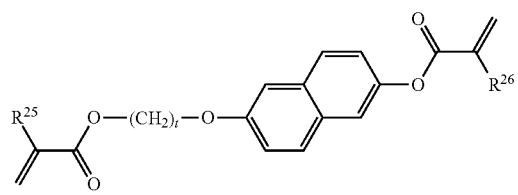
(M-5)
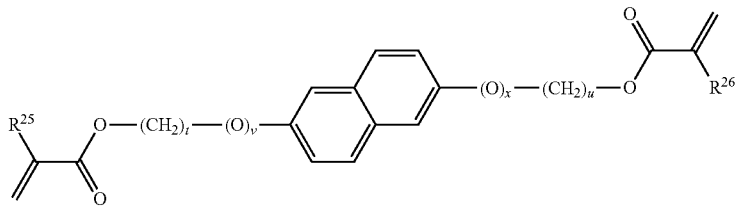
(M-6)
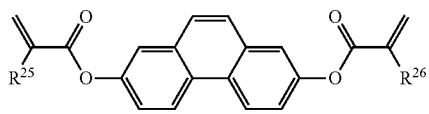
(M-7)
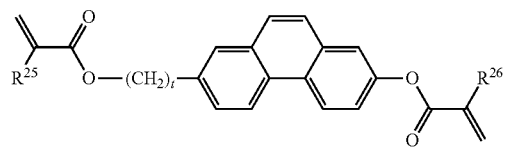
(M-8)
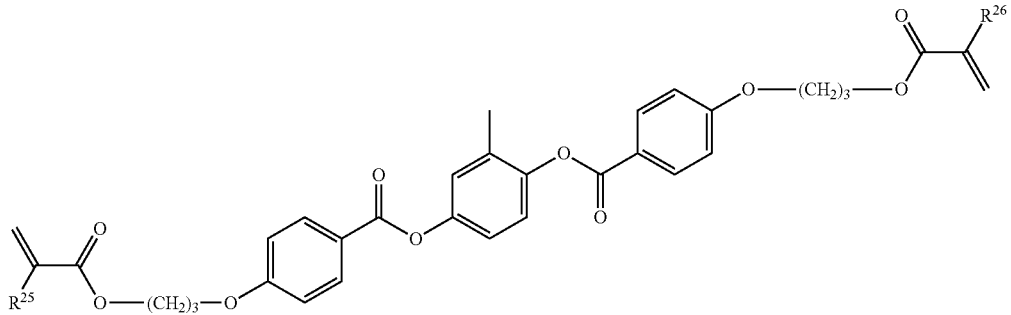
(M-9)

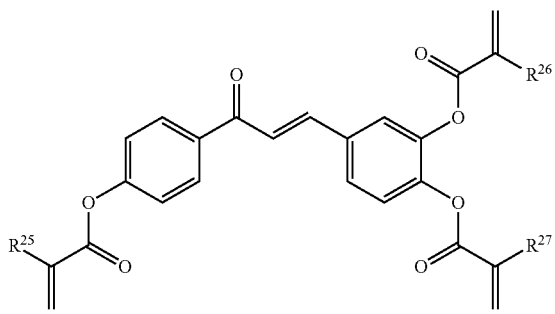
(M-10)
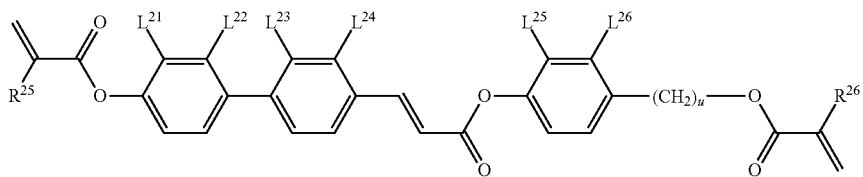
(M-11)
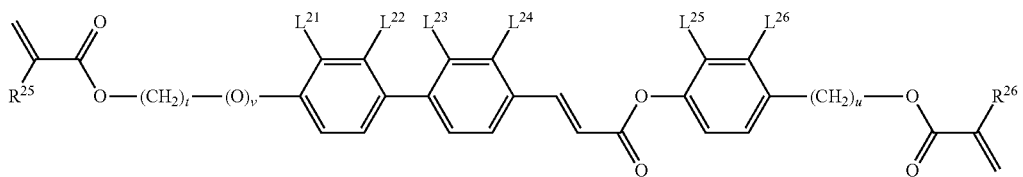
(M-12)
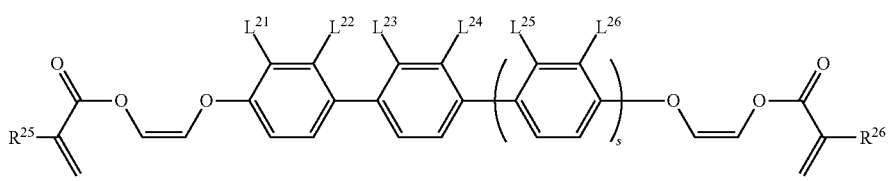
(M-13)
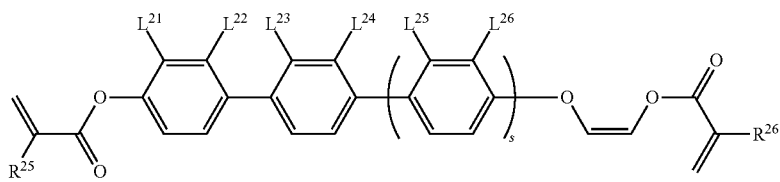
(M-14)
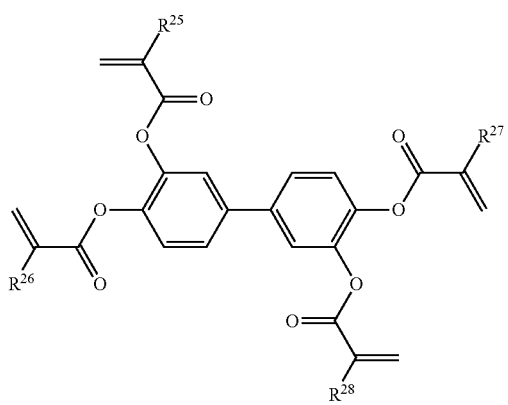
(M-15)

-continued

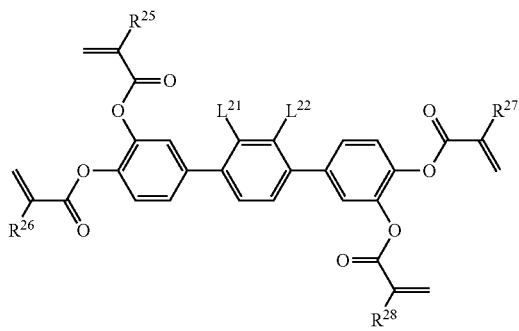
(M-16)

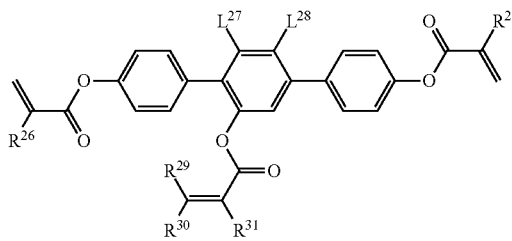
(M-17)

The polymerizable compound can smoothly be polymerized by the addition of a polymerization initiator. The amount of the remaining polymerizable compound can be decreased by optimizing the reaction temperature. Examples of a photo-radical polymerization initiator are TPO, 1173 and 4265 of Darocur series, and 184, 369, 500, 651, 784, 819, 907, 1300, 1700, 1800, 1850 and 2959 of Irgacure series, at BASF SE.

Additional examples of the photo-radical polymerization initiators are 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a mixture of benzophenone/Michler's ketone, a mixture of hexaarylbiimidazole/mercaptobenzimidazole, 1-(4-isopropylphenyl)-2-hydroxy-2-methylpropan-1-one, benzyldimethylketal, 2-methyl-1-[4-(methylthio)phenyl]-2-morphorinopropan-1-one, a mixture of 2,4-diethylxanthone/methyl p-dimethylaminobenzoate and a mixture of benzophenone/methyltriethanolamine.

The polymerization can be carried out by irradiation with ultraviolet light under the conditions of an applied electric field, after a photo-radical polymerization initiator had been added to a liquid crystal composition. However, the unreacted polymerization initiator or the degradation product of the polymerization initiator may cause a poor display such as image burn-in to the device. The photo-polymerization may be carried out without the polymerization initiator in order to avoid it. Desirable wavelengths of the irradiated light are in the range of 150 nm to 500 nm. More desirable wavelengths are in the range of 250 nm to 450 nm, and the most desirable wavelengths are in the range of 300 nm to 400 nm.

A polymerization inhibitor may be added in order to prevent the polymerization when a polymerizable compound is kept in storage. The polymerizable compound is usually added to a composition without removing the polymerization inhibitor. Examples of the polymerization inhibitor include hydroquinone derivatives such as hydroquinone and methylhydroquinone, 4-t-butylcatechol, 4-methoxyphenol and phenothiazine.

An optically active compound is effective in inducing a helical structure in liquid crystal molecules, giving a necessary twist angle and thus preventing a reverse twist. A helical pitch can be adjusted by the addition of the optically active compound. Two or more optically active compounds may be added for the purpose of adjusting the temperature dependence of the helical pitch. Desirable examples of the optically active compound include the following compounds (Op-1) to (Op-18). In compound (Op-18), ring J is 1,4-cyclohexylene or 1,4-phenylene, and $R^{28}$ is alkyl having 1 to 10 carbons.

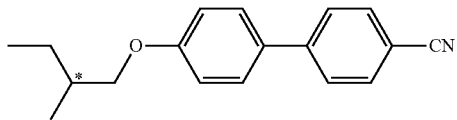
(Op-1)

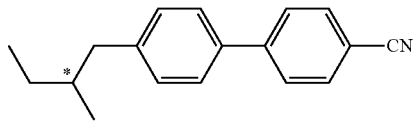
(Op-2)

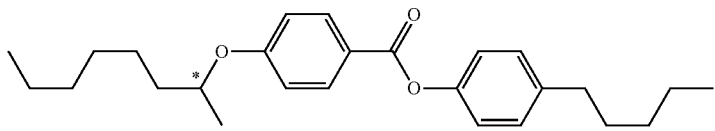
(Op-3)

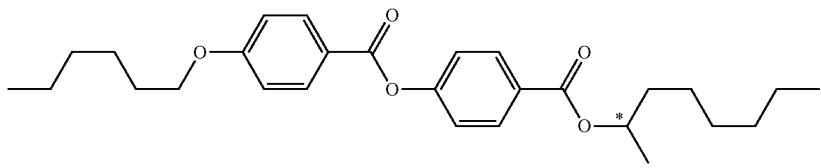
(Op-4)

-continued
(Op-5)
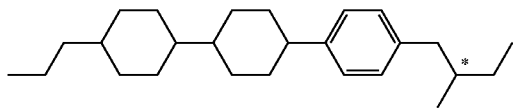
(Op-6)
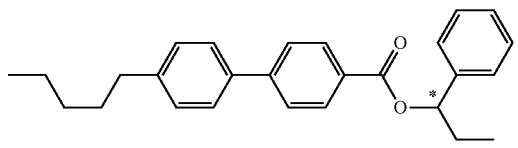
(Op-7)
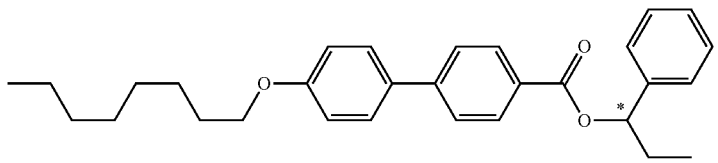
(Op-8)
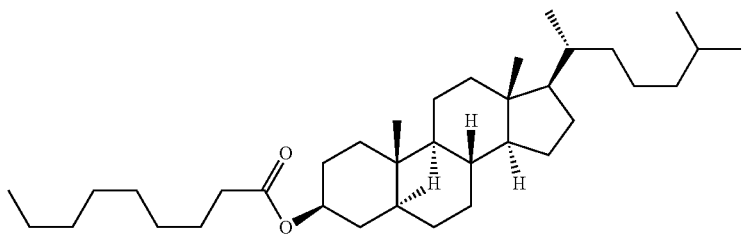
(Op-9)
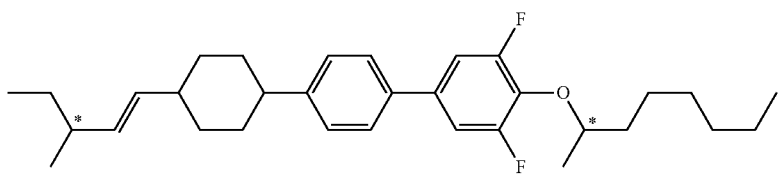
(Op-10)
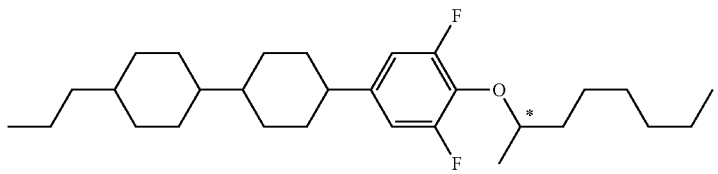
(Op-11)
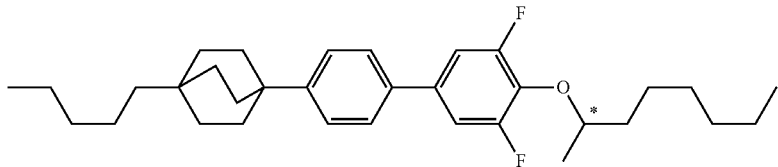
(Op-12)
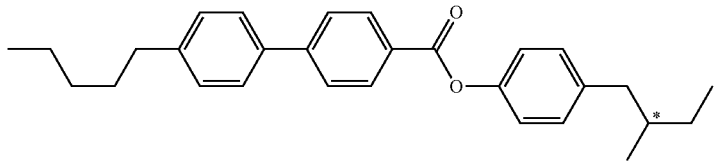
(Op-13)
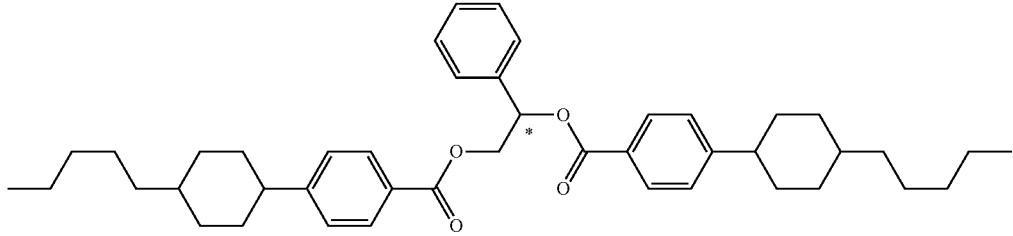

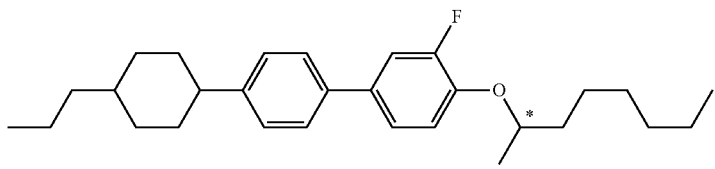

(Op-14)

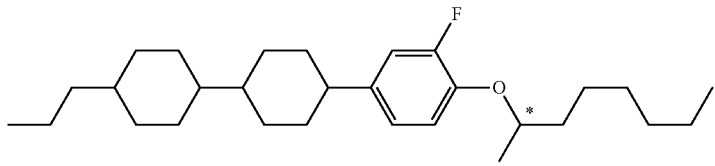

(Op-15)

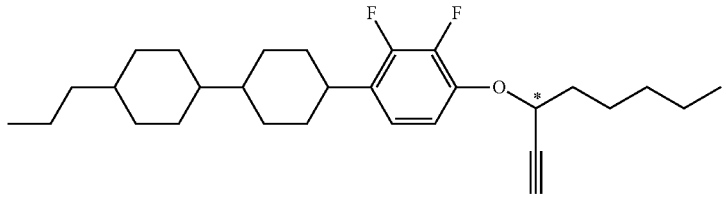

(Op-16)

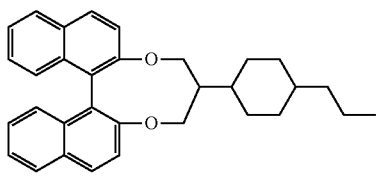

(Op-17)

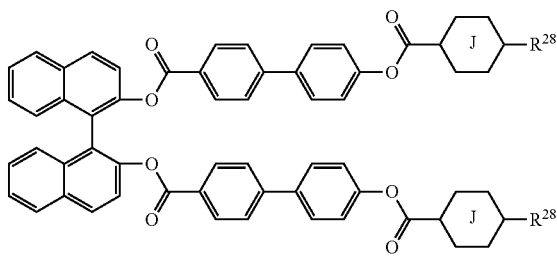

(Op-18)

An antioxidant is effective in maintaining a large voltage holding ratio. Desirable examples of the antioxidant include compounds (AO-1) and (AO-2) described below; and Irganox 415, Irganox 565, Irganox 1010, Irganox 1035, Irganox 3114 and Irganox 1098 (trade name of BASF SE). An ultraviolet light absorber is effective for preventing a decrease in the maximum temperature. Desirable examples of the ultraviolet light absorber include benzophenone derivatives, benzoate derivatives and triazole derivatives. Specific examples include compounds (AO-3) and (AO-4) described below; Tinuvin 329, Tinuvin P, Tinuvin 326, Tinuvin 234, Tinuvin 213, Tinuvin 400, Tinuvin 328, Tinuvin 99-2 (trade name of BASF SE); and 1,4-diazabicyclo[2.2.2]octane (DABCO).

A light stabilizer such as amines with steric hindrance is also desirable for maintaining a large voltage holding ratio. Desirable examples of the light stabilizer include compounds (AO-5) and (AO-6) described below; and Tinuvin 144, Tinuvin 765 and Tinuvin 770DF (trade name of BASF SE). A thermal stabilizer is also effective in maintaining a large voltage holding ratio. Desirable examples include Irgafos 168 (trade name of BASF SE). A dichroic dye such as an azo dye or an anthraquinone dye is added to the composition for adjusting to a device having a guest host (GH) mode. An antifoaming agent is effective in preventing foam formation. Desirable examples of the antifoaming agent include dimethyl silicone oil and methyl phenyl silicone oil.

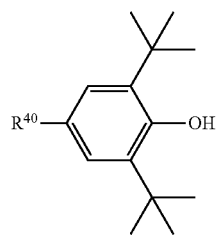

(AO-1)

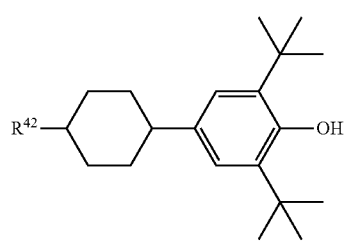

(AO-2)

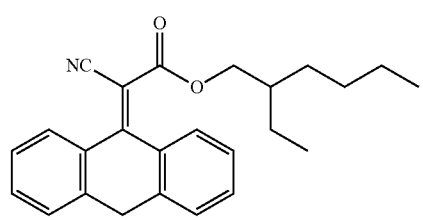

(AO-3)

-continued (AO-4)

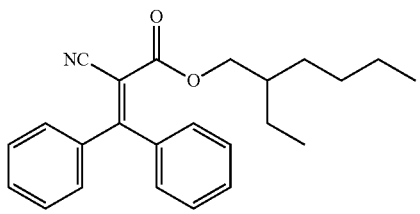

(AO-5)

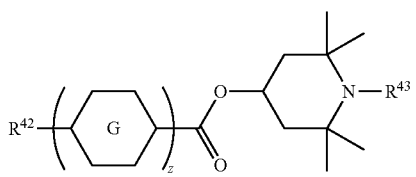

(AO-6)

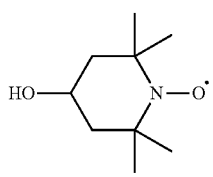

In compound (AO-1), $R^{40}$ is alkyl having 1 to 20 carbons, alkoxy having 1 to 20 carbons, —COOR$^{41}$ or —CH$_2$CH$_2$COOR$^{41}$, where $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O. (oxygen radical); ring G is 1,4-cyclohexylene or 1,4-phenylene; and z is 1, 2 or 3.

4. Liquid Crystal Display Devices

The liquid crystal composition can be used for a liquid crystal display device having a driving mode such as PC, TN, STN, OCB or PSA, which is driven by means of an active matrix mode. The composition can also be used for a liquid crystal display device having a driving mode such as PC, TN, STN, OCB, VA or IPS, which is driven by means of a passive matrix mode. These devices can be applied to any of a reflection type, a transmission type or a semi-transmission type.

The composition is suitable for a NCAP (nematic curvilinear aligned phase) device, where the composition is micro-encapsulated. The composition can be used for a polymer-distributed liquid crystal display device (PDLCD) or and for a polymer network liquid crystal display device (PNLCD). In these compositions, a large amount of a polymerizable compound is added. In contrast, a liquid crystal display device having a PSA mode is produced when the added amount of the polymerizable compound is 10% by weight or less based on the weight of this liquid crystal composition. A desirable ratio is in the range of 0.1% by weight to 2% by weight. A more desirable ratio is in the range of 0.2% by weight to 1.0% by weight. The device having a PSA mode can be driven by way of a driving mode such as an active matrix or a passive matrix. Such a device can be applied to any of a reflection type, a transmission type or a semi-transmission type.

EXAMPLES

The invention will be explained in more detail by way of Examples (including Synthetic Examples and Use Examples). The invention is not limited to Examples. The invention includes a mixture of the composition in Use Example 1 and the composition in Use Example 2. The invention also includes a composition prepared by mixing at least two compositions in Use Examples.

1. Examples of Compound (1a)

Compound (1a) was prepared according to the procedures described below. Compounds prepared herein were identified by methods such as NMR analysis. The physical properties of compounds or compositions and the characteristics of devices were measured by the methods described below.

NMR Analysis: A model DRX-500 apparatus made by Bruker BioSpin Corporation was used for measurement. In the measurement of $^1$H-NMR, a sample was dissolved in a deuterated solvent such as CDCl$_3$, and measured under the conditions of room temperature, 500 MHz and the accumulation of 16 scans. Tetramethylsilane was used as an internal standard. In the measurement of $^{19}$F-NMR, CFCl$_3$ was used as an internal standard, and 24 scans were accumulated. In the explanation of the nuclear magnetic resonance spectra, the symbols s, d, t, q, quin, sex, m and br stand for a singlet, a doublet, a triplet, a quartet, a quintet, a sextet, a multiplet and line-broadening, respectively.

Gas Chromatographic Analysis: A gas chromatograph Model GC-2010 made by Shimadzu Corporation was used for measurement. The column used was a capillary column DB-1 (length 60 meters, bore 0.25 millimeters, film thickness 0.25 micrometers) made by Agilent Technologies, Inc. The carrier gas was helium (1 milliliter per minute). The sample injector and the detector (FID) were set to 300° C. A sample was dissolved in acetone to give a 0.1% solution by weight, and 1 microliter of the solution was injected into the sample injector. A recorder used was Model GC Solution System made by Shimadzu Corporation or the like.

HPLC Analysis: Model Prominence (LC-20AD; SPD-20A) made by Shimadzu Corporation was used for measurement. A column YMC-Pack ODS-A (length 150 millimeters, bore 4.6 millimeters, particle size 5 micrometers) made by YMC Co., Ltd. was used. Acetonitrile and water were properly mixed and used as eluent. A detector such as a UV detector, a RI detector or a Corona detector was properly used. The measurement wavelength was 254 nanometers when the UV detector was used. A sample was dissolved in acetonitrile to give a 0.1% by weight solution, and then 1 microliter of the solution was injected into the sample injector. Model C-R7Aplus made by Shimadzu Corporation was used as a recorder.

Ultraviolet and Visible Spectrophotometric Analysis: Model PharmaSpec UV-1700 made by Shimadzu Corporation was used for measurement. Wavelengths in the range of 190 nm to 700 nm were used for the detection. A sample was dissolved in acetonitrile, giving a 0.01 mmol/L solution, which was placed in a quartz cell (optical path length: 1 cm) and measured.

Sample for measurement: A compound itself was used as a sample when the phase structure and the transition temperature (a clearing point, a melting point, a starting temperature of polymerization or the like) were measured. A mixture of the compound and mother liquid crystals was used as a sample when physical properties such as the maximum temperature of a nematic phase, viscosity, optical anisotropy and dielectric anisotropy were measured.

When a sample was prepared by mixing a compound and mother liquid crystals, the measurement was carried out according to the following method. The sample was prepared by mixing 20% by weight of the compound and 80% by weight of the mother liquid crystals. Extrapolated values were calculated from the measured values of the sample by means of an extrapolation method represented by the following equation, and their values were reported. [Extrapolated value]=(100×[Measured value of sample]−[% by weight of mother liquid crystals]×[Measured value of mother liquid crystals])/[% by weight of compound].

When crystals (or a smectic phase) deposited at 25° C. even at this ratio of the compound to the mother liquid crystals, the ratio of the compound to the mother liquid crystals was changed in the order of (15% by weight: 85% by weight), (10% by weight: 90% by weight), (5% by weight: 95% by weight) and (1% by weight: 99% by weight). The physical properties of the sample were measured at the ratio in which the crystals (or the smectic phase) did not deposit at 25° C. Incidentally, the ratio of the compound to the mother liquid crystals was (20% by weight: 80% by weight), unless otherwise noted.

Mother liquid crystals (i) composed of the following fluorine-containing compounds were used as mother liquid crystals. The ratio of each component is expressed as a percentage by weight.

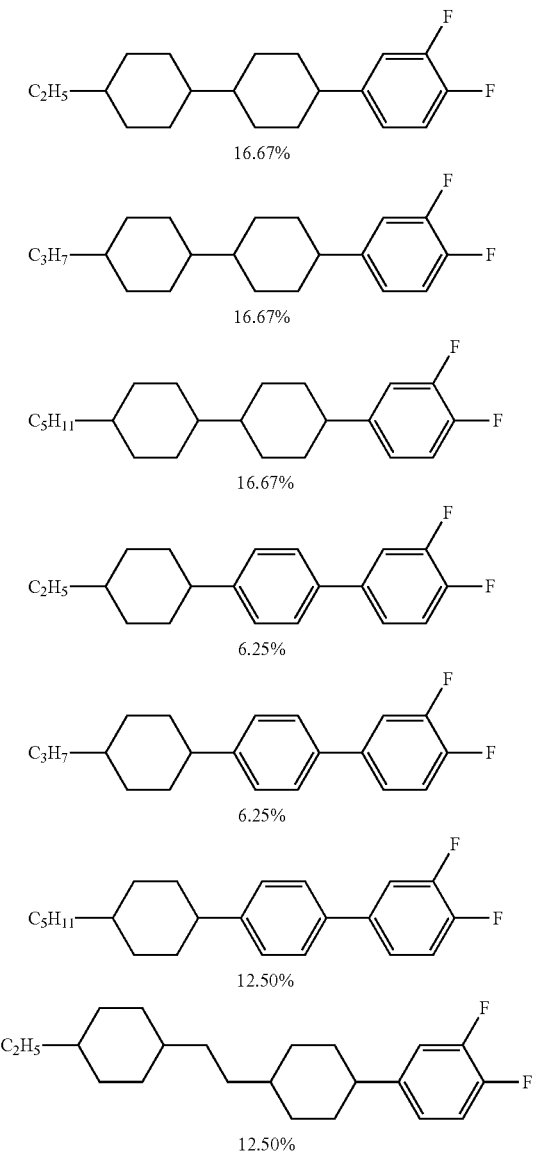

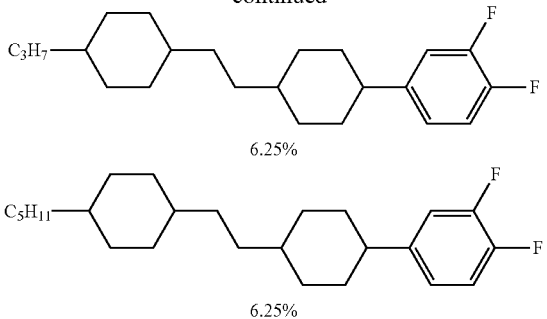

Measurement method: The physical properties were measured according to the following methods. Most of them are described in the JEITA standards (JEITA-ED-2521B) which was deliberated and established by Japan Electronics and Information Technology Industries Association (abbreviated to JEITA). A modified method was also used. No TFT was attached to a TN device used for measurement.

(1) Phase structure: A sample was placed on a hot plate of a melting point apparatus (Hot Stage Model FP-52 made by Mettler Toledo International Inc.) equipped with a polarizing microscope, and the phase conditions and their changes were observed with the polarizing microscope while the sample was heated at the rate of 3° C. per minute, and the type of phase was specified.

(2) Transition temperature (° C.): A differential scanning calorimeter, a Diamond DSC System made by PerkinElmer Inc. or a X-DSC7000 high sensitivity differential scanning analyzer made by SII NanoTechnology Inc. was used for measurement. A sample was heated and then cooled at the rate of 3° C. per minute, and the starting point of an endothermic peak or an exothermic peak caused by the phase change of the sample was obtained by means of the extrapolation, and thus the transition temperature was determined. The melting point and a starting temperature of polymerization of a compound were also measured by use of this apparatus. The transition temperature of a compound from solid to a liquid crystal phase such as a smectic phase or a nematic phase may be abbreviated to "the minimum temperature of a liquid crystal phase". The transition temperature of a compound from a liquid crystal phase to liquid may be abbreviated to "a clearing point".

The symbol C stood for crystals. When the type of crystals was distinguishable, each was expressed as $C_1$ or $C_2$. The symbols S and N stood for a smectic phase and a nematic phase, respectively. When a smectic A phase, a smectic B phase, a smectic C phase or a smectic F was distinguishable in the smectic phases, it was expressed as $S_A$, $S_B$, $S_C$ or $S_F$, respectively. The symbol I stood for a liquid (isotropic). Transition temperatures were expressed as, for example, "C 50.0 N 100.0 Iso", which means that the transition temperature from crystals to a nematic phase was 50.0° C., and the transition temperature from the nematic phase to a liquid was 100.0° C.

(3) Compatibility at low temperatures: Samples were prepared by mixing a compound with mother liquid crystals so that the ratio of the compound became 20% by weight, 15% by weight, 10% by weight, 5% by weight, 3% by weight and 1% by weight, and placed in glass vials. After these glass vials had been kept in a freezer at −10° C. or -20° C. for a certain period of time, they were observed as to whether or not crystals (or a smectic phase) deposited.

(4) Maximum temperature of a nematic phase ($T_{NI}$ or NI; ° C.): A sample was placed on a hot plate in a melting point apparatus equipped with a polarizing microscope and was heated at the rate of 1° C. per minute. The temperature was measured when part of the sample began to change from a nematic phase to an isotropic liquid. The symbol $T_{NI}$ means that the sample was a mixture of compound (1a) and mother liquid crystals. The symbol NI means that the sample was a mixture of a compound (1a) and a compound such as component B, C and D. A higher limit of the temperature range of a nematic phase may be abbreviated to "the maximum temperature."

(5) Minimum temperature of a nematic phase ($T_c$; ° C.): A sample having a nematic phase was placed in a glass vials and kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., $T_c$ was expressed as <−20° C. A lower limit of the temperature range of a nematic phase may be abbreviated to "the minimum temperature."

(6) Viscosity (bulk viscosity; η; measured at 20° C.; mPa·s): An E-type viscometer made by Tokyo Keiki Inc. was used for measurement.

(7) Viscosity (rotational viscosity; Y1; measured at 25° C.; mPa·s): Measurement was carried out according to the method described in M. Imai, et al., Molecular Crystals and Liquid Crystals, Vol. 259, 37 (1995). A sample was poured into a TN device in which the twist angle was 0 degrees and the distance between the two glass substrates (cell gap) was 5 micrometers. A voltage in the range of 16 to 19.5 volts was applied stepwise to the device with an increment of 0.5 volts. After a period of 0.2 seconds with no voltage, a voltage was applied repeatedly under the conditions of only one rectangular wave (rectangular pulse; 0.2 seconds) and of no voltage (2 seconds). The peak current and the peak time of the transient current generated by the applied voltage were measured. The value of rotational viscosity was obtained from the measured values and the calculating equation (8) on page 40 of the paper presented by M. Imai, et al. The value of dielectric anisotropy necessary for this calculation was obtained by use of the device that had been used for the measurement of rotational viscosity, according to the method that will be described below.

(8) Optical anisotropy (refractive index anisotropy; Δn; measured at 25° C.): Measurement was carried out using an Abbe refractometer with a polarizing plate attached to the ocular, using light at a wavelength of 589 nanometers. The surface of the main prism was rubbed in one direction, and then a sample was placed on the main prism. The refractive index (n∥) was measured when the direction of the polarized light was parallel to that of the rubbing. The refractive index (n⊥) was measured when the direction of polarized light was perpendicular to that of the rubbing. The value of the optical anisotropy (Δn) was calculated from the equation: Δn=n∥−n⊥.

(9) Dielectric anisotropy (Δ∈; measured at 25° C.): A sample was poured into a TN device in which the distance between the two glass substrates (cell gap) was 9 micrometers and the twist angle was 80 degrees. Sine waves (10 V, 1 kHz) were applied to this device, and the dielectric constant (∈∥) in a major axis direction of liquid crystal molecules was measured after 2 seconds. Sine waves (0.5 V, 1 kHz) were applied to the device and the dielectric constant (∈⊥) in a minor axis direction of the liquid crystal molecules was measured after 2 seconds. The value of dielectric anisotropy was calculated from the equation:

$$\Delta\epsilon = \epsilon_\parallel - \epsilon_\perp.$$

(10) Elastic constant (K; measured at 25° C.; pN): A LCR meter Model HP 4284-A made by Yokokawa Hewlett-Packard, Ltd. was used for measurement. A sample was poured into a homogeneous device in which the distance between the two glass substrates (cell gap) was 20 micrometers. An electric charge of 0 volts to 20 volts was applied to the device, and the electrostatic capacity and the applied voltage were measured. The measured values of the electric capacity (C) and the applied voltage (V) were fitted to the equation (2.98) and the equation (2.101) in page 75 of the "Ekisho Debaisu Handobukku" (Liquid Crystal Device Handbook, in English; The Nikkan Kogyo Shimbun, Ltd., Japan) and the values of $K_{11}$ and $K_{33}$ were obtained from the equation (2.99). Next, the value of $K_{22}$ was calculated from the equation (3.18) in page 171 and the values of $K_{11}$ and $K_{33}$ thus obtained. The elastic constant K was expressed as an average value of $K_{11}$, $K_{22}$ and $K_{33}$.

(11) Threshold voltage (Vth; measured at 25° C.; V): An LCD evaluation system Model LCD-5100 made by Otsuka Electronics Co., Ltd. was used for measurement. The light source was a halogen lamp. A sample was poured into a TN device having a normally white mode, in which the distance between the two glass substrates (cell gap) was 4.45/An (micrometers) and the twist angle was 80 degrees. Voltage to be applied to the device (32 Hz, rectangular waves) was stepwise increased in 0.02 V increments from 0 V up to 10 V. The device was vertically irradiated with light simultaneously, and the amount of light passing through the device was measured. A voltage-transmittance curve was prepared, in which the maximum amount of light corresponded to 100% transmittance and the minimum amount of light corresponded to 0% transmittance. The threshold voltage was expressed as voltage at 90% transmittance.

(12) Voltage Holding Ratio (VHR-1; measured at 25° C.; %): A TN device used for measurement had a polyimide-alignment film, and the distance between the two glass substrates (cell gap) was 5 micrometers. A sample was poured into the device, and then the device was sealed with an adhesive curable on irradiation with ultraviolet light. A pulse voltage (60 microseconds at 5 V) was applied to the device and the device was charged. A decreasing voltage was measured for 16.7 milliseconds with a high-speed voltmeter, and area A between a voltage curve and a horizontal axis in a unit cycle was obtained. Area B was an area without the decrease. The voltage holding ratio was a percentage of area A to area B.

(13) Voltage Holding Ratio (VHR-2; measured at 80° C.; %): The voltage holding ratio was measured by the method described above, except that it was measured at 80° C. instead of 25° C. The resulting value was represented by the symbol VHR-2.

(14) Specific Resistance (ρ; measured at 25° C.; Ω cm): A sample of 1.0 milliliter was poured into a vessel equipped with electrodes. A DC voltage (10 V) was applied to the vessel, and the DC current was measured after 10 seconds. The specific resistance was calculated from the following equation: (specific resistance)=[(voltage)×(electric capacity of vessel)]/[(DC current)×(dielectric constant in vacuum)].

(15) Response Time (τ; measured at 25° C.; millisecond): An LCD evaluation system Model LCD-5100 made by Otsuka Electronics Co., Ltd. was used for measurement. The light source was a halogen lamp. The low-pass filter was set at 5 kHz. A sample was poured into a TN device having a normally white mode, in which the distance between the two glass substrates (cell gap) was 5.0 micrometers and the twist angle was 80 degrees. Rectangular waves (60 Hz, 5 V, 0.5 seconds) were applied to this device. The device was vertically irradiated with light simultaneously, and the amount of light passing through the device was measured. The transmittance was regarded as 100% when the amount of light reached a maximum. The transmittance was regarded as 0% when the amount of light reached a minimum. Rise time (τr; millisecond) was the time required for a change from 90% to 10% transmittance. Fall time (τf; millisecond) was the time required for a change from 10% to 90% transmittance. The response time was expressed as the sum of the rise time and the fall time thus obtained.

Materials: Solmix A-11 (registered trademark) was a mixture of ethanol (85.5%), methanol (13.4%) and isopropanol (1.1%), and was available from Japan Alcohol Trading Co., Ltd.

Synthetic Example 1

Preparation of Compound (No. 2)

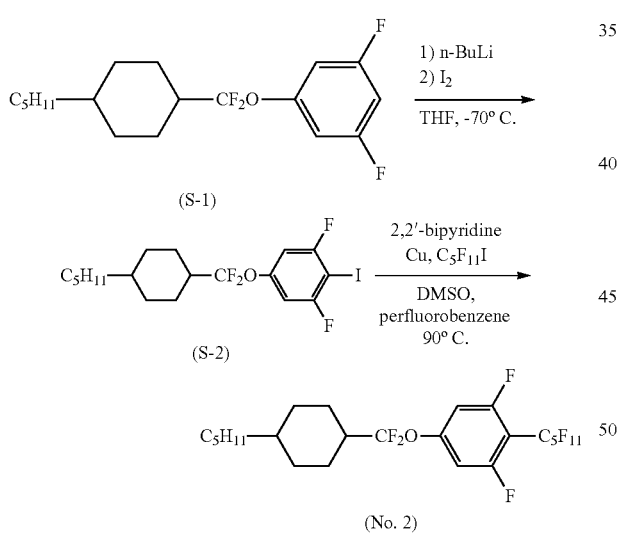

First Step:

Compound (S-1) prepared by known methods (5.44 g) and THF (100 ml) were placed in a reaction vessel under an atmosphere of nitrogen, and the mixture was cooled to −70° C. n-Butyllithium (1.59 M; cyclohexane solution; 10.8 ml) was slowly added dropwise. After 1 hour of stirring, iodine (4.98 g) in THF (10 ml) solution was slowly added dropwise, and the reaction mixture was warmed to room temperature. The reaction mixture was poured into water, and the aqueous layer was extracted with ethyl acetate. The combined organic layers were washed with water and brine, and then dried over anhydrous magnesium sulfate. The solution was concentrated under reduced pressure, and the residue was purified by silica gel chromatography (heptane). Further purification by recrystallization from solmix gave compound (S-2) (5.35 g; 71%).

Second Step:

Compound (S-2) (5.35 g), 2,2'-bipyridine (0.13 g), copper powder (1.63 g), $C_5F_{11}I$ (18.5 g), dimethylsulfoxide (25 ml) and perfluorobenzene (50 ml) were placed in a reaction vessel under an atmosphere of nitrogen, and the mixture was heated to 90° C. and stirred for 16 hours. The reaction mixture was poured into water, to which toluene was added. After filtration through Celite, the aqueous layer was extracted with toluene. The combined organic layers were washed with water and brine, and then dried over anhydrous magnesium sulfate. The solution was concentrated under reduced pressure, and the residue was purified by silica gel chromatography (heptane). Further purification by recrystallization from solmix gave compound (No. 2) (0.68 g; 10%).

$^1$H-NMR (ppm; $CDCl_3$): δ6.90-6.86 (m, 2H), 2.08-1.96 (m, 3H), 1.87 (d, J=12.6, 2H), 1.40-1.17 (m, 11H), 0.98-0.87 (m, 5H).

Transition temperature: C 23.0 I.

Maximum temperature ($T_{NI}$)=−7.4° C.; optical anisotropy (Δn)=0.053; dielectric anisotropy (Δ∈)=9.60; viscosity (η)=38.6 mPa·s.

Synthetic Example 2

Preparation of Compound (No. 201)

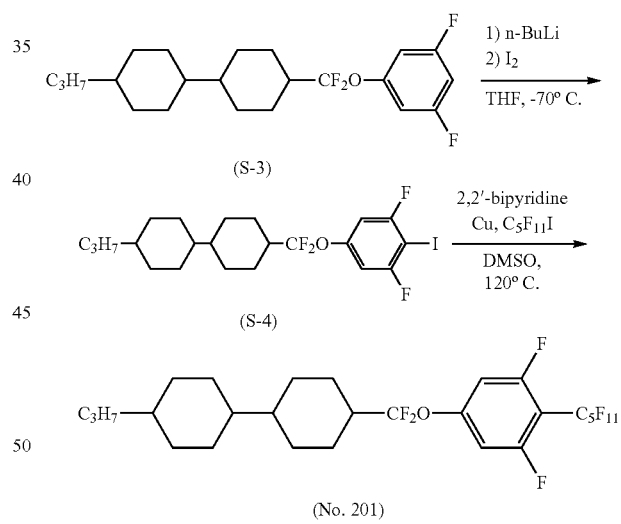

First Step:

Compound (S-3) (15.1 g) prepared by known methods and THF (450 ml) were placed in a reaction vessel under an atmosphere of nitrogen, and the mixture was cooled to −70° C. n-Butyllithium (1.59 M; cyclohexane solution; 25.7 ml) was slowly added dropwise. After 1 hour of stirring, iodine (11.9 g) in THF (50 ml) solution was slowly added dropwise, and the reaction mixture was warmed to room temperature. The reaction mixture was poured into water, and the aqueous layer was extracted with ethyl acetate. The combined organic layers were washed with water and brine, and then dried over anhydrous magnesium sulfate. The solution was concentrated under reduced pressure, and the residue was purified by silica gel chromatography (heptane). Further purification by recrystallization from heptane gave compound (S-4) (15.4 g; 77%).

Second Step:

Compound (S-4) (15.4 g), 2,2'-bipyridine (0.33 g), copper powder (4.21 g), $C_5F_{11}I$ (23.8 g) and dimethyl sulfoxide (250 ml) were placed in a reaction vessel under an atmosphere of nitrogen, and the mixture was heated to 120° C. and stirred for 11 hours. The reaction mixture was poured into water, and toluene was added. After filtration through Celite, the aqueous layer was extracted with toluene. The combined organic layers were washed with water and brine, and then dried over anhydrous magnesium sulfate. The solution was concentrated under reduced pressure, and the residue was purified by silica gel chromatography (heptane). Further purification by recrystallization from 2-propanol gave compound (No. 201) (1.18 g; 6%).

$^1$H-NMR (ppm; $CDCl_3$): δ6.89-6.85 (m, 2H), 2.05-1.96 (m, 3H), 1.89-1.82 (m, 2H), 1.79-1.67 (m, 4H), 1.38-1.25 (m, 4H), 1.20-0.79 (m, 14H).

Transition temperature: C 68.5 N 121.8 I.

Maximum temperature ($T_{NI}$)=104.1° C.; optical anisotropy (Δn)=0.078; dielectric anisotropy (Δ∈)=11.2; viscosity (η)=58.2 mPa·s.

Synthetic Example 3

Preparation of (No. 274)

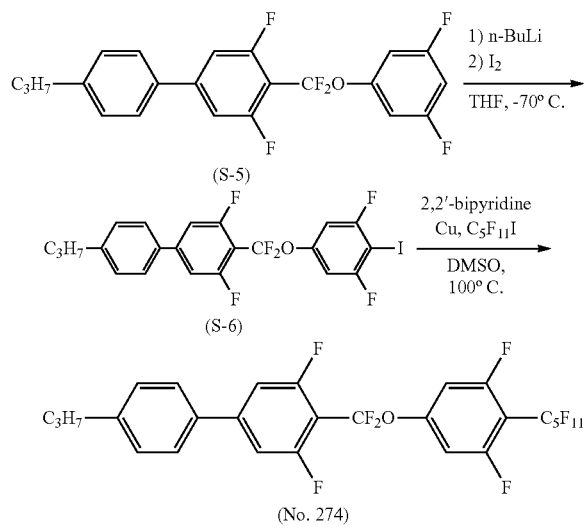

First Step:

Compound (S-5) (15.5 g) prepared by known methods and THF (250 ml) were placed in a reaction vessel under an atmosphere of nitrogen, and the mixture was cooled to −70° C. n-Butyllithium (1.59 M; cyclohexane solution; 24.9 ml) was slowly added dropwise. After 1 hour of stirring, iodine (11.5 g) in THF (50 ml) solution was slowly added dropwise, and the reaction mixture was warmed to room temperature. The reaction mixture was poured into water, and the aqueous layer was extracted with ethyl acetate. The combined organic layers were washed with water and brine, and then dried over anhydrous magnesium sulfate. The solution was concentrated under reduced pressure, and the residue was purified by silica gel chromatography (heptane:ethyl acetate=10:1 by volume). Further purification by recrystallization from a mixed solvent of 2-propanol and ethyl acetate (1:1 by volume) gave compound (S-6) (16.4 g; 81%).

Second Step:

Compound (S-6) (3.57 g), 2,2'-bipyridine (0.07 g), copper powder (0.93 g), $C_5F_{11}I$ (6.60 g) and dimethylsulfoxide (50 ml) were placed in a reaction vessel under an atmosphere of nitrogen, and the mixture was heated to 100° C. and stirred for 16 hours. The reaction mixture was poured into water, and toluene was added. After filtration through Celite, the aqueous layer was extracted with toluene. The combined organic layers were washed with water and brine, and then dried over anhydrous magnesium sulfate. The solution was concentrated under reduced pressure, and the residue was purified by silica gel chromatography (heptane). Further purification by recrystallization from 2-propanol gave compound (No. 274) (0.89 g; 20%).

$^1$H-NMR (ppm; $CDCl_3$): δ7.51-7.47 (m, 2H), 7.30 (d, J=8.10, 2H), 7.23 (d, J=10.6, 2H), 7.03-6.98 (m, 2H), 2.65 (t, J=7.50, 2H), 1.71-1.65 (m, 2H), 0.97 (t, J=7.40, 3H).

Transition temperature: C 38.7 ($S_A$ 38.0) I.

Maximum temperature ($T_{NI}$)=22.6° C.; optical anisotropy (Δn)=0.118; dielectric anisotropy (Δ∈)=22.1; viscosity (η)=51.5 mPa·s.

Synthetic Example 4

Preparation of Compound (No. 275)

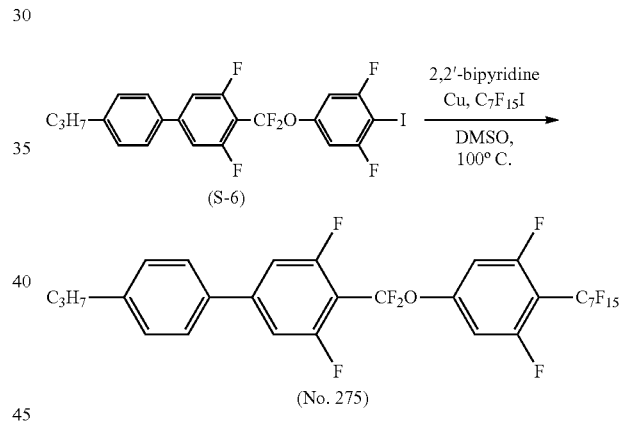

First Step:

compound (S-6) (8.27 g), 2,2'-bipyridine (0.17 g), copper powder (2.16 g), $C_7F_{15}I$ (15.3 g) and dimethylsulfoxide (160 ml) were placed in a reaction vessel under an atmosphere of nitrogen, and the mixture was heated to 100° C. and stirred for 16 hours. The reaction mixture was poured into water, and toluene was added. After filtration through Celite, the aqueous layer was extracted with toluene. The combined organic layers were washed with water and brine, and then dried over anhydrous magnesium sulfate. The solution was concentrated under reduced pressure, and the residue was purified by silica gel chromatography (heptane). Further purification by recrystallization from 2-propanol gave compound (No. 275) (1.66 g; 14%).

$^1$H-NMR (ppm; $CDCl_3$): δ7.49 (d, J=8.15, 2H), 7.30 (d, J=8.15, 2H), 7.23 (d, J=10.7, 2H), 7.00 (d, J=10.4, 2H), 2.65 (t, J=7.50, 2H), 1.72-1.64 (m, 2H), 0.97 (t, J=7.35, 3H).

Transition temperature: C 51.6 $S_A$ 70.9 I.

Maximum temperature ($T_{NI}$)=46.8° C.; optical anisotropy (Δn)=0.120; dielectric anisotropy (Δ∈)=19.8; viscosity (η)=50.3 mPa·s.

Incidentally, a sample in which the ratio of the compound to the mother liquid crystals was 15% by weight: 85% by weight was used for measurement of the maximum temperature, the optical anisotropy, dielectric anisotropy and the viscosity.

Synthetic Example 5

Preparation of Compound (No. 458)

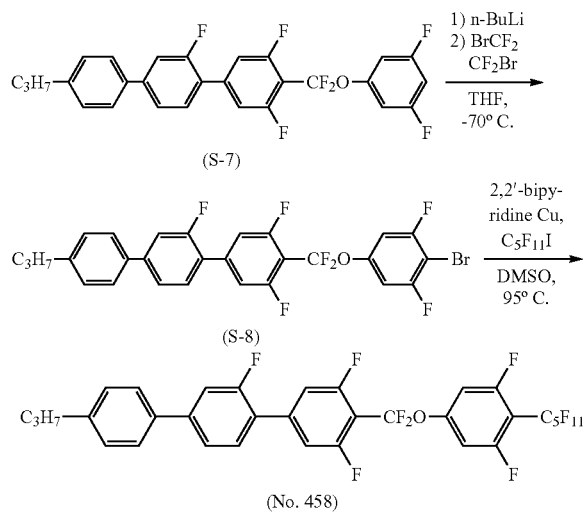

First Step:

Compound (S-7) (5.04 g) prepared by known methods and THF (100 ml) were placed in a reaction vessel under an atmosphere of nitrogen, and the mixture was cooled to −70° C. n-Butyllithium (1.59 M; cyclohexane solution; 6.60 ml) was slowly added dropwise. After 1 hour of stirring, 1,2-dibromo-1,1,2,2-tetrafluoroethane (3.12 g) was slowly added dropwise, and the reaction mixture was warmed to room temperature. The reaction mixture was poured into water, and the aqueous layer was extracted with ethyl acetate. The combined organic layers were washed with water and brine, and then dried over anhydrous magnesium sulfate. The solution was concentrated under reduced pressure, and the residue was purified by silica gel chromatography (heptane:ethyl acetate=10:1 by volume). Further purification by recrystallization from a mixed solvent of 2-propanol and ethyl acetate (1:1 by volume) gave compound (S-8) (4.79 g; 82%).

Second Step:

Compound (S-8) (4.29 g), 2,2'-bipyridine (0.08 g), copper powder (1.03 g), $C_5F_{11}I$ (5.82 g) and dimethylsulfoxide (85 ml) were placed in a reaction vessel under an atmosphere of nitrogen, and the mixture was heated to 95° C. and stirred for 15 hours. The reaction mixture was poured into water, and toluene was added. After filtration through Celite, the aqueous layer was extracted with toluene. The combined organic layers were washed with water and brine, and then dried over anhydrous magnesium sulfate. The solution was concentrated under reduced pressure, and the residue was purified by silica gel chromatography (heptane:ethyl acetate=9:1 by volume). Further purification by recrystallization from a mixed solvent of 2-propanol and toluene (1:1 by volume) gave compound (No. 458) (0.97 g; 17%).

$^1$H-NMR (ppm; $CDCl_3$): δ7.54 (d, J=8.10, 2H), 7.52-7.48 (m, 2H), 7.43 (d, J=12.2, 1H), 7.33-7.25 (m, 4H), 7.02 (d, J=10.3, 2H), 2.65 (t, J=7.45, 2H), 1.74-1.64 (m, 2H), 0.98 (t, J=7.35, 3H).

Transition temperature: C 82.5 $S_A$ 153.2 I.

Maximum temperature ($T_{NI}$)=118° C.; optical anisotropy (Δn)=0.173; dielectric anisotropy (Δ∈)=27.1; viscosity (η)=58.1 mPa·s.

Incidentally, a sample in which the ratio of the compound to the mother liquid crystals was 5% by weight: 95% by weight was used for measurement of the maximum temperature, the optical anisotropy, dielectric anisotropy and the viscosity.

Synthetic Example 6

Preparation of Compound (No. 457)

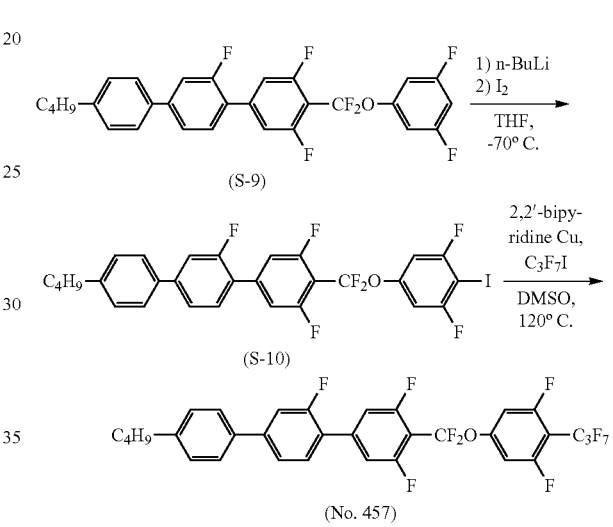

First Step:

Compound (S-9) (10.8 g) prepared by known methods and THF (170 ml) were placed in a reaction vessel under an atmosphere of nitrogen, and the mixture was cooled to −70° C. n-Butyllithium (1.65 M; cyclohexane solution; 13.2 ml) was slowly added dropwise. After 1 hour of stirring, iodine (6.34 g) in THF (30 ml) solution was slowly added dropwise, and the reaction mixture was warmed to room temperature. The reaction mixture was poured into water, and the aqueous layer was extracted with ethyl acetate. The combined organic layers were washed with water and brine, and then dried over anhydrous magnesium sulfate. The solution was concentrated under reduced pressure, and the residue was purified by silica gel chromatography (heptane:ethyl acetate=10:1 by volume). Further purification by recrystallization from mixed solvent of 2-propanol and ethyl acetate (1:1 by volume) gave compound (S-10) (11.2 g; 84%).

Second Step:

Compound (S-10) (5.50 g), 2,2'-bipyridine (0.09 g), copper powder (1.19 g), $C_3F_7I$ (5.05 g) and dimethylsulfoxide (110 ml) were placed in a reaction vessel under an atmosphere of nitrogen, and the mixture was heated to 120° C. and stirred to 16 hours. The reaction mixture was poured into water, and toluene was added. After filtration through Celite, the aqueous layer was extracted with toluene. The combined organic layers were washed with water and brine, and then dried over anhydrous magnesium sulfate. The solution was concentrated under reduced pressure, and the residue was purified by silica gel chromatography (heptane:ethyl acetate=20:1 by volume) Further purification by recrystallization from 2-propanol gave compound (No. 457) (1.04 g; 18%).

$^1$H-NMR (ppm; CDCl$_3$): δ7.54 (d, J=8.10, 2H), 7.51-7.48 (m, 2H), 7.43 (d, J=12.4, 1H), 7.33-7.25 (m, 4H), 7.02 (d, J=10.4, 2H), 2.68 (t, J=7.70, 2H), 1.68-1.60 (m, 2H), 1.44-1.35 (m, 2H), 0.95 (t, J=7.20, 3H).

Transition temperature: C 72.2 S$_A$ 118 N 123 I.

Maximum temperature (T$_{NI}$)=93.6° C.; optical anisotropy (Δn)=0.183; dielectric anisotropy (Δ∈)=33.6; viscosity (η)=80.6 mPa·s.

Synthetic Example 7

Preparation of Compound (No. 459)

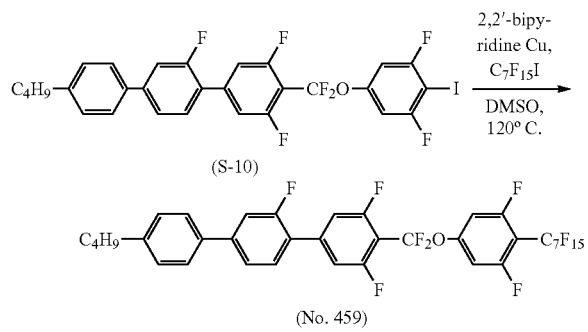

First Step:

Compound (S-10) (5.50 g), 2,2'-bipyridine (0.09 g), copper powder (1.19 g), C$_7$F$_{15}$I (8.47 g) and dimethylsulfoxide (110 ml) were placed in a reaction vessel under an atmosphere of nitrogen, and the mixture was heated to 120° C. and stirred for 16 hours. The reaction mixture was poured into water, and toluene was added. After filtration through Celite, the aqueous layer was extracted with toluene. The combined organic layers were washed with water and brine, and then dried over anhydrous magnesium sulfate. The solution was concentrated under reduced pressure, and the residue was purified by silica gel chromatography (heptane:toluene=15:1 by volume). Further purification by recrystallization from a mixed solvent of 2-propanol and heptane (1:1 by volume) gave compound (No. 459) (1.91 g; 25%).

$^1$H-NMR (ppm; CDCl$_3$): δ7.54 (d, J=8.10, 2H), 7.51-7.48 (m, 2H), 7.43 (d, J=12.5, 1H), 7.32-7.26 (m, 4H), 7.02 (d, J=10.3, 2H), 2.68 (t, J=7.75, 2H), 1.68-1.60 (m, 2H), 1.45-1.37 (m, 2H), 0.96 (t, J=7.45, 3H).

Transition temperature: C 74.7 S$_A$ 169 I.

Maximum temperature (T$_{NI}$)=124° C.; optical anisotropy (Δn)=0.153; dielectric anisotropy (Δ∈)=25.1; viscosity (η)=66.1 mPa·s.

Incidentally, a sample in which the ratio of the compound to the mother liquid crystals was 5% by weight: 95% by weight was used for measurement of the maximum temperature, the optical anisotropy, dielectric anisotropy and the viscosity.

Comparative Example 1

The following compound (C-1) was selected for comparison. This is because this compound is different from the compound of the invention in view of the right-terminal group being fluorine. The compound was prepared according to the description in WO 96/011897 A.

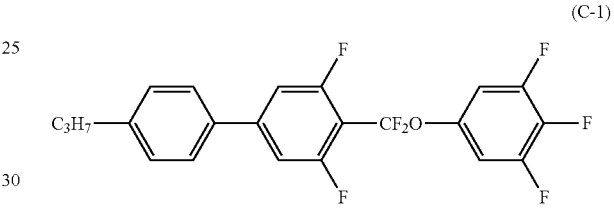

$^1$H-NMR (ppm; CDCl$_3$): δ7.49 (d, J=8.00 Hz, 2H), 7.29 (d, J=8.00 Hz, 2H), 7.21 (d, J=10.5 Hz, 2H), 7.03-6.94 (m, 2H), 2.65 (t, J=7.50 Hz, 2H), 1.75-1.64 (m, 2H), 0.97 (t, J=7.50 Hz, 3H).

Transition temperature: C 46.1 I.

Maximum temperature (T$_{NI}$)=−17.9° C.; optical anisotropy (Δn)=0.115; dielectric anisotropy (Δ∈)=25.7.

The maximum temperatures (T$_{NI}$) of compound (No. 274), compound (No. 275) and comparative compound (C-1) are summarized in Table 1 below. As is clear from Table 1, the compound of the invention is superior to the comparative compound in view of the fact that the maximum temperature is high.

TABLE 1

| | Comparison of the Maximum Temperature | |
|---|---|---|
| Examples | Compounds | Maximum Temperature (T$_{NI}$)[1)] |
| Synthetic Example 3 | (No. 274) C$_3$H$_7$—⌬—⌬—CF$_2$O—⌬—C$_5$F$_{11}$ | 22.6° C. |
| Synthetic Example 4 | (No. 275) C$_3$H$_7$—⌬—⌬—CF$_2$O—⌬—C$_3$F$_{15}$ | 46.8° C. |

TABLE 1-continued

Comparison of the Maximum Temperature

| Examples | Compounds | Maximum Temperature ($T_{NI}$)[1] |
|---|---|---|
| Comparative Example 1 | 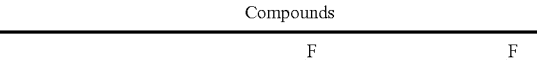 (C-1) | −17.9° C. |

[1] The maximum temperature ($T_{NI}$) of a nematic phase was measured using a mixture of the compound and the mother liquid crystals as a sample and calculated by extrapolating from the measured value.

The following compounds (No. 1) to (No. 108), compounds (No. 200) to (No. 349), compounds (No. 400) to (No. 565) and compounds (No. 600) to (No. 675) are prepared according to the synthetic methods of compound (1a) described above and the synthetic procedures described in Synthetic Examples 1 to 7.

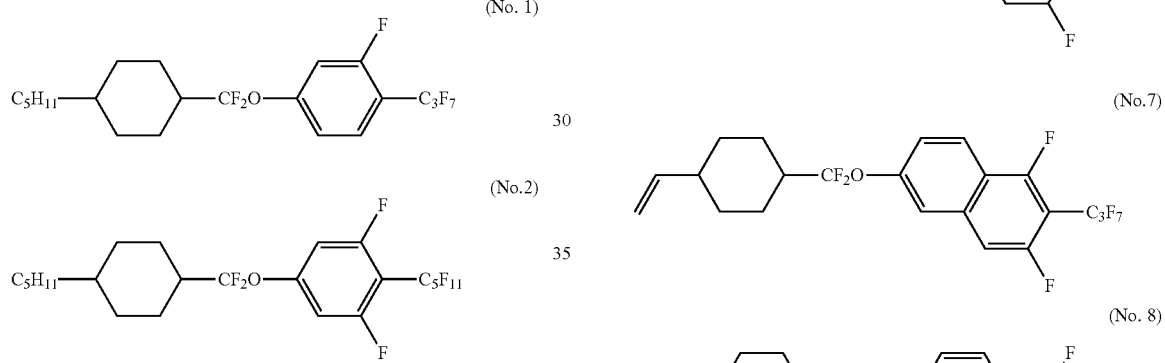

C 23.01
$T_{NI} = 7.4°$ C., $\Delta\varepsilon = 9.6$, $\Delta n = 0.053$

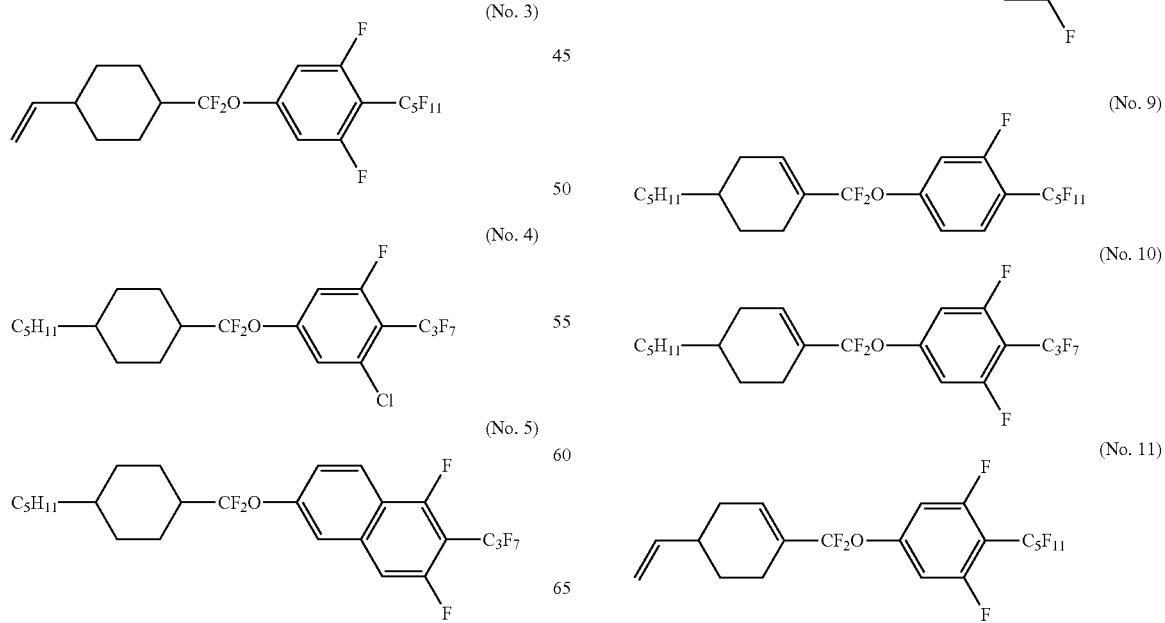

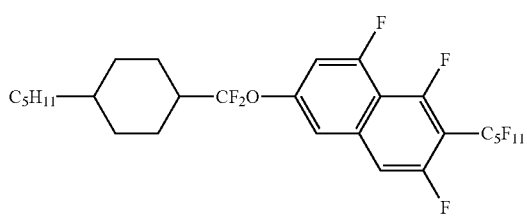

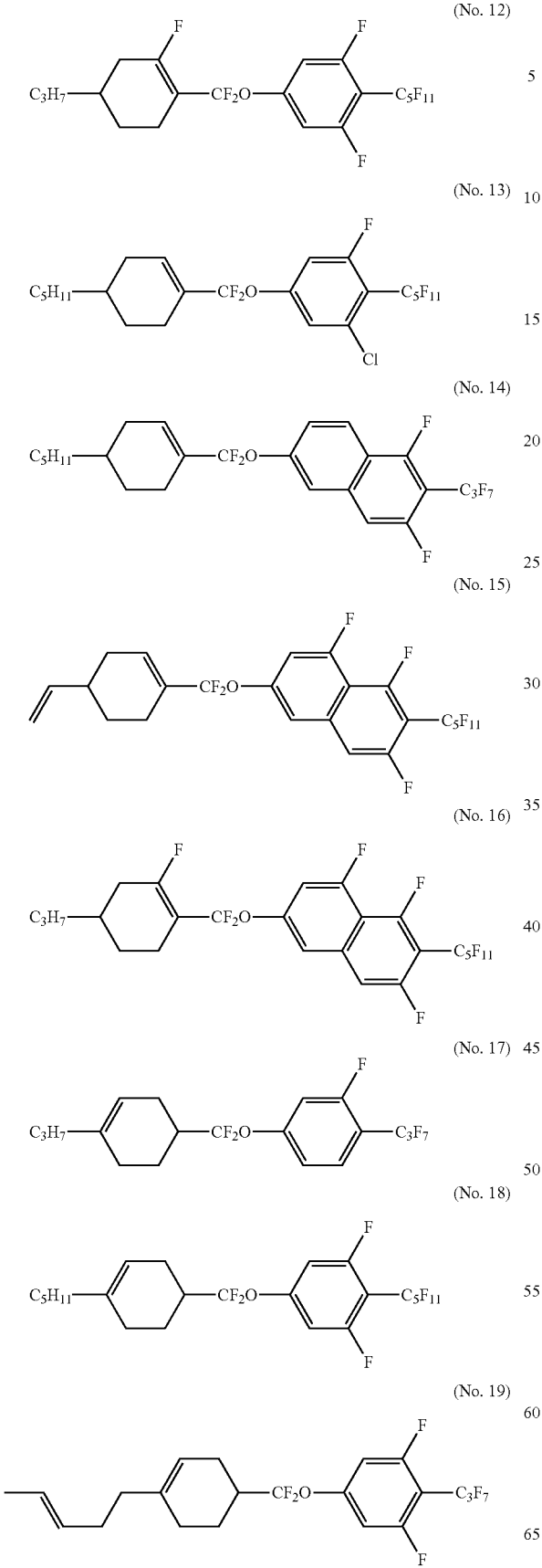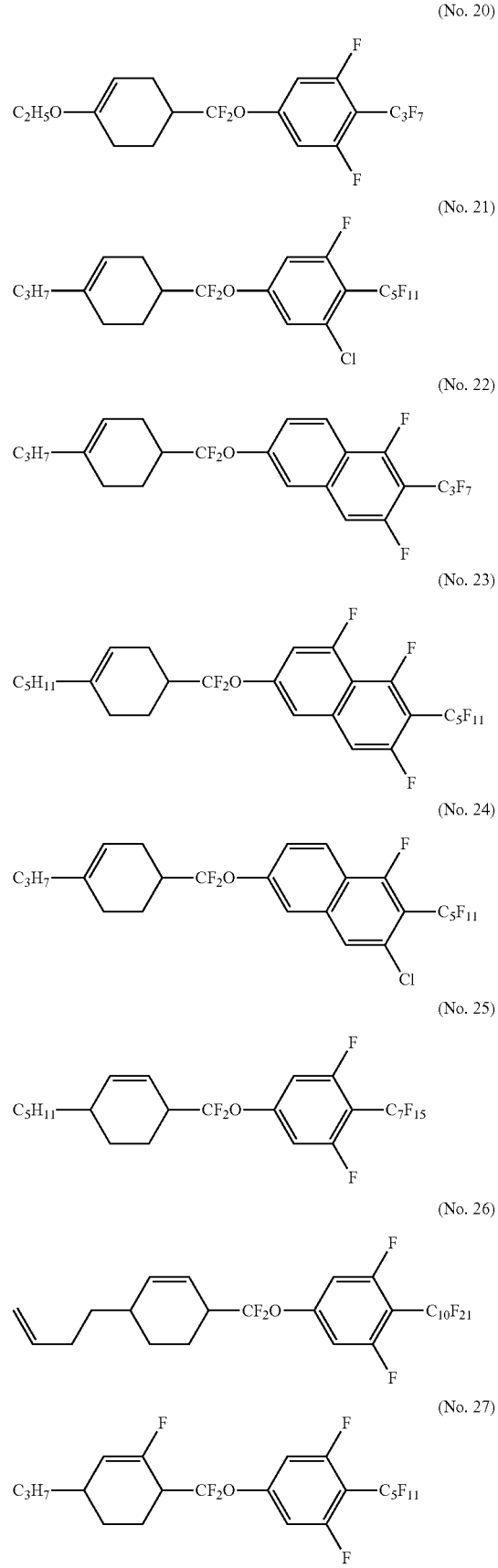

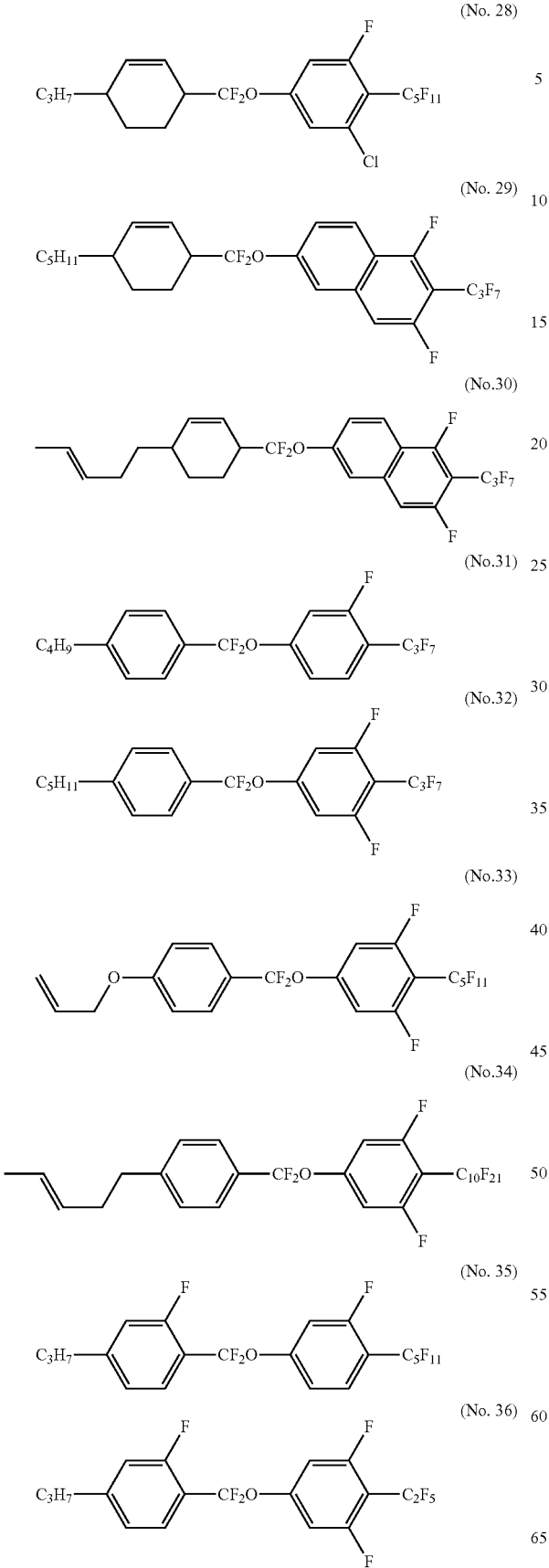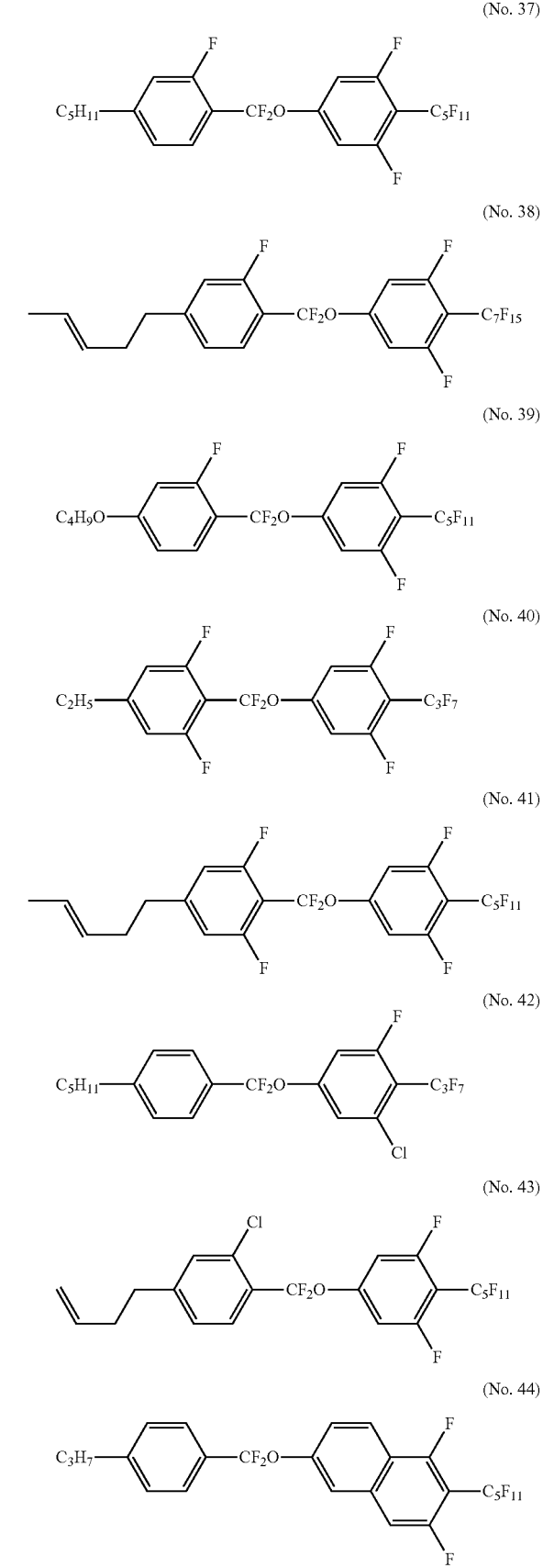

(No. 45)
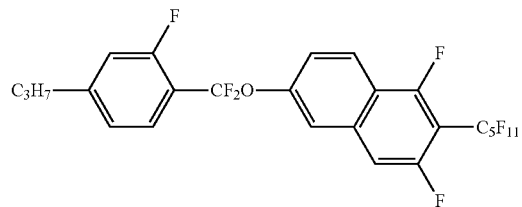
(No. 46)
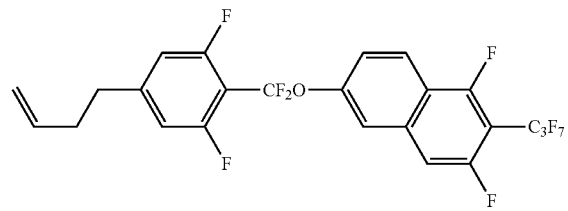
(No. 47)
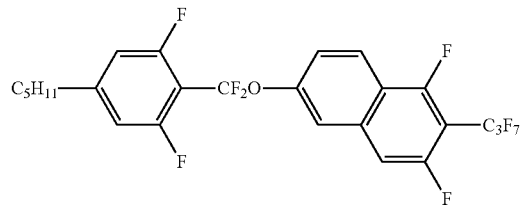
(No. 48)
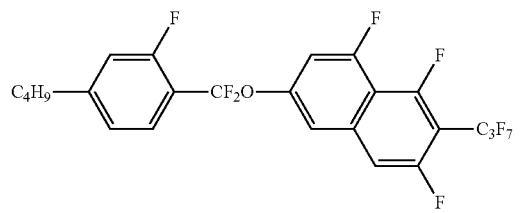
(No. 49)
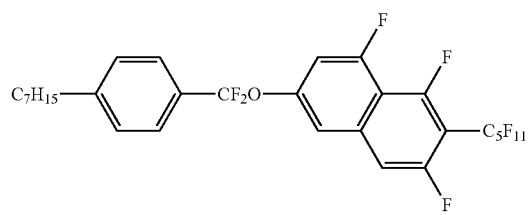
(No. 50)
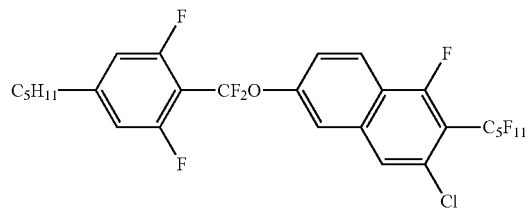
(No. 51)
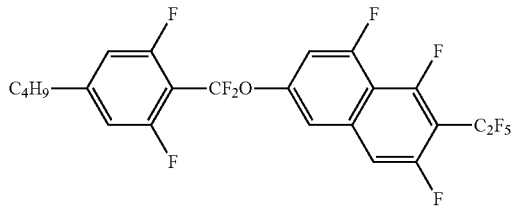
(No. 52)
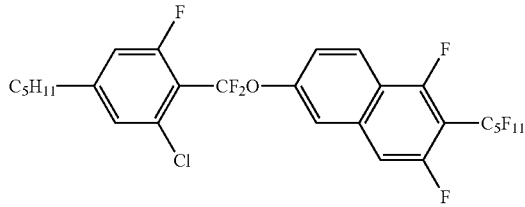
(No. 53)
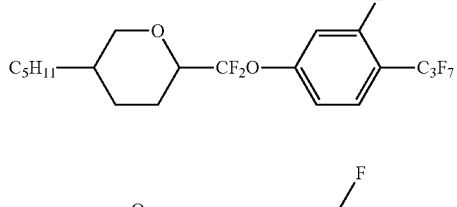
(No. 54)
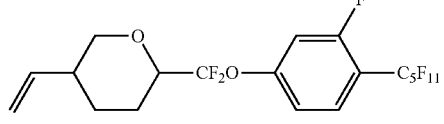
(No. 55)
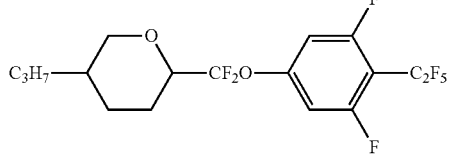
(No. 56)
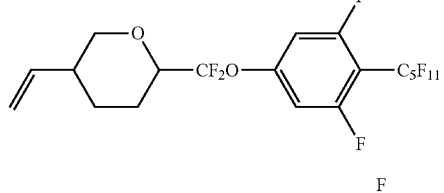
(No. 57)
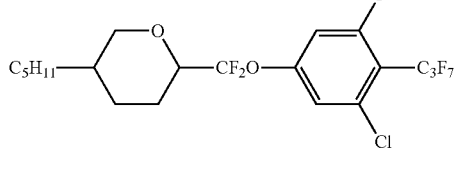
(No. 58)
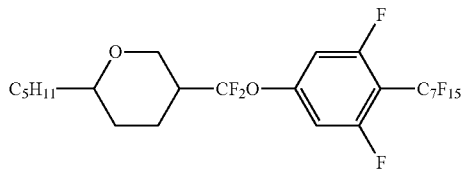

(No.59)
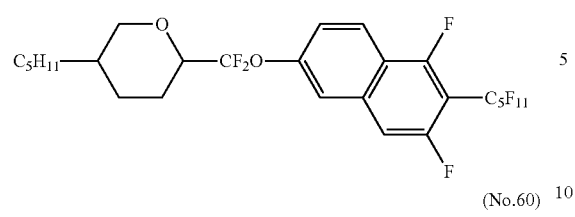
(No.60)
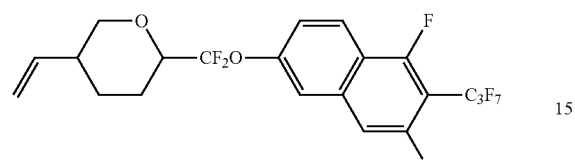
(No.61)
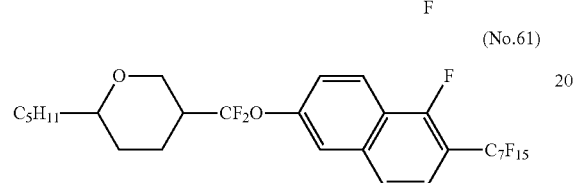
(No.62)
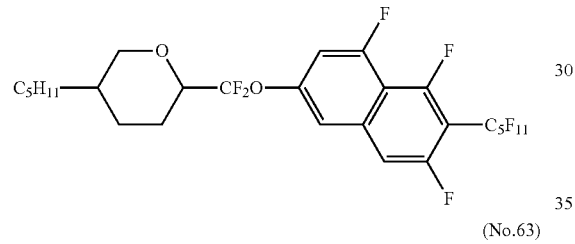
(No.63)
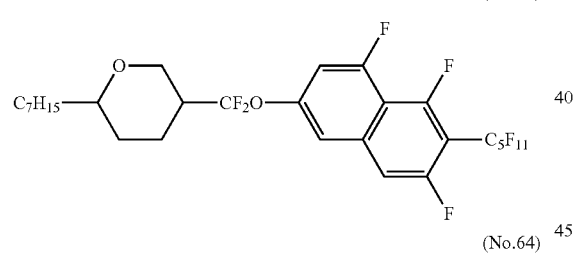
(No.64)
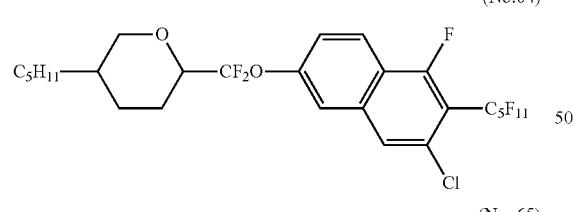
(No.65)
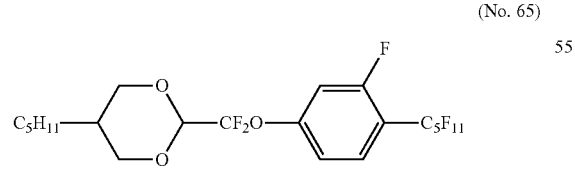
(No.66)
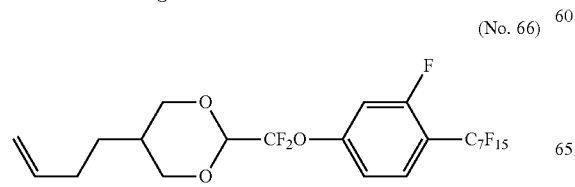
(No. 67)
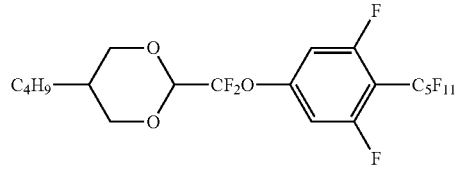
(No. 68)
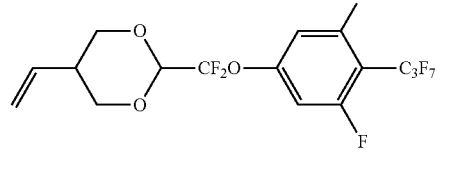
(No. 69)
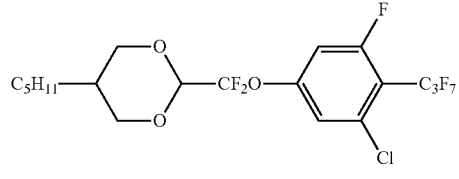
(No.70)
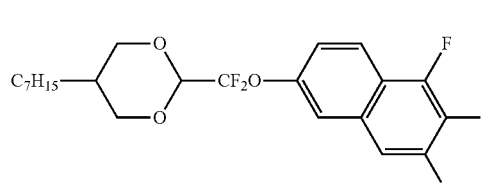
(No.71)
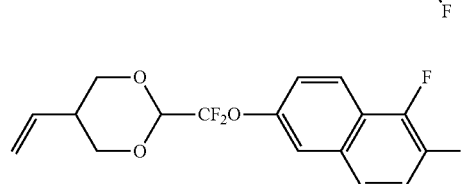
(No. 72)
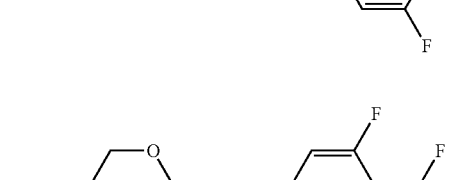
(No. 73)
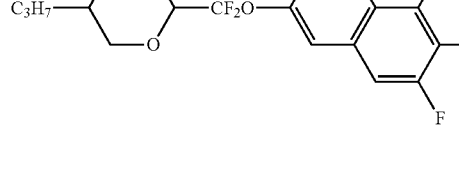
(No. 74)
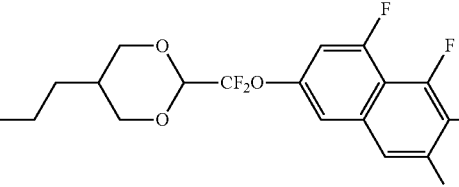

-continued
(No. 75)
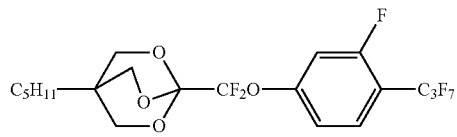
(No. 76)
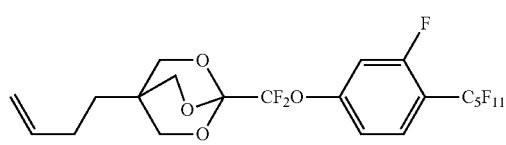
(No. 77)
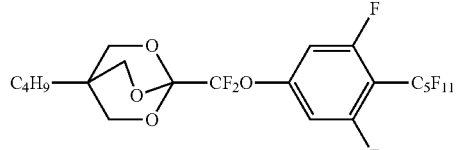
(No. 78)
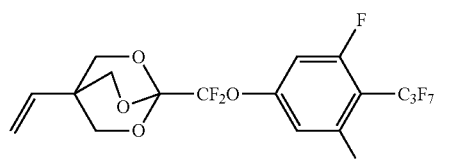
(No. 79)
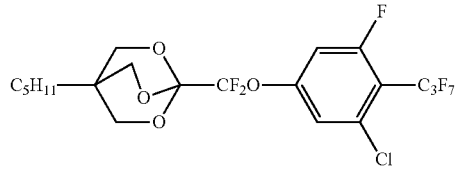
(No. 80)
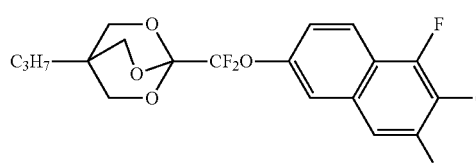
(No. 81)
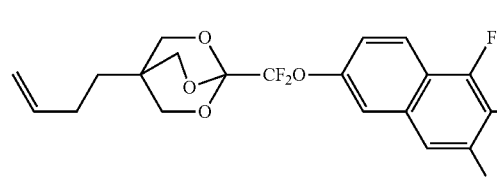
(No. 82)
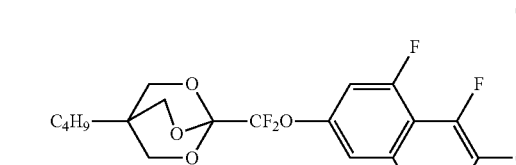
(No. 83)
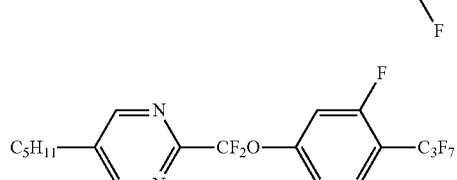
-continued
(No. 84)
(No. 85)
(No. 86)
(No. 87)
(No. 88)
(No. 89)
(No. 90)
(No. 91)

(chemical structure diagrams Nos. 92–106)

-continued
(No. 107)
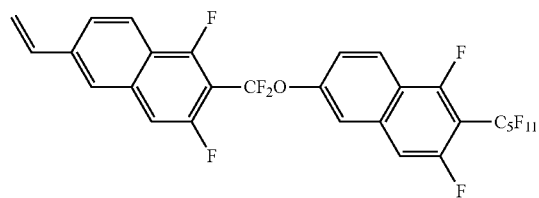
(No. 108)
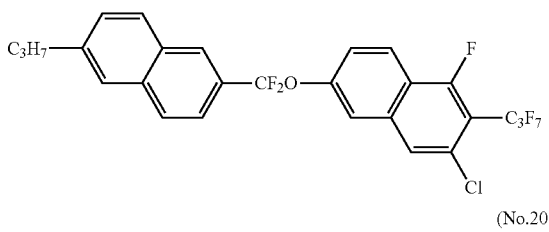
(No. 200)
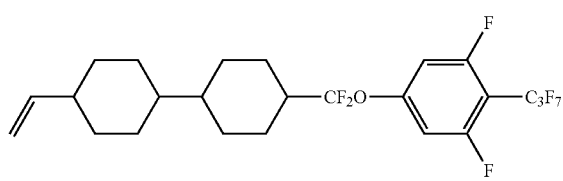
C 68.5N 1221
$T_{NI} = 104.1°$ C., $\Delta\varepsilon = 11.2$, $\Delta n = 0.078$
(No. 201)
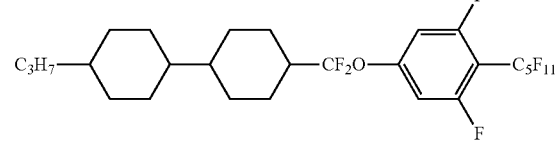
(No. 202)
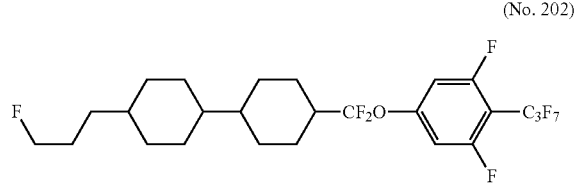
(No. 203)
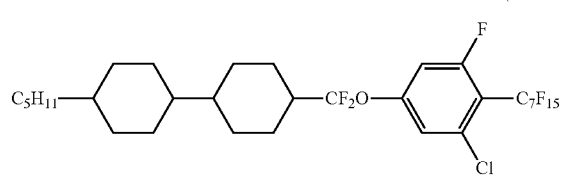
(No. 204)
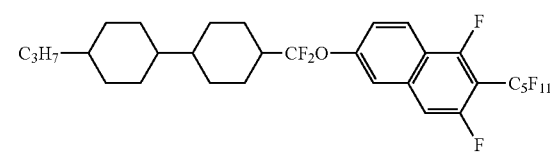
-continued
(No. 205)
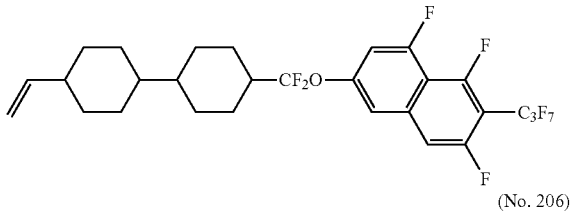
(No. 206)
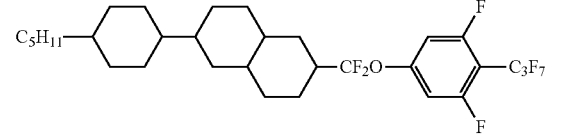
(No. 207)
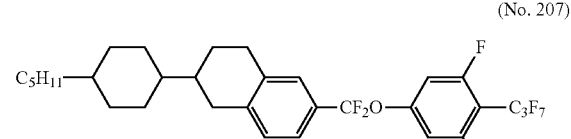
(No. 208)
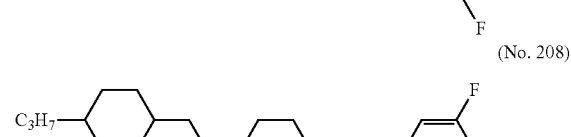
(No. 209)
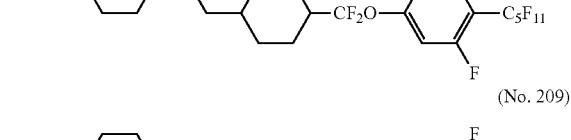
(No. 210)
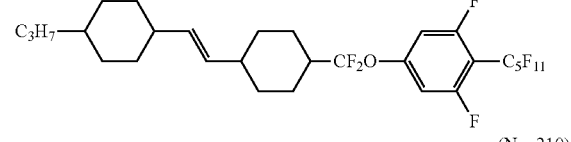
(No. 211)
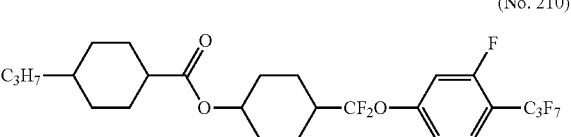
(No. 212)
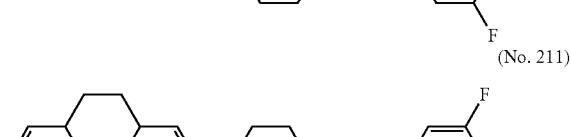
(No. 213)
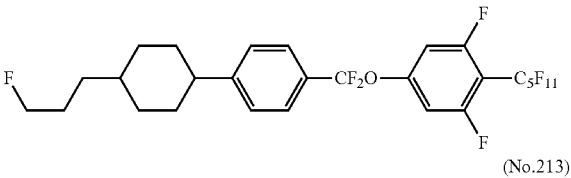

(No.214)
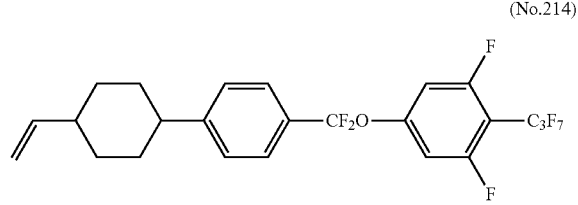
(No.215)
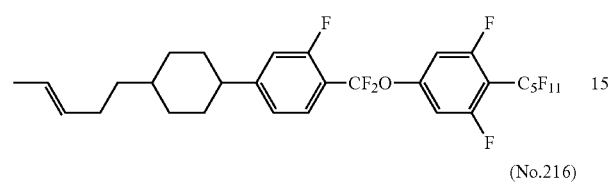
(No.216)
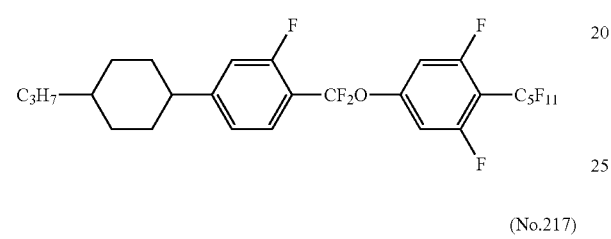
(No.217)
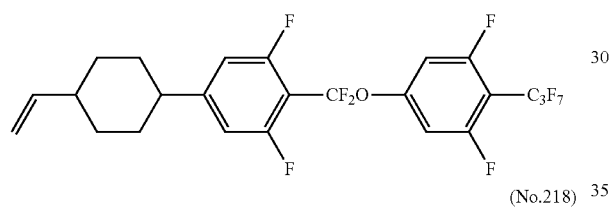
(No.218)
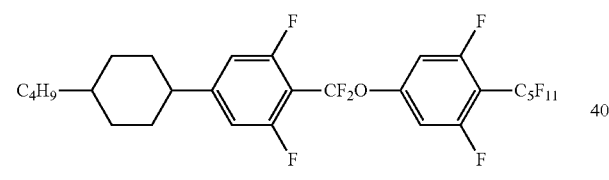
(No.219)
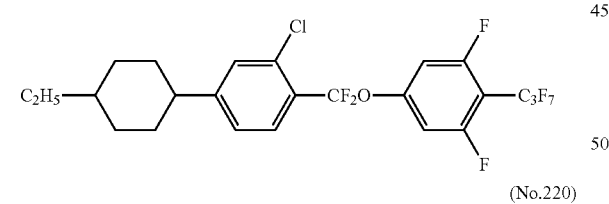
(No.220)
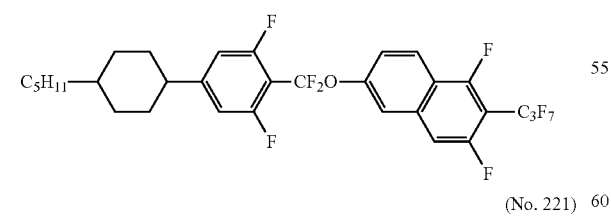
(No.221)
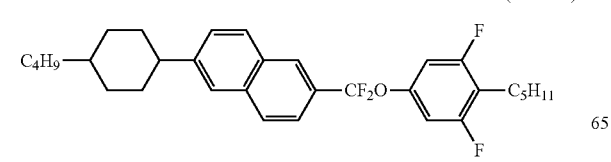
(No. 222)
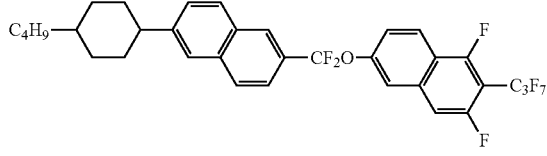
(No. 223)
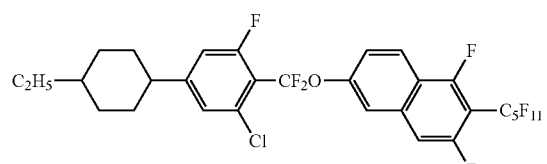
(No. 224)
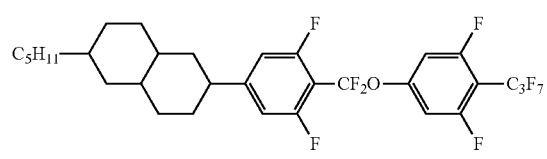
(No. 225)
(No. 226)
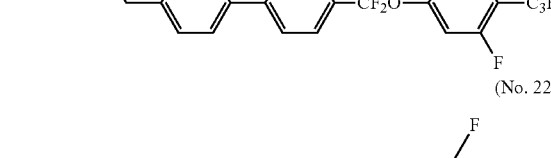
(No. 227)
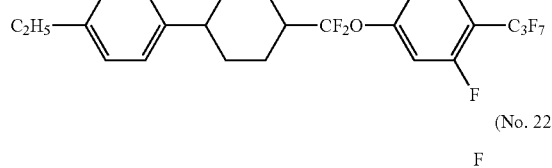
(No. 228)
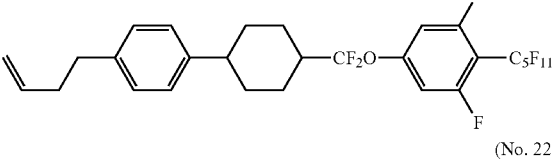
(No. 229)
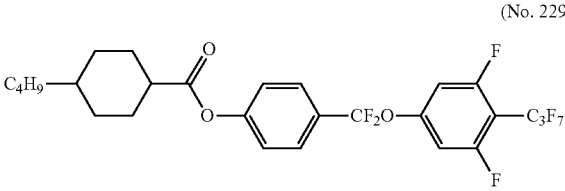

(No. 230)
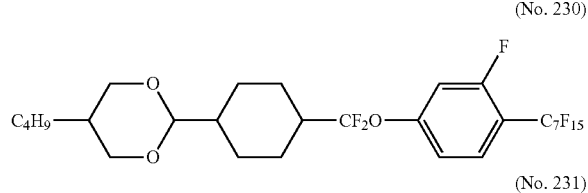
(No. 231)
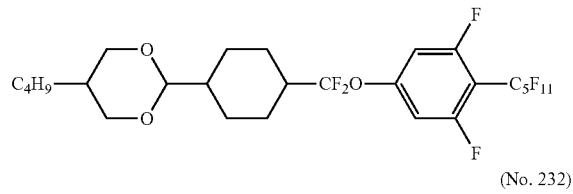
(No. 232)
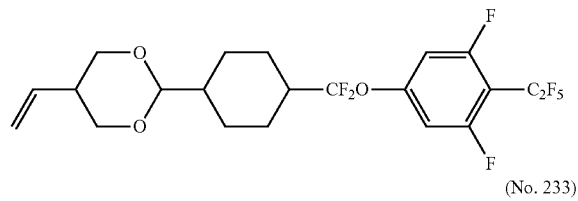
(No. 233)
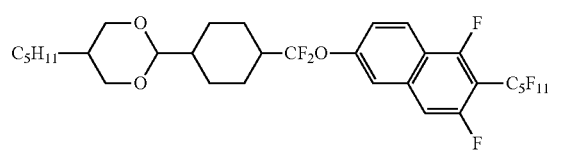
(No. 238)
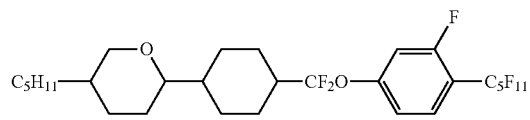
(No. 240)
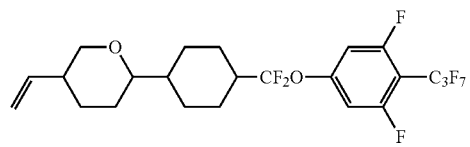
(No. 242)
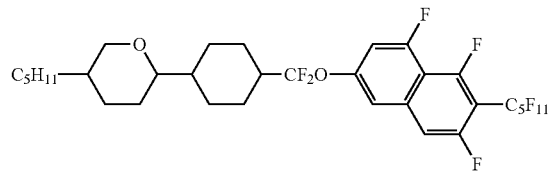
(No. 244)
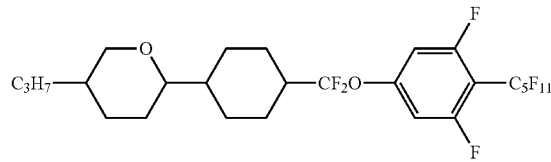
(No. 234)
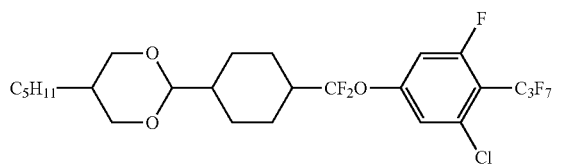
(No. 235)
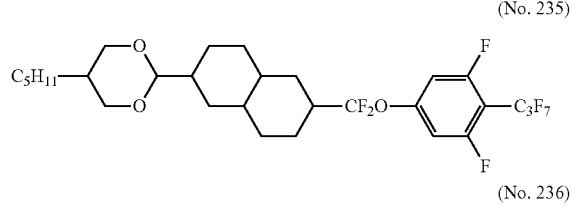
(No. 236)
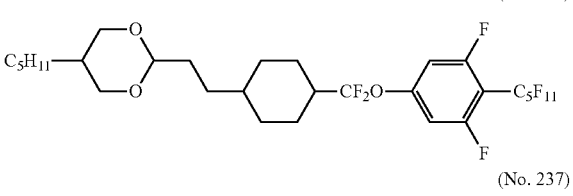
(No. 237)
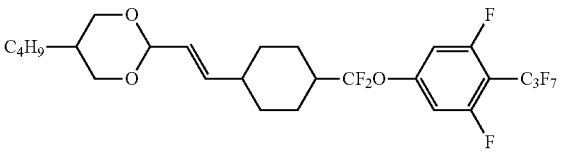
(No. 239)
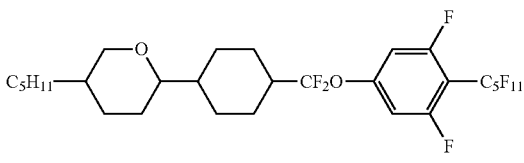
(No. 241)
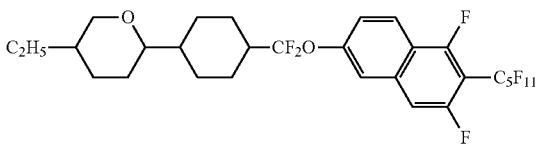
(No. 243)
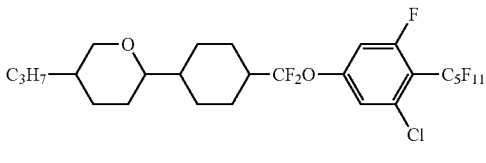
(No. 245)
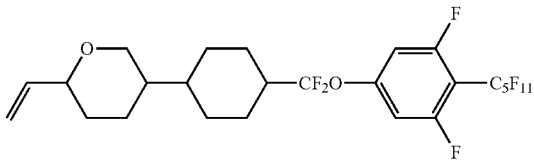

-continued
(No.246)
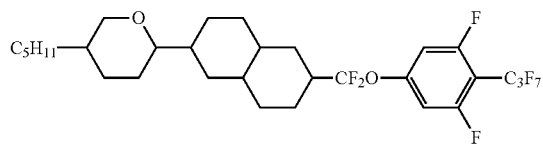
(No.247)
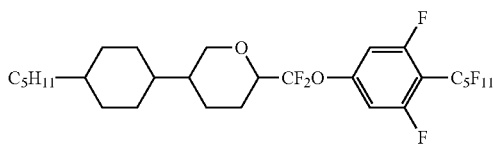
(No.248)
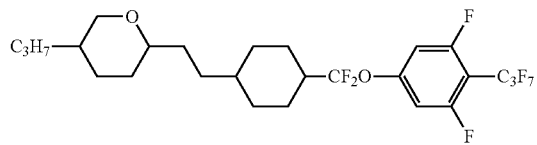
(No.249)
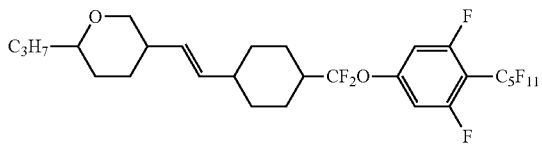
(Nlo. 250)
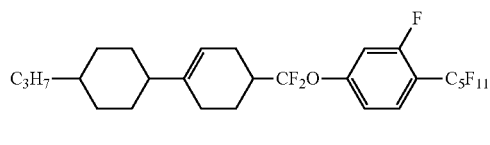
(Nlo. 251)
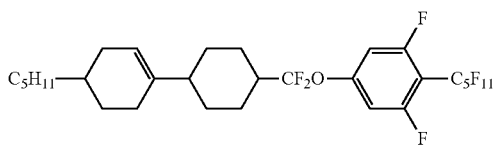
(Nlo. 252)
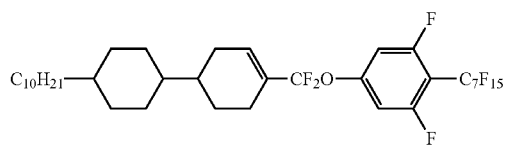
(Nlo. 253)
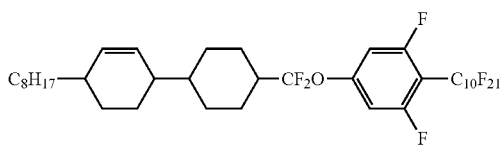
(Nlo. 254)
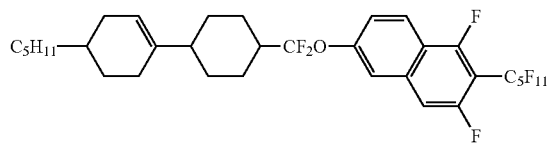
(Nlo. 255)
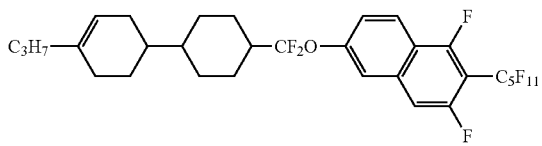
(Nlo. 256)
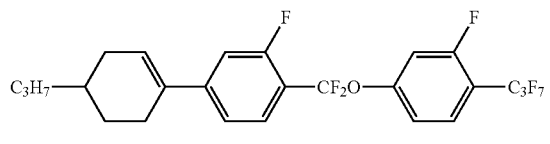
(Nlo. 257)
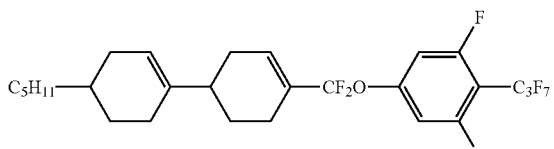
(Nlo. 258)
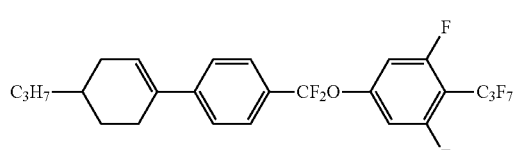
(Nlo. 259)
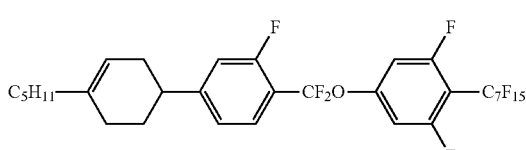
(Nlo. 260)
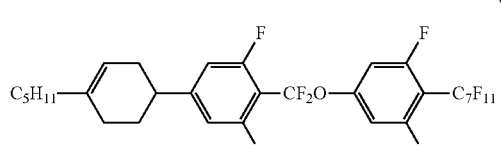
(Nlo. 261)
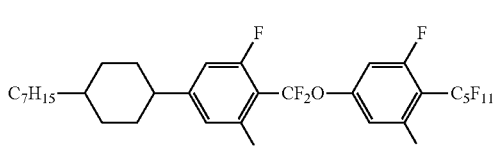
(Nlo. 262)
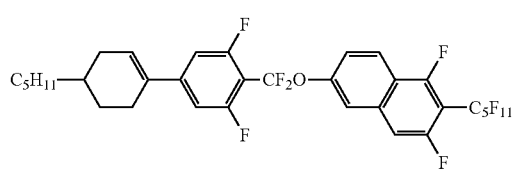
(Nlo. 263)
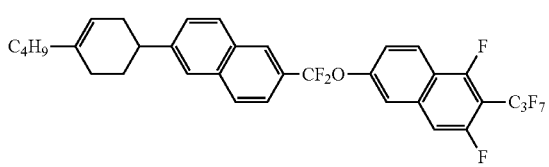

-continued
(No. 264)
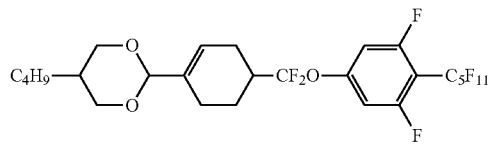
(No. 265)
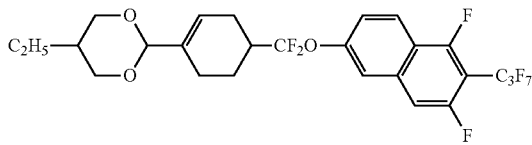
(No. 266)
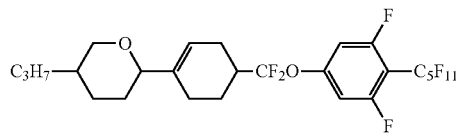
(No. 267)
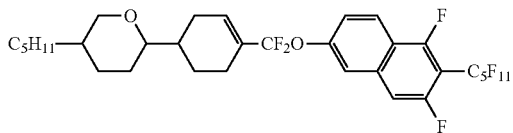
(No. 268)
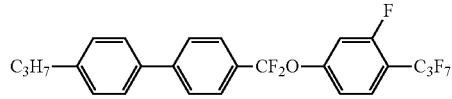
(No. 269)
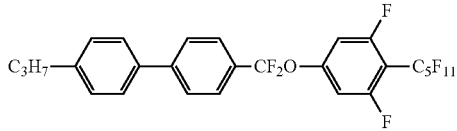
(No. 270)
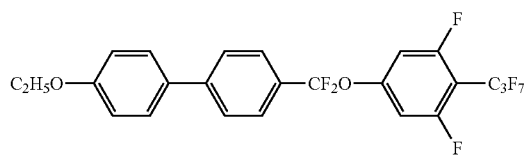
(No. 271)
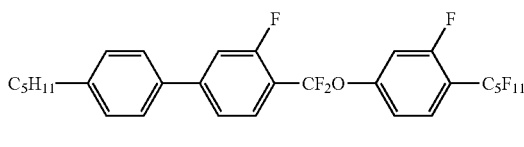
(No. 272)
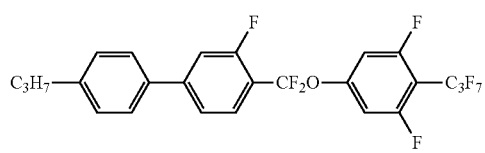
(No. 273)
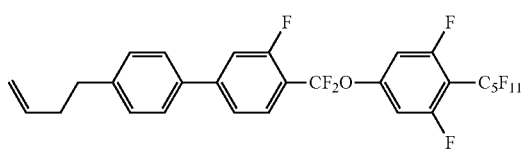
(No. 274)
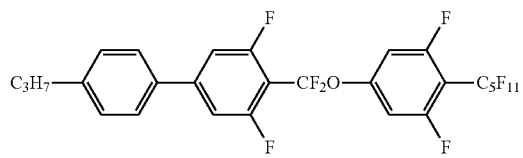
C 38.7 I
$T_{NI} = 22.6°$ C., $\Delta\varepsilon = 22.1$, $\Delta n = 0.118$
(No. 275)
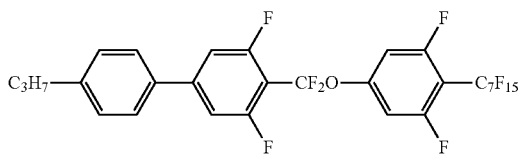
C 51.6 $S_A$ 70.9 I
$T_{NI} = 46.8°$ C., $\Delta\varepsilon = 19.8$, $\Delta n = 0.120$
(No. 276)
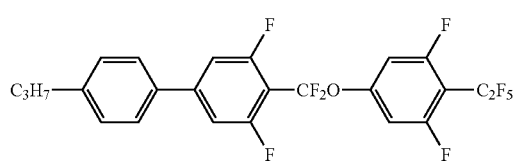
(No. 277)
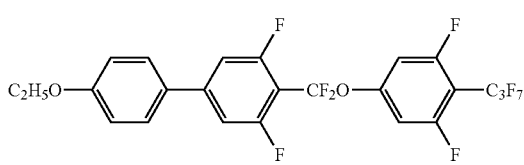
(No. 278)
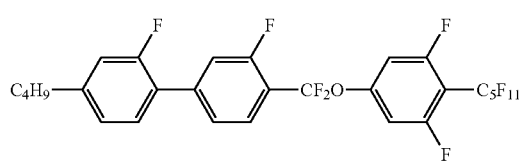
(No. 279)
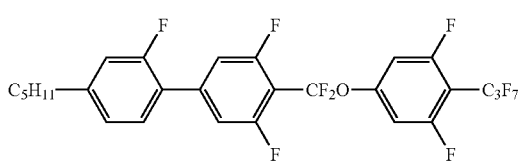
(No. 280)
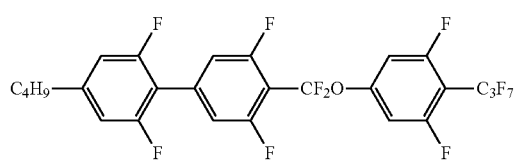
(No. 281)
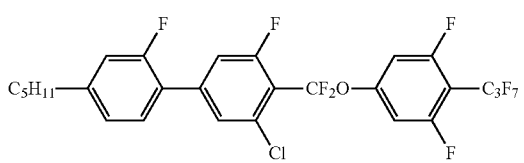

-continued (No. 282)

(No. 283)

(No. 284)

(No. 285)

(No. 286)

(No. 287)

(No. 288)

(No. 289)

(No.290)

(No.291)

(No.292)

(No.293)

(No.294)

(No.295)

(No.296)

(No.297)

(No.298)

(No.299)

-continued
(No. 300)
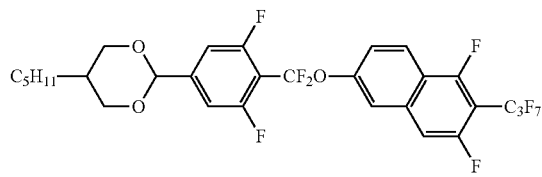
(No. 301)
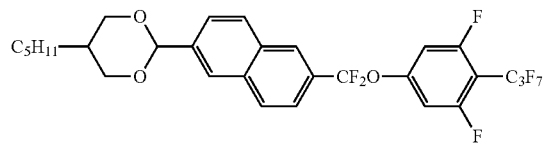
(No. 302)
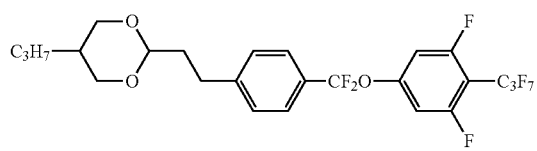
(No. 303)
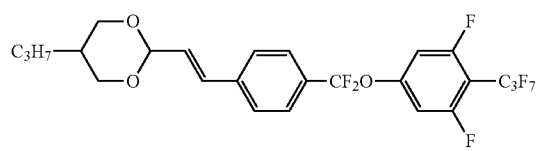
(No. 304)
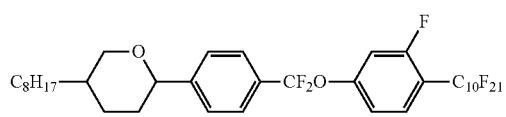
(No. 305)
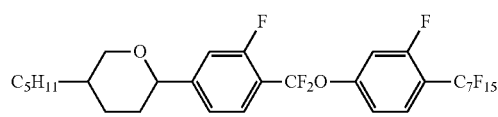
(No. 306)
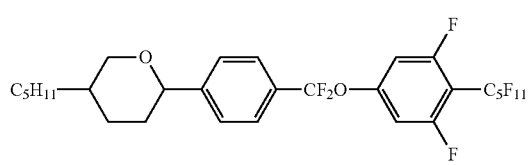
(No. 307)
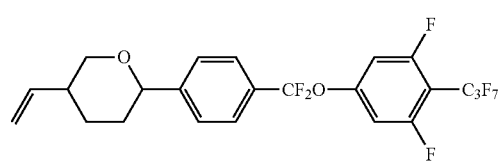
(No. 308)
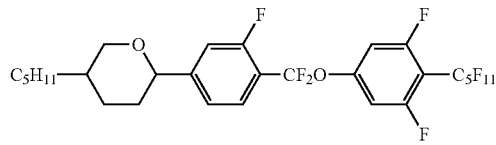
(No. 309)
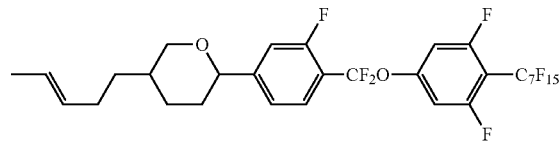
(No. 310)
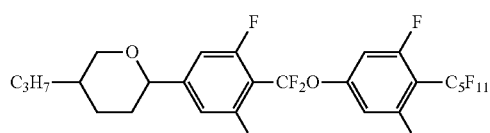
(No. 311)
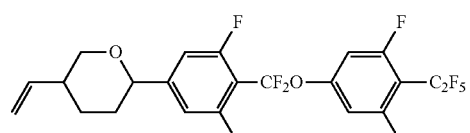
(No. 312)
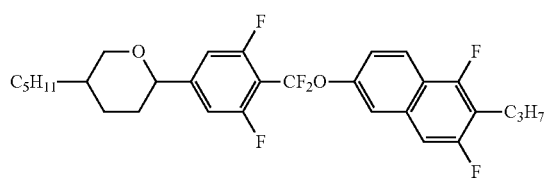
(No. 313)
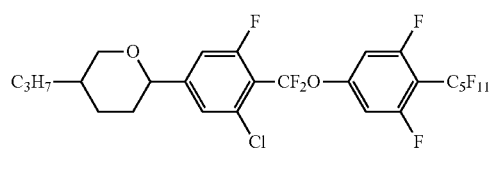
(No. 314)
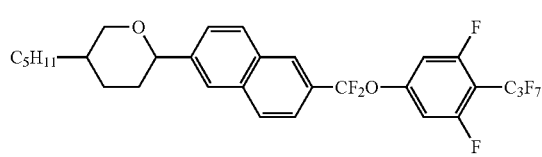
(No. 315)
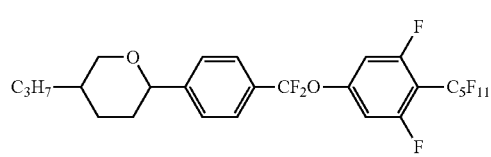
(No. 316)
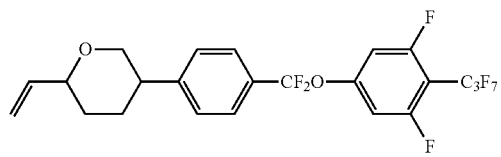
(No. 317)
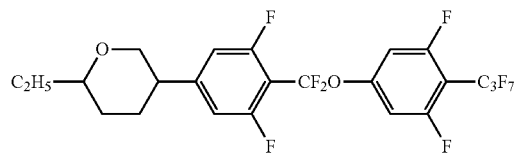

-continued
(No. 318)
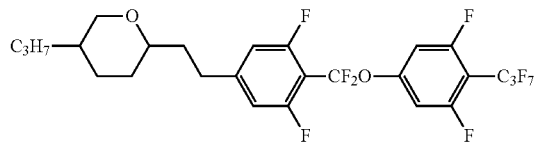
(No. 319)
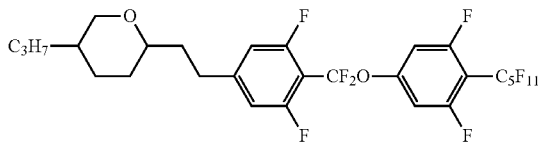
(No. 320)
(No. 321)
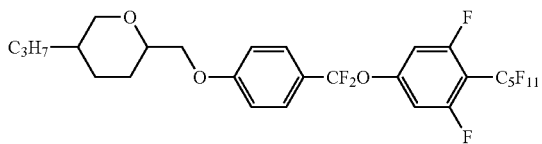
(No. 322)
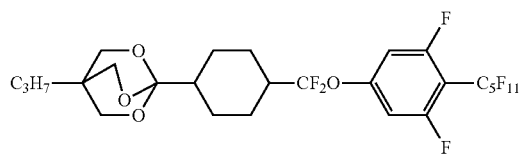
(No. 323)
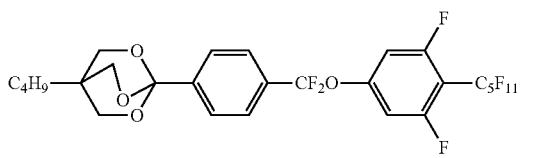
(No. 324)
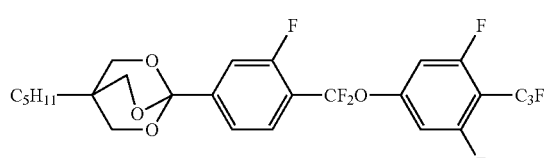
(No. 325)
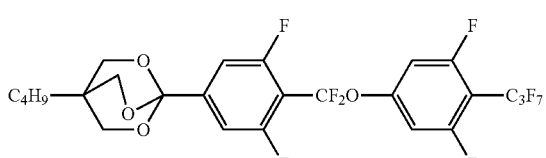
(No. 326)
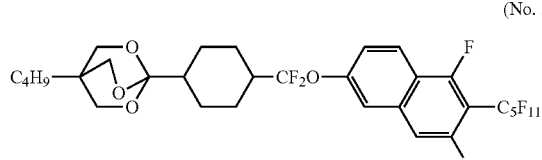
(No. 327)
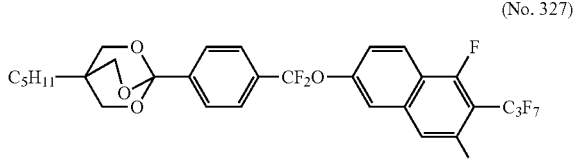
(No. 328)
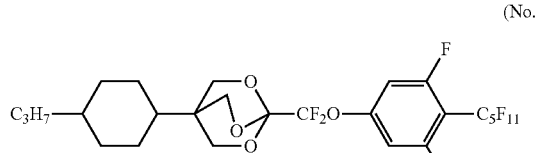
(No. 329)
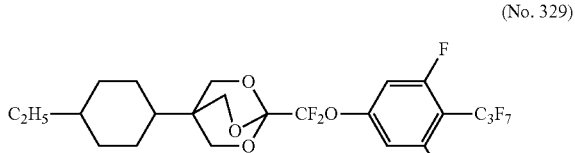
(No. 330)
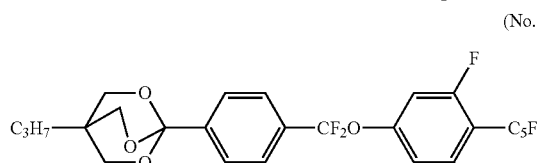
(No. 331)
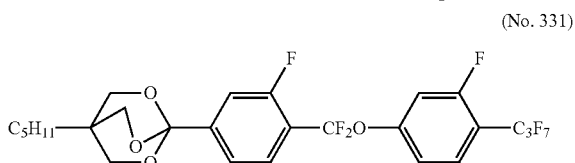
(No. 332)
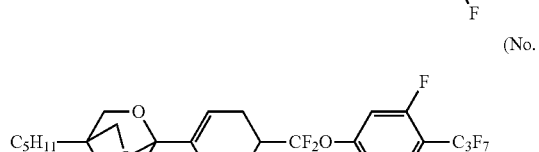
(No. 333)
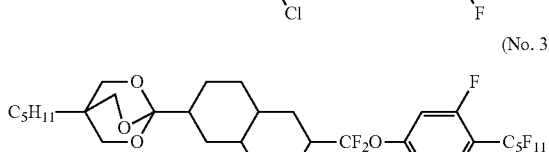
(No. 334)
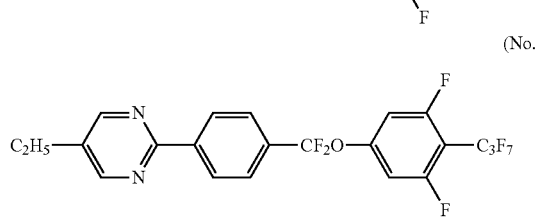
(No. 335)
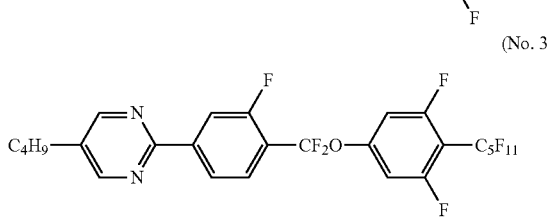

-continued
(No. 336)
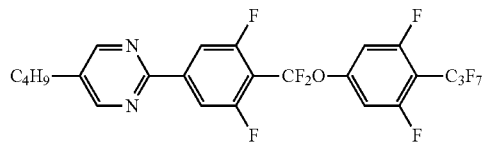
(No. 337)
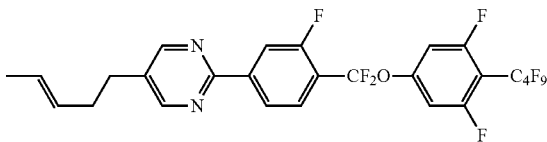
(No. 338)
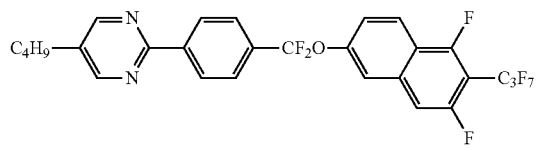
(No. 339)
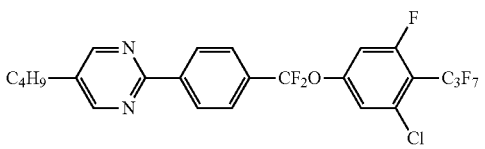
(No. 340)
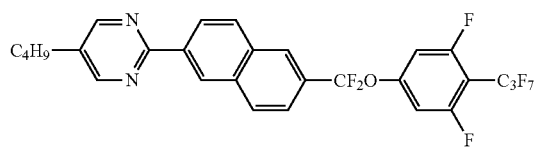
(No. 341)
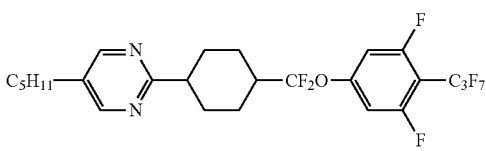
(No. 342)
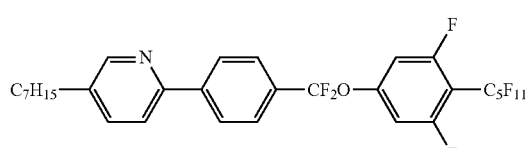
(No. 343)
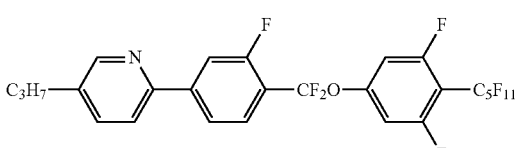
(No. 344)
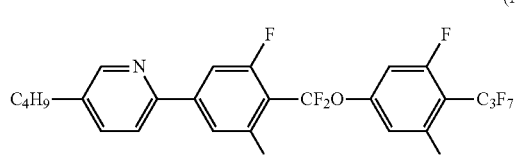
(No. 345)
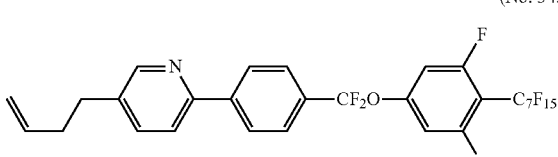
(No. 346)
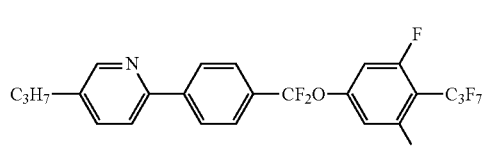
(No. 347)
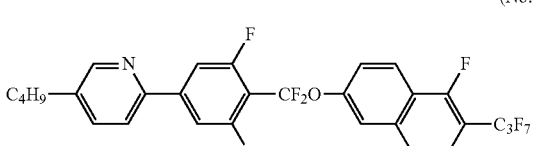
(No. 348)
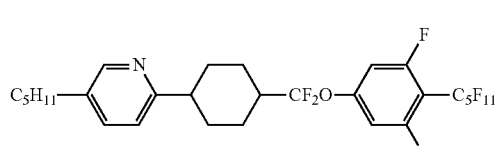
(No. 349)
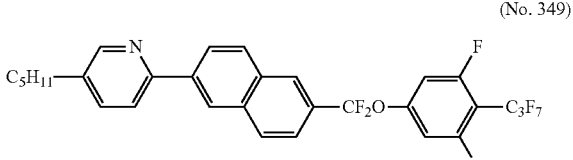
(No. 400)
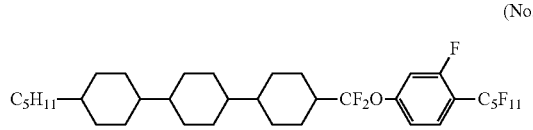
(No. 401)
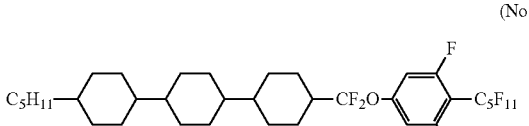
(No. 402)
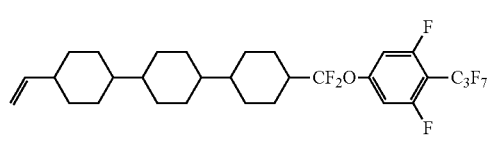
(No. 403)
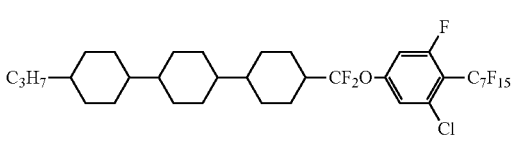

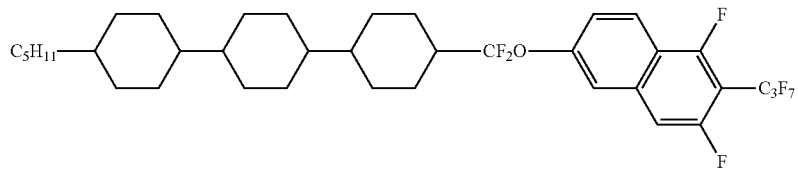
(No. 404)
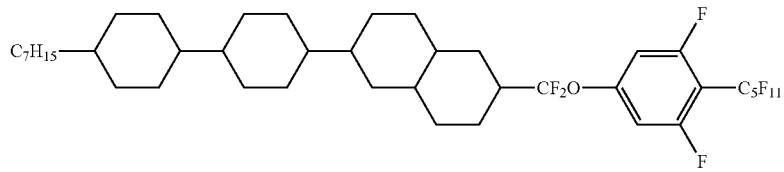
(No. 405)
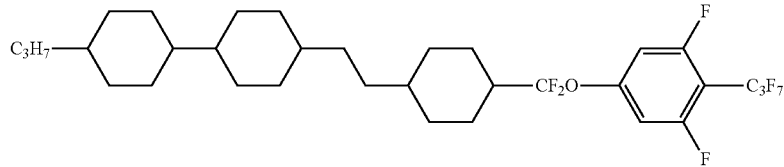
(No. 406)
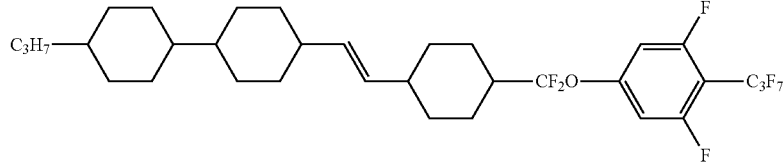
(No. 407)
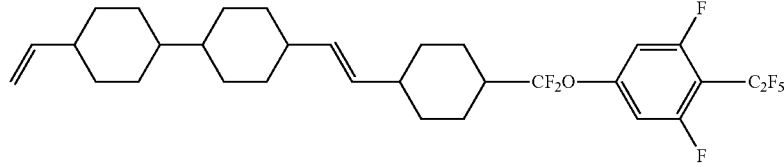
(No. 408)
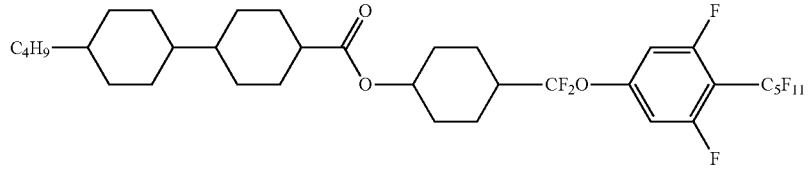
(No. 409)
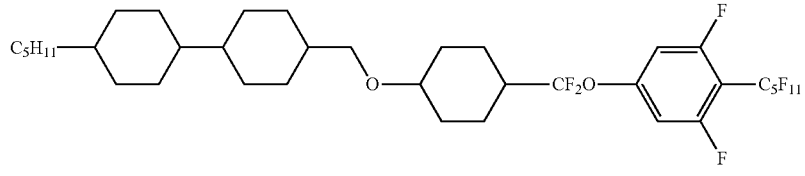
(No. 410)
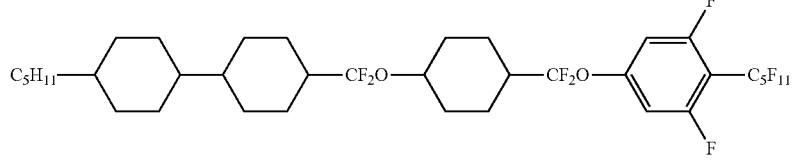
(No. 411)
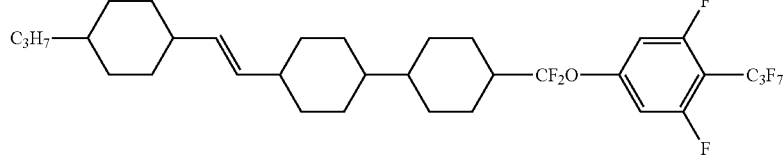
(No. 412)

-continued
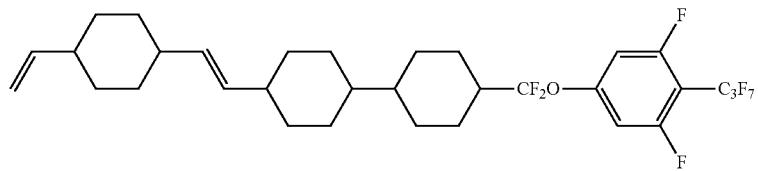
(No. 413)
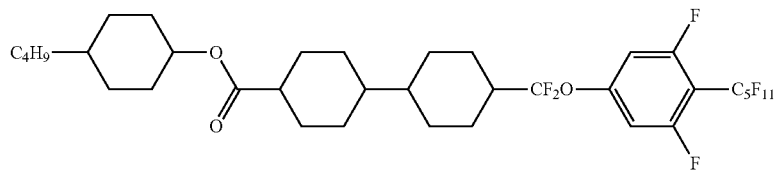
(No. 414)
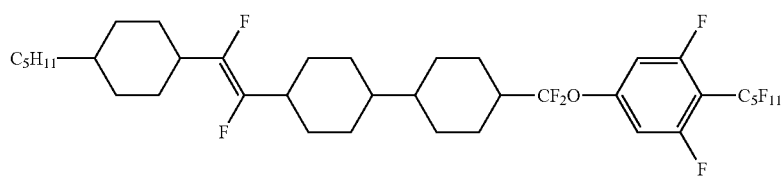
(No. 415)
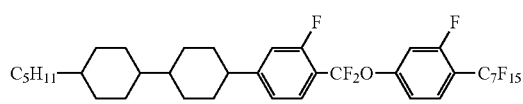
(No. 416)
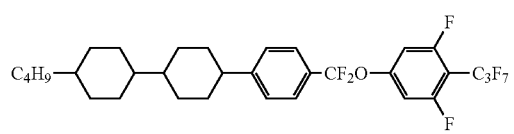
(No. 417)
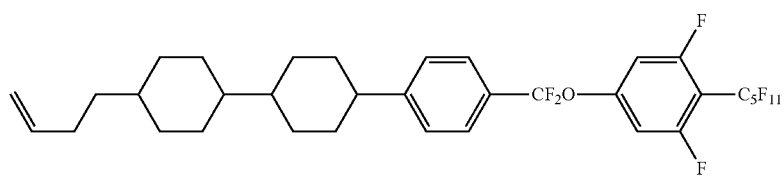
(No. 418)
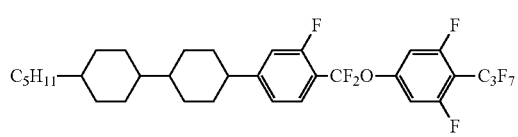
(No. 419)
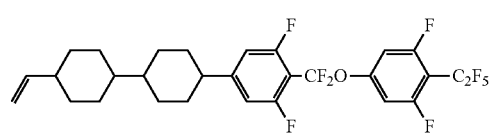
(No. 420)
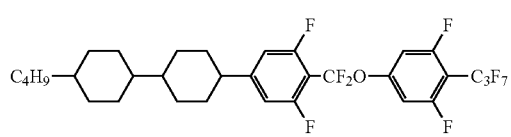
(No. 421)
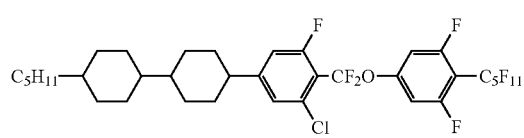
(No. 422)
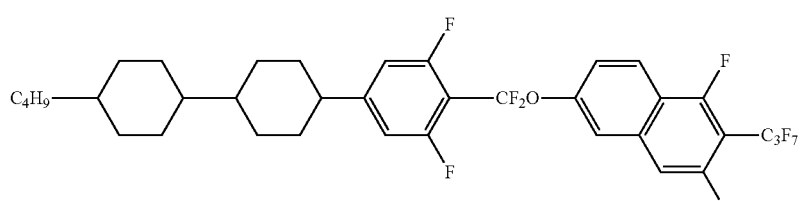
(No. 423)
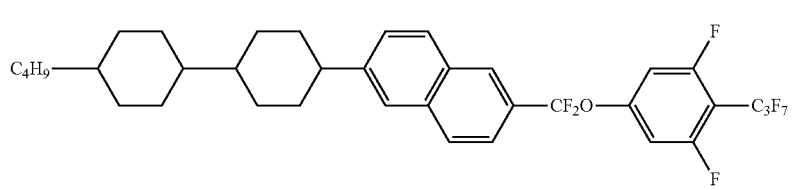
(No. 424)

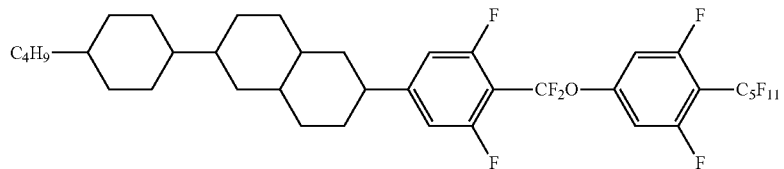
(No. 425)
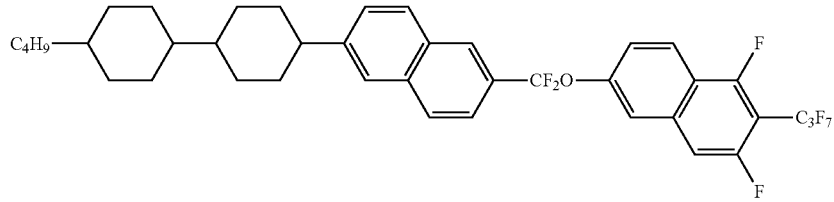
(No. 426)
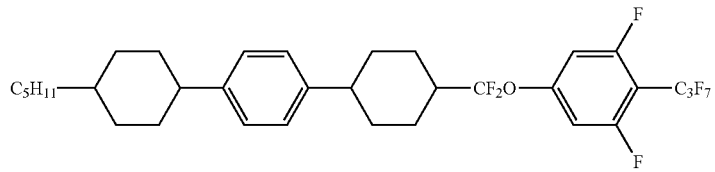
(No. 427)
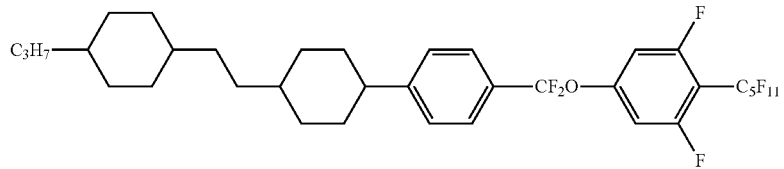
(No. 428)
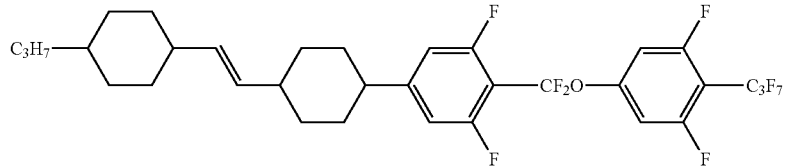
(No. 429)
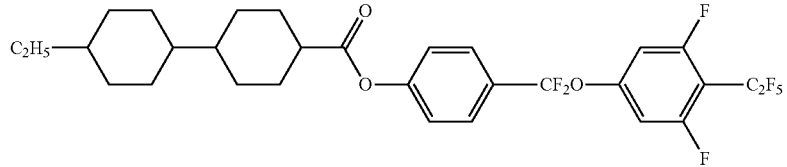
(No. 430)
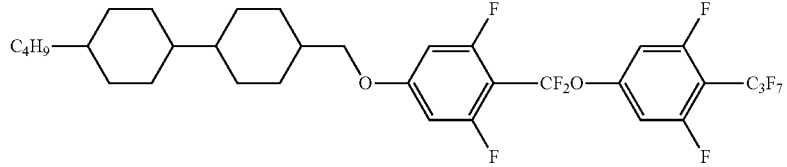
(No. 431)
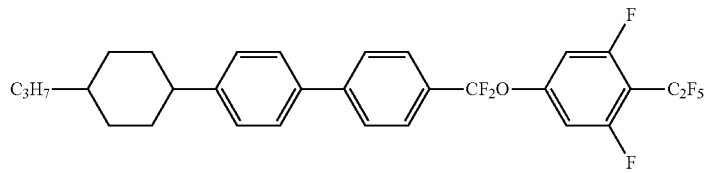
(No. 432)

-continued
(No. 433)
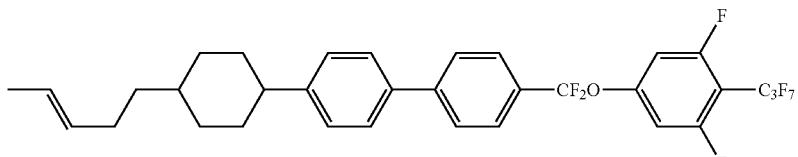
(No. 434)
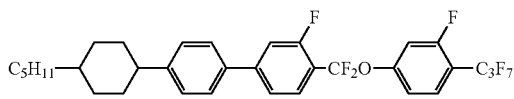
(No. 435)
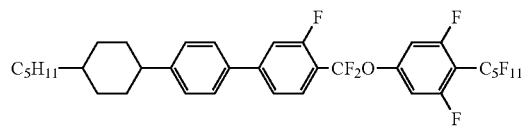
(No. 436)
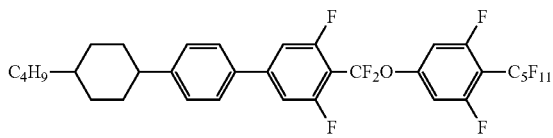
(No. 437)
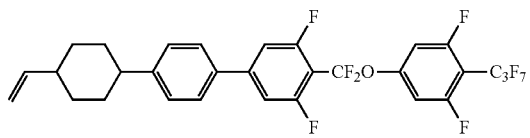
(No. 438)
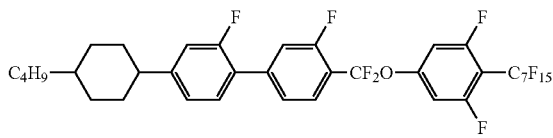
(No. 439)
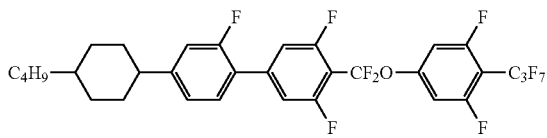
(No. 440)
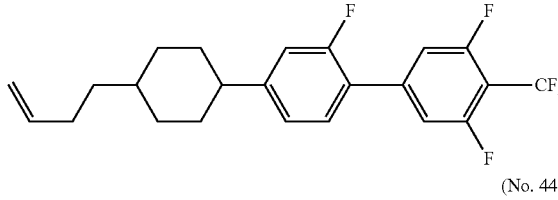
(No. 441)
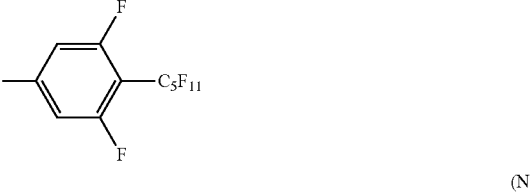
(No. 442)
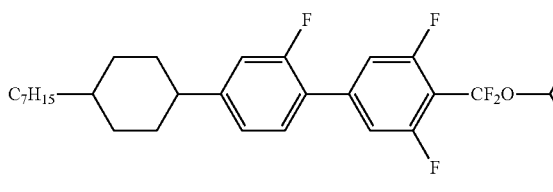
(No. 443)
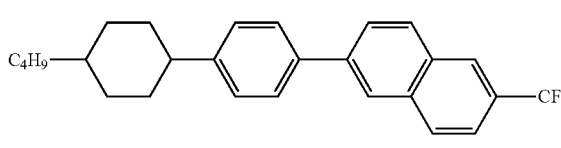
(No. 444)
(No. 445)
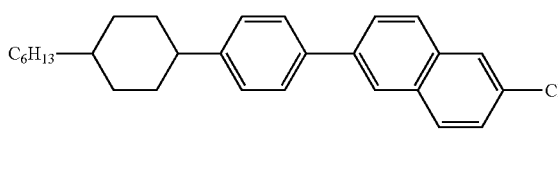

-continued
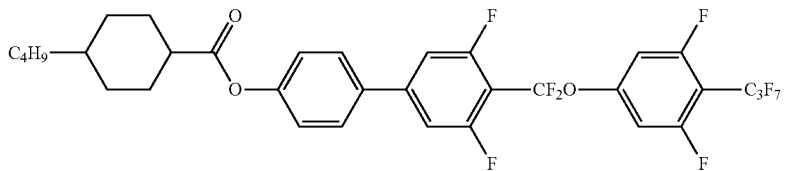
(No. 446)
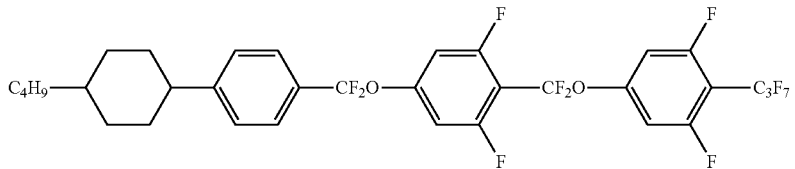
(No. 447)
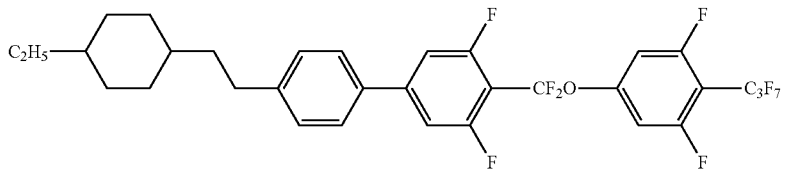
(No. 448)
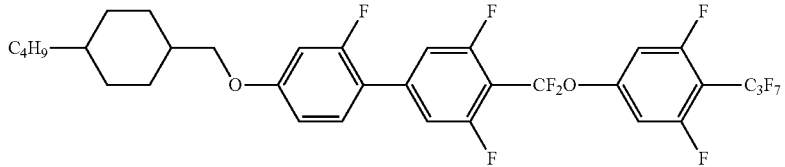
(No. 449)
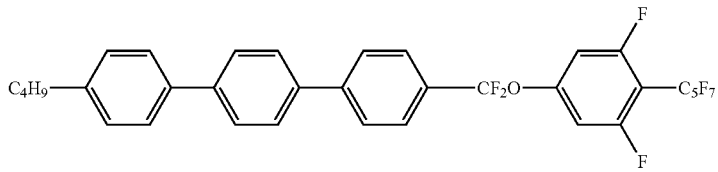
(No. 450)
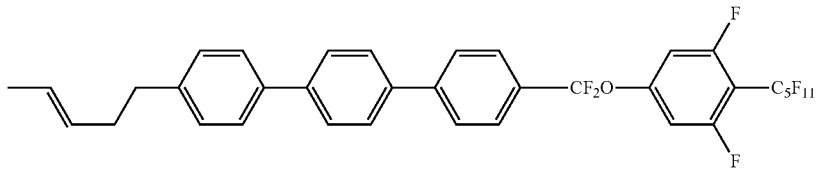
(No. 451)
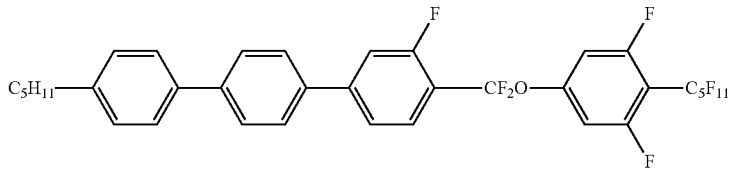
(No. 452)
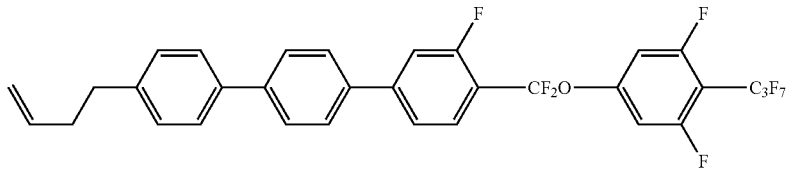
(No. 453)
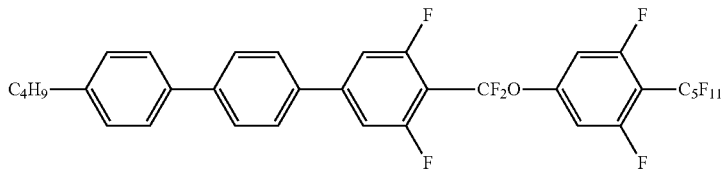
(No. 454)

-continued
(No. 455)
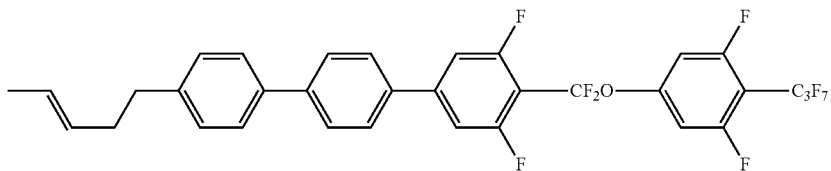
(No. 456)
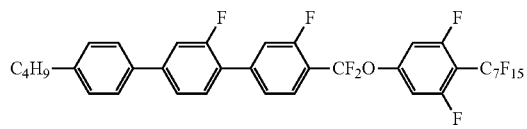
(No. 457)
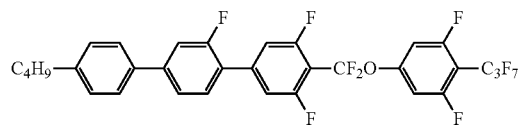
C 72.2 S$_A$ 118 N 123 I
T$_{NI}$ = 93.6° C., Δε = 33.6, Δn = 0.183
(No. 458)
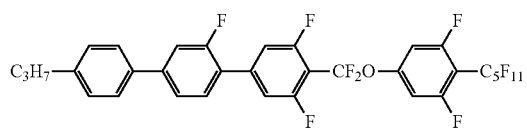
C 82.5 S$_A$ 153 I
T$_{NI}$ = 118° C., Δε = 27.1, Δn = 0.173
(No. 459)
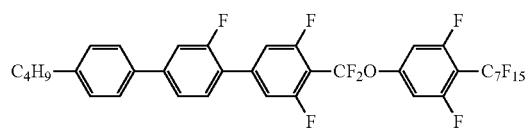
C 74.7 S$_A$ 169 I
T$_{NI}$ = 124° C., Δε = 25.1, Δn = 0.153
(No. 460)
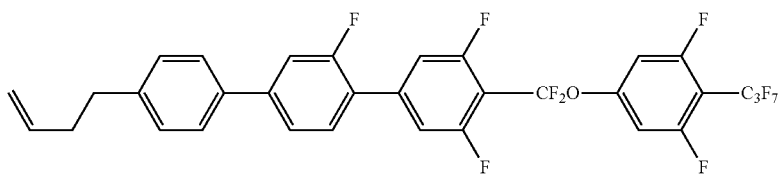
(No. 461)
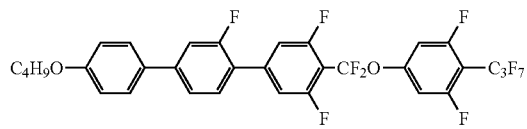
(No. 462)
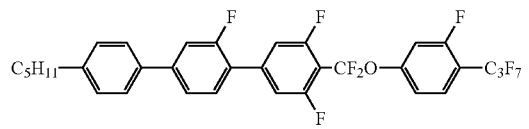
(No. 463)
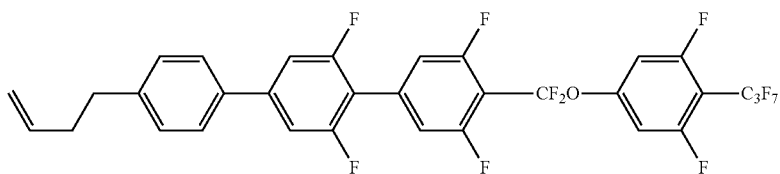
(No. 464)
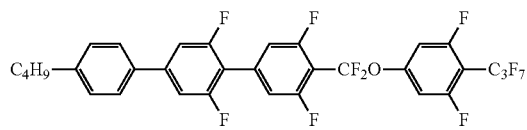
(No. 465)
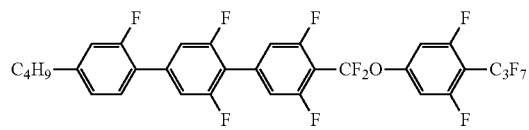
(No. 466)
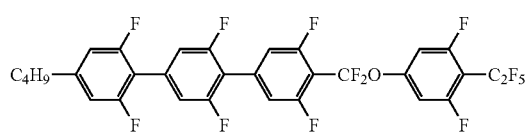
(No. 467)
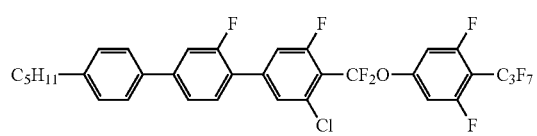

-continued
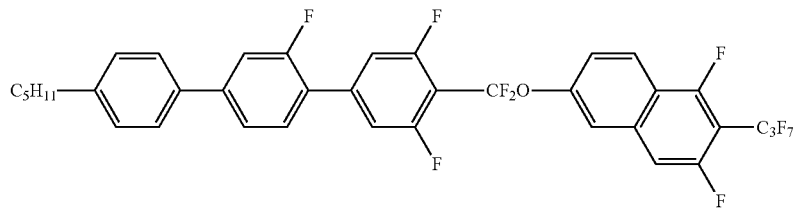 (No. 468)
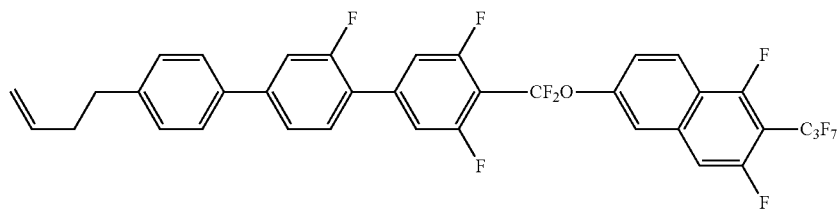 (No. 469)
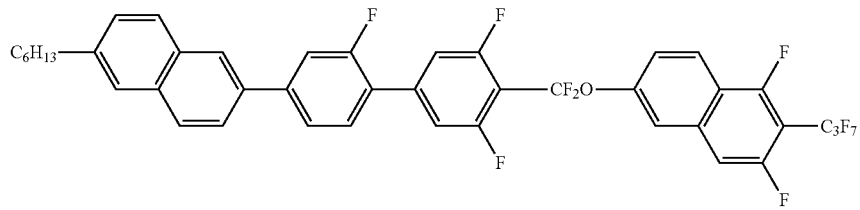 (No. 470)
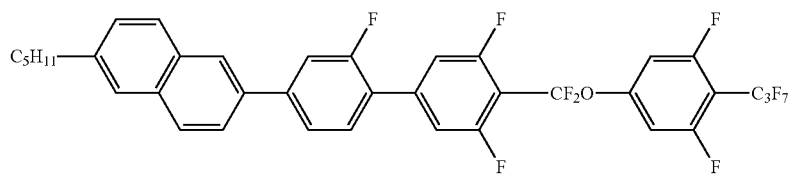 (No. 471)
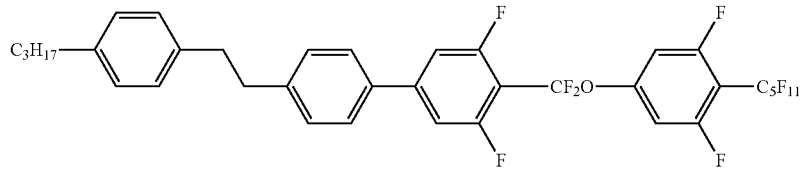 (No. 472)
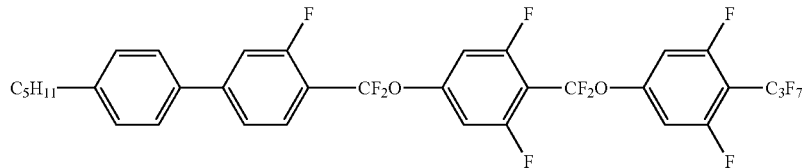 (No. 473)
(No. 474)　　　　　　　　　　　　　　　(No. 475)
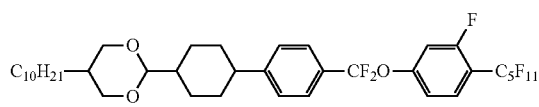　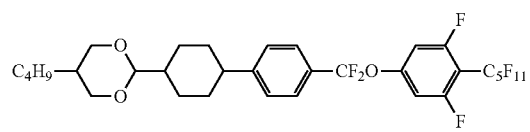
(No. 476)　　　　　　　　　　　　　　　(No. 477)
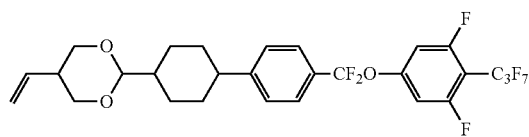　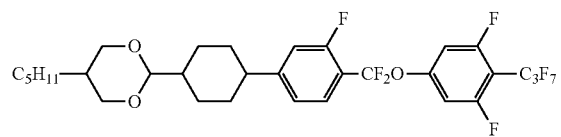

-continued
(No. 478)
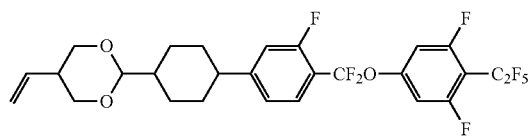
(No. 479)
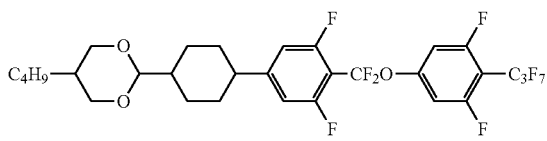
(No. 480)
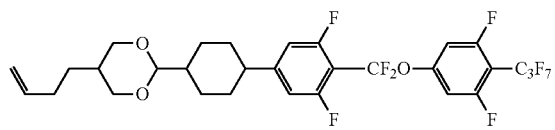
(No. 481)
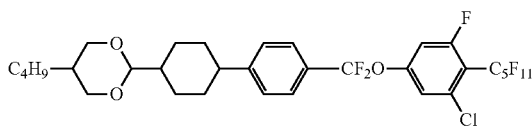
(No. 482)
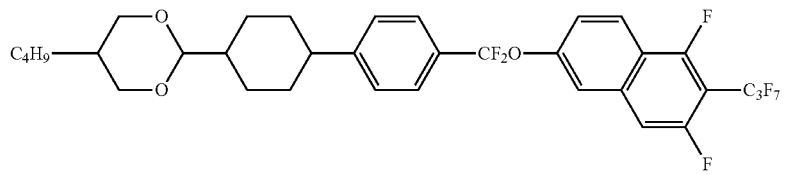
(No. 483)
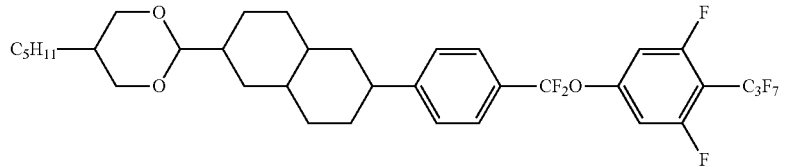
(No. 484)
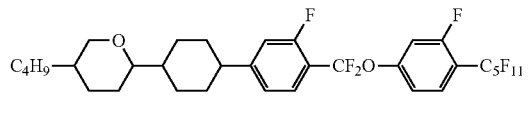
(No. 485)
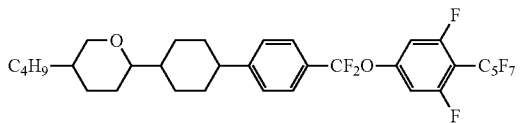
(No. 486)
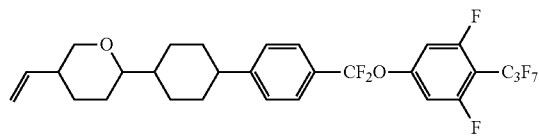
(No. 487)
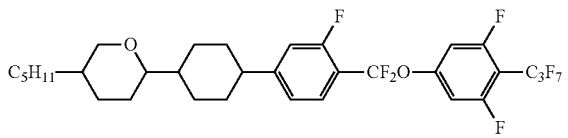
(No. 488)
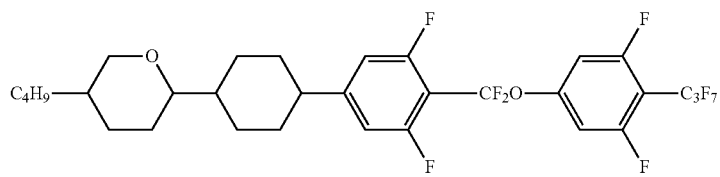
(No. 489)
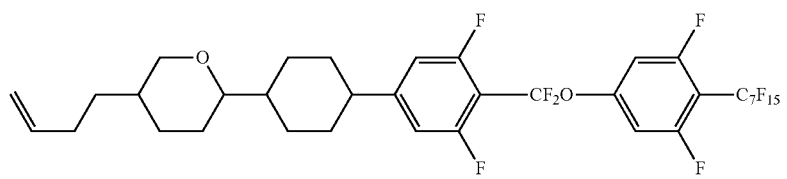
(No. 490)
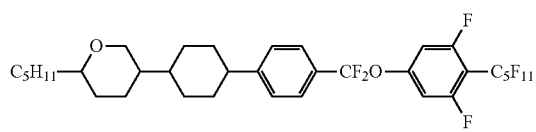
(No. 491)
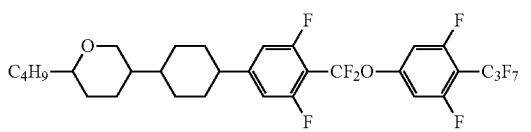

-continued
(No. 492)
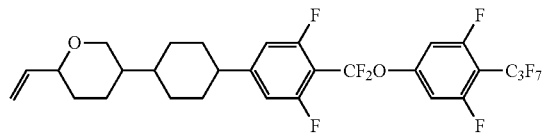
(No. 493)
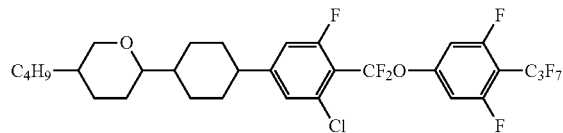
(No. 494)
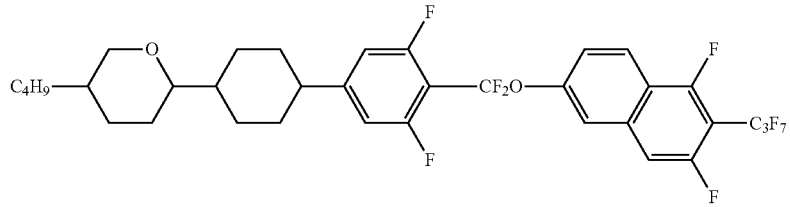
(No. 495)
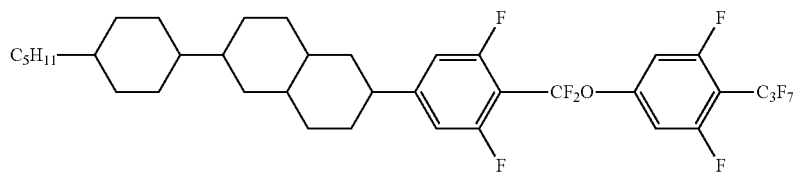
(No. 496)
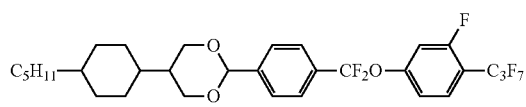
(No. 497)
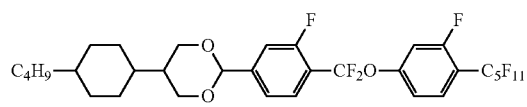
(No. 498)
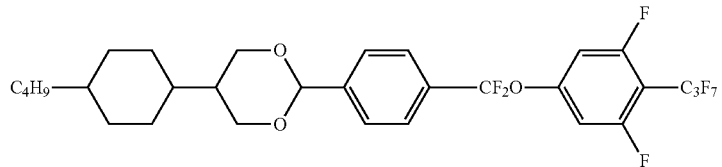
(No. 499)
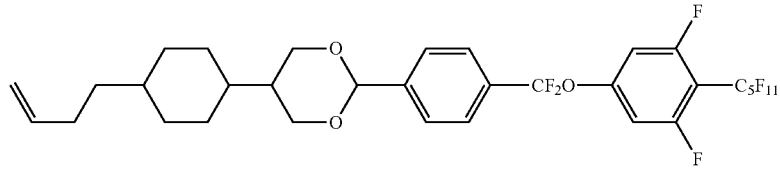
(No. 500)
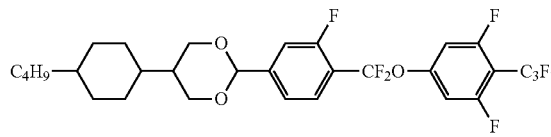
(No. 501)
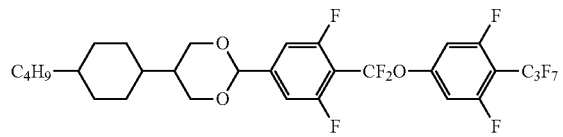
(No. 502)
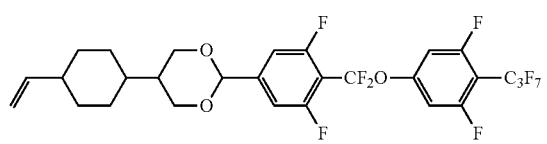
(No. 503)
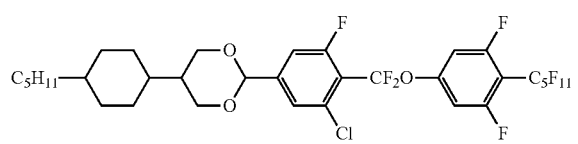
(No. 504)
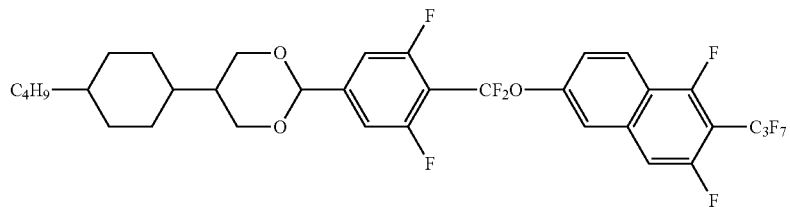

-continued
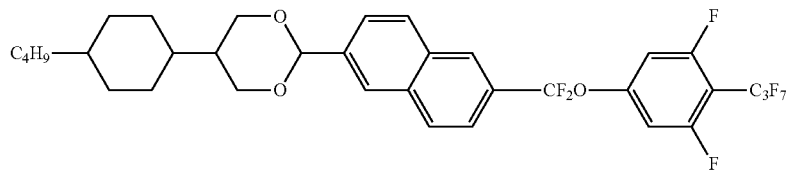
(No.505)
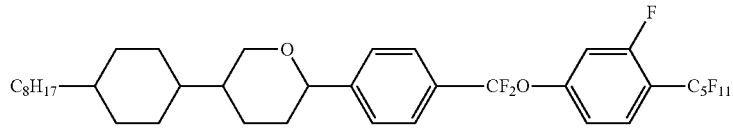
(No.506)
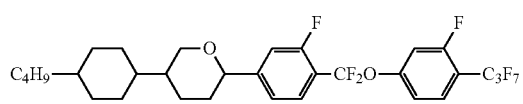
(No. 507)
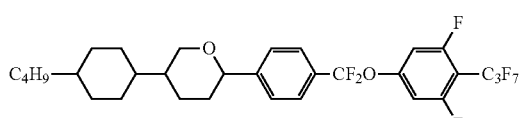
(No. 508)
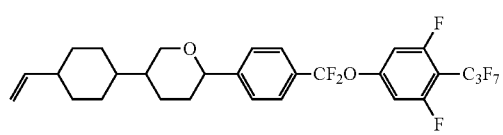
(No. 509)
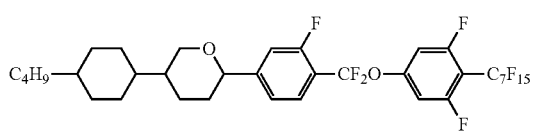
(No. 510)
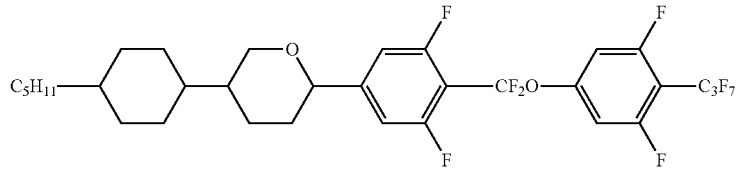
(No. 511)
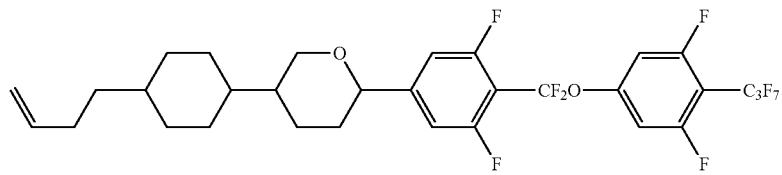
(No. 512)
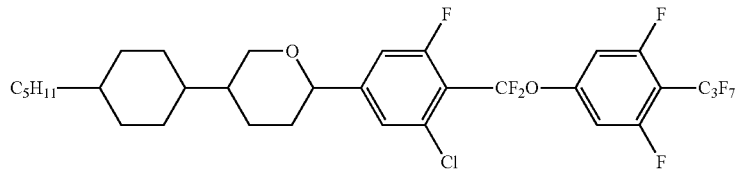
(No. 513)
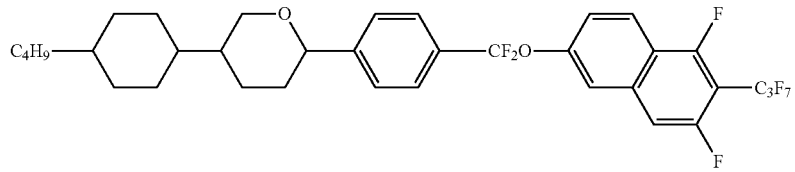
(No. 514)
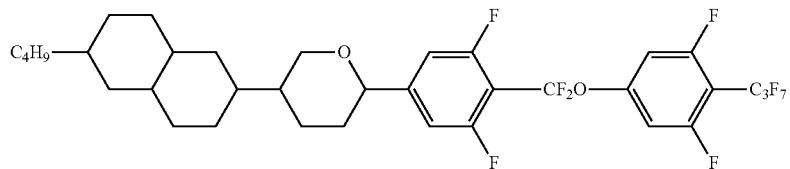
(No. 515)

-continued (No. 516)
(No. 517)
(No. 518)
(No. 519)
(No. 520)
(No. 521)
(No. 522)
(No. 523)
(No. 524)
(No. 525)
(No. 526)
(No. 527)
(No. 528)
(No. 529)
(No. 530)
(No. 531)
(No. 532)

(No. 533)
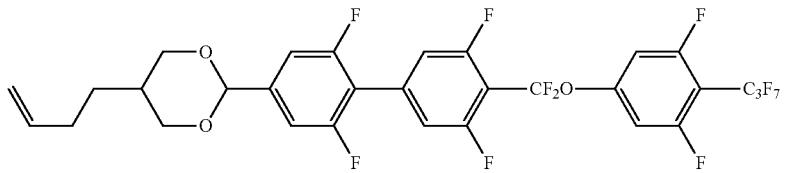
(No. 534)
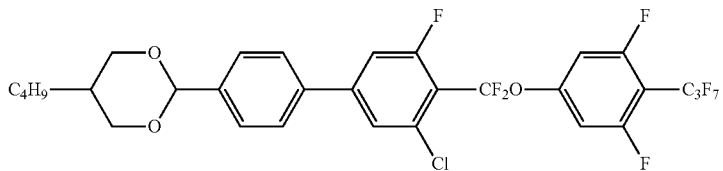
(No. 535)
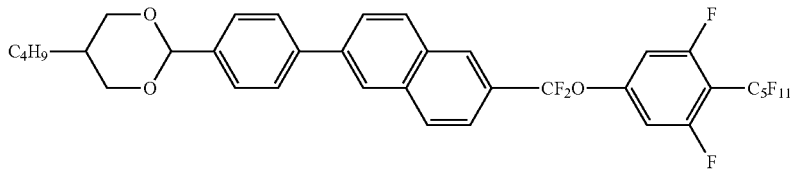
(No. 536)
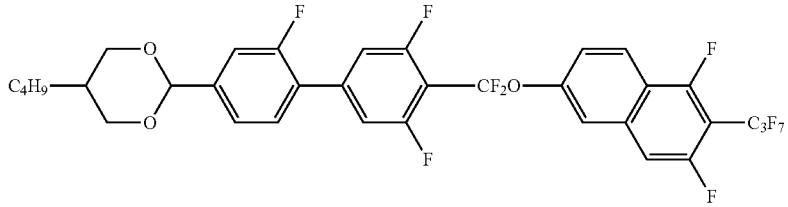
(No. 537)
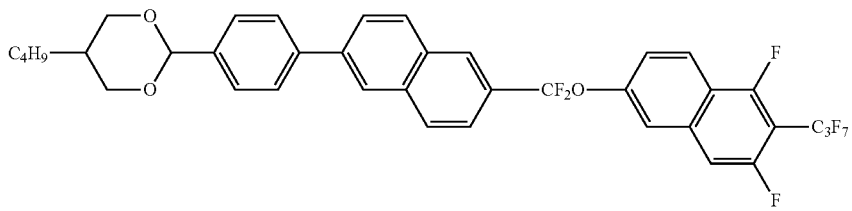
(No. 538)
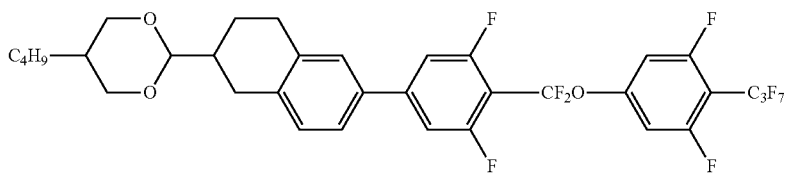
(No. 539)
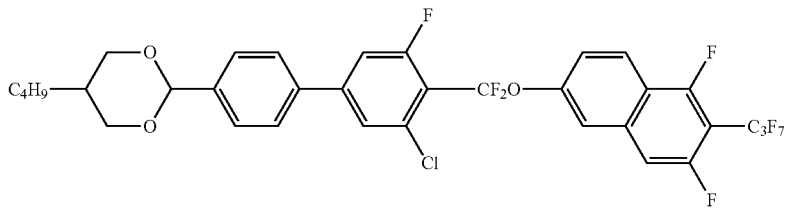
(No. 540)
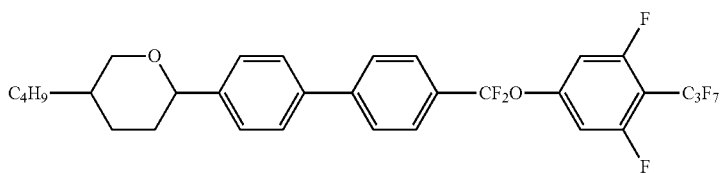

(No. 541)
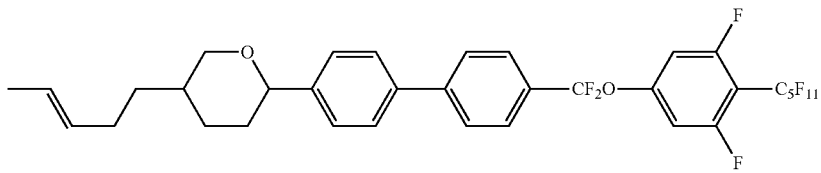
(No. 542)                                    (No. 543)
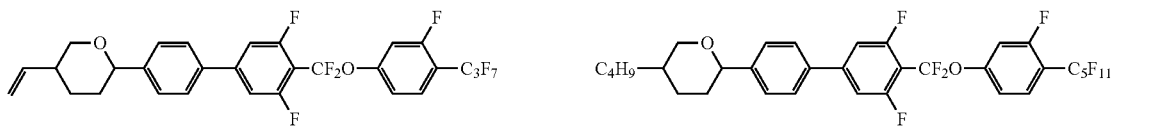
(No. 544)
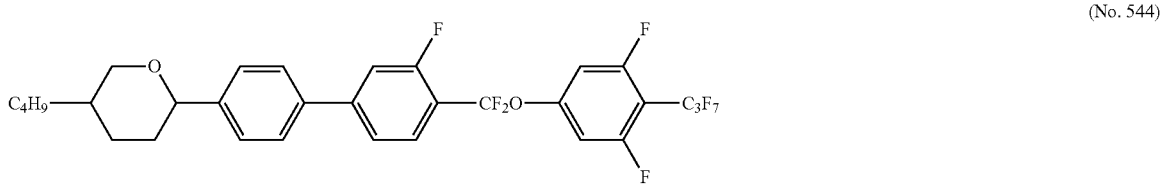
(No. 545)
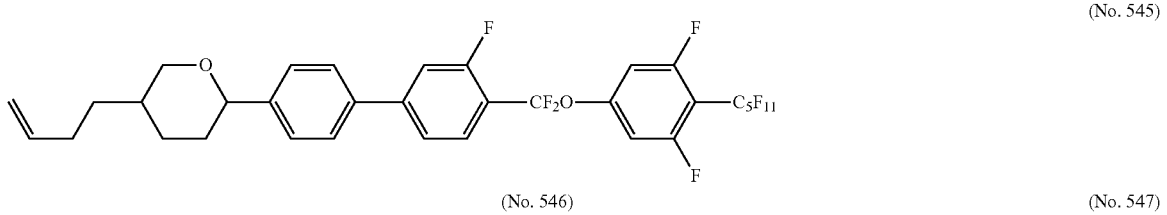
(No. 546)                                    (No. 547)
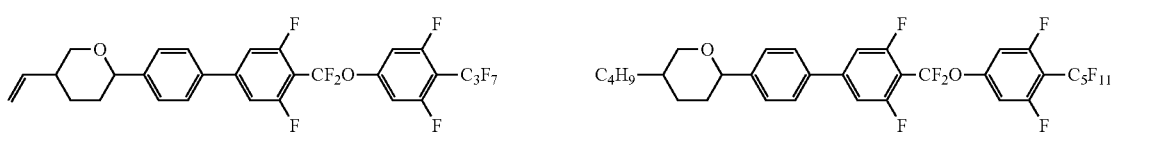
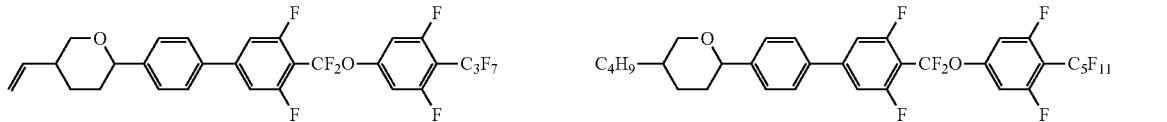
(No. 548)
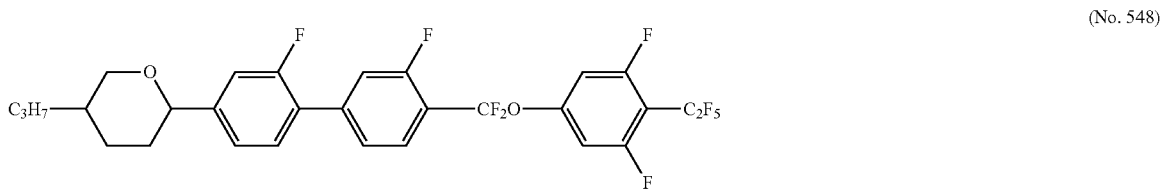
(No. 549)
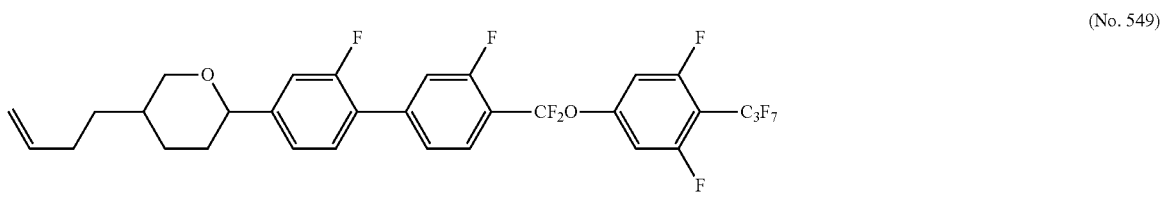
(No. 550)                                    (No. 551)
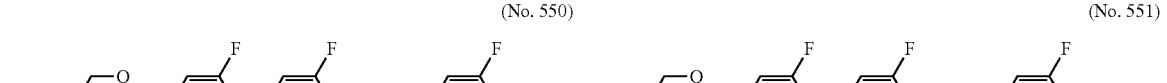
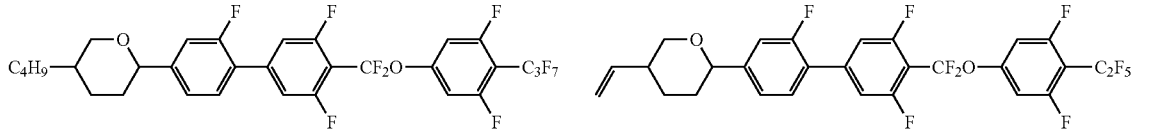
(No. 552)                                    (No. 553)
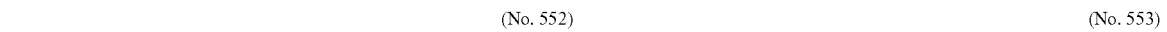
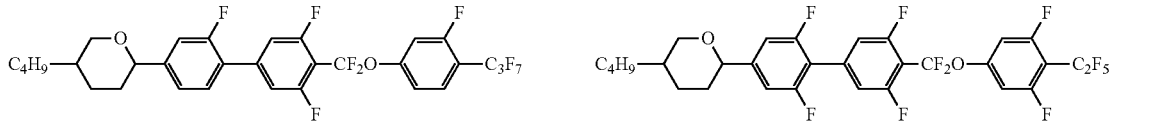

-continued
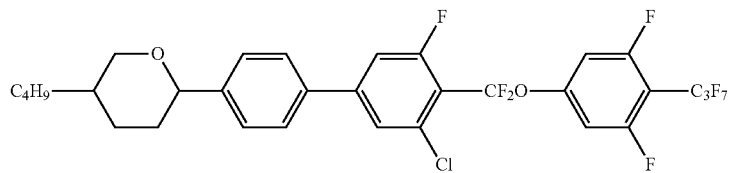
(No. 554)
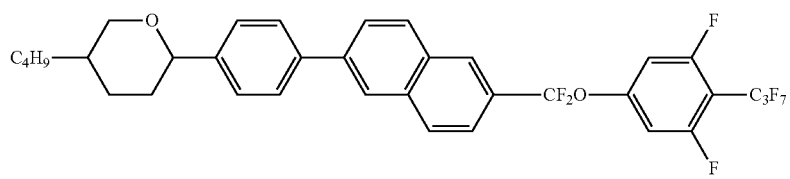
(No. 555)
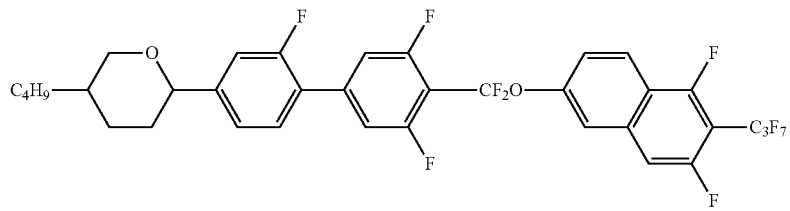
(No. 556)
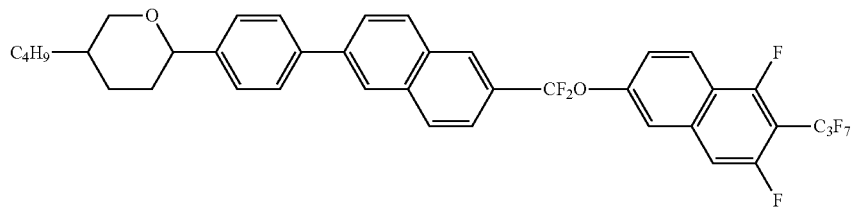
(No. 557)
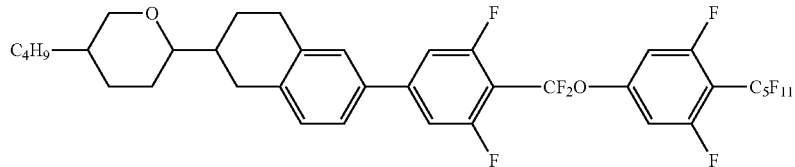
(No. 558)
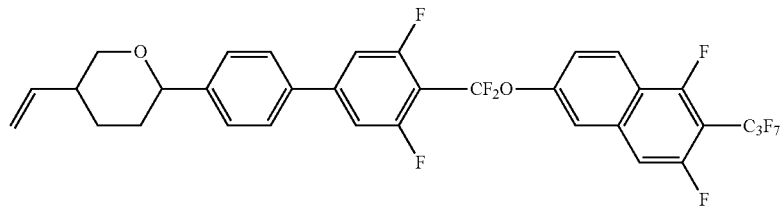
(No. 559)
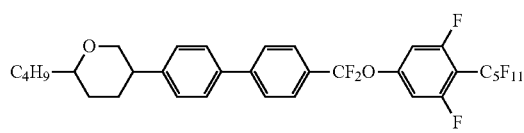
(No. 560)
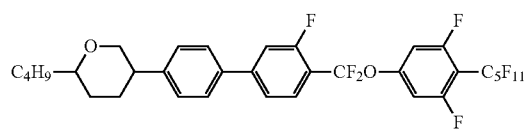
(No. 561)
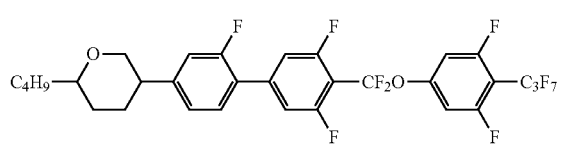
(No. 562)
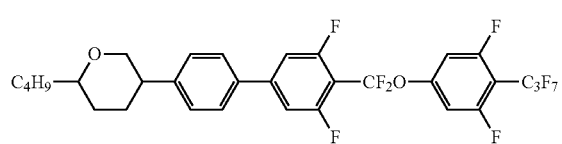
(No. 563)

-continued
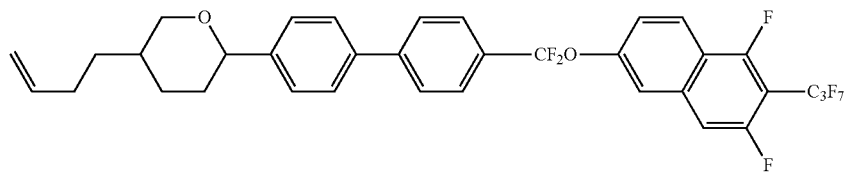
(No. 564)
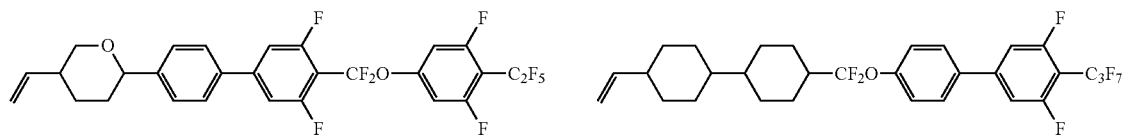
(No. 565)
(No.600)
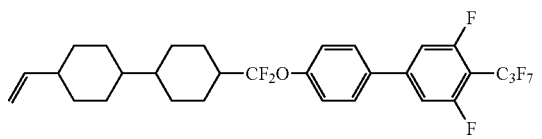
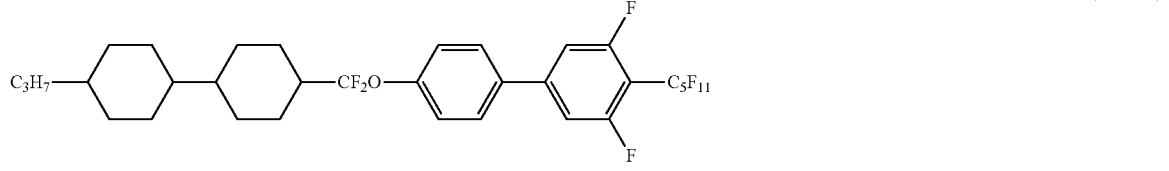
(No. 601)
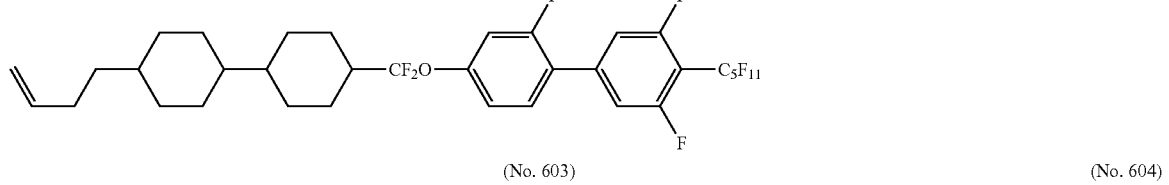
(No. 602)
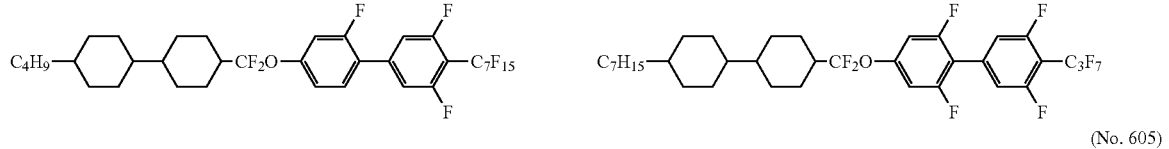
(No. 603)
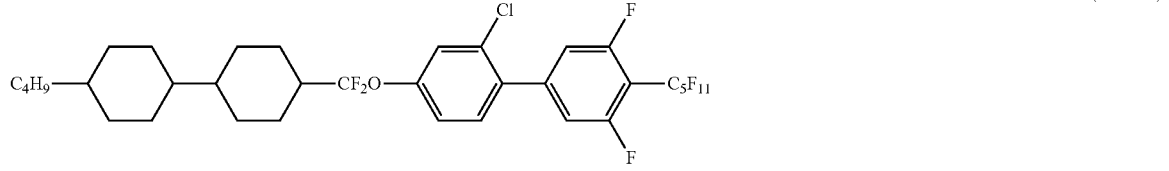
(No. 604) (No. 605)
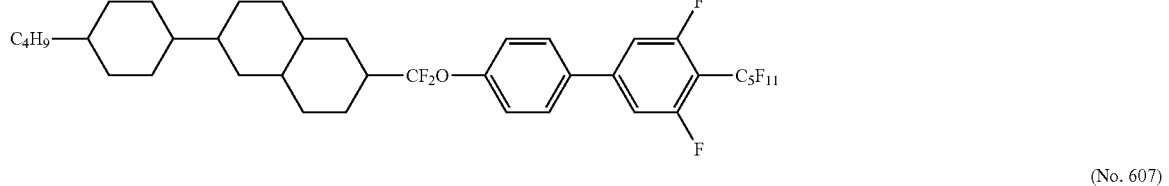
(No. 606)
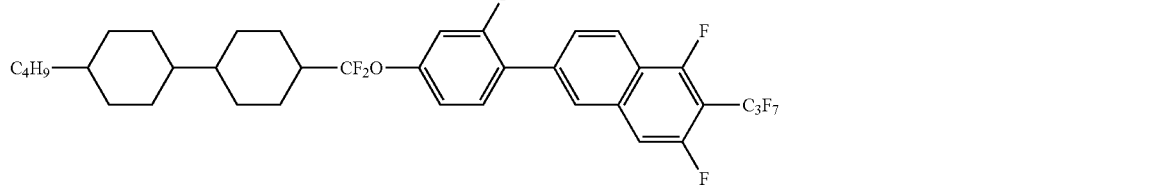
(No. 607)
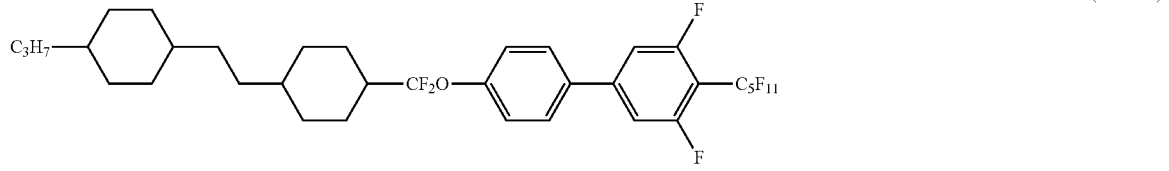
(No. 608)

-continued
(No. 609)
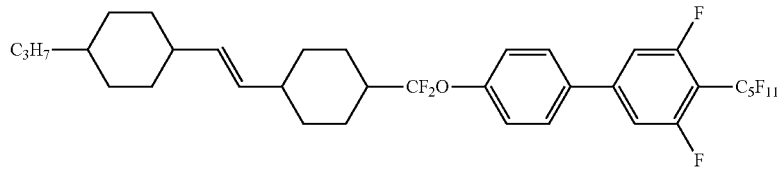
(No. 610)
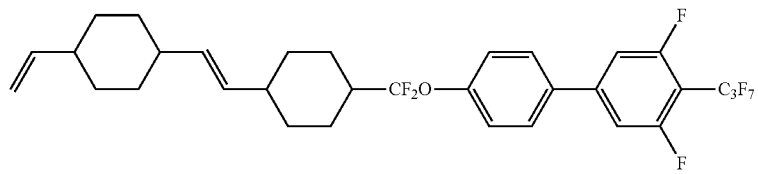
(No. 611)
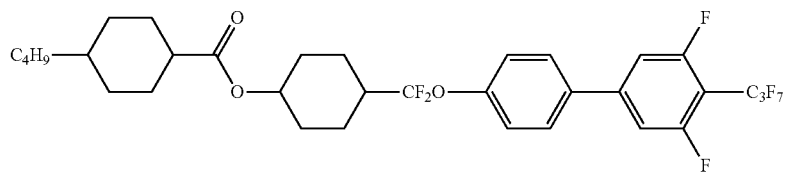
(No. 612)
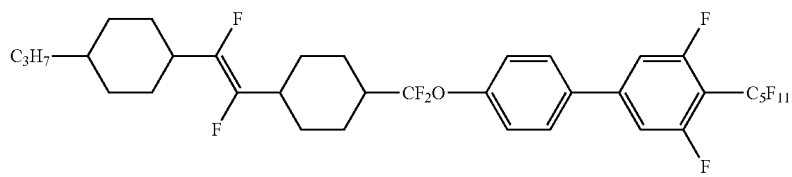
(No. 613)
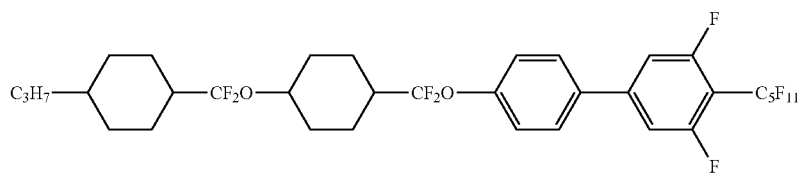
(No. 614)
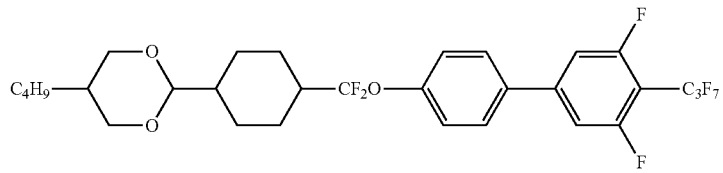
(No. 615)
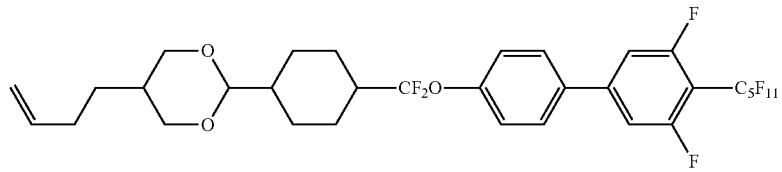
(No. 616)
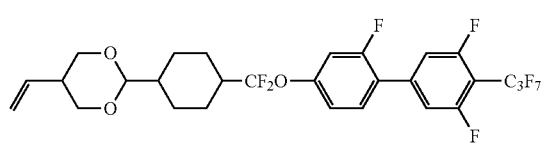
(No. 617)
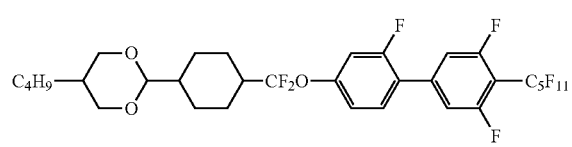
(No. 618)
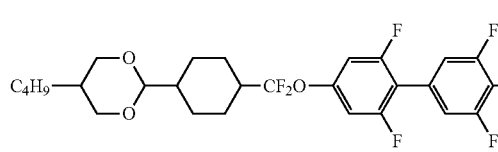
(No. 619)
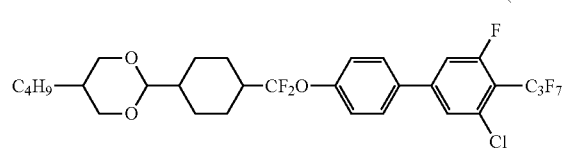

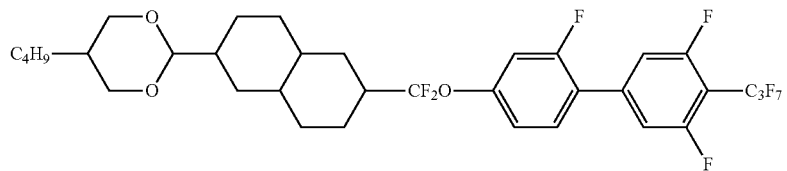
(No. 620)
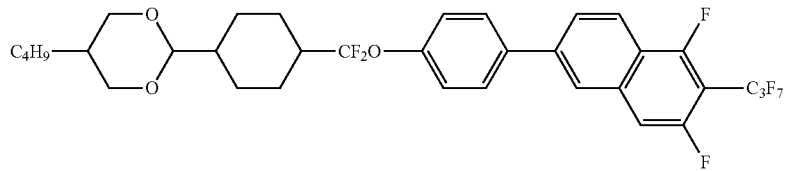
(No. 621)
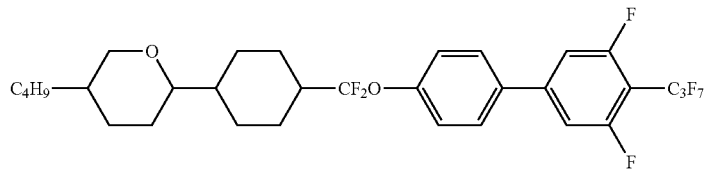
(No. 622)
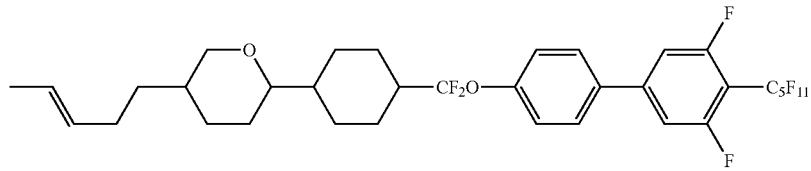
(No. 623)
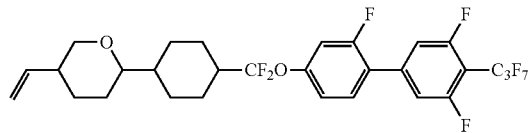
(No. 624)
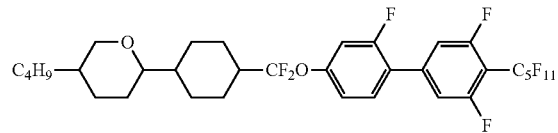
(No. 625)
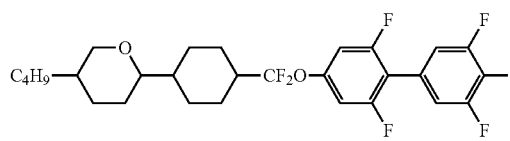
(No. 626)
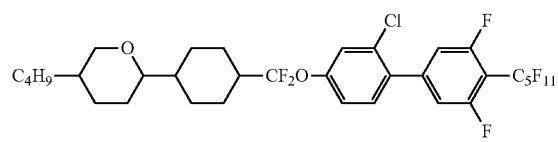
(No. 627)
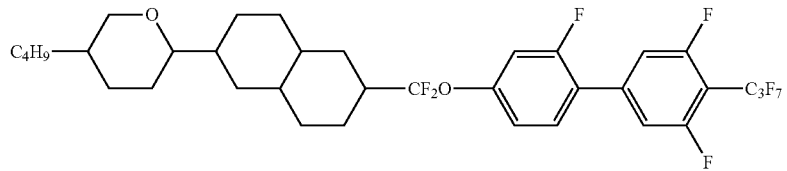
(No. 628)
(No. 629)
(No. 630)
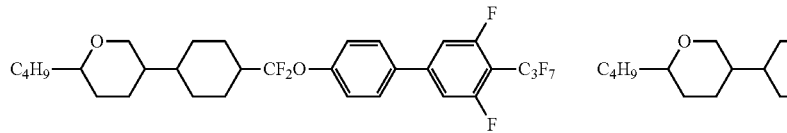
(No. 631)

(No. 632)
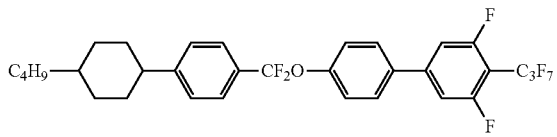
(No. 633)
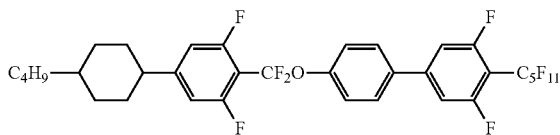
(No. 634)
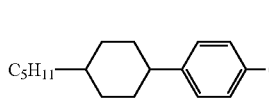
(No. 635)
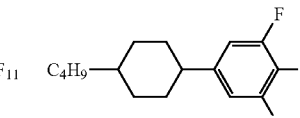
(No. 636)
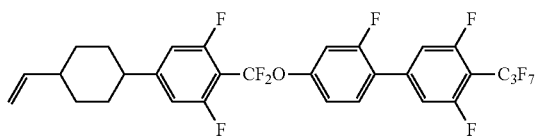
(No. 637)
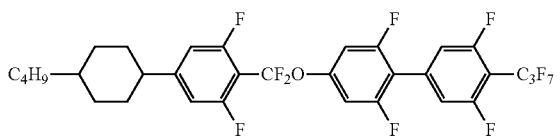
(No. 638)
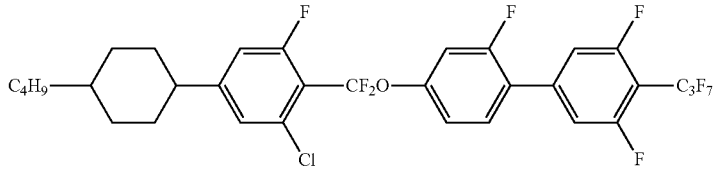
(No. 639)
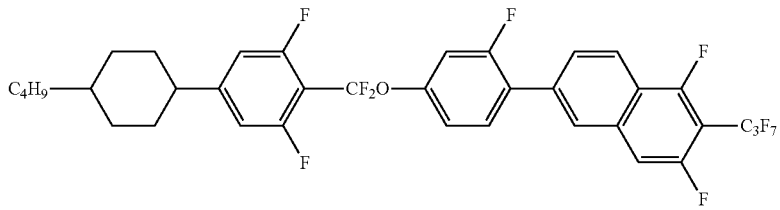
(No. 640)
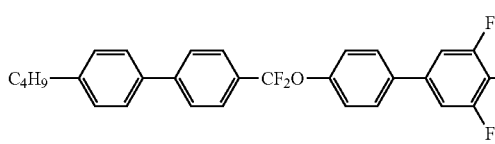
(No. 641)
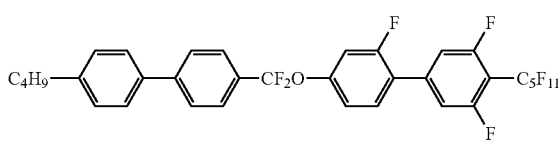
(No. 642)
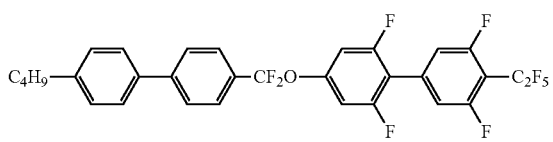
(No. 643)
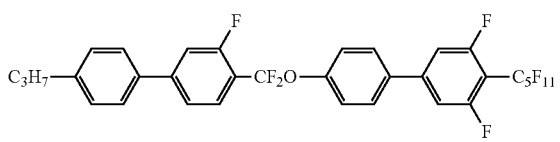
(No. 644)
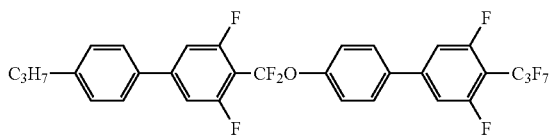
(No. 645)
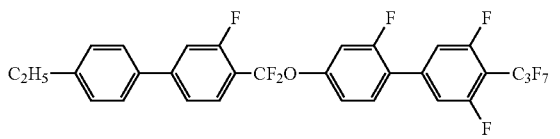
(No. 646)
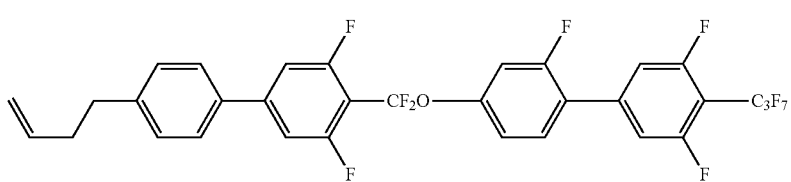

-continued
(No. 647)
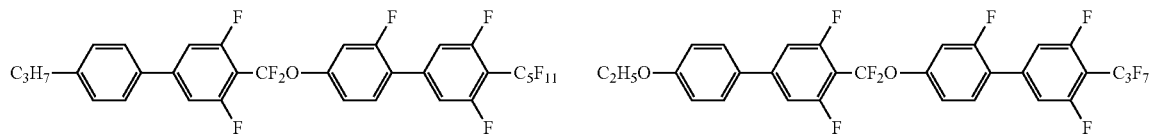
(No. 648)
(No. 649)
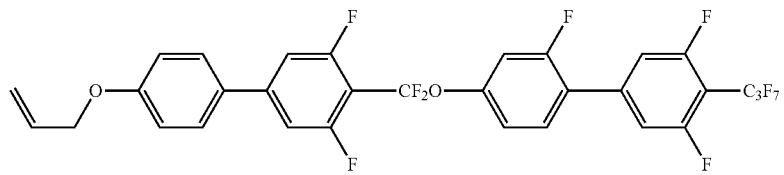
(No. 650)
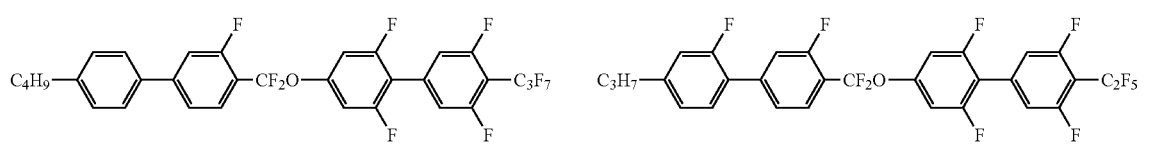
(No. 651)
(No. 652)
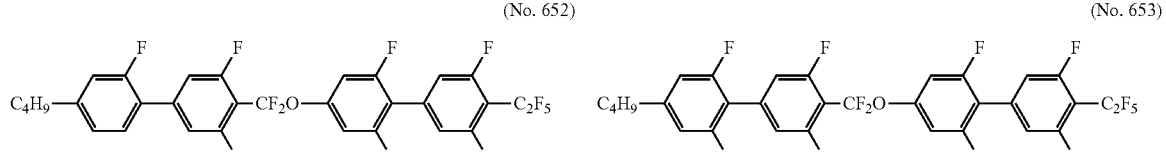
(No. 653)
(No. 654)
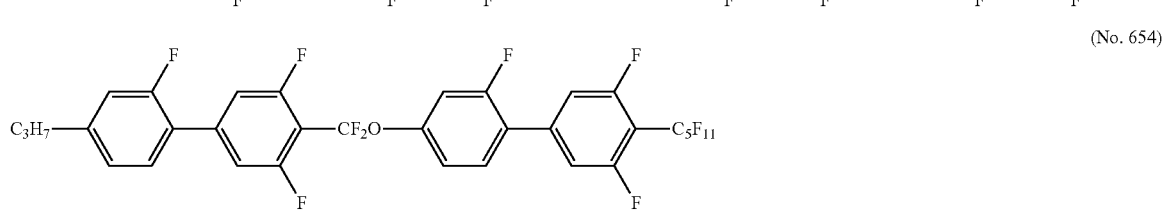
(No. 655)
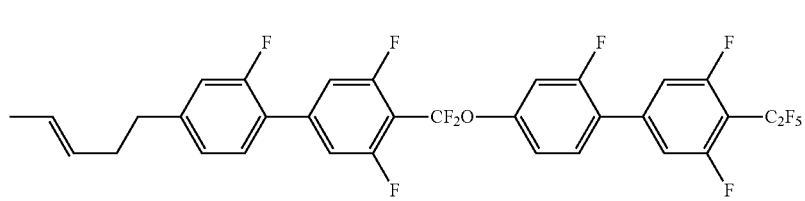
(No. 656)
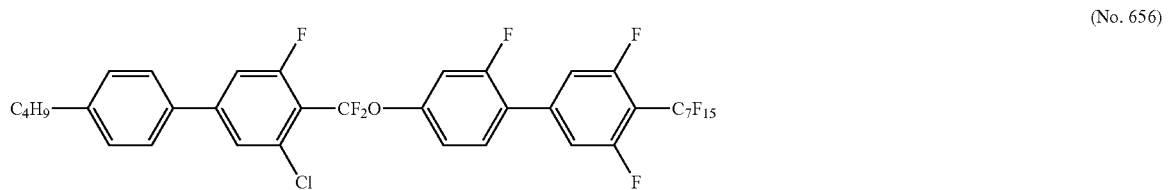
(No. 657
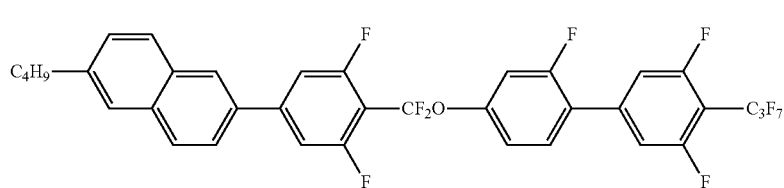
(No. 658)
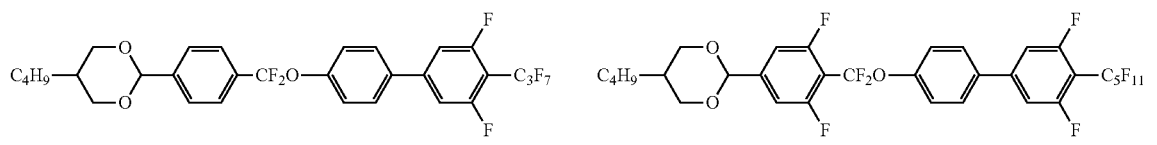
(No. 659)

-continued
(No. 660)
(No. 661)
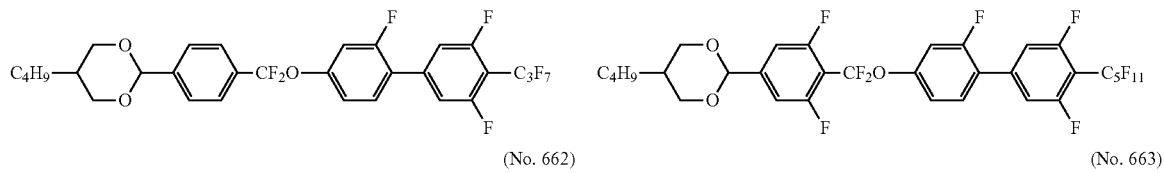
(No. 662)
(No. 663)
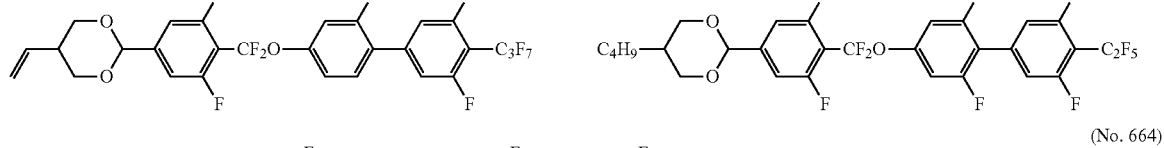
(No. 664)
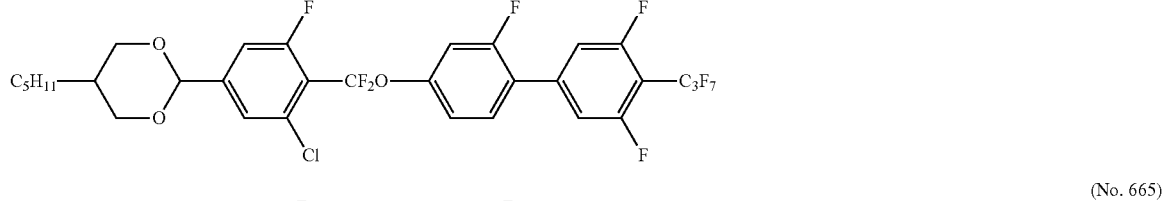
(No. 665)
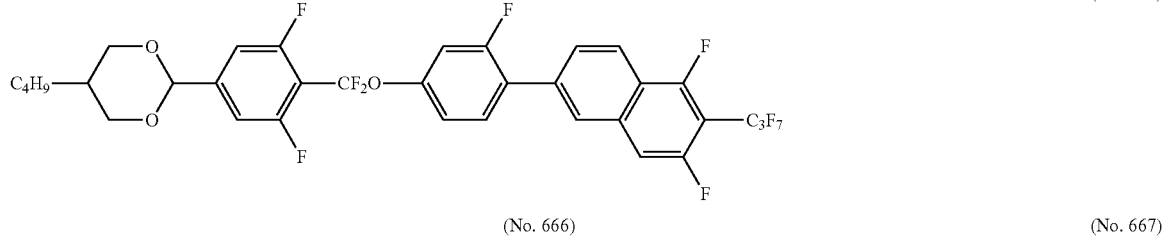
(No. 666)
(No. 667)
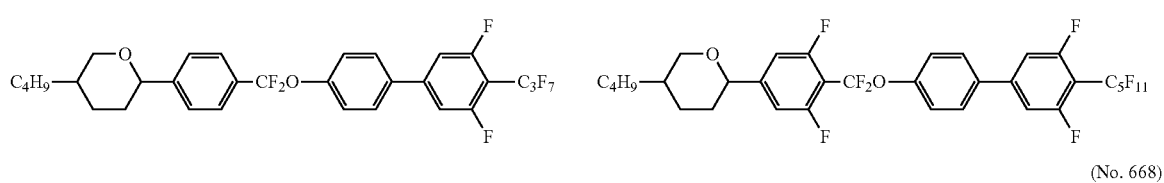
(No. 668)
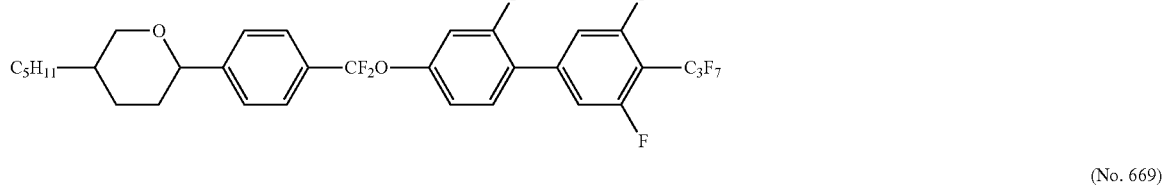
(No. 669)
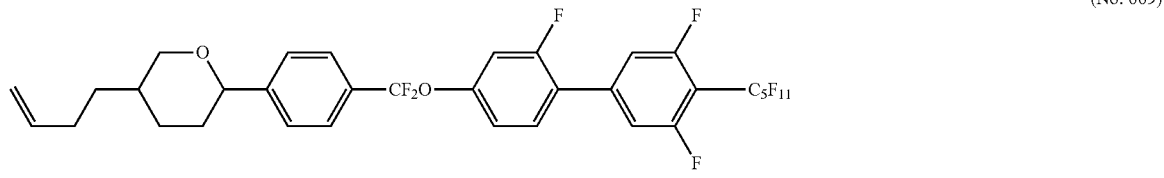
(No. 670)
(No. 671)
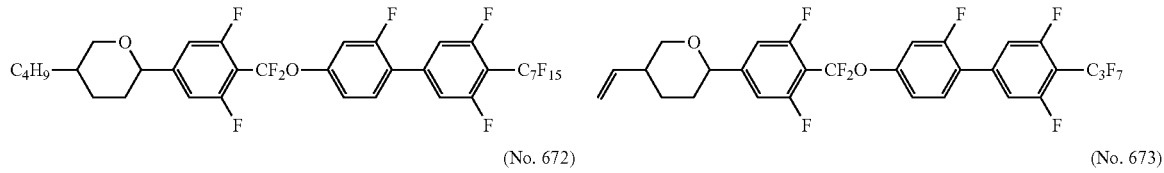
(No. 672)
(No. 673)
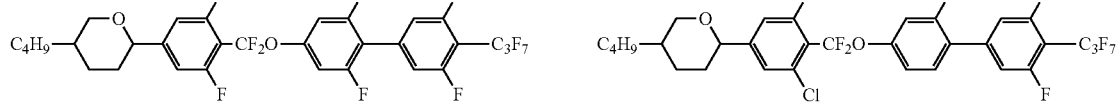

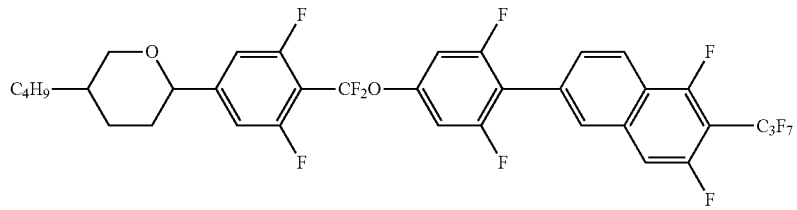
(No. 674)

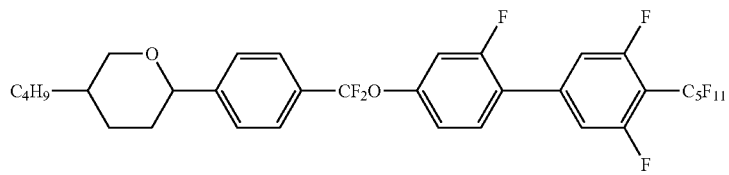
(No. 675)

2. Examples of the Composition

The invention will be explained in more detail by way of Examples. The invention includes a mixture of the composition in Use Example 1 and the composition in Use Example 2. The invention also includes a mixture prepared by mixing at least two compositions in Use Examples. The compounds described in Examples were expressed in terms of symbols based on the definition in Table 2 described below. In Table 2, the configuration of 1,4-cyclohexylene is trans. A parenthesized number next to a symbolized compound in Example represents the chemical formula to which the compound belongs. The symbol "(-)" means any other liquid crystal compound. The ratio (percentage) of a liquid crystal compound means the percentages by weight (% by weight) based on the weight of the liquid crystal composition. Last, physical property-values of the composition are summarized. Physical properties were measured according to the method described above, and the measured value was reported as it was (without extrapolation).

TABLE 2

| Method of Description of Compounds using Symbols R—(A$_1$)—Z$_1$—. . . .—Z$_n$—(A$_n$)—R' | |
|---|---|
| 1) Left-terminal Group R— | Symbol |
| C$_n$H$_{2n+1}$— | n- |
| C$_n$H$_{2n+1}$O— | nO— |
| C$_m$H$_{2m+1}$OC$_n$H$_{2n}$— | mOn- |
| CH$_2$=CH— | V— |
| C$_n$H$_{2n+1}$—CH=CH— | nV— |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF— |
| CF$_2$=CH—C$_n$H$_{2n}$— | VFFn- |
| 2) Right—terminal Group —R' | Symbol |
| —C$_n$H$_{2n+1}$ | -n |
| —OC$_n$H$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | -nV |
| —C$_m$H$_{2m}$—CH=CH—C$_n$H$_{2n+1}$ | -mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |

TABLE 2-continued

| Method of Description of Compounds using Symbols R—(A$_1$)—Z$_1$—. . . .—Z$_n$—(A$_n$)—R' | |
|---|---|
| —C≡N | —C |
| —C$_n$F$_{2n+1}$ | —Rfn |
| 3) Bonding Group —Z$_n$— | Symbol |
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring —A$_n$— | Symbol |
| 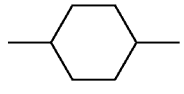 | H |
| 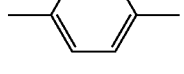 | B |
| 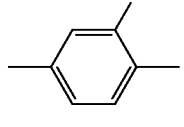 | B(F) |
| 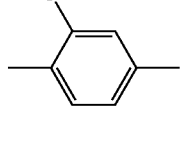 | B(2F) |
| 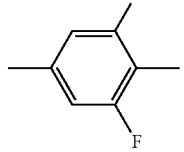 | B(F,F) |

TABLE 2-continued

Method of Description of Compounds using Symbols
R—(A₁)—Z₁—.....—Zₙ—(Aₙ)—R'

| Structure | Symbol |
|---|---|
| 2,5-difluoro-1,4-phenylene | B(2F,5F) |
| 2,3-difluoro-1,4-phenylene | B(2F,3F) |
| pyrimidine | Py |
| 1,3-dioxane | G |
| tetrahydropyran (2,5) | dh |
| tetrahydropyran (2,6) | Dh |
| 7,8-difluorochroman | Cro |
| 3-chloro-2-fluoro-1,4-phenylene | B(2F,3CL) |

5) Examples of Description

Example 1. 3-HH—V

Example 2. 3-BB(F,F)XB(F,F)—Rf7

Use Example 1

| | | |
|---|---|---|
| 3-BB(F)B(F,F)XB(F,F)-Rf5 | (No. 458) | 1% |
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 9% |
| 4-PyBB-F | (6-80) | 9% |
| 5-PyBB-F | (6-80) | 9% |
| 5-HBB(F)B-2 | (4-5) | 10% |
| 5-HBB(F)B-3 | (4-5) | 10% |

NI = 98.7° C.; η = 40.1 mPa · s; Δn = 0.188; Δε = 8.3.

Use Example 2

| | | |
|---|---|---|
| 4-BB(F)B(F,F)XB(F,F)-Rf3 | (No. 457) | 2% |
| 5-HXB(F,F)-Rf5 | (No. 2) | 2% |
| 2-HB-C | (8-1) | 5% |
| 3-HB-C | (8-1) | 12% |
| 3-HB-O2 | (2-5) | 15% |
| 2-BTB-1 | (2-10) | 3% |
| 3-HHB-F | (6-1) | 4% |
| 3-HHB-1 | (3-1) | 8% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 5% |
| 3-HHB(F)-F | (6-2) | 7% |
| 5-HHB(F)-F | (6-2) | 7% |
| 3-HHB(F,F)-F | (6-3) | 3% |

NI = 99.2° C.; η = 19.1 mPa · s; Δn = 0.102; Δε = 5.1.

Use Example 3

| | | |
|---|---|---|
| 3-HHXB(F,F)-Rf5 | (No. 201) | 5% |
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 10% |
| 2-HBB(F)-F | (6-23) | 7% |
| 3-HBB(F)-F | (6-23) | 6% |
| 5-HBB(F)-F | (6-23) | 16% |
| 2-HBB-F | (6-22) | 4% |
| 3-HBB-F | (6-22) | 4% |
| 5-HBB-F | (6-22) | 3% |
| 3-HBB(F,F)-F | (6-24) | 5% |
| 5-HBB(F,F)-F | (6-24) | 10% |

NI = 87.0° C.; η = 26.1 mPa · s; Δn = 0.112; Δε = 5.9.

Use Example 4

| | | |
|---|---|---|
| 3-BB(F,F)XB(F,F)-Rf7 | (No. 275) | 4% |
| 5-HB-CL | (5-2) | 16% |
| 3-HH-4 | (2-1) | 12% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 9% |
| 5-HHB(F)-F | (6-2) | 9% |
| 7-HHB(F)-F | (6-2) | 5% |
| 5-HBB(F)-F | (6-23) | 3% |
| 1O1-HBBH-5 | (4-1) | 3% |
| 3-HHBB(F,F)-F | (7-6) | 2% |
| 4-HHBB(F,F)-F | (7-6) | 3% |

-continued

| | | |
|---|---|---|
| 5-HHBB(F,F)-F | (7-6) | 3% |
| 3-HH2BB(F,F)-F | (7-15) | 3% |
| 4-HH2BB(F,F)-F | (7-15) | 3% |

NI = 111.8° C.; η = 19.5 mPa · s; Δn = 0.092; Δε = 4.3.

Use Example 5

| | | |
|---|---|---|
| 3-BB(F,F)XB(F,F)-Rf5 | (No. 274) | 5% |
| 3-HHB(F,F)-F | (6-3) | 9% |
| 3-H2HB(F,F)-F | (6-15) | 8% |
| 4-H2HB(F,F)-F | (6-15) | 8% |
| 5-H2HB(F,F)-F | (6-15) | 8% |
| 3-HBB(F,F)-F | (6-24) | 20% |
| 5-HBB(F,F)-F | (6-24) | 19% |
| 3-H2BB(F,F)-F | (6-27) | 8% |
| 5-HHBB(F,F)-F | (7-6) | 2% |
| 5-HHEBB-F | (7-17) | 2% |
| 3-HH2BB(F,F)-F | (7-15) | 3% |
| 1O1-HBBH-4 | (4-1) | 4% |
| 1O1-HBBH-5 | (4-1) | 4% |

NI = 94.9° C.; η = 35.5 mPa · s; Δn = 0.116; Δε = 9.6.

The helical pitch was 63.9 micrometers when optically active compound (Op-5) was added to the preceding composition in the ratio of 0.25% by weight.

Use Example 6

| | | |
|---|---|---|
| 3-BB(F,F)XB(F,F)-Rf2 | (No. 276) | 5% |
| 5-HB-F | (5-2) | 10% |
| 6-HB-F | (5-2) | 7% |
| 7-HB-F | (5-2) | 6% |
| 2-HHB-OCF3 | (6-1) | 7% |
| 3-HHB-OCF3 | (6-1) | 7% |
| 4-HHB-OCF3 | (6-1) | 7% |
| 5-HHB-OCF3 | (6-1) | 5% |
| 3-HH2B-OCF3 | (6-4) | 4% |
| 5-HH2B-OCF3 | (6-4) | 4% |
| 3-HHB(F,F)-OCF2H | (6-3) | 4% |
| 3-HHB(F,F)-OCF3 | (6-3) | 5% |
| 3-HH2B(F)-F | (6-5) | 3% |
| 3-HBB(F)-F | (6-23) | 10% |
| 5-HBB(F)-F | (6-23) | 10% |
| 5-HBBH-3 | (4-1) | 3% |
| 3-HB(F)BH-3 | (4-2) | 3% |

Use Example 7

| | | |
|---|---|---|
| 3-B(F)B(F,F)XB(F)B(F,F)-Rf5 | (No. 654) | 1% |
| 3-GB(F,F)XB(F,F)-Rf3 | (No. 296) | 3% |
| 5-HB-CL | (5-2) | 11% |
| 3-HH-4 | (2-1) | 8% |
| 3-HHB-1 | (3-1) | 5% |
| 3-HHB(F,F)-F | (6-3) | 7% |
| 3-HBB(F,F)-F | (6-24) | 20% |
| 5-HBB(F,F)-F | (6-24) | 14% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 3% |
| 5-HBEB(F,F)-F | (6-39) | 3% |
| 3-HHBB(F,F)-F | (7-6) | 6% |

Use Example 8

| | | |
|---|---|---|
| 4-BB(F)B(F,F)XB(F,F)-Rf7 | (No. 459) | 2% |
| 3-dhBB(F,F)XB(F,F)-Rf5 | (No. 547) | 1% |
| 3-HB-CL | (5-2) | 6% |
| 5-HB-CL | (5-2) | 4% |
| 3-HHB-OCF3 | (6-1) | 5% |
| 3-H2HB-OCF3 | (6-13) | 5% |
| 5-H4HB-OCF3 | (6-19) | 13% |
| V-HHB(F)-F | (6-2) | 4% |
| 3-HHB(F)-F | (6-2) | 5% |
| 5-HHB(F)-F | (6-2) | 5% |
| 3-H4HB(F,F)-CF3 | (6-21) | 8% |
| 5-H4HB(F,F)-CF3 | (6-21) | 10% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 10% |
| 3-HBEB(F,F)-F | (6-39) | 5% |

Use Example 9

| | | |
|---|---|---|
| 3-BB(F)B(F,F)XB(F,F)-Rf5 | (No. 458) | 1% |
| 4-BB(F)B(F,F)XB(F,F)-Rf3 | (No. 457) | 2% |
| 5-HB-CL | (5-2) | 17% |
| 7-HB(F,F)-F | (5-4) | 3% |
| 3-HH-4 | (2-1) | 10% |
| 3-HH-5 | (2-1) | 5% |
| 3-HB-O2 | (2-5) | 15% |
| 3-HHB-1 | (3-1) | 8% |
| 3-HHB-O1 | (3-1) | 4% |
| 2-HHB(F)-F | (6-2) | 7% |
| 3-HHB(F)-F | (6-2) | 6% |
| 5-HHB(F)-F | (6-2) | 6% |
| 3-HHB(F,F)-F | (6-3) | 6% |
| 3-H2HB(F,F)-F | (6-15) | 5% |
| 4-H2HB(F,F)-F | (6-15) | 5% |

NI = 70.0° C.; η = 14.9 mPa · s; Δn = 0.077; Δε = 3.6.

Use Example 10

| | | |
|---|---|---|
| 3-HHXB(F,F)-Rf5 | (No. 201) | 3% |
| 5-HB-CL | (5-2) | 3% |
| 7-HB(F)-F | (5-3) | 7% |
| 3-HH-4 | (2-1) | 9% |
| 3-HH-EMe | (2-2) | 23% |
| 3-HHEB-F | (6-10) | 8% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 5% |
| 2-H2GB(F,F)-F | (6-106) | 4% |
| 3-H2GB(F,F)-F | (6-106) | 5% |
| 5-GHB(F,F)-F | (6-109) | 5% |

NI = 81.0° C.; η = 19.9 mPa · s; Δn = 0.064; Δε = 5.5.

Use Example 11

| | | |
|---|---|---|
| 3-BB(F,F)XB(F,F)-Rf7 | (No. 275) | 5% |
| 3-HB-O1 | (2-5) | 16% |
| 3-HH-4 | (2-1) | 5% |
| 3-HB(2F,3F)-O2 | (9-1) | 12% |
| 5-HB(2F,3F)-O2 | (9-1) | 10% |
| 2-HHB(2F,3F)-1 | (10-1) | 10% |

-continued

| | | |
|---|---|---|
| 3-HHB(2F,3F)-1 | (10-1) | 12% |
| 3-HHB(2F,3F)-O2 | (10-1) | 11% |
| 5-HHB(2F,3F)-O2 | (10-1) | 13% |
| 3-HHB-1 | (3-1) | 6% |

NI = 83.5° C.; $\eta$ = 35.6 mPa · s; $\Delta n$ = 0.091; $\Delta \epsilon$ = −3.1.

Use Example 12

| | | |
|---|---|---|
| 3-BB(F,F)XB(F,F)-Rf5 | (No. 274) | 5% |
| 2-HH-5 | (2-1) | 3% |
| 3-HH-4 | (2-1) | 15% |
| 3-HH-5 | (2-1) | 4% |
| 3-HB-O2 | (2-5) | 12% |
| 3-H2B(2F,3F)-O2 | (9-4) | 13% |
| 5-H2B(2F,3F)-O2 | (9-4) | 15% |
| 3-HHB(2F,3CL)-O2 | (10-12) | 5% |
| 2-BBB(2F,3F)-O2 | (10-7) | 3% |
| 3-BBB(2F,3F)-O2 | (10-7) | 8% |
| 5-BBB(2F,3F)-O2 | (10-7) | 7% |
| 3-HHB-1 | (3-1) | 3% |
| 3-HHB-3 | (3-1) | 4% |
| 3-HHB-O1 | (3-1) | 3% |

NI = 72.0° C.; $\eta$ = 20.0 mPa · s; $\Delta n$ = 0.092; $\Delta \epsilon$ = −3.8.

Use Example 13

| | | |
|---|---|---|
| 3-BB(F,F)XB(F,F)-Rf2 | (No. 276) | 4% |
| 2-HH-3 | (2-1) | 18% |
| 3-HH-4 | (2-1) | 9% |
| 1-BB-3 | (2-8) | 9% |
| 3-HB-O2 | (2-5) | 2% |
| 3-BB(2F,3F)-O2 | (9-3) | 9% |
| 5-BB(2F,3F)-O2 | (9-3) | 5% |
| 2-HH1OB(2F,3F)-O2 | (10-5) | 13% |
| 3-HH1OB(2F,3F)-O2 | (10-5) | 21% |
| 3-HHB-1 | (3-1) | 5% |
| 3-HHB-O1 | (3-1) | 3% |
| 5-B(F)BB-2 | (3-8) | 2% |

Use Example 14

| | | |
|---|---|---|
| 3-B(F)B(F,F)XB(F)B(F,F)-Rf5 | (No. 654) | 1% |
| 3-GB(F,F)XB(F,F)-Rf3 | (No. 296) | 3% |
| 2-HH-3 | (2-1) | 16% |
| 7-HB-1 | (2-5) | 10% |
| 5-HB-O2 | (2-5) | 8% |
| 3-HB(2F,3F)-O2 | (9-1) | 17% |
| 5-HB(2F,3F)-O2 | (9-1) | 14% |
| 3-HHB(2F,3CL)-O2 | (10-12) | 3% |
| 4-HHB(2F,3CL)-O2 | (10-12) | 3% |
| 3-HH1OCro(7F,8F)-5 | (13-6) | 5% |
| 5-HBB(F)B-2 | (4-5) | 10% |
| 5-HBB(F)B-3 | (4-5) | 10% |

Use Example 15

| | | |
|---|---|---|
| 4-BB(F)B(F,F)XB(F,F)-Rf7 | (No. 459) | 2% |
| 3-dhBB(F,F)XB(F,F)-Rf5 | (No. 547) | 1% |
| 1-BB-3 | (2-8) | 10% |
| 3-HH-V | (2-1) | 27% |

-continued

| | | |
|---|---|---|
| 3-BB(2F,3F)-O2 | (9-3) | 12% |
| 2-HH1OB(2F,3F)-O2 | (10-5) | 20% |
| 3-HH1OB(2F,3F)-O2 | (10-5) | 14% |
| 3-HHB-1 | (3-1) | 8% |
| 5-B(F)BB-2 | (3-8) | 6% |

Use Example 16

| | | |
|---|---|---|
| 3-BB(F)B(F,F)XB(F,F)-Rf5 | (No. 458) | 1% |
| 4-BB(F)B(F,F)XB(F,F)-Rf3 | (No. 457) | 2% |
| 2-HH-3 | (2-1) | 6% |
| 3-HH-V1 | (2-1) | 10% |
| 1V2-HH-1 | (2-1) | 8% |
| 1V2-HH-3 | (2-1) | 7% |
| 3-BB(2F,3F)-O2 | (9-3) | 8% |
| 5-BB(2F,3F)-O2 | (9-3) | 4% |
| 3-H1OB(2F,3F)-O2 | (9-5) | 6% |
| 2-HH1OB(2F,3F)-O2 | (7-5) | 7% |
| 3-HH1OB(2F,3F)-O2 | (10-5) | 19% |
| 3-HDhB(2F,3F)-O2 | (10-5) | 6% |
| 3-HHB-1 | (3-1) | 3% |
| 3-HHB-3 | (3-1) | 2% |
| 2-BB(2F,3F)B-3 | (11-1) | 11% |

NI = 85.5° C.; $\eta$ = 22.1 mPa · s; $\Delta n$ = 0.111; $\Delta \epsilon$ = −4.2.

Use Example 17

| | | |
|---|---|---|
| 5-HXB(F,F)-Rf5 | (No. 2) | 5% |
| 1V2-BEB(F,F)-C | (8-15) | 5% |
| 3-HB-C | (8-1) | 18% |
| 2-BTB-1 | (2-10) | 10% |
| 5-HH-VFF | (2-1) | 30% |
| 3-HHB-1 | (3-1) | 3% |
| VFF-HHB-1 | (3-1) | 8% |
| VFF2-HHB-1 | (3-1) | 11% |
| 3-H2BTB-2 | (3-17) | 3% |
| 3-H2BTB-3 | (3-17) | 4% |
| 3-H2BTB-4 | (3-17) | 3% |

NI = 74.3° C.; $\eta$ = 12.3 mPa · s; $\Delta n$ = 0.123; $\Delta \epsilon$ = 6.1.

Use Example 18

| | | |
|---|---|---|
| 3-HHXB(F,F)-Rf5 | (No. 201) | 5% |
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 5% |
| 5-BB(F)B(F,F)XB(F,F)-F | (7-47) | 3% |
| 3-HH-V | (2-1) | 41% |
| 3-HH-V1 | (2-1) | 7% |
| 3-HHEH-5 | (3-13) | 3% |
| 3-HHB-1 | (3-1) | 3% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 9% |
| 3-HHBB(F,F)-F | (7-6) | 3% |

NI = 83.8° C.; $\eta$ = 12.4 mPa · s; $\Delta n$ = 0.102; $\Delta \epsilon$ = 5.6.

Use Example 19

| | | |
|---|---|---|
| 3-BB(F,F)XB(F,F)-Rf7 | (No. 275) | 4% |
| 3-GB(F)B(F,F)XB(F,F)-F | (7-57) | 5% |

| | | |
|---|---|---|
| 3-BB(F)B(F,F)XB(F,F)-F | (7-47) | 3% |
| 4-BB(F)B(F,F)XB(F,F)-F | (7-47) | 5% |
| 5-BB(F)B(F,F)XB(F,F)-F | (7-47) | 3% |
| 3-HH-V | (2-1) | 41% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 5% |
| 3-GB(F,F)XB(F,F)-F | (6-113) | 4% |
| 3-HHBB(F,F)-F | (7-6) | 3% |

NI = 81.5° C.; η = 12.5 mPa · s; Δn = 0.102; Δε = 6.9.

INDUSTRIAL APPLICABILITY

The liquid crystal compound of the invention satisfies at least one of physical properties such as a high stability to heat or light, a high clearing point (or a high maximum temperature), a low minimum temperature of a liquid crystal phase, a small viscosity, a suitable optical anisotropy, a large dielectric anisotropy, a suitable elastic constant and an excellent compatibility with any other liquid crystal compound. The compound has an especially high maximum temperature. The liquid crystal composition of the invention includes this compound and satisfies at least one of physical property such as a high stability to heat or light, a high maximum temperature, a low minimum temperature, a small viscosity, a suitable optical anisotropy, a large dielectric anisotropy, a large specific resistance and a suitable elastic constant. The composition has a suitable balance between at least two of physical properties. The liquid crystal display device of the invention includes this composition and has a wide temperature range in which a device can be used, a short response time, a large voltage holding ratio, a low threshold voltage, a large contrast ratio and a long service life. The device can be used for a liquid crystal projector, a liquid crystal television and so forth, accordingly.

What is claimed is:

1. A compound represented by formula (1a):

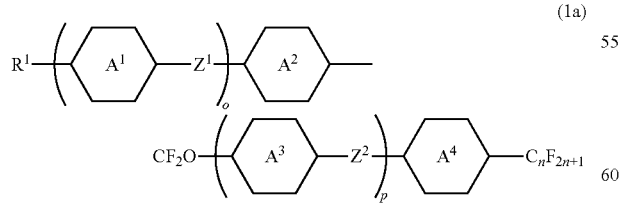

(1a)

in formula (1a),
$R^1$ is alkyl having 1 to 15 carbons, and in the alkyl at least one —$CH_2$— may be replaced by —O— or —S— and at least one —$CH_2CH_2$— may be replaced by —CH=CH—;

ring $A^1$, ring $A^2$ and ring $A^3$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl or 1,2,3,4-tetrahydronaphthalene-2,6-diyl, and in these rings at least one hydrogen may be replaced by fluorine or chlorine;

ring $A^4$ is 1,4-phenylene or naphthalene-2,6-diyl, and in these rings at least one hydrogen may be replaced by fluorine or chlorine;

$Z^1$ and $Z^2$ are independently a single bond, —$CH_2CH_2$—, —CH=CH—, —C≡C—, —COO—, —OCO—, —$CH_2O$—, —$OCH_2$—, —$CF_2O$—, —$OCF_2$— or —CF=CF—;

o and p are independently 0, 1 or 2, and the sum of o and p is 0, 1 or 2; and n is an integer from 2 to 10.

2. The compound according to claim 1, wherein in formula (1a) according to claim 1, ring $A^3$ is 1,4-phenylene, 1,4-phenylene in which at least one hydrogen has been replaced by fluorine or chlorine, naphthalene-2,6-diyl or naphthalene-2,6-diyl in which at least one hydrogen has been replaced by fluorine or chlorine.

3. The compound according to claim 1, wherein the compound is represented by formula (1b):

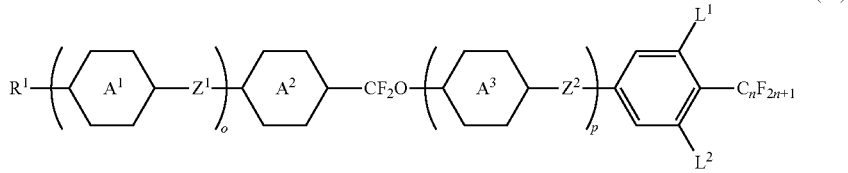

(1b)

in formula (1b),
$R^1$ is alkyl having 1 to 15 carbons, and in the alkyl at least one —$CH_2$— may be replaced by —O— and at least one —$CH_2CH_2$— may be replaced by —CH=CH—;

ring $A^1$ is 1,4-cyclohexylene, 1,4-phenylene, 1,4-phenylene in which at least one hydrogen has been replaced by fluorine or chlorine, naphthalene-2,6-diyl, naphthalene-2,6-diyl in which at least one hydrogen has been replaced by fluorine or chlorine, 1,3-dioxane-2,5-diyl, tetrahydropyran-2,5-diyl or 2,6,7-trioxabicyclo[2.2.2]octane-1,4-diyl;

ring $A^2$ is 1,4-cyclohexylene, 1,4-phenylene, 1,4-phenylene in which at least one hydrogen has been replaced by fluorine or chlorine, naphthalene-2,6-diyl or naphthalene-2,6-diyl in which at least one hydrogen has been replaced by fluorine or chlorine;

ring $A^3$ is 1,4-phenylene, 1,4-phenylene in which at least one hydrogen has been replaced by fluorine or chlorine, naphthalene-2,6-diyl or naphthalene-2,6-diyl in which at least one hydrogen has been replaced by fluorine or chlorine;

$Z^1$ and $Z^2$ are independently a single bond, —$CH_2CH_2$—, —CH=CH—, —C≡C—, —COO—, —OCO—, —$CH_2O$—, —$OCH_2$—, —$CF_2O$—, —$OCF_2$— or —CF=CF—;

L¹ and L² are independently hydrogen, fluorine or chlorine;

o and p are independently 0, 1 or 2, and the sum of o and p is 0, 1 or 2; and n is an integer from 2 to 10.

4. The compound according to claim 3, wherein in formula (1b) according to claim 3, R¹ is alkyl having 1 to 15 carbons, alkoxy having 1 to 14 carbons, alkenyl having 2 to 15 carbons or alkenyloxy having 2 to 14 carbons; and Z¹ and Z² are independently a single bond, —CH₂CH₂—, —CH=CH—, —CF₂O— or —COO—.

5. The compound according to claim 1, wherein the compound is represented by any one of formulas (1-1) to (1-4):

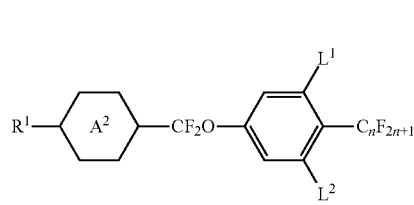
(1-1)

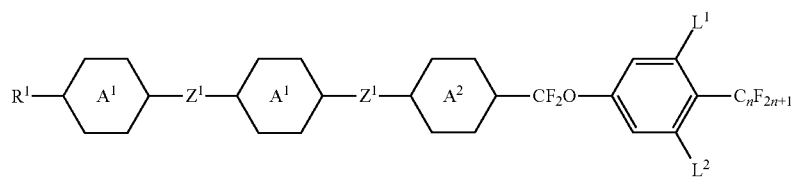
(1-2)

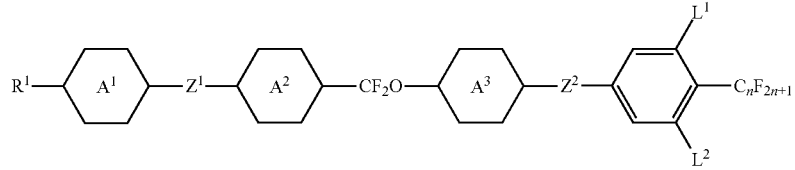
(1-3)

(1-4)

in formulas (1-1) to (1-4),
   R¹ is alkyl having 1 to 15 carbons, alkoxy having 1 to 14 carbons, alkenyl having 2 to 15 carbons or alkenyloxy having 2 to 14 carbons;
   ring A¹ is 1,4-cyclohexylene, 1,4-phenylene, 1,4-phenylene in which at least one hydrogen has been replaced by fluorine or chlorine, naphthalene-2,6-diyl, naphthalene-2,6-diyl in which at least one hydrogen has been replaced by fluorine or chlorine, 1,3-dioxane-2,5-diyl or tetrahydropyran-2,5-diyl;
   ring A² is 1,4-cyclohexylene, 1,4-phenylene or 1,4-phenylene in which at least one hydrogen has been replaced by fluorine or chlorine, naphthalene-2,6-diyl or naphthalene-2,6-diyl in which at least one hydrogen has been replaced by fluorine or chlorine;
   ring A³ is 1,4-phenylene or 1,4-phenylene in which at least one hydrogen has been replaced by fluorine or chlorine, naphthalene-2,6-diyl or naphthalene-2,6-diyl in which at least one hydrogen has been replaced by fluorine or chlorine;
   Z¹ and Z² are independently a single bond, —CH₂CH₂— or —CH=CH—;
   L¹ and L² are independently hydrogen or fluorine; and
   n is an integer from 2 to 10.

6. The compound according to claim 5, wherein in formulas (1-1) to (1-4) according to claim 5, R¹ is alkyl having 1 to 15 carbons or alkenyl having 2 to 15 carbons.

7. The compound according to claim 1, wherein the compound is represented by any one of formulas (1-5) to (1-37):

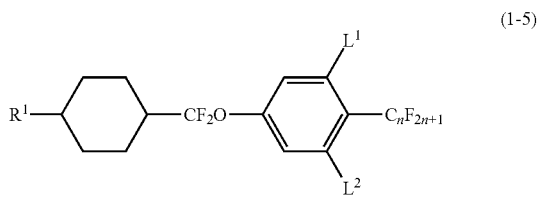
(1-5)

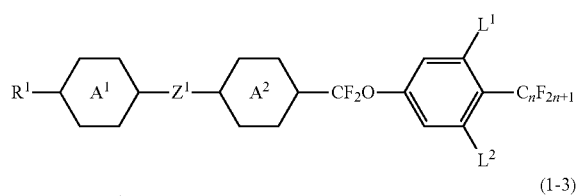
(1-6)

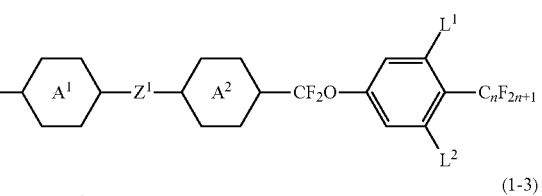

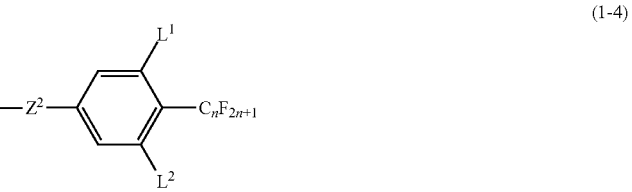
(1-7)

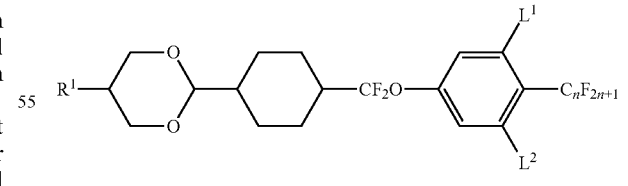
(1-8)

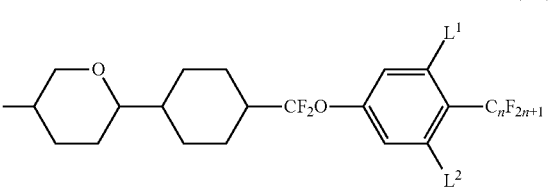

(1-9)
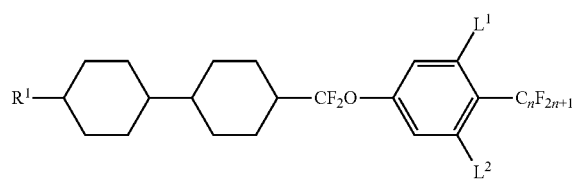
(1-17)
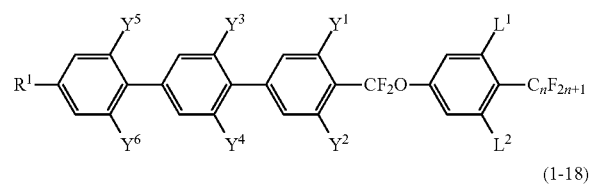
(1-10)
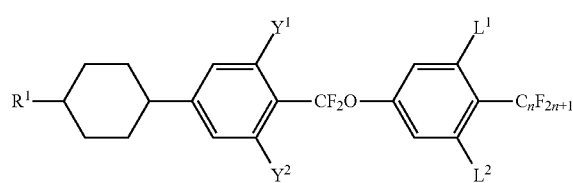
(1-18)
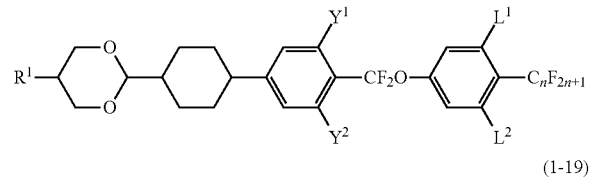
(1-11)
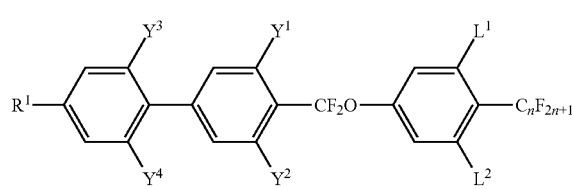
(1-19)
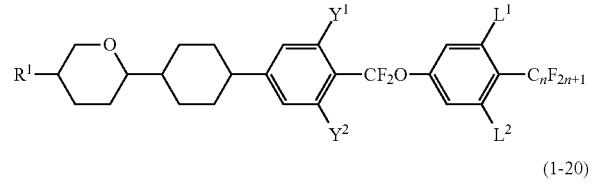
(1-12)
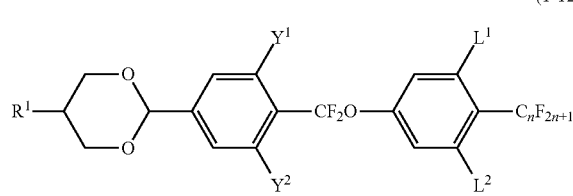
(1-20)
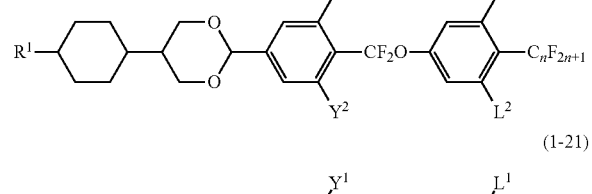
(1-13)
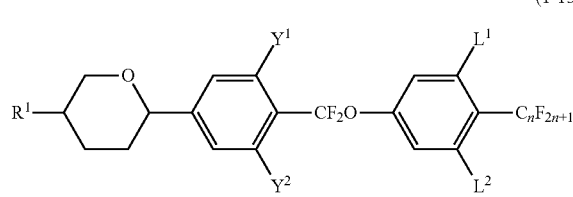
(1-21)
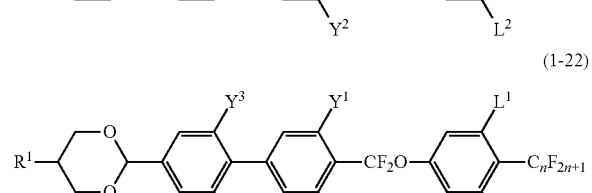
(1-14)
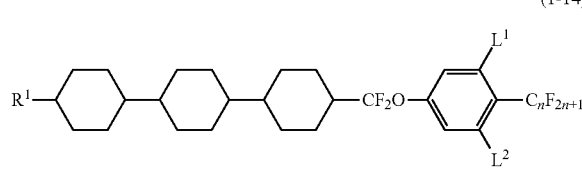
(1-22)
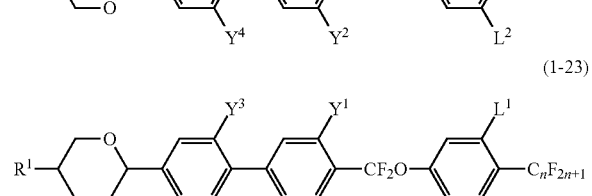
(1-15)
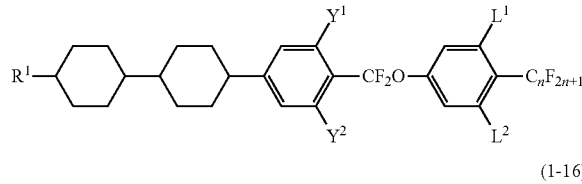
(1-23)
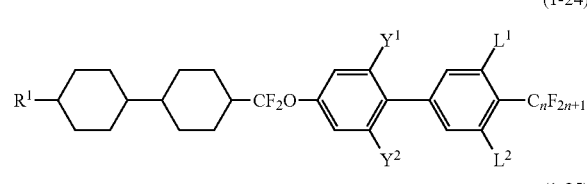
(1-16)
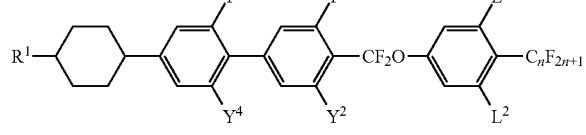
(1-24)
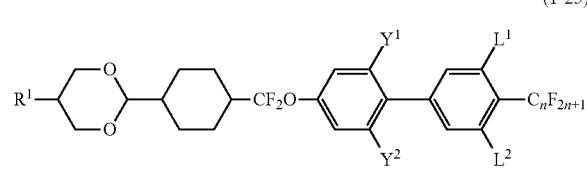
(1-25)

(1-26)
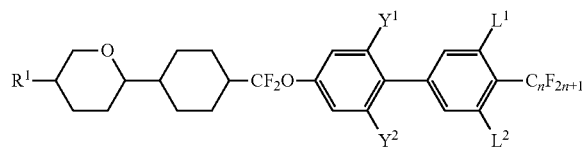
(1-27)
(1-28)
(1-29)
(1-30)
(1-31)
(1-32)
(1-33)
(1-34)
(1-35)
(1-36)
(1-37)
in formulas (1-5) to (1-37), $R^1$ is alkyl having 1 to 10 carbons or alkenyl having 2 to 10 carbons; $L^1$ and $L^2$ are independently hydrogen or fluorine; $Y^1$, $Y^2$, $Y^3$, $Y^4$, $Y^5$ and $Y^6$ are independently hydrogen or fluorine; $Z^1$ is a single bond, —CH$_2$CH$_2$— or —CH=CH—; and n is an integer from 2 to 10.
8. The compound according to claim 1, wherein the compound is represented by any one of formulas (1-38) to (1-45):
(1-38)
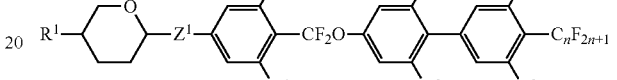
(1-39)
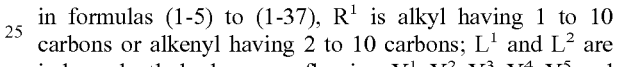
(1-40)
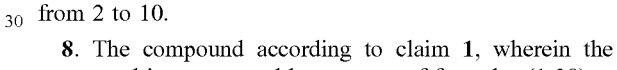
(1-41)

-continued (1-42)
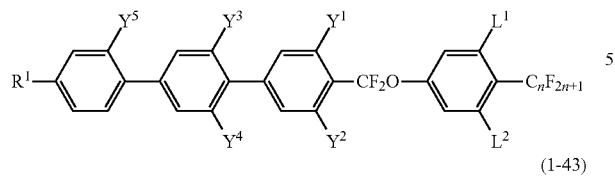

(1-43)
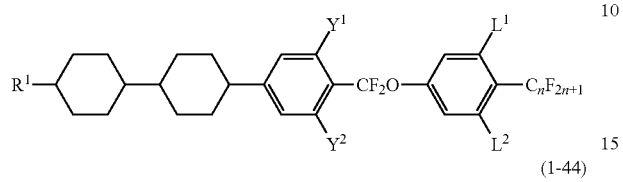

(1-44)
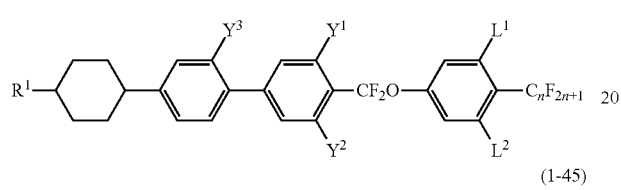

(1-45)
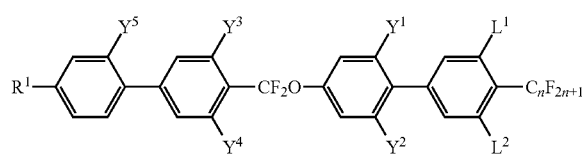

in formulas (1-38) to (1-45), $R^1$ is alkyl having 1 to 10 carbons or alkenyl having 2 to 10 carbons; $L^1$ and $L^2$ are independently hydrogen or fluorine; $Y^1$, $Y^2$, $Y^3$, $Y^4$ and $Y^5$ are independently hydrogen or fluorine; and n is an integer from 2 to 10.

9. The compound according to claim 8, wherein in formulas (1-38) to (1-45) according to claim 8, $R^1$ is alkyl having 1 to 10 carbons; $L^1$ and $L^2$ are fluorine; and $Y^1$, $Y^2$, $Y^3$, $Y^4$, $Y^5$ and $Y^6$ are independently hydrogen or fluorine.

10. A liquid crystal composition including at least one of compounds according to claim 1.

11. The liquid crystal composition according to claim 10, further including at least one compound selected from the group of compounds represented by formulas (2) to (4):

(2)
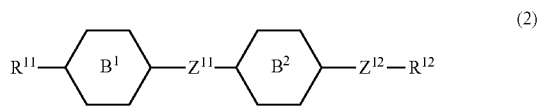

(3)
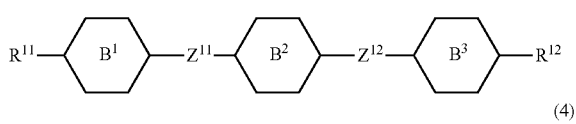

(4)
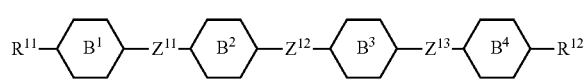

in formulas (2) to (4),
$R^{11}$ and $R^{12}$ are independently alkyl having 1 to 10 carbons or alkenyl having 2 to 10 carbons, and in the alkyl and alkenyl at least one —$CH_2$— may be replaced by —O— and at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

12. The liquid crystal composition according to claim 10, further including at least one compound selected from the group of compounds represented by formulas (5) to (7):

(5)
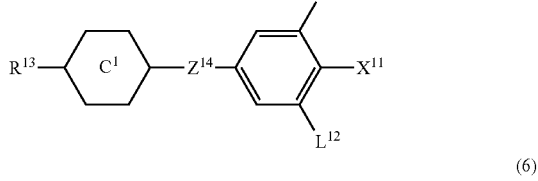

(6)
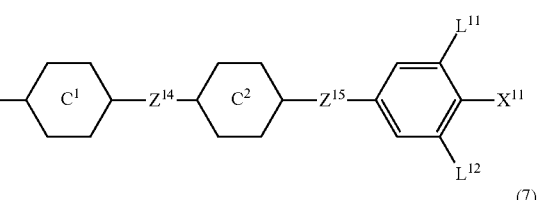

(7)
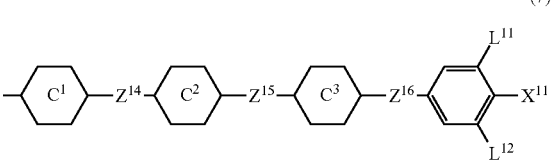

in formula (5) to (7),
$R^{13}$ is alkyl having 1 to 10 carbons or alkenyl having 2 to 10 carbons, and in the alkyl and alkenyl at least one —$CH_2$— may be replaced by —O— and at least one hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

13. The liquid crystal composition according to claim 10, further including at least one compound selected from the group of compounds represented by formula (8):

(8)
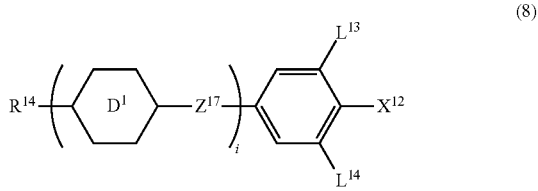

in formula (8),
- $R^{14}$ is alkyl having 1 to 10 carbons or alkenyl having 2 to 10 carbons, and in the alkyl and alkenyl at least one —CH$_2$— may be replaced by —O— and at least one hydrogen may be replaced by fluorine;
- $X^{12}$ is —C≡N or —C≡C—C≡N;
- ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
- $Z^{17}$ is a single bond, —CH$_2$CH$_2$—, —C≡C—, —COO—, —CF$_2$O—, —OCF$_2$— or —CH$_2$O—;
- $L^{13}$ and $L^{14}$ are independently hydrogen or fluorine; and
- i is 1, 2, 3 or 4.

14. The liquid crystal composition according to claim 10, further including at least one compound selected from the group of compounds represented by formulas (9) to (15):

- ring $E^1$, ring $E^2$, ring $E^3$ and ring $E^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;
- ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;
- $Z^{18}$, $Z^{19}$, $Z^{20}$ and $Z^{21}$ are independently a single bond, —CH$_2$CH$_2$—, —COO—, —CH$_2$O—, —OCF$_2$— or —OCF$_2$CH$_2$CH$_2$—;
- $L^{15}$ and $L^{16}$ are independently fluorine or chlorine;
- $S^{11}$ is hydrogen or methyl;
- X is —CHF— or —CF$_2$—; and
- j, k, m, n, p, q, r and s are independently 0 or 1, the sum of k, m, n and p is 1 or 2, and the sum of q, r and s is 0, 1, 2 or 3, and t is 1, 2 or 3.

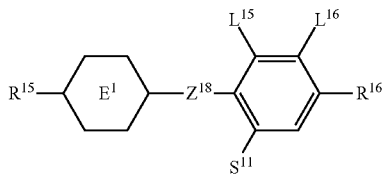

(9)

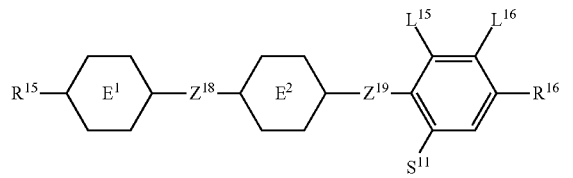

(10)

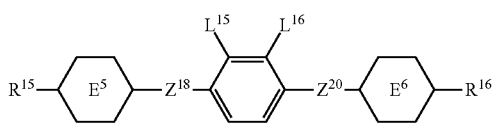

(11)

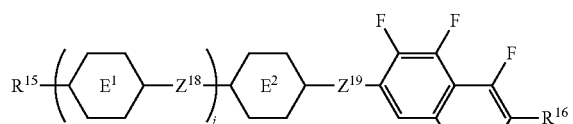

(12)

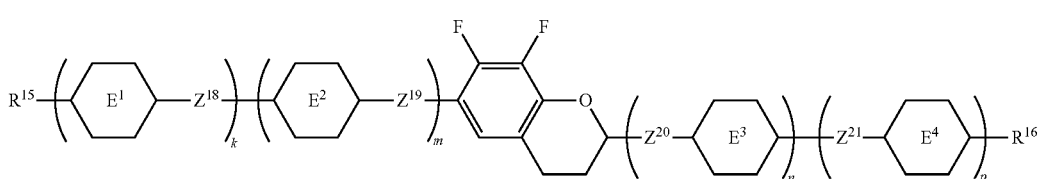

(13)

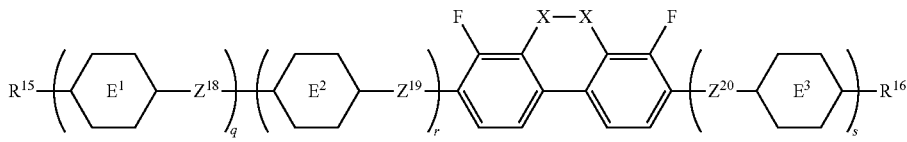

(14)

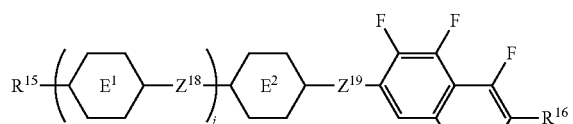

(15)

in formulas (9) to (15),
- $R^{15}$ and $R^{16}$ are independently alkyl having 1 to 10 carbons or alkenyl having 2 to 10 carbons, and in the alkyl and alkenyl at least one —CH$_2$— may be replaced by —O— and at least one hydrogen may be replaced by fluorine;
- $R^{17}$ is hydrogen, fluorine, alkyl having 1 to 10 carbons or alkenyl having 2 to 10 carbons, and in the alkyl and alkenyl at least one —CH$_2$— may be replaced by —O— and at least one hydrogen may be replaced by fluorine;

15. The liquid crystal composition according to claim 10, further including at least one additive selected from the group of a polymerizable compound, a polymerization initiator, a polymerization inhibitor, an optically active compound, an antioxidant, an ultraviolet light absorber, a light stabilizer, a thermal stabilizer, a coloring matter and an antifoaming agent.

16. A liquid crystal display device including the liquid crystal composition according to claim 10.

* * * * *